US007125878B2

(12) United States Patent
Zhang et al.

(10) Patent No.: US 7,125,878 B2
(45) Date of Patent: Oct. 24, 2006

(54) SUBSTITUTED PYRROLINE KINASE INHIBITORS

(75) Inventors: Han-Cheng Zhang, Lansdale, PA (US); Gee-Hong Kuo, Scotch Plains, NJ (US); Bruce E. Maryanoff, Forest Grove, PA (US); Hong Ye, Lansdale, PA (US); David O'Neill, Flemington, NJ (US); Lan Shen, Clinton, NJ (US); Keith Demarest, Flemington, NJ (US); Bruce R. Conway, Doylestown, PA (US); David F. McComsey, Warminster, PA (US)

(73) Assignee: Janssen Pharmaceutica, Beerse (BE)

( * ) Notice: Subject to any disclaimer, the term of this patent is extended or adjusted under 35 U.S.C. 154(b) by 115 days.

(21) Appl. No.: 10/430,000

(22) Filed: May 6, 2003

(65) Prior Publication Data

US 2004/0006095 A1    Jan. 8, 2004

Related U.S. Application Data

(60) Provisional application No. 60/378,503, filed on May 8, 2002.

(51) Int. Cl.
*A61K 31/495*   (2006.01)
*C07D 241/02*   (2006.01)
*C07D 403/04*   (2006.01)

(52) U.S. Cl. ............... 514/255.05; 544/242; 544/336; 544/410; 546/152; 546/268.1; 546/276.4; 514/252.1

(58) Field of Classification Search ............... 544/336, 544/410, 242; 514/252.1, 255.05; 546/152, 546/288.1, 276.4
See application file for complete search history.

(56) References Cited

U.S. PATENT DOCUMENTS 5,057,614 A    10/1991  Davis et al.
6,828,327 B1 * 12/2004  Kuo et al. ................... 514/279

FOREIGN PATENT DOCUMENTS

EP      0328026 A1    2/1989
WO      WO 95/07910 A1    3/1995
WO      WO 00/21927 A2    4/2000
WO      WO 00/38675 A1    7/2000

OTHER PUBLICATIONS

Slater et al (1995): STN International CAPLUS database, (Columbus, Ohio), Accession No. 1995:858526.*
International Search Report mailed Aug. 25, 2003 for PCT/US03/14113.
Davis, et al., J. Med Chem 1992, 35, 177-194.
Ref. International J. Pharm. 1986, 33, 201-217.
J. Pharm Sci., 1977 (Jan.), 66, 1, 1.
P. Xia, et al., "J. Clin. Invest.", 1996, 98, 2018.
H. Ishii, et al., "J. Mol. Med.", 1998, 76, 21.
Inoguchi, et al., "Proc. Natl. Acad. Sci. USA", 1992, 89, 11059-11065.
Bastyr III, E.J. and Lu, J., "Diabetes", 1993, 42 (Suppl. 1) 97A.
Hsieh, et al., "Proc. Natl. Acad. Sci. USA", 1991, 88, 9315-9319.
Hsieh, et al., "J. Biol. Chem." 1993, 268, 15118-15126.
Murray, et al., "J. Biol. Chem.", 1993, 268, 15847-15853.
Bilder, G.E. et al., J. Pharmacol. Exp. Ther. 1990, 252, 526-530.
Matsumoto, H. and Sasaki, Y., Biochem. Biophys. Res. Commun., 1989, 158, 105-109.
Yan, S-F, et al, J. boil. Chem., 2000, 275, 16-11921-11928.
Ren, S. et al., Am. J. Physiol. 2000, 278, (4, Pt. 1), E656-E662.
Muid, R.E., et al., FEBS Lett., 1990, 293, 169-172.
Sonoki, H. et al., Kokyo-To Junkan, 1989, 37, 669-674.
Kobayashi, et al., Amer. Phys. Soc. 1994, H1214-H1220.
Toullec, D. et al., J. Biol. Chem 1991, 266, 15771-15781.
Karasik, A., et al., J. Biol. Chem., 1990, 265, 10226-10231.
Chen, K.S., et al. Trans. Assoc. Am. Physicians, 1991, 104, 206-212.
Chin, J.E. et al., J. Biol. Chem., 1993, 268, 6338-6347.
Lee, T-S., et al., J. Clin. Invest., 1989, 83, 90-94.
Lee, T-S., et al., Proc. Natl. Acad. Sci. USA, 1989, 86, 5141-5145.
Craven, PA and DeRubertis, F.R., J. Clin. Invest., 1989, 87, 1667-1675.
Wolf, B.A. et al., J. Clin. Invest., 1991, 87, 31-38.
Tesfamariam, B., et al., J. Clin. Invest., 1991, 87, 1643-1648.
Ishii, H., et al., Science, 1996, 272, 728-731.
X. Gu, et al., Circ. Res., 1994, 75, 926.
R.H. Strasser, et al., Circulation, 1996, 94, 1551.
H. Wakasaki, et al., Proc. Natl. Acad. Sci. USA, 1997, 94, 9320.
Twoemy, B., et al., Biochem. Biophys. Res. Commun., 1990, 191, 1087-1092.
Mulqueen, M.J., et al., Agents Actions, 1992, 37, 85-89.
Nechushtan, H., et al., Blood, 2000 (Mar.), 95, 5, 1752-1757.
Ren, S., et al., A. J. Physiol., 2000, 278, (4, Pt. 1), E656-E662).
Nagpala, P.G., et al, J. Cell Physiol., 1996, 2, 249-55.
Dekker, L.V., et al., Biochem. J., 2000, 347, 285-289.
Slater, J.J., et al., Biorg. & Med. Chem., 1999, 7, 1067-1074.
Rabbi, M.F., et al., Virology, 1998 (Jun. 5), 245, 2, 257-69.
Leitges, M., et al., Science (Wash., D.C.), 1996), 273, 5276, 788-789.
Horn, F., et al., J. Invest. Dermatol., 1987, 88, 220-222.
Raynaud, F. and Evain-Brion, D., Br. J. Dermatol., 1991, 124, 542-546.
Hegemann, L., et al., Arch. Dermatol. Res., 1991, 283, 456-460.
Bollag, W.B., et al., J. Invest. Dermatol., 1993, 100, 240-246.
Rotenberg, S.A. and Weinstein, I.B., Biochem. Mol. Aspects Sel. Cancer, 1991, 1, 25-73.
Ahmad, et al., Molecular Pharmacology, 1993, 43, 858-862.
Meyer, T., et al., Int. J. Cancer, 1989, 43, 851-856.
Akinagaka, S., et al., Cancer Res., 1991, 51, 4888-4892.
Sauma, S., et al., Cell Growth Differ., 1996, 7, 5, 587-94.
Konig, A., et al., Blood, 1997, 90, 10, Suppl. 1 Pt. 2.
Danso, D., et al., Proc. Am. Assoc. Cancer Res., 1997, 38, 88 Meet. 92.

(Continued)

*Primary Examiner*—Golam M. M. Shameem
(74) *Attorney, Agent, or Firm*—Yurity Stercho

(57) ABSTRACT

The present invention is directed to novel substituted pyrroline compounds useful as kinase inhibitors and methods for treating or ameliorating a kinase mediated disorder.

26 Claims, No Drawings

OTHER PUBLICATIONS

Harrington, E.O., et al., J. Biol. Chem., 1997, 272, 11, 7390-7397.
Begemann, M., et al., Anticancer Res. (Greece), 1998 (Jul.-Aug.), 18, 4A, 2275-82.
Teicher, B.A., et al., Proc. Am. Assoc. Cancer Res., 1998, 39, 89 Meet. 384.
Teicher, B.A., et al., Clinical Cancer Research, 2001 (Mar.), 7, 634-640.
Huang, K.P., Trends Neurosci., 1989, 12, 425-432.
Shimohama, S., et al., Neurology, 1993, 43, 1407-1413.
Hara, H., et al., J. Cereb. Blood Flow Metabl., 1990, 10, 646-653.
Shibata, s., et al., Brain Res., 1992, 594, 290-294.
Beldhuis, H.J.A., et al., Neuroscience, 1993, 55, 4, 965-73.
Miletic, V., et al., Neurosci. Lett., 2000, 288, 3, 199-202.
Chen, C., et al., Science (Wash., D.C.), 1997, 278, 5336, 279-283.
Embi, et al, Eur. J. Biochem, 1980, 107, 519-527.
Cross, et al., Biochemical Journal, 1994, 303, 21-26.
Villar-Palasi C. and Larner J., Biochim. Biophys. Acta, 1960, 39, 171-173.
Parker P.J., et al., Eur. J. Biochem, 1983, 130, 227-234.
Cohen P., Bochem. Soc. Trans. 1993, 21, 555-567.
Srivastava A.K. and Pandey S.K., Mol. and Cellular Biochem., 1998, 182, 135-141.
Chen, et al., Diabetes, 1994, 43, 1234-1241.
Eldar-Finkelman, et al., PNAS, 1996, 93, 10228-10233.
Eldar-Finkelman and Krebs, PNAS, 1997, 94, 9660-9664.
Eldar-Finkelman, et al., Diabetes, 1999, 48, 1662-1666.
Gat, et al., Cell, 1998, 95, 605-614.
Hoeflich K.P., et al., Nature, 2000, 406, 86-90.
Pap and Cooper, J. Biol. Chem., 1998, 273, 19929-19932.
D'Mello, et al., Exp. Cell Res., 1994, 211, 332-338.
Nonaka and Chuang, Neuroreport, 1998, 9(9), 2081-2084.
Hong M. et al., J. Biol. Chem., 1997, 272 (40), 25326-32.
Ikeda, et al., EMBO J., 1998, 17, 1371-1384.
Eastman, Grosschedl, Curr. Opin. Cell Biol., 1999, 11, 233.
Cotter D., et al., Neuroreport, 1998, 9, 1379-1383.
Lijam N., et al., Cell, 1997, 90, 895-905.
Manji, et al., J. Clin. Psychiatry, 1999, 60, (Suppl 2) 27-39.
Jones, R.G.,J. Am. Chem. Soc. 1953, 75, 4048.
Robinson, J. Amer. Chem. Soc., 78, 1956, 1247-1249.

* cited by examiner

SUBSTITUTED PYRROLINE KINASE INHIBITORS

CROSS REFERENCE TO RELATED APPLICATIONS

This application claims benefit of provisional patent application Ser. No. 60/378,503, filed on May 8, 2002, which is hereby incorporated by reference herein.

FIELD OF THE INVENTION

This invention is directed to certain novel compounds, methods for producing them and methods for treating or ameliorating a kinase mediated disorder. More particularly, this invention is directed to substituted pyrroline compounds useful as selective kinase inhibitors, methods for producing such compounds and methods for treating or ameliorating a kinase mediated disorder.

BACKGROUND OF THE INVENTION

Patent application WO 00/38675 discloses disubstituted maleimide compounds of Formula compounds as GSK-3 (glycogen synthase kinase-3) inhibitors of Formula (A), (B) and (C):

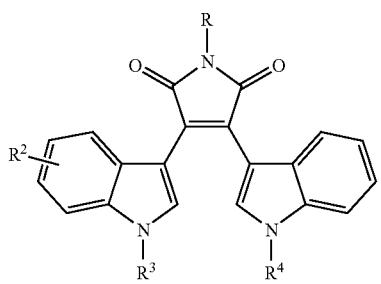

(A)

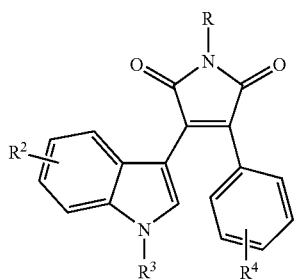

(B)

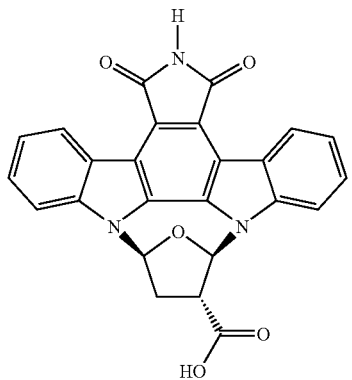

(C)

wherein, for Formula (A), R is hydrogen; $R^2$ is hydrogen, 5-O-n-Pr, 5-Ph, 5-$CO_2$Me or 5-$NO_2$; $R^3$ is Me or $(CH_2)_3OH$, and; $R^4$ is Me, n-Pr, —$(CH_2)_3X$, wherein X is selected from CN, $NH_2$, $CO_2H$, $CONH_2$ or OH; and, wherein, for Formula (B), R is hydrogen; $R^2$ is hydrogen; $R^3$ is Me or a group —$(CH_2)_3Y$, wherein Y is $NH_2$ or OH; and, $R^4$ is 2-Cl or 2,4-di-Cl.

Patent application WO 00/21927 describes 3-amino-4-arymaleimide compounds of Formula (I):

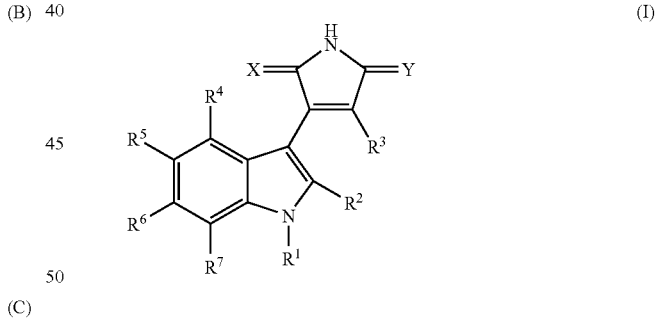

(I)

or a pharmaceutically acceptable derivative thereof, wherein: R is hydrogen, alkyl, aryl or aralkyl; $R^1$ is hydrogen, alkyl, aralkyl, hydroxyalkyl or alkoxyalkyl; $R^2$ is substituted or unsubstituted aryl or substituted or unsubstituted heterocyclyl; $R^3$ is hydrogen, substituted or unsubstituted alkyl, cycloalkyl, alkoxyalkyl, substituted or unsubstituted aryl, substituted or unsubstituted heterocyclyl or aralkyl wherein the aryl moiety is substituted or unsubstituted; or, $R^1$ and $R^3$ together with the nitrogen to which they are attached form a single or fused, optionally substituted, saturated or unsaturated heterocyclic ring and a method for the treatment of conditions associated with a need for inhibition of GSK-3, such as diabetes, dementias such as Alzheimer's disease and manic depression.

U.S. Pat. No. 5,057,614 to Davis, et. al., describes substituted pyrrole compounds of formula (I):

(I)

wherein $R^1$ signifies hydrogen, alkyl, aryl (limited to phenyl), aralkyl (limited to phenylalkyl), alkoxyalkyl, hydroxyalkyl, haloalkyl, aminoalkyl, monoalkylaminoalkyl, dialkylaminoalkyl, trialkylaminoalkyl, aminoalkylaminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl or a group of the formula —$(CH_2)_n$—W-Het (a), —$(CH_2)_n$-T-C(=V)-Z (b), —$(CH_2)_n$—NH—C(=O)-Im (c), or —$(CH_2)_n$—NH—C(=NH)—Ar (d)

in which Het signifies a heterocyclyl group, W signifies NH, S or a bond, T signifies NH or S, V signifies O, S, NH, NNO$_2$, NCN or CHNO$_2$, Z signifies alkylthio, amino, monoalkylamino or dialkylamino, Im signifies 1-imidazolyl, Ar signifies aryl, and n stands for 2–6; R$^2$ signifies hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonylaminoalkyl, mercaptoalkyl, alkylthioalkyl, carboxyalkyl, alkoxycarbonylalkyl, aminocarbonylalkyl, alkylthio or alkylsulphinyl; R$^3$ signifies a carbocyclic or heterocyclic aromatic group; R$^4$, R$^5$, R$^6$ and R$^7$ each independently signify hydrogen, halogen, hydroxy, alkoxy, aryloxy, haloalkyl, nitro, amino, acylamino, monoalkylamino, dialkylamino, alkylthio, alkylsulphinyl or alkylsulphonyl; and one of X and Y signifies O and the other signifies O, S, (H,OH) or (H,H); with the proviso that R$^1$ has a significance different from hydrogen when R$^2$ signifies hydrogen, R$^3$ signifies 3-indolyl or 6-hydroxy-3-indolyl, R$^4$, R$^5$ and R$^7$ each signify hydrogen, R$^6$ signifies hydrogen or hydroxy and X and Y both signify O and when R$^2$ signifies hydrogen, R$^3$ signifies 3-indolyl, R$^4$, R$^5$, R$^6$ and R$^7$ each signify hydrogen, X signifies (H,H) and Y signifies O; as well as pharmaceutically acceptable salts of acidic compounds of formula I with bases and of basic compounds of formula I with acids, as protein kinase C inhibitors and as therapeutically active substances for the use in control or prevention of inflammatory, immunological, bronchopulmonary and cardiovascular disorders.

An associated published paper (Davis, et. al., *J. Med. Chem.* 1992, 35, 177–184), disclosed a compound of formula (I) wherein R$^4$, R$^5$, R$^6$ and R$^7$ signify hydrogen; R$^1$ signifies methyl; X and Y signify O; and R$^3$ signifies 3-(7-aza-1-methylindolyl) as a protein kinase C inhibitor (IC$_{50}$=2.9 µM).

Patent application WO 95/07910 describes heterocyclylindole derivatives of formula (I):

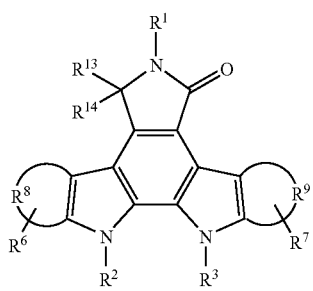

as antiviral agents. Preparation of compounds of formula (I) include use of indolyl(7-azaindolyl)maleimide compounds and bis(7-azaindolyl)maleimide compounds as reaction intermediates.

The substituted pyrroline compounds of the present invention have not been heretofore disclosed.

Accordingly, it is an object of the present invention to provide substituted pyrroline compounds useful as a kinase or dual-kinase inhibitor (in particular, a kinase selected from protein kinase C or glycogen synthase kinase-3; and, more particularly, a kinase selected from protein kinase C α, protein kinase C β-II, protein kinase C γ or glycogen synthase kinase-3β), methods for their production and methods for treating or ameliorating a kinase or dual-kinase mediated disorder.

SUMMARY OF THE INVENTION

The present invention is directed to substituted pyrroline compounds of Formula (I):

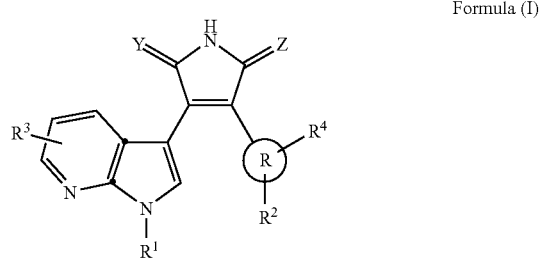

Formula (I)

wherein
R is selected from the group consisting of R$_a$, —C$_{1-8}$alkyl-R$_a$, —C$_{2-8}$alkenyl-R$_a$, —C$_{2-8}$alkynyl-R$_a$ and cyano;
R$_a$ is selected from the group consisting of cycloalkyl, heterocyclyl, aryl and heteroaryl;
R$^1$ is selected from the group consisting of hydrogen, —C$_{1-8}$alkyl-R$^5$, —C$_{2-8}$alkenyl-R$^5$, —C$_{2-8}$alkynyl-R$^5$, —C(O)—(C$_{1-8}$)alkyl-R$^9$, —C(O)-aryl-R$^8$, —C(O)—O—(C$_{1-8}$)alkyl-R$^9$, —C(O)—O-aryl-R$^8$, —C(O)—NH(C$_{1-8}$alkyl-R$^9$), —C(O)—NH(aryl-R$^8$), —C(O)—N(C$_{1-8}$alkyl-R$^9$)$_2$, —SO$_2$—(C$_{1-8}$)alkyl-R$^9$, —SO$_2$-aryl-R$^8$, -cycloalkyl-R$^6$, -heterocyclyl-R$^6$, -aryl-R$^6$ and -heteroaryl-R$^6$; wherein heterocyclyl and heteroaryl are attached to the azaindole nitrogen atom in the one position via a heterocyclyl or heteroaryl ring carbon atom;
R$^5$ is 1 to 2 substituents independently selected from the group consisting of hydrogen, —O—(C$_{1-8}$)alkyl, —O-aryl-R$^6$, —O—(C$_{1-8}$)alkyl-OH, —O—(C$_{1-8}$)alkyl-O—(C$_{1-8}$)alkyl, —O—(C$_{1-8}$)alkyl-NH$_2$, —O—(C$_{1-8}$)alkyl-NH(C$_{1-8}$alkyl), —O—(C$_{1-8}$)alkyl-N(C$_{1-8}$alkyl)$_2$, —O—(C$_{1-8}$)alkyl-S—(C$_{1-8}$)alkyl, —O—(C$_{1-8}$)alkyl-SO$_2$—(C$_{1-8}$)alkyl, —O—(C$_{1-8}$)alkyl-SO$_2$—NH$_2$, —O—(C$_{1-8}$)alkyl-SO$_2$—NH(C$_{1-8}$alkyl), —O—(C$_{1-8}$)alkyl-SO$_2$—N(C$_{1-8}$alkyl)$_2$, —O—C(O)H, —O—C(O)—(C$_{1-8}$)alkyl, —O—C(O)—NH$_2$, —O—C(O)—NH(C$_{1-8}$alkyl), —O—C(O)—N(C$_{1-8}$alkyl)$_2$, —O—(C$_{1-8}$)alkyl-C(O)H, —O—(C$_{1-8}$)alkyl-C(O)—(C$_{1-8}$)alkyl, —O—(C$_{1-8}$)alkyl-CO$_2$H, —O—(C$_{1-8}$)alkyl-C(O)—O—(C$_{1-8}$)alkyl, —O—(C$_{1-8}$)alkyl-C(O)—NH$_2$, —O—(C$_{1-8}$)alkyl-C(O)—NH(C$_{1-8}$alkyl), —O—(C$_{1-8}$)alkyl-C(O)—N(C$_{1-8}$alkyl)$_2$, —C(O)H, —C(O)—(C$_{1-8}$)alkyl, —CO$_2$H, —C(O)—O—(C$_{1-8}$)alkyl, —C(O)—NH$_2$, —C(NH)—NH$_2$, —C(O)—NH(C$_{1-8}$alkyl), —C(O)—N(C$_{1-8}$alkyl)$_2$, —SH, —S—(C$_{1-8}$)alkyl, —S—(C$_{1-8}$)alkyl-S—(C$_{1-8}$)alkyl, —S—(C$_{1-8}$)alkyl-O—(C$_{1-8}$)alkyl, —S—(C$_{1-8}$)alkyl-O—(C$_{1-8}$)alkyl-OH, —S—(C$_{1-8}$)alkyl-O—(C$_{1-8}$)alkyl-NH$_2$, —S—(C$_{1-8}$)alkyl-O—(C$_{1-8}$)alkyl-NH(C$_{1-8}$alkyl), —S—(C$_{1-8}$)alkyl-O—(C$_{1-8}$)alkyl-N(C$_{1-8}$alkyl)$_2$, —S—(C$_{1-8}$)alkyl-NH(C$_{1-8}$alkyl), —SO$_2$—(C$_{1-8}$)alkyl, —SO$_2$—NH$_2$, —SO$_2$—NH(C$_{1-8}$alkyl), —SO$_2$—N(C$_{1-8}$alkyl)$_2$, —N—R$^7$, cyano, (halo)$_{1-3}$, hydroxy, nitro, oxo, -cycloalkyl-R$^6$, -heterocyclyl-R$^6$, -aryl-R$^6$ and -heteroaryl-R$^6$;
R$^6$ is 1 to 4 substituents attached to a carbon or nitrogen atom independently selected from the group consisting of hydrogen, —C$_{1-8}$alkyl, —C$_{2-8}$alkenyl, —C$_{2-8}$alkynyl, —C(O)H, —C(O)—(C$_{1-8}$)alkyl, —CO$_2$H, —C(O)—O—(C$_{1-8}$)alkyl, —C(O)—NH$_2$, —C(NH)—NH$_2$, —C(O)—NH(C$_{1-8}$alkyl), —C(O)—N(C$_{1-8}$alkyl)$_2$, —SO$_2$—(C$_{1-8}$)

alkyl, —SO$_2$—NH$_2$, —SO$_2$—NH(C$_{1-8}$alkyl), —SO$_2$—N(C$_{1-8}$alkyl)$_2$, —(C$_{1-8}$)alkyl-N—R$^7$, —(C$_{1-8}$)alkyl-(halo)$_{1-3}$, —(C$_{1-8}$)alkyl-OH, -aryl-R$^8$, —(C$^{1-8}$)alkyl-aryl-R$^8$ and —(C$_{1-8}$)alkyl-heteroaryl-R$^8$;

with the proviso that, when R$^6$ is attached to a carbon atom, R$^6$ is further selected from the group consisting of —C$_{1-8}$alkoxy, —(C$_{1-8}$)alkoxy-(halo)$_{1-3}$, —SH, —S—(C$_{1-8}$)alkyl, —N—R$^7$, cyano, halo, hydroxy, nitro, oxo and -heteroaryl-R$^8$;

R$^7$ is 2 substituents independently selected from the group consisting of hydrogen, —C$_{1-8}$alkyl, —C$_{2-8}$alkenyl, —C$_{2-8}$alkynyl, —(C$_{1-8}$)alkyl-OH, —(C$_{1-8}$)alkyl-O—(C$_{1-8}$)alkyl, —(C$_{1-8}$)alkyl-NH$_2$, —(C$_{1-8}$)alkyl-NH(C$_{1-8}$alkyl), —(C$_{1-8}$)alkyl-N(C$_{1-8}$alkyl)$_2$, —(C$_{1-8}$)alkyl-S—(C$_{1-8}$)alkyl, —C(O)H, —C(O)—(C$_{1-8}$)alkyl, —C(O)—O—(C$_{1-8}$)alkyl, —C(O)—NH$_2$, —C(O)—NH(C$_{1-8}$alkyl), —C(O)—N(C$_{1-8}$alkyl)$_2$, —SO$_2$—(C$_{1-8}$)alkyl, —SO$_2$—NH$_2$, —SO$_2$—NH(C$_{1-8}$alkyl), —SO$_2$—N(C$_{1-8}$alkyl)$_2$, —C(N)—NH$_2$, -cycloalkyl-R$^8$, —(C$_{1-8}$)alkyl-heterocyclyl-R$^8$, -aryl-R$^8$, —(C$_{1-8}$)alkyl-aryl-R$^8$ and —(C$_{1-8}$)alkyl-heteroaryl-R$^8$;

R$^8$ is 1 to 4 substituents attached to a carbon or nitrogen atom independently selected from the group consisting of hydrogen, —C$_{1-8}$alkyl, —(C$_{1-8}$)alkyl-(halo)$_{1-3}$ and —(C$_{1-8}$)alkyl-OH;

with the proviso that, when R$^8$ is attached to a carbon atom, R$^8$ is further selected from the group consisting of —C$_{1-8}$alkoxy, —NH$_2$, —NH(C$_{1-8}$alkyl), —N(C$_{1-8}$alkyl)$_2$, cyano, halo, —(C$_{1-8}$)alkoxy-(halo)$_{1-3}$, hydroxy and nitro;

R$^9$ is 1 to 2 substituents independently selected from the group consisting of hydrogen, —C$_{1-8}$alkoxy, —NH$_2$, —NH(C$_{1-8}$alkyl), —N(C$_{1-8}$alkyl)$_2$, cyano, (halo)$_{1-3}$, hydroxy and nitro;

R$^2$ is one substituent attached to a carbon or nitrogen atom selected from the group consisting of hydrogen, —C$_{1-8}$alkyl-R$^5$, —C$_{2-8}$alkenyl-R$^5$, —C$_{2-8}$alkynyl-R$^5$, —C(O)H, —C(O)—(C$_{1-8}$)alkyl-R$^9$, —C(O)—NH$_2$, —C(O)—NH(C$_{1-8}$alkyl-R$^9$), —C(O)—N(C$_{1-8}$alkyl-R$^9$)$_2$, —C(O)—NH(aryl-R$^8$), —C(O)-cycloalkyl-R$^8$, —C(O)-heterocyclyl-R$^8$, —C(O)-aryl-R$^8$, —C(O)-heteroaryl-R$^8$, —CO$_2$H, —C(O)—O—(C$_{1-8}$)alkyl-R$^9$, —C(O)—O-aryl-R$^8$, —SO$_2$—(C$_{1-8}$)alkyl-R$^9$, —SO$_2$-aryl-R$^8$, -cycloalkyl-R$^6$, -aryl-R$^6$ and —(C$_{1-8}$)alkyl-N—R$^7$;

with the proviso that, when R$^2$ is attached to a carbon atom, R$^2$ is further selected from the group consisting of —C$_{1-8}$alkoxy-R$^5$, —N—R$^7$, cyano, halogen, hydroxy, nitro, oxo, -heterocyclyl-R$^6$ and -heteroaryl-R$^6$;

R$^3$ is 1 to 3 substituents attached to a carbon atom independently selected from the group consisting of hydrogen, —C$_{1-8}$alkyl-R$^{10}$, —C$_{2-8}$alkenyl-R$^{10}$, —C$_{2-8}$alkynyl-R$^{10}$, —C$_{1-8}$alkoxy-R$^{10}$, —C(O)H, —C(O)—(C$_{1-8}$)alkyl-R$^9$, —C(O)—NH$_2$, —C(O)—NH(C$_{1-8}$alkyl-R$^9$), —C(O)—N(C$_{1-8}$alkyl-R$^9$)$_2$, —C(O)-cycloalkyl-R$^8$, —C(O)-heterocyclyl-R$^8$, —C(O)-aryl-R$^8$, —C(O)-heteroaryl-R$^8$, —C(NH)—NH$_2$, —CO$_2$H, —C(O)—O—(C$_{1-8}$)alkyl-R$^9$, —C(O)—O-aryl-R$^8$, —SO$_2$—(C$_{1-8}$)alkyl-R$^9$, —SO$_2$-aryl-R$^8$, —N—R$^7$, cyano, halogen, hydroxy, nitro, -cycloalkyl-R$^8$, -heterocyclyl-R$^8$, -aryl-R$^8$ and -heteroaryl-R$^8$;

R$^4$ is 1 to 4 substituents attached to a carbon atom independently selected from the group consisting of hydrogen, —C$_{1-8}$alkyl-R$^{10}$, —C$_{2-8}$alkenyl-R$^{10}$, —C$_{2-8}$alkynyl-R$^{10}$, —C$_{1-8}$alkoxy-R$^{10}$, —C(O)H, —C(O)—(C$_{1-8}$)alkyl-R$^9$, —C(O)—NH$_2$, —C(O)—NH(C$_{1-8}$alkyl-R$^9$), —C(O)—N(C$_{1-8}$alkyl-R$^9$)$_2$, —C(O)-cycloalkyl-R$^8$, —C(O)-heterocyclyl-R$^8$, —C(O)-aryl-R$^8$, —C(O)-heteroaryl-R$^8$, —C(NH)—NH$_2$, —CO$_2$H, —C(O)—O—(C$_{1-8}$)alkyl-R$^9$, —C(O)—O-aryl-R$^8$, —SH, —S—(C$_{1-8}$)alkyl-R$^{10}$, —SO$_2$—(C$_{1-8}$)alkyl-R$^9$, —SO$_2$-aryl-R$^8$, —SO$_2$—NH$_2$, —SO$_2$—NH(C$_{1-8}$alkyl-R$^9$), —SO$_2$—N(C$_{1-8}$alkyl-R$^9$)$_2$, —N—R$^7$, cyano, halogen, hydroxy, nitro, -cycloalkyl-R$^8$, -heterocyclyl-R$^8$, -aryl-R$^8$ and -heteroaryl-R$^8$;

R$^{10}$ is 1 to 2 substituents independently selected from the group consisting of hydrogen, —NH$_2$, —NH(C$_{1-8}$alkyl), —N(C$_{1-8}$alkyl)$_2$, cyano, (halo)$_{1-3}$, hydroxy, nitro and oxo; and, Y and Z are independently selected from the group consisting of O, S, (H,OH) and (H,H); with the proviso that one of Y and Z is O and the other is selected from the group consisting of O, S, (H,OH) and (H,H);

and pharmaceutically acceptable salts thereof.

The present invention is directed to substituted pyrroline compounds useful as a selective kinase or dual-kinase inhibitor; in particular, a kinase selected from protein kinase C or glycogen synthase kinase-3; and, more particularly, a kinase selected from protein kinase C α, protein kinase C β (e.g. protein kinase C β-I and protein kinase C β-II), protein kinase C γ or glycogen synthase kinase-3β.

The present invention is also directed to methods for producing the instant substituted pyrroline compounds and pharmaceutical compositions and medicaments thereof.

The present invention is further directed to methods for treating or ameliorating a kinase mediated disorder. In particular, the method of the present invention is directed to treating or ameliorating a kinase mediated disorder such as, but not limited to, cardiovascular diseases, diabetes, diabetes-associated disorders, inflammatory diseases, immunological disorders, dermatological disorders, oncological disorders and CNS disorders.

DETAILED DESCRIPTION OF THE INVENTION

Embodiments of the present invention include compounds of Formula (I) wherein, preferably, R is selected from the group consisting of R$_a$, —C$_{1-4}$alkyl-R$_a$, —C$_{2-4}$alkenyl-R$_a$, —C$_{2-4}$alkynyl-R$_a$ and cyano.

Embodiments of the present invention include compounds of Formula (I) wherein, preferably, R$_a$ is selected from the group consisting of heterocyclyl, aryl and heteroaryl.

More preferably, R$_a$ is selected from the group consisting of dihydro-pyranyl, phenyl, naphthyl, thienyl, pyrrolyl, imidazolyl, pyrazolyl, pyridinyl, azaindolyl, indazolyl, benzofuryl, benzothienyl, dibenzofuryl and dibenzothienyl.

Embodiments of the present invention include compounds of Formula (I) wherein, preferably, R$^1$ is selected from the group consisting of hydrogen, —C$_{1-4}$alkyl-R$^5$, —C$_{2-4}$alkenyl-R$^5$, —C$_{2-4}$alkynyl-R$^5$, —C(O)—(C$_{1-4}$)alkyl-R$^9$, —C(O)-aryl-R$^8$, —C(O)—O—(C$_{1-4}$)alkyl-R$^9$, —C(O)—O-aryl-R$^8$, —C(O)—NH(C$_{1-4}$alkyl-R$^9$), —C(O)—NH(aryl-R$^8$), —C(O)—N(C$_{1-4}$alkyl-R$^9$)$_2$, —SO$_2$—(C$_{1-4}$)alkyl-R$^9$, —SO$_2$-aryl-R$^8$, -cycloalkyl-R$^6$, -heterocyclyl-R$^6$, -aryl-R$^6$ and -heteroaryl-R$^6$; wherein heterocyclyl and heteroaryl are attached to the azaindole nitrogen atom in the one position via a heterocyclyl or heteroaryl ring carbon atom.

More preferably, R$^1$ is selected from the group consisting of hydrogen, —C$_{1-4}$alkyl-R$^5$, -aryl-R$^6$ and -heteroaryl-R$^6$; wherein heteroaryl is attached to the azaindole nitrogen atom in the one position via a heteroaryl ring carbon atom.

Most preferably, R$^1$ is selected from the group consisting of hydrogen, —C$_{1-4}$alkyl-R$^5$ and -naphthyl-R$^6$.

Embodiments of the present invention include compounds of Formula (I) wherein, preferably, $R^5$ is 1 to 2 substituents independently selected from the group consisting of hydrogen, —O—$(C_{1-4})$alkyl, —O-aryl-$R^6$, —O—$(C_{1-4})$alkyl-OH, —O—$(C_{1-4})$alkyl-O—$(C_{1-4})$alkyl, —O—$(C_{1-4})$alkyl-NH$_2$, —O—$(C_{1-4})$alkyl-NH$(C_{1-4}$alkyl), —O—$(C_{1-4})$alkyl-N$(C_{1-4}$alkyl)$_2$, —O—$(C_{1-4})$alkyl-S—$(C_{1-4})$alkyl, —O—$(C_{1-4})$alkyl-SO$_2$—$(C_{1-4})$alkyl, —O—$(C_{1-4})$alkyl-SO$_2$—NH$_2$, —O—$(C_{1-4})$alkyl-SO$_2$—NH$(C_{1-4}$alkyl), —O—$(C_{1-4})$alkyl-SO$_2$—N$(C_{1-4}$alkyl)$_2$, —O—C(O)H, —O—C(O)—$(C_{1-4})$alkyl, —O—C(O)—NH$_2$, —O—C(O)—NH$(C_{1-4}$alkyl), —O—C(O)—N$(C_{1-4}$alkyl)$_2$, —O—$(C_{1-4})$alkyl-C(O)H, —O—$(C_{1-4})$alkyl-C(O)—$(C_{1-4})$alkyl, —O—$(C_{1-4})$alkyl-CO$_2$H, —O—$(C_{1-4})$alkyl-C(O)—O—$(C_{1-4})$alkyl, —O—$(C_{1-4})$alkyl-C(O)—NH$_2$, —O—$(C_{1-4})$alkyl-C(O)—NH$(C_{1-4}$alkyl), —O—$(C_{1-4})$alkyl-C(O)—N$(C_{1-4}$alkyl)$_2$, —C(O)H, —C(O)—$(C_{1-4})$alkyl, —CO$_2$H, —C(O)—O—$(C_{1-4})$alkyl, —C(O)—NH$_2$, —C(NH)—NH$_2$, —C(O)—NH$(C_{1-4}$alkyl), —C(O)—N$(C_{1-4}$alkyl)$_2$, —SH, —S—$(C_{1-4})$alkyl, —S—$(C_{1-4})$alkyl-S—$(C_{1-4})$alkyl, —S—$(C_{1-4})$alkyl-O—$(C_{1-4})$alkyl, —S—$(C_{1-4})$alkyl-O—$(C_{1-4})$alkyl-OH, —S—$(C_{1-4})$alkyl-O—$(C_{1-4})$alkyl-NH$_2$, —S—$(C_{1-4})$alkyl-O—$(C_{1-4})$alkyl-NH$(C_{1-4}$alkyl), —S—$(C_{1-4})$alkyl-O—$(C_{1-4})$alkyl-N$(C_{1-4}$alkyl)$_2$, —S—$(C_{1-4})$alkyl-NH$(C_{1-4}$alkyl), —SO$_2$—NH$_2$, —SO$_2$—NH$(C_{1-4}$alkyl), —SO$_2$—N$(C_{1-4}$alkyl)$_2$, —N—$R^7$, cyano, (halo)$_{1-3}$, hydroxy, nitro, oxo, -cycloalkyl-$R^6$, -heterocyclyl-$R^6$, -aryl-$R^6$ and -heteroaryl-$R^6$.

More preferably, $R^5$ is 1 to 2 substituents independently selected from the group consisting of hydrogen, —O—$(C_{1-4})$alkyl, —O-aryl-$R^6$, —N—$R^7$, hydroxy and -heteroaryl-$R^6$.

Most preferably, $R^5$ is 1 to 2 substituents independently selected from the group consisting of hydrogen, —O—$(C_{1-4})$alkyl, —O-aryl-$R^6$, —N—$R^7$, hydroxy, -imidazolyl-$R^6$, -triazolyl-$R^6$ and -tetrazolyl-$R^6$.

Embodiments of the present invention include compounds of Formula (I) wherein, preferably, $R^6$ is 1 to 4 substituents attached to a carbon or nitrogen atom independently selected from the group consisting of hydrogen, —$C_{1-4}$alkyl, —$C_{2-4}$alkenyl, —$C_{2-4}$alkynyl, —C(O)H, —C(O)—$(C_{1-4})$alkyl, —CO$_2$H, —C(O)—O—$(C_{1-4})$alkyl, —C(O)—NH$_2$, —C(NH)—NH$_2$, —C(O)—NH$(C_{1-4}$alkyl), —C(O)—N$(C_{1-4}$alkyl)$_2$, —SO$_2$—$(C_{1-4})$alkyl, —SO$_2$—NH$_2$, —SO$_2$—NH$(C_{1-4}$alkyl), —SO$_2$—N$(C_{1-4}$alkyl)$_2$, —$(C_{1-4})$alkyl-N—$R^7$, —$(C_{1-4})$alkyl-(halo)$_{1-3}$, —$(C_{1-4})$alkyl-OH, -aryl-$R^8$, —$(C_{1-4})$alkyl-aryl-$R^8$ and —$(C_{1-4})$alkyl-heteroaryl-$R^8$;
with the proviso that, when $R^6$ is attached to a carbon atom, $R^6$ is further selected from the group consisting of —$C_{1-4}$alkoxy, —$(C_{1-4})$alkoxy-(halo)$_{1-3}$, —SH, —S-$(C_{1-4})$alkyl, —N—$R^7$, cyano, halo, hydroxy, nitro, oxo and -heteroaryl-$R^8$.

More preferably, $R^6$ is hydrogen.

Embodiments of the present invention include compounds of Formula (I) wherein, preferably, $R^7$ is 2 substituents independently selected from the group consisting of hydrogen, —$C_{1-4}$alkyl, —$C_{2-4}$alkenyl, —$C_{2-4}$alkynyl, —$(C_{1-4})$alkyl-OH, —$(C_{1-4})$alkyl-O—$(C_{1-4})$alkyl, —$(C_{1-4})$alkyl-NH$_2$, —$(C_{1-4})$alkyl-NH$(C_{1-4}$alkyl), —$(C_{1-4})$alkyl-N$(C_{1-4}$alkyl)$_2$, —$(C_{1-4})$alkyl-S—$(C_{1-4})$alkyl, —C(O)H, —C(O)—$(C_{1-4})$alkyl, —C(O)—O—$(C_{1-4})$alkyl, —C(O)—NH$_2$, —C(O)—NH$(C_{1-4}$alkyl), —C(O)—N$(C_{1-4}$alkyl)$_2$, —SO$_2$—$(C_{1-4})$alkyl, —SO$_2$—NH$_2$, —SO$_2$—NH$(C_{1-4}$alkyl), —SO$_2$—N$(C_{1-4}$alkyl)$_2$, —C(N)—NH$_2$, -cycloalkyl-$R^8$, —$(C_{1-4})$alkyl-heterocyclyl-$R^8$, -aryl-$R^8$, —$(C^{1-4})$alkyl-aryl-$R^8$ and —$(C_{1-4})$alkyl-heteroaryl-$R^8$.

More preferably, $R^7$ is 2 substituents independently selected from the group consisting of of hydrogen, —$C_{1-4}$alkyl, —C(O)H, —C(O)—$(C_{1-4})$alkyl, —C(O)—O—$(C_{1-4})$alkyl, —SO$_2$—NH$_2$, —SO$_2$—NH$(C_{1-4}$alkyl) and —SO$_2$—N$(C_{1-4}$alkyl)$_2$.

Embodiments of the present invention include compounds of Formula (I) wherein, preferably, $R^8$ is 1 to 4 substituents attached to a carbon or nitrogen atom independently selected from the group consisting of hydrogen, —$C_{1-4}$alkyl, —$(C_{1-4})$alkyl-(halo)$_{1-3}$ and —$(C_{1-4})$alkyl-OH;
with the proviso that, when $R^8$ is attached to a carbon atom, $R^8$ is further selected from the group consisting of —$C_{1-4}$alkoxy, —NH$_2$, —NH$(C_{1-4}$alkyl), —N$(C_{1-4}$alkyl)$_2$, cyano, halo, —$(C_{1-4})$alkoxy-(halo)$_{1-3}$, hydroxy and nitro.

More preferably, $R^8$ is hydrogen.

Embodiments of the present invention include compounds of Formula (I) wherein, preferably, $R^9$ is 1 to 2 substituents independently selected from the group consisting of hydrogen, —$C_{1-4}$alkoxy, —NH$_2$, —NH$(C_{1-4}$alkyl), —N$(C_{1-4}$alkyl)$_2$, cyano, (halo)$_{1-3}$, hydroxy and nitro.

More preferably, $R^9$ is hydrogen.

Embodiments of the present invention include compounds of Formula (I) wherein, preferably, $R^2$ is one substituent attached to a carbon or nitrogen atom selected from the group consisting of hydrogen, —$C_{1-4}$alkyl-$R^5$, —$C_{2-4}$alkenyl-$R^5$, —$C_{2-4}$alkynyl-$R^5$, —C(O)H, —C(O)—$(C_{1-4})$alkyl-$R^9$, —C(O)—NH$_2$, —C(O)—NH$(C_{1-4}$alkyl-$R^9$), —C(O)—N$(C_{1-4}$alkyl-$R^9$)$_2$, —C(O)—NH(aryl-$R^8$), —C(O)-cycloalkyl-$R^8$, —C(O)-heterocyclyl-$R^8$, —C(O)-aryl-$R^8$, —C(O)-heteroaryl-$R^8$, —CO$_2$H, —C(O)—O—$(C_{1-4})$alkyl-$R^9$, —C(O)—O-aryl-$R^8$, —SO$_2$—$(C_{1-4})$alkyl-$R^9$, —SO$_2$-aryl-$R^8$, -cycloalkyl-$R^6$, -aryl-$R^6$ and —$(C_{1-4})$alkyl-N—$R^7$;
with the proviso that, when $R^2$ is attached to a carbon atom, $R^2$ is further selected from the group consisting of —$C_{1-4}$alkoxy-$R^5$, —N—$R^7$, cyano, halogen, hydroxy, nitro, oxo, -heterocyclyl-$R^6$ and -heteroaryl-$R^6$.

More preferably, $R^2$ is one substituent attached to a carbon or nitrogen atom selected from the group consisting of hydrogen, —$C_{1-4}$alkyl-$R^5$, —$C_{2-4}$alkenyl-$R^5$, —$C_{2-4}$alkynyl-$R^5$, —CO$_2$H, —C(O)—O—$(C_{1-4})$alkyl-$R^9$, -cycloalkyl-$R^6$, -aryl-$R^6$ and —$(C_{1-4})$alkyl-N—$R^7$;
with the proviso that, when $R^2$ is attached to a nitrogen atom, a quaternium salt is not formed; and, with the proviso that, when $R^2$ is attached to a carbon atom, $R^2$ is further selected from the group consisting of —$C_{1-4}$alkoxy-$R^5$, —N—$R^7$, cyano, halogen, hydroxy, nitro, oxo, -heterocyclyl-$R^6$ and -heteroaryl-$R^6$.

Most preferably, $R^2$ is one substituent attached to a carbon or nitrogen atom selected from the group consisting of hydrogen, —$C_{1-4}$alkyl-$R^5$ and -aryl-$R^6$; with the proviso that, when $R^2$ is attached to a nitrogen atom, a quaternium salt is not formed; and, with the proviso that when $R^2$ is attached to a carbon atom, $R^2$ is further selected from the group consisting of —N—$R^7$, halogen, hydroxy and -heteroaryl-$R^6$.

Embodiments of the present invention include compounds of Formula (I) wherein, preferably, $R^3$ is 1 to 3 substituents attached to a carbon atom independently selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —C(O)—$(C_{1-4})$alkyl-$R^9$, —C(O)—NH$_2$, —C(O)—NH$(C_{1-4}$alkyl-$R^9$), —C(O)—N$(C_{1-4}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—NH$_2$, —CO₂H, —C(O)—O—(C_{1-4})alkyl-R⁹, —C(O)—O-aryl-R⁸, —SO₂—(C_{1-8})alkyl-R⁹, —SO₂-aryl-R⁸, —N—R⁷, —(C_{1-4})alkyl-N—R⁷, cyano, halogen, hydroxy, nitro, -cycloalkyl-R⁸, -heterocyclyl-R⁸, -aryl-R⁸ and -heteroaryl-R⁵.

More preferably, R³ is one substituent attached to a carbon atom selected from the group consisting of hydrogen, —C_{1-4}alkyl-R¹⁰, —C_{2-4}alkenyl-R¹⁰, —C_{2-4}alkynyl-R¹⁰, —C_{1-4}alkoxy-R¹⁰, —C(O)H, —CO₂H, —NH₂, —NH(C_{1-4}alkyl), —N(C_{1-4}alkyl)₂, cyano, halogen, hydroxy and nitro.

Most preferably, R³ is one substituent attached to a carbon atom selected from the group consisting of hydrogen, —C_{1-4}alkyl-R¹⁰, —NH₂, —NH(C_{1-4}alkyl), —N(C_{1-4}alkyl)₂, halogen and hydroxy.

Embodiments of the present invention include compounds of Formula (I) wherein, R⁴ is 1 to 4 substituents attached to a carbon atom independently selected from the group consisting of hydrogen, —C_{1-4}alkyl-R¹⁰, —C_{2-4}alkenyl-R¹⁰, —C_{2-4}alkynyl-R¹⁰, —C_{1-4}alkoxy-R¹⁰, —C(O)H, —C(O)—(C_{1-4})alkyl-R⁹, —C(O)—NH₂, —C(O)—NH(C_{1-4} alkyl-R⁹), —C(O)—N(C_{1-4}alkyl-R⁹)₂, —C(O)-cycloalkyl-R⁸, —C(O)-heterocyclyl-R⁸, —C(O)-aryl-R⁸, —C(O)-heteroaryl-R⁸, —C(NH)—NH₂, —CO₂H, —C(O)—O—(C_{1-4})alkyl-R⁹, —C(O)—O-aryl-R⁸, —SH, —S—(C_{1-4})alkyl-R¹⁰, —SO₂—(C_{1-4})alkyl-R⁹, —SO₂-aryl-R⁸, —SO₂—NH₂, —SO₂—NH(C_{1-4}alkyl-R⁹), —SO₂—N(C_{1-4}alkyl-R⁹)₂, —N—R⁷, cyano, halogen, hydroxy, nitro, -cycloalkyl-R⁸, -heterocyclyl-R⁸, -aryl-R⁸ and -heteroaryl-R⁸.

Preferably, R⁴ is 1 to 4 substituents attached to a carbon atom independently selected from the group consisting of hydrogen, —C_{1-4}alkyl-R¹⁰, —C_{2-4}alkenyl-R¹⁰, —C_{2-4}alkynyl-R¹⁰, —C_{1-4}alkoxy-R¹⁰, —C(O)H, —CO₂H, —NH₂, —NH(C_{1-4}alkyl), —N(C_{1-4}alkyl)₂, cyano, halogen, hydroxy, nitro, -cycloalkyl, -heterocyclyl, -aryl and -heteroaryl.

More preferably, R⁴ is 1 to 4 substituents attached to a carbon atom independently selected from the group consisting of hydrogen, C_{1-4}alkyl-R¹⁰, C_{1-4}alkoxy-R¹, —NH₂, —NH(C_{1-4}alkyl), —N(C_{1-4}alkyl)₂, halogen and hydroxy.

Most preferably, R⁴ is 1 to 4 substituents attached to a carbon atom independently selected from the group consisting of hydrogen, C_{1-4}alkyl-R¹⁰, C_{1-4}alkoxy-R¹⁰, —NH₂, —NH(C_{1-4}alkyl), —N(C_{1-4}alkyl)₂, chlorine, fluorine and hydroxy.

Embodiments of the present invention include compounds of Formula (I) wherein, preferably, R¹⁰ is 1 to 2 substituents independently selected from the group consisting of hydrogen, —NH₂, —NH(C_{1-4}alkyl), —N(C_{1-4}alkyl)₂, cyano, (halo)_{1-3}, hydroxy, nitro and oxo.

More preferably, R¹⁰ is 1 to 2 substituents independently selected from the group consisting of hydrogen and (halo)_{1-3}.

Most preferably, R¹⁰ is 1 to 2 substituents independently selected from the group consisting of hydrogen and (fluoro)₃.

Embodiments of the present invention include compounds of Formula (I) wherein, preferably, Y and Z are independently selected from the group consisting of O, S, (H,OH) and (H,H); with the proviso that one of Y and Z is O and the other is selected from the group consisting of O, S, (H,OH) and (H,H).

More preferably, Y and Z are independently selected from the group consisting of O and (H,H); with the proviso that one of Y and Z is O, and the other is selected from the group consisting of O and (H,H).

Most preferably, Y and Z are independently selected from O.

Exemplified compounds of Formula (I) include compounds selected from Formula (Ia):

TABLE 1

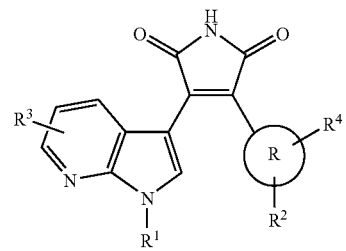

Formula (Ia)

wherein R, R¹, R², R³ and R⁴ are dependently selected from:

| Cpd | R¹ | R³ | R | R² | R⁴ |
|-----|----|----|---|----|----|
| 1 | HO(CH₂)₃ | H | Ph | H | 2-Cl; |
| 2 | Me₂N(CH₂)₃ | H | Ph | H | 2-Cl; |
| 3 | HO(CH₂)₃ | H | 1-naphthyl | H | H; |
| 4 | Me₂N(CH₂)₃ | H | 1-naphthyl | H | H; |
| 5 | HO(CH₂)₃ | H | 3-benzo[b]thienyl | — | 5-Cl; |
| 6 | HO(CH₂)₃ | H | 3-indazolyl | H | H; |
| 7 | HO(CH₂)₃ | H | 7-azaindol-3-yl | N-1-ethyl | H; |
| 8 | HO(CH₂)₃ | H | Ph | H | 2-OMe; |
| 9 | HO(CH₂)₃ | H | Ph | H | 3-OMe; |
| 10 | HO(CH₂)₃ | H | Ph | H | 2-Cl-4-F; |
| 11 | HO(CH₂)₃ | H | Ph | H | 2-CF₃; |
| 12 | HO(CH₂)₃ | H | 2-pyridinyl | H | H; |
| 13 | HO(CH₂)₃ | H | 2-pyridinyl | H | 3-Cl-5-CF₃; |
| 14 | HO(CH₂)₃ | H | 2-thienyl | H | H; |
| 15 | HO(CH₂)₃ | H | 3-thienyl | H | 2,5-Cl₂; |

TABLE 1-continued

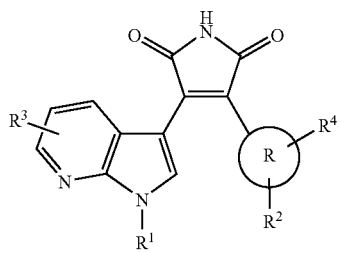

Formula (Ia)

wherein R, $R^1$, $R^2$, $R^3$ and $R^4$ are dependently selected from:

| Cpd | $R^1$ | $R^3$ | R | $R^2$ | $R^4$ |
|---|---|---|---|---|---|
| 16 | $HO(CH_2)_3$ | H | 1H-pyrazol-3-yl | N-1-$HO(CH_2)_3$ | H; |
| 17 | $HO(CH_2)_3$ | H | 1H-imidazol-2-yl | H | H; |
| 18 | $HO(CH_2)_3$ | H | 1H-imidazol-4-yl | N-1-$HO(CH_2)_3$ | H; |
| 19 | $HO(CH_2)_3$ | H | 1H-imidazol-4-yl | N-1-$HO(CH_2)_2$ | H; |
| 20 | 2-naphthyl | H | 3-indazolyl | N-1-$Me_2N(CH_2)_3$ | H; |
| 21 | 2-naphthyl | H | 3-indazolyl | N-1-$HO(CH_2)_3$. | H; |
| 22 | $HO(CH_2)_3$ | H | $(CH)_2Ph$ | H | 4-F; |
| 23 | $HO(CH_2)_3$ | H | 3,4-dihydro-2H-pyran-6-yl | H | H; |
| 24 | $HO(CH_2)_3$ | H | 3-1H-pyrrolyl | H | H; |
| 25 | $HO(CH_2)_3$ | H | 2-benzo[b]furyl | H | H; |
| 26 | $HO(CH_2)_3$ | H | 1H-pyrazol-3-yl | N-1-$CH_3$ | H; |
| 27 | $HO(CH_2)_3$ | H | CN | — | — |
| 28 | $HO(CH_2)_3$ | H | dibenzo[b,d]thien-4-yl | H | H; |
| 29 | $HO(CH_2)_3$ | H | 4-dibenzofuryl | H | H; |
| 30 | $MeO(CH_2)_3$ | H | Ph | H | 2-OH; |
| 31 | $MeO(CH_2)_3$ | H | Ph | H | 3,4-$(OMe)_2$; |
| 32 | $HO(CH_2)_3$ | H | Ph | H | 3,4-$(OH)_2$; |
| 33 | 2-naphthyl | H | Ph | H | 2-OMe; |
| 34 | Boc-$NH(CH_2)_3$ | H | Ph | H | 2-OMe; |
| 35 | MeOC(O)—$NH(CH_2)_3$ | H | Ph | H | 2-OMe |
| 36 | Boc-$NH(CH_2)_3$ | H | Ph | H | 2-$CF_3$; |
| 37 | MeOC(O)—$NH(CH_2)_3$ | H | Ph | H | 2-$CF_3$ |
| 38 | $H_2N(CH_2)_3$ | H | Ph | H | 2-OMe; |
| 39 | $H_2N$—$SO_2$—$NH(CH_2)_3$ | H | Ph | H | 2-OMe |
| 40 | $HO(CH_2)_3$ | H | Pyrimidin-5-yl | 2-OMe | 4-OMe |
| 41 | $HO(CH_2)_3$ | H | Pyrimidin-5-yl | H | H |
| 42 | $HO(CH_2)_3$ | H | Quinolin-8-yl | H | H |
| 43 | $HO(CH_2)_3$ | H | Benzo[b]thiophen | H | H |
| 44 | $HO(CH_2)_3$ | H | isoxazol-4-yl | 3-Me | 5-Me |
| 45 | $HO(CH_2)_3$ | H | 2-oxo-2H-pyran-3-yl | H | H |
| 46 | $HO(CH_2)_3$ | H | 1H-Pyrroly-3-yl | 1-Me | H |
| 47 | $HO(CH_2)_3$ | H | pyrazin-2-yl | H | H |
| 48 | $HO(CH_2)_3$ | H | 1H-Pyrroly-3-yl | 1-benzyl | H |
| 49 | $HO(CH_2)_3$ | H | oxazol-5-yl | 2-phenyl | H |
| 50 | $HO(CH_2)_3$ | H | 5,6-Dihydro-4H-pyrrolo[1,2-b]pyrazol-2-yl | H | H |
| 51 | $HO(CH_2)_3$ | H | 5,6-Dihydro-[1,4]dioxin-2-yl | H | H |
| 52 | $HO(CH_2)_3$ | H | 1H-pyrazol-4-yl | 1-Me | H |
| 53 | $HO(CH_2)_3$ | H | Furan-2-yl | H | H |
| 54 | $HO(CH_2)_3$ | H | 4,5,6,7-tetrahydro-pyrazolo[1,5-a]pyridin-2-yl | H | H |
| 55 | $HO(CH_2)_3$ | H | thiazol-2-yl | H | H |
| 56 | $HO(CH_2)_3$ | H | pyrimidin-2-yl | H | H |
| 57 | $Ph(CH_2)_3$ | H | pyrimidin-5-yl | 2-MeO | 4-MeO |
| 58 | $Ph(CH_2)_3$ | H | pyrimidin-5-yl | H | H |

TABLE 1-continued

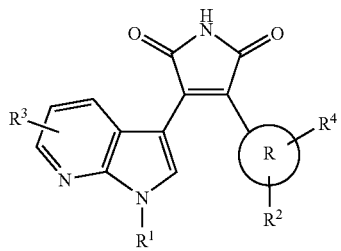

Formula (Ia)

wherein R, R¹, R², R³ and R⁴ are dependently selected from:

| Cpd | R¹ | R³ | R | R² | R⁴ |
|---|---|---|---|---|---|
| 59 | Ph(CH₂)₃ | H | 5,6-Dihydro-4H-pyrrolo[1,2-b]pyrazol-2-yl | H | H |
| 60 | Ph(CH₂)₃ | H | pyrazin-2-yl | H | H |
| 61 | Ph(CH₂)₃ | H | 5,6-Dihydro-4H-pyran-2-yl | H | H |
| 62 | NC(CH₂)₃ | H | pyrimidin-5-yl | 2-Meo | 4-MeO |
| 63 | NC(CH₂)₃ | H | pyrazin-2-yl | H | H |
| 64 | NC(CH₂)₃ | H | 1H-pyrazol-3-yl | 1-Me | H |
| 65 | PhO(CH₂)₃ | H | 5,6-Dihydro-4H-pyrrolo[1,2-b]pyrazol-2-yl | H | H |
| 66 | HO(CH₂)₃ | H | 2H-pyrazol-3-yl | 2-Me | H |
| 67 | HO(CH₂)₃ | H | 3-Furan-3-yl | H | H |
| 68 | HO(CH₂)₃ | H | 1H-pyrimidine-2,4-dione-5-yl | H | H |
| 69 | NC(CH₂)₂ | H | 1H-pyrazol-3-yl | 1-Me | H |
| 70 | HO(CH₂)₃ | H | CH₃(CH₂)₃ | — | — |
| 71 | MeO(CH₂)₂ | H | pyrimidin-5-yl | 2-MeO | 4-MeO |
| 72 | PhCH₂ | H | pyrimidin-5-yl | 2-MeO | 4-MeO |
| 73 | Ph(CH₂)₂ | H | pyrimidin-5-yl | 2-MeO | 4-MeO |
| 74 | 3-thiophen-2-yl-propyl | H | pyrimidin-5-yl | 2-MeO | 4-MeO |
| 75 | 2-(4-fluoro-phenoxy)-ethyl | H | pyrimidin-5-yl | 2-MeO | 4-MeO |
| 76 | PhO(CH₂)₃ | H | pyrimidin-5-yl | 2-MeO | 4-MeO |
| 77 | MeC(O)—NH(CH₂)₃ | H | Ph | H | 2-OMe |
| 78 | HC(O)—NH(CH₂)₃ | H | Ph | H | 2-OMe |
| 79 | MeSO₂—NH(CH₂)₃ | H | Ph | H | 2-OMe |

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201–217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "independently" means that when a group is substituted with more than one substituent that the substituents may be the same or different. The term "dependently" means that the substituents are specified in an indicated combination of structure variables.

Unless specified otherwise, the term "alkyl" refers to a saturated straight or branched chain consisting solely of 1–8 hydrogen substituted carbon atoms; preferably, 1–6 hydrogen substituted carbon atoms; and, most preferably, 1–4 hydrogen substituted carbon atoms. The term "alkenyl" refers to a partially unsaturated straight or branched chain consisting solely of 2–8 hydrogen substituted carbon atoms that contains at least one double bond. The term "alkynyl" refers to a partially unsaturated straight or branched chain consisting solely of 2–8 hydrogen substituted carbon atoms that contains at least one triple bond. The term "alkoxy" refers to —O-alkyl, where alkyl is as defined supra. The term "hydroxyalkyl" refers to radicals wherein the alkyl chain terminates with a hydroxy radical of the formula HO-alkyl, where alkyl is as defined supra. Alkyl, alkenyl and alkynyl chains are optionally substituted within the alkyl chain or on a terminal carbon atom.

The term "cycloalkyl" refers to a saturated or partially unsaturated monocyclic alkyl ring consisting of 3–8 hydrogen substituted carbon atoms or a saturated or partially unsaturated bicyclic ring consisting of 8 or 11 hydrogen substituted carbon atoms. Examples include, and are not limited to, cyclopropyl, cyclopentyl, cyclohexyl or cycloheptyl.

The term "heterocyclyl" as used herein refers to an unsubstituted or substituted stable three to seven membered monocyclic saturated or partially unsaturated ring system which consists of carbon atoms and from one to three heteroatoms selected from N, O or S, or a stable eight to twelve membered bicyclic saturated or partially saturated ring system which consists of carbon atoms and from one to four heteroatoms selected from N, O, or S. In either the monocyclic or bicyclic rings the nitrogen or sulfur heteroatoms may optionally be oxidized, and the nitrogen heteroatom may optionally be quaternized. Preferred are saturated or partially unsaturated rings having five or six members of which at least one member is a N, O or S atom and which optionally contains one additional N, O or S atoms; saturated or partially unsaturated bicyclic rings having nine or ten members of which at least one member is a N, O or S atom and which optionally contains one or two additional N, O or S atoms; wherein said nine or ten membered bicyclic rings may have one aromatic ring and one nonaromatic ring. In another embodiment of this invention the previously defined heterocyclyl have as the additional heteroatom N, wherein at most two nitrogens atoms are adjacent. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl, piperazinyl, 5,6-dihydro-4H-pyrrolo[1,2-b]prazolyl and 4,5,6,7-tetrahydro-pyrazolo[1,5-a]pyridinyl.

The term "aryl" refers to an aromatic monocyclic ring containing 6 hydrogen substituted carbon atoms, an aromatic bicyclic ring system containing 10 hydrogen substituted carbon atoms or an aromatic tricyclic ring system containing 14 hydrogen substituted carbon atoms. Examples include, and are not limited to, phenyl, naphthalenyl or anthracenyl.

The term "heteroaryl" as used herein represents an unsubstituted or substituted stable five or six membered monocyclic aromatic ring system or an unsubstituted or substituted stable nine or ten membered benzo-fused heteroaromatic ring system (wherein both rings of the benzo-fused system are aromatic) or bicyclic heteroaromatic ring system and unsubstituted or substituted stable twelve to fourteen membered tricyclic ring systems which consists of carbon atoms and from one to four heteroatoms selected from N, O or S, and wherein the nitrogen or sulfur heteroatoms of any of these heteroaryls may optionally be oxidized, and the nitrogen heteroatom may optionally be quaternized. Preferred heteroaryl are aromatic monocyclic rings containing five members of which at least one member is a N, O or S atom and which optionally contains one, two or three additional N atoms; an aromatic monocyclic ring having six members of which one, two or three members are a N atoms; an aromatic bicyclic ring having nine members of which at least one member is a N, O or S atom and which optionally contains one, two or three additional N atoms; an aromatic bicyclic ring having ten members of which of which one, two, three or four members are N atoms; or, an aromatic tricyclic ring system containing 13 members of which at least one member is a N, O or S atom and which optionally contains one, two or three additional N atoms. In another embodiment of this invention, the previously defined heteroaryls have as the additional heteroatom N, wherein at most two nitrogens atoms are adjacent. Examples include, and are not limited to, furyl, thienyl, pyrrolyl, oxazolyl, thiazolyl, imidazolyl, triazolyl, tetrazolyl, pyrazolyl, isoxazolyl, isothiazolyl, pyridinyl, pyridazinyl, pyrimidinyl, pyrazinyl, indolyl, indazolyl, benzo(b)thienyl, benzofuryl, quinolinyl, isoquinolinyl, quinazolinyl, dibenzofuryl or dibenzo[b,d]thienyl.

The "carboxyl" as used herein refers to the organic radical terminal group: R—C(O)OH.

Whenever the term "alkyl" or "aryl" or either of their prefix roots appear in a name of a substituent (e.g., aralkyl, alkylamino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

Unless indicated otherwise, under standard nomenclature rules used throughout this disclosure, the terminal portion of the designated side chain is described first, followed by the adjacent functionality toward the point of attachment. Thus, for example, a "phenyl($C_{1-6}$)alkylamido($C_{1-6}$)alkyl" substituent refers to a group of the formula:

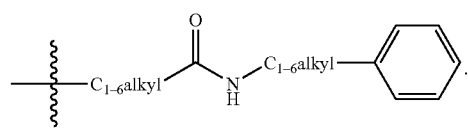

When the substituent's point of attachment is not otherwise clear, a dashed line is used to indicate the point of attachment, followed by the adjacent functionality and ending with the terminal functionality such as, for example, —($C_{1-4}$)alkyl-NH—($C_{1-4}$)alkyl.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

An embodiment of the invention is a pharmaceutical composition comprising a pharmaceutically acceptable carrier and any of the compounds described above. Illustrative of the invention is a pharmaceutical composition made by mixing any of the compounds described above and a pharmaceutically acceptable carrier. Another illustration of the invention is a process for making a pharmaceutical composition comprising mixing any of the compounds described above and a pharmaceutically acceptable carrier. Further illustrative of the present invention are pharmaceutical compositions comprising one or more compounds of this invention in association with a pharmaceutically acceptable carrier.

As used herein, the term "composition" is intended to encompass a product comprising the specified ingredients in the specified amounts, as well as any product which results, directly or indirectly, from combinations of the specified ingredients in the specified amounts.

The compounds of the present invention are selective kinase inhibitors and some compounds are dual-kinase inhibitors useful in a method for treating or ameliorating a kinase or dual-kinase mediated disorder. In particular, the kinase is selected from protein kinase C or glycogen synthase kinase-3. More particularly, the kinase is selected from protein kinase C α, protein kinase C β (e.g. protein kinase C β-I and protein kinase C β-II), protein kinase C γ or glycogen synthase kinase-3β.

Protein Kinase C Isoforms

Protein kinase C is known to play a key role in intracellular signal transduction (cell-cell signaling), gene expression and in the control of cell differentiation and growth. The PKC family is composed of twelve isoforms that are further classified into 3 subfamilies: the calcium dependent classical PKC isoforms alpha (α), beta-I (β-I), beta-II (β-II) and gamma (γ); the calcium independent PKC isoforms delta (γ), epsilon (δ), eta (η), theta (θ) and mu (μ); and, the a typical PKC isoforms zeta (ζ), lambda (λ) and iota (ι).

Certain disease states tend to be associated with elevation of particular PKC isoforms. The PKC isoforms exhibit distinct tissue distribution, subcellular localization and activation-dependent cofactors. For example, the α and β isoforms of PKC are selectively induced in vascular cells stimulated with agonists such as vascular endothelial growth factor (VEGF) (P. Xia, et al., *J. Clin. Invest.*, 1996, 98, 2018) and have been implicated in cellular growth, differentiation, and vascular permeability (H. Ishii, et al., *J. Mol. Med.*, 1998, 76, 21). The elevated blood glucose levels found in diabetes leads to an isoform-specific elevation of the β-II isoform in vascular tissues (Inoguchi, et al., *Proc. Natl. Acad. Sci. USA*, 1992, 89, 11059–11065). A diabetes-linked elevation of the β isoform in human platelets has been correlated with their altered response to agonists (Bastyr III, E. J. and Lu, J., *Diabetes*, 1993, 42, (Suppl. 1) 97A). The human vitamin D receptor has been shown to be selectively phosphorylated by PKCβ. This phosphorylation has been linked to alterations in the functioning of the receptor (Hsieh, et al., *Proc. Natl. Acad. Sci. USA*, 1991, 88, 9315–9319; Hsieh, et al., *J. Biol. Chem.*, 1993, 268, 15118–15126). In addition, the work has shown that the β-II isoform is responsible for erythroleukemia cell proliferation while the ox isoform is involved in megakaryocyte differentiation in these same cells (Murray, et al., *J. Biol. Chem.*, 1993, 268, 15847–15853).

Cardiovascular Diseases

PKC activity plays an important role in cardiovascular diseases. Increased PKC activity in the vasculature has been shown to cause increased vasoconstriction and hypertension (Bilder, G. E., et al., *J. Pharmacol. Exp. Ther.*, 1990, 252, 526–530). PKC inhibitors block agonist-induced smooth muscle cell proliferation (Matsumoto, H. and Sasaki, Y., *Biochem. Biophys. Res. Commun.*, 1989, 158, 105–109). PKC β triggers events leading to induction of Egr-1 (Early Growth Factor-1) and tissue factor under hypoxic conditions (as part of the oxygen deprivation-mediated pathway for triggering procoagulant events) (Yan, S-F, et al., *J. Biol. Chem.*, 2000, 275, 16, 11921–11928). PKC β is suggested as a mediator for production of PAI-1 (Plaminogen Activator Inhibitor-1) and is implicated in the development of thrombosis and atherosclerosis (Ren, S, et al., *Am. J. Physiol.*, 2000, 278, (4, Pt. 1), E656–E662). PKC inhibitors are useful in treating cardiovascular ischemia and improving cardiac function following ischemia (Muid, R. E., et al., *FEBS Lett.*, 1990, 293, 169–172; Sonoki, H. et al., *Kokyu-To Junkan*, 1989, 37, 669–674). Elevated PKC levels have been correlated with an increased platelet function response to agonists (Bastyr III, E. J. and Lu, J., *Diabetes*, 1993, 42, (Suppl. 1) 97A). PKC has been implicated in the biochemical pathway in the platelet-activating factor (PAF) modulation of microvascular permeability (Kobayashi, et al., *Amer. Phys. Soc.*, 1994, H1214–H1220). PKC inhibitors affect agonist-induced aggregation in platelets (Toullec, D., et al., *J. Biol. Chem.*, 1991, 266, 15771–15781). Accordingly, PKC inhibitors may be indicated for use in treating cardiovascular disease, ischemia, thrombotic conditions, atherosclerosis and restenosis.

Diabetes

Excessive activity of PKC has been linked to insulin signaling defects and therefore to the insulin resistance seen in Type II diabetes (Karasik, A., et al., *J. Biol. Chem.*, 1990, 265, 10226–10231; Chen, K. S., et al., *Trans. Assoc. Am. Physicians*, 1991, 104, 206–212; Chin, J. E., et al., *J. Biol. Chem.*, 1993, 268, 6338–6347).

Diabetes-Associated Disorders

Studies have demonstrated an increase in PKC activity in tissues known to be susceptible to diabetic complications when exposed to hyperglycemic conditions (Lee, T-S., et al., *J. Clin. Invest.*, 1989, 83, 90–94; Lee, T-S., et al., *Proc. Natl. Acad. Sci. USA*, 1989, 86, 5141–5145; Craven, P. A. and DeRubertis, F. R., *J. Clin. Invest.*, 1989, 87, 1667–1675; Wolf, B. A., et al., *J. Clin. Invest.*, 1991, 87, 31–38; Tesfamariam, B., et al., *J. Clin. Invest.*, 1991, 87, 1643–1648). For example, activation of the PKC-β-II isoform plays an important role in diabetic vascular complications such as retinopathy (Ishii, H., et al., *Science*, 1996, 272, 728–731) and PKCβ has been implicated in development of the cardiac hypertrophy associated with heart failure (X. Gu, et al., *Circ. Res.*, 1994, 75, 926; R. H. Strasser, et al., *Circulation*, 1996, 94, 1551). Overexpression of cardiac PKCβII in transgenic mice caused cardiomyopathy involving hypertrophy, fibrosis and decreased left ventricular function (H. Wakasaki, et al., *Proc. Natl. Acad. Sci. USA*, 1997, 94, 9320).

Inflammatory Diseases

PKC inhibitors block inflammatory responses such as the neutrophil oxidative burst, CD3 down-regulation in T-lymphocytes and phorbol-induced paw edema (Twoemy, B., et al., *Biochem. Biophys. Res. Commun.*, 1990, 171, 1087–1092; Mulqueen, M. J., et al. *Agents Actions*, 1992, 37, 85–89). PKC β has an essential role in the degranulation of bone marrow-derived mast cells, thus affecting cell capacity to produce IL-6 (Interleukin-6) (Nechushtan, H., et al., *Blood*, 2000 (March), 95, 5, 1752–1757). PKC plays a role in enhanced ASM (Airway Smooth Muscle) cell growth in rat models of two potential risks for asthma: hyperresponsiveness to contractile agonists and to growth stimuli (Ren, S, et al., *Am. J. Physiol.*, 2000, 278, (4, Pt. 1), E656–E662). PKC β-1 overexpression augments an increase in endothelial permeability, suggesting an important function in the regulation of the endothelial barrier (Nagpala, P. G., et al., *J. Cell Physiol.*, 1996, 2, 249–55). PKC β mediates activation of neutrophil NADPH oxidase by PMA and by stimulation of Fcγ receptors in neutrophils (Dekker, L. V., et al., *Biochem. J.*, 2000, 347, 285–289). Thus, PKC inhibitors may be indicated for use in treating inflammation and asthma.

Immunological Disorders

PKC may be useful in treating or ameliorating certain immunological disorders. While one study suggests that HCMV (Human Cytomegalovirus) inhibition is not correlated with PKC inhibition (Slater, M. J., et al., *Biorg. & Med. Chem.*, 1999, 7, 1067–1074), another study showed that the PKC signal transduction pathway synergistically interacted with the cAMP-dependent PKA pathway to activate or increase HIV-1 transcription and viral replication and was abrogated with a PKC inhibitor (Rabbi, M. F., et al., *Virology*, 1998 (June 5), 245, 2, 257–69). Therefore, an immunological disorder may be treated or ameliorated as a function of the affected underlying pathway's response to up- or down-regulation of PKC.

PKC β deficiency also results in an immunodeficiency characterized by impaired humoral immune responses and a reduced B cell response, similar to X-linked immunodeficiency in mice, playing an important role in antigen receptor-mediated signal transduction (Leitges, M., et al., *Science* (Wash., D.C.), 1996, 273, 5276, 788–789). Accordingly, transplant tissue rejection may be ameliorated or prevented by suppressing the immune response using a PKC β inhibitor.

Dermatological Disorders

Abnormal activity of PKC has been linked to dermatological disorders characterized by abnormal proliferation of keratinocytes, such as psoriasis (Horn, F., et al., *J. Invest. Dermatol.*, 1987, 88, 220–222; Raynaud, F. and Evain-Brion, D., *Br. J. Dermatol.*, 1991, 124, 542–546). PKC inhibitors have been shown to inhibit keratinocyte proliferation in a dose-dependent manner (Hegemann, L., et al., *Arch. Dermatol. Res.*, 1991, 283, 456–460; Bollag, W. B., et al., *J. Invest. Dermatol.*, 1993, 100, 240–246).

Oncological Disorders

PKC activity has been associated with cell growth, tumor promotion and cancer (Rotenberg, S. A. and Weinstein, I. B., *Biochem. Mol. Aspects Sel. Cancer*, 1991, 1, 25–73; Ahmad, et al., *Molecular Pharmacology*, 1993, 43, 858–862); PKC inhibitors are known to be effective in preventing tumor growth in animals (Meyer, T., et al., *Int. J. Cancer*, 1989, 43, 851–856; Akinagaka, S., et al., *Cancer Res.*, 1991, 51, 4888–4892). PKC β-1 and β-2 expression in differentiated HD3 colon carcinoma cells blocked their differentiation, enabling them to proliferate in response to basic FGF (Fibroblast Growth Factor) like undifferentiated cells, increasing their growth rate and activating several MBP (Myelin-Basic Protein) kinases, including p57 MAP (Mitogen-Activated Protein) kinase (Sauma, S., et al., *Cell Growth Differ.*, 1996, 7, 5, 587–94). PKC α inhibitors, having an additive therapeutic effect in combination with other anti-cancer agents, inhibited the growth of lymphocytic leukemia cells (Konig, A., et al., *Blood*, 1997, 90, 10, Suppl. 1 Pt. 2). PKC inhibitors enhanced MMC (Mitomycin-C) induced apoptosis in a time-dependent fashion in a gastric cancer cell-line, potentially indicating use as agents for chemotherapy-induced apoptosis (Danso, D., et al., *Proc. Am. Assoc. Cancer Res.*, 1997, 38, 88 Meet., 92). Therefore, PKC inhibitors may be indicated for use in ameliorating cell and tumor growth, in treating or ameliorating cancers (such as leukemia or colon cancer) and as adjuncts to chemotherapy.

PKC α (by enhancing cell migration) may mediate some proangiogenic effects of PKC activation while PKC δ may direct antiangiogenic effects of overall PKC activation (by inhibiting cell growth and proliferation) in capillary endothelial cells, thus regulating endothelial proliferation and angiogenesis (Harrington, E. O., et al., *J. Biol. Chem.*, 1997, 272, 11, 7390–7397). PKC inhibitors inhibit cell growth and induce apoptosis in human glioblastoma cell lines, inhibit the growth of human astrocytoma xenografts and act as radiation sensitizers in glioblastoma cell lines (Begemann, M., et al., *Anticancer Res.* (Greece), 1998 (Jul–Aug), 18, 4A, 2275–82). PKC inhibitors, in combination with other anti-cancer agents, are radiation and chemosensitizers useful in cancer therapy (Teicher, B. A., et al., *Proc. Am. Assoc. Cancer Res.*, 1998, 39, 89 Meet., 384). PKC β inhibitors (by blocking the MAP kinase signal transduction pathways for VEGF (Vascular Endothelial Growth Factor) and bFGF (basic Fibrinogen Growth Factor) in endothelial cells), in a combination regimen with other anti-cancer agents, have an anti-angiogenic and antitumor effect in a human T98G glioblastoma multiforme xenograft model (Teicher, B. A., et al., *Clinical Cancer Research*, 2001 (March), 7, 634–640). Accordingly, PKC inhibitors may be indicated for use in ameliorating angiogenesis and in treating or ameliorating cancers (such as breast, brain, kidney, bladder, ovarian or colon cancers) and as adjuncts to chemotherapy and radiation therapy.

Central Nervous System Disorders

PKC activity plays a central role in the functioning of the central nervous system (CNS) (Huang, K. P., *Trends Neurosci.*, 1989, 12, 425–432) and PKC is implicated in Alzheimer's disease (Shimohama, S., et al., *Neurology*, 1993, 43, 1407–1413) and inhibitors have been shown to prevent the damage seen in focal and central ischemic brain injury and brain edema (Hara, H., et al., *J. Cereb. Blood Flow Metab.*, 1990, 10, 646–653; Shibata, S., et al., *Brain Res.*, 1992, 594, 290–294). Accordingly, PKC inhibitors may be indicated for use in treating Alzheimer's disease and in treating neurotraumatic and ischemia-related diseases.

The long-term increase in PKC γ (as a component of the phosphoinositide $2^{nd}$ messenger system) and muscarinic acetylcholine receptor expression in an amygdala-kindled rat model has been associated with epilepsy, serving as a basis for the rat's permanent state of hyperexcitability (Beldhuis, H. J. A., et al., *Neuroscience*, 1993, 55, 4, 965–73). Therefore, PKC inhibitors may be indicated for use in treating epilepsy.

The subcellular changes in content of the PKC γ and PKC β-II isoenzymes for animals in an in-vivo thermal hyperalgesia model suggests that peripheral nerve injury contributes to the development of persistent pain (Miletic, V., et al., *Neurosci. Lett.*, 2000, 288, 3, 199–202). Mice lacking PKC γ display normal responses to acute pain stimuli, but almost completely fail to develop a neuropathic pain syndrome after partial sciatic nerve section (Chen, C., et al., *Science* (Wash., D.C.), 1997, 278, 5336, 279–283). PKC modulation may thus be indicated for use in treating chronic pain and neuropathic pain.

PKC has demonstrated a role in the pathology of conditions such as, but not limited to, cardiovascular diseases, diabetes, diabetes-associated disorders, inflammatory diseases, immunological disorders, dermatological disorders, oncological disorders and central nervous system disorders. Glycogen Synthase Kinase-3 Glycogen synthase kinase-3 (GSK-3) is a serine/threonine protein kinase composed of two isoforms (α and β) which are encoded by distinct genes. GSK-3 is one of several protein kinases which phosphorylate glycogen synthase (GS) (Embi, et al., *Eur. J. Biochem*, 1980, 107, 519–527). The α and β isoforms have a monomeric structure of 49 and 47 kD respectively and are both found in mammalian cells. Both isoforms phosphorylate muscle glycogen synthase (Cross, et al., *Biochemical Journal*, 1994, 303, 21–26) and these two isoforms show good homology between species (human and rabbit GSK-3α are 96% identical).

Diabetes

Type II diabetes (or Non-Insulin Dependent Diabetes Mellitus, NIDDM) is a multifactorial disease. Hyperglycemia is due to insulin resistance in the liver, muscle and other tissues coupled with inadequate or defective secretion of insulin from pancreatic islets. Skeletal muscle is the major site for insulin-stimulated glucose uptake and in this tissue glucose removed from the circulation is either metabolised through glycolysis and the TCA (tricarboxylic acid) cycle or stored as glycogen. Muscle glycogen deposition plays the more important role in glucose homeostasis and Type II diabetic subjects have defective muscle glycogen storage. The stimulation of glycogen synthesis by insulin in skeletal muscle results from the dephosphorylation and activation of glycogen synthase (Villar-Palasi C. and Larner J., *Biochim. Biophys. Acta*, 1960, 39, 171–173, Parker P. J., et al., *Eur. J. Biochem.*, 1983, 130, 227–234, and Cohen P., *Biochem. Soc. Trans.*, 1993, 21, 555–567). The phosphorylation and dephosphorylation of GS are mediated by specific kinases and phosphatases. GSK-3 is responsible for phosphorylation and deactivation of GS, while glycogen bound protein phosphatase 1 (PP1G) dephosphorylates and activates GS. Insulin both inactivates GSK-3 and activates PP1G (Srivastava A. K. and Pandey S. K., *Mol. and Cellular Biochem.*, 1998, 182, 135–141).

Studies suggest that an increase in GSK-3 activity might be important in Type II diabetic muscle (Chen, et al., *Diabetes*, 1994, 43, 1234–1241). Overexpression of GSK-3β and constitutively active GSK-3β (S9A, S9e) mutants in HEK-293 cells resulted in suppression of glycogen synthase activity (Eldar-Finkelman, et al., *PNAS*, 1996, 93, 10228–10233) and overexpression of GSK-3β in CHO cells, expressing both insulin receptor and insulin receptor substrate 1 (IRS-1) resulted in impairment of insulin action (Eldar-Finkelman and Krebs, *PNAS*, 1997, 94, 9660–9664). Recent evidence for the involvement of elevated GSK-3 activity and the development of insulin resistance and Type II diabetes in adipose tissue has emerged from studies undertaken in diabetes and obesity prone C57BL/6J mice (Eldar-Finkelman, et al., *Diabetes*, 1999, 48, 1662–1666).

Dermatological Disorders

The finding that transient β-catenin stabilization may play a role in hair development (Gat, et al., *Cell*, 1998, 95, 605–614) suggests that GSK-3 inhibitors could also be used in the treatment of baldness.

Inflammatory Diseases

Studies on fibroblasts from the GSK-3β knockout mouse indicate that inhibition of GSK-3 may be useful in treating inflammatory disorders or diseases through the negative regulation of NFkB activity (Hoeflich K. P., et al., *Nature*, 2000, 406, 86–90).

Central Nervous System Disorders

In addition to modulation of glycogen synthase activity, GSK-3 also plays an important role in the CNS disorders. GSK-3 inhibitors may be of value as neuroprotectants in the treatment of acute stroke and other neurotraumatic injuries (Pap and Cooper, *J. Biol. Chem.*, 1998, 273, 19929–19932). Lithium, a low mM inhibitor of GSK-3, has been shown to protect cerebellar granule neurons from death (D'Mello, et al., *Exp. Cell Res.*, 1994, 211, 332–338) and chronic lithium treatment has demonstrable efficacy in the middle cerebral artery occlusion model of stroke in rodents (Nonaka and Chuang, Neuroreport, 1998, 9(9), 2081–2084).

Tau and β-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease and is postulated to promote microtubule disassembly. Lithium has been reported to reduce the phosphorylation of tau, enhance the binding of tau to microtubules and promote microtubule assembly through direct and reversible inhibition of GSK-3 (Hong M. et al *J. Biol. Chem.*, 1997, 272 (40), 25326–32). β-catenin is phosphorylated by GSK-3 as part of a tripartite axin protein complex resulting in β-catenin degradation (Ikeda, et al., *EMBO J.*, 1998, 17, 1371–1384). Inhibition of GSK-3 activity is involved in the stabilization of catenin hence promotes β-catenin-LEF-1/TCF transcriptional activity (Eastman, Grosschedl, *Curr. Opin. Cell Biol.*, 1999, 11, 233). Studies have also suggested that GSK-3 inhibitors may also be of value in treatment of schizophrenia (Cotter D., et al. *Neuroreport*, 1998, 9, 1379–1383; Lijam N., et al., *Cell*, 1997, 90, 895–905) and manic depression (Manji, et al., *J. Clin. Psychiatry*, 1999, 60, (Suppl 2) 27–39 for review).

Accordingly, compounds found useful as GSK-3 inhibitors could have further therapeutic utility in the treatment of diabetes, dermatological disorders, inflammatory diseases and central nervous system disorders.

Embodiments of the method of the present invention include a method for treating or ameliorating a kinase or dual-kinase mediated disorder in a subject in need thereof comprising administering to the subject a therapeutically effective amount of an instant compound or pharmaceutical composition thereof. The therapeutically effective amount of the compounds of Formula (I) exemplified in such a method is from about 0.001 mg/kg/day to about 300 mg/kg/day.

Embodiments of the present invention include the use of a compound of Formula (I) for the preparation of a medicament for treating or ameliorating a kinase or dual-kinase mediated disorder in a subject in need thereof.

In accordance with the methods of the present invention, an individual compound of the present invention or a pharmaceutical composition thereof can be administered separately at different times during the course of therapy or concurrently in divided or single combination forms. The instant invention is therefore to be understood as embracing all such regimes of simultaneous or alternating treatment and the term "administering" is to be interpreted accordingly.

Embodiments of the present method include a compound or pharmaceutical composition thereof advantageously co-administered in combination with other agents for treating or ameliorating a kinase or dual-kinase mediated disorder. For example, in the treatment of diabetes, especially Type II diabetes, a compound of Formula (I) or pharmaceutical composition thereof may be used in combination with other agents, especially insulin or antidiabetic agents including, but not limited to, insulin secretagogues (such as sulphonylureas), insulin sensitizers including, but not limited to, glitazone insulin sensitizers (such as thiazolidinediones) or biguamides or a glucosidase inhibitors.

The combination product comprises co-administration of a compound of Formula (I) or pharmaceutical composition thereof and an additional agent for treating or ameliorating a kinase or dual-kinase mediated disorder, the sequential administration of a compound of Formula (I) or pharmaceutical composition thereof and an additional agent for treating or ameliorating a kinase or dual-kinase mediated disorder, administration of a pharmaceutical composition containing a compound of Formula (I) or pharmaceutical composition thereof and an additional agent for treating or ameliorating a kinase or dual-kinase mediated disorder or the essentially simultaneous administration of a separate pharmaceutical composition containing a compound of Formula (I) or pharmaceutical composition thereof and a separate pharmaceutical composition containing an additional agent for treating or ameliorating a kinase or dual-kinase mediated disorder.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The ubiquitous nature of the PKC and GSK isoforms and their important roles in physiology provide incentive to produce highly selective PKC and GSK inhibitors. Given the evidence demonstrating linkage of certain isoforms to disease states, it is reasonable to assume that inhibitory compounds that are selective to one or two PKC isoforms or to a GSK isoform relative to the other PKC and GSK isoforms and other protein kinases are superior therapeutic agents. Such compounds should demonstrate greater efficacy and lower toxicity by virtue of their specificity. Accordingly, it will be appreciated by one skilled in the art that a compound of Formula (I) is therapeutically effective for certain kinase or dual-kinase mediated disorders based on the modulation of the disorder by selective kinase or dual-kinase inhibition. The usefulness of a compound of Formula (I) as a selective kinase or dual-kinase inhibitor can be determined according to the methods disclosed herein and the scope of such use includes use in one or more kinase or dual-kinase mediated disorders.

Therefore, the term "kinase or dual-kinase mediated disorders" as used herein, includes, and is not limited to, cardiovascular diseases, diabetes, diabetes-associated disorders, inflammatory diseases, immunological disorders, dermatological disorders, oncological disorders and CNS disorders.

Cardiovascular diseases include, and are not limited to, acute stroke, heart failure, cardiovascular ischemia, thrombosis, atherosclerosis, hypertension, restenosis, retinopathy of prematurity or age-related macular degeneration. Diabetes includes insulin dependent diabetes or Type II non-insulin dependent diabetes mellitus. Diabetes-associated disorders include, and are not limited to, impaired glucose tolerance, diabetic retinopathy, proliferative retinopathy, retinal vein occlusion, macular edema, cardiomyopathy, nephropathy or neuropathy. Inflammatory diseases include, and are not limited to, vascular permeability, inflammation, asthma, rheumatoid arthritis or osteoarthritis. Immunological disorders include, and are not limited to, transplant tissue rejection, HIV-1 or immunological disorders treated or ameliorated by PKC modulation. Dermatological disorders include, and are not limited to, psoriasis, hair loss or baldness. Oncological disorders include, and are not limited to, cancers or tumor growth (such as breast, brain, kidney, bladder, ovarian or colon cancer or leukemia), proliferative angiopathy and angiogenesis; and, includes use for compounds of Formula (I) as an adjunct to chemotherapy and radiation therapy. CNS disorders include, and are not limited to, chronic pain, neuropathic pain, epilepsy, chronic neurodegenerative conditions (such as dementia or Alzheimer's disease), mood disorders (such as schizophrenia), manic depression or neurotraumatic, cognitive decline and ischemia-related diseases {as a result of head trauma (from acute ischemic stroke, injury or surgery) or transient ischemic stroke (from coronary bypass surgery or other transient ischemic conditions)}.

A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending on the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets*, Second Edition, Revised and Expanded, Volumes 1–3, edited by Lieberman, et al.; *Pharmaceutical Dosage Forms: Parenteral Medications*, Volumes 1–2, edited by Avis, et al.; and *Pharmaceutical Dosage Forms: Disperse Systems*, Volumes 1–2, edited by Lieberman, et al.; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 300 mg (preferably, from about 0.1 mg to about 100 mg; and, more preferably, from about 0.1 mg to about 30 mg) and may be given at a dosage of from about 0.01 mg/kg/day to about 300 mg/kg/day (preferably, from about 0.1 mg/kg/day to about 100 mg/kg/day; and, more preferably, from about 0.1 mg/kg/day to about 30 mg/kg/day). Preferably, in the method for the treatment of kinase mediated disorders described in the present invention and using any of the compounds as defined herein, the dosage form will contain a pharmaceutically acceptable carrier containing between about 0.01 mg and 100 mg; and, more preferably, between about 5 mg and 50 mg of the compound; and, may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and glidants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable glidants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropylcellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, I- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treatment of kinase mediated disorders, particularly protein kinase or glycogen synthase kinase mediated disorders, is required for a subject in need thereof.

The daily dose of a pharmaceutical composition of the present invention may be varied over a wide range from about 0.7 mg to about 21,000 mg per 70 kilogram (kg) adult human per day; preferably in the range of from about 7 mg to about 7,000 mg per adult human per day; and, more preferably, in the range of from about 7 mg to about 2,100 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. A therapeutically effective amount of the drug is ordinarily supplied at a dosage level of from about 0.01 mg/kg to about 300 mg/kg of body weight per day. Preferably, the range is from about 0.1 mg/kg to about 100 mg/kg of body weight per day; and, most preferably, from about 0.1 mg/kg to about 30 mg/kg of body weight per day. Advantageously, compounds of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Abbreviations used in the instant specification, particularly the Schemes and Examples, are as follows:

| | |
|---|---|
| ATP = | adenosinetriphosphate |
| BSA = | bovine serum albumin |
| DCM = | dichloromethane |
| DMF = | N,N-dimethylformamide |
| DMSO = | dimethylsulfoxide |
| EDTA = | ethylenediaminetetraacetic acid |
| EGTA = | ethylenebis(oxyethylenenitrilo)tetraacetic acid |
| h = | hour |
| HEPES = | 4-(2-hydroxyethyl)-1-piperazine-ethanesulfonic acid |
| min = | minute |
| NT = | not tested |
| rt = | room temperature |
| TBAF = | tert-butylammonium fluoride |
| TCA = | trichloroacetic acid |
| THF = | tetrahydrofuran |
| TFA = | trifluoroacetic acid |
| SEM = | 2-(trimethylsilyl)ethoxymethyl |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

The following schemes describe general synthetic methods whereby intermediate and target compounds of the present invention may be prepared.

Additional representative compounds of the present invention can be synthesized using the intermediates prepared in accordance with the schemes and other materials, compounds and reagents known to those skilled in the art.

In Scheme AA, the 7-azaindole Compound AA1 (optionally substituted with $R^3$) was treated with ethylmagnesium bromide followed by alkylation with $(C_{1-2})$alkylchlorooxoacetate to give Compound AA2.

Compound AA2 was then alkylated with an appropriate alkylating agent in the presence of a base such as cesium or potassium carbonate in a dipolar aprotic solvent such as DMF to give Compound AA3 (wherein $R^1$ was a substituted or unsubstituted alkyl group).

The glyoxylate ester Compound AA3 was then reacted with an acetamide Compound AA4 (substituted with $R(R_2, R_4)$; wherein the "R" group is selected from cycloalkyl, heterocyclyl, aryl and heteroaryl; and, is preferably selected from an aromatic, heteroaromatic or partially saturated heterocyclic ring system) stirred in an aprotic solvent such as THF with ice bath cooling and a base, such as potassium tert-butoxide or sodium hydride, to give a target Compound AA5.

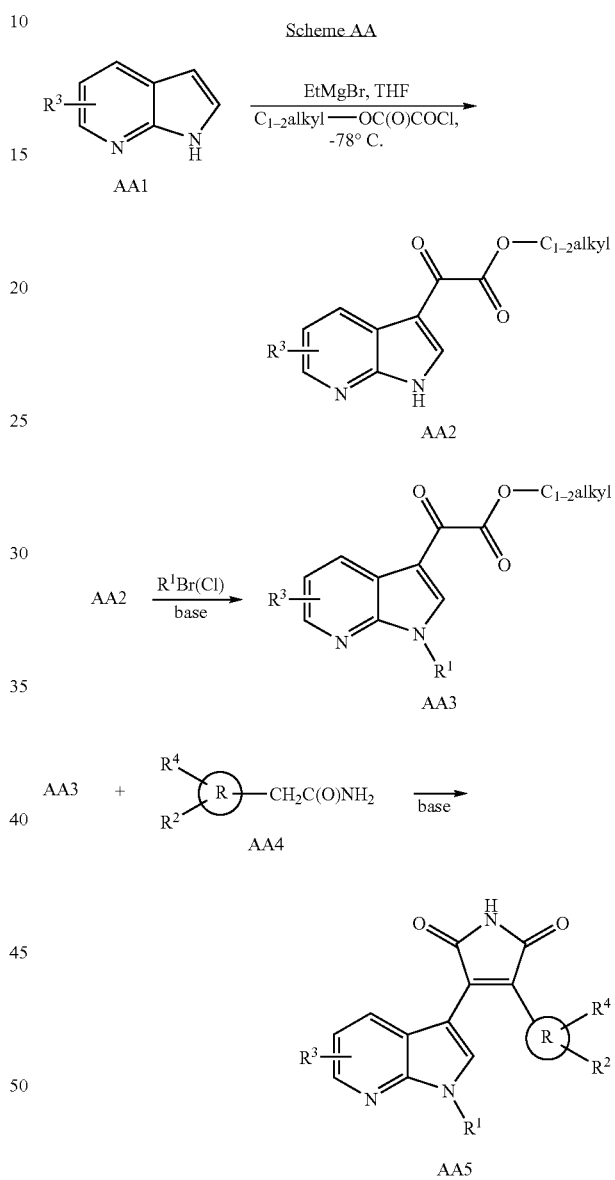

Alternatively, in Scheme AB, Compound AA1 was treated with an appropriate alkylating agent under basic conditions (wherein $R^1$ was a substituted or unsubstituted alkyl group), or an appropriate aryl or heteroaryl halide in the presence of a base such as cesium or potassium carbonate and copper oxide in a dipolar aprotic solvent such as DMF (wherein $R^1$ was a substituted or unsubstituted aryl or heteroaryl group) to give Compound AB1. Acylation of AB1 with oxalyl chloride in an aprotic solvent such as diethyl ether or DCM followed by addition of methanol or sodium methoxide afforded Compound AA3.

Scheme AB

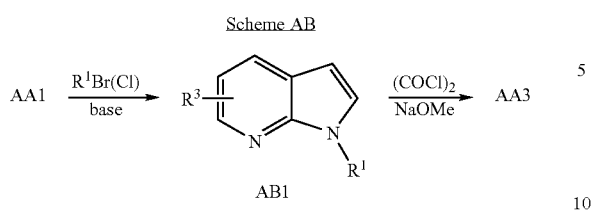

In Scheme AC, the 7-azaindole Compound AC1 (optionally substituted with $R^3$) was reacted with a halogenated $R^1$ group (optionally protected with a suitable protecting group) to give Compound AC2. The pyrrolinylene moiety on Compound AC4 was then synthesized via Compound AC3 and was converted to the chloride or —$OSO_2CF_3$ (triflate) substituted Compound AC5. Using a palladium-catalyzed cross-coupling reaction, Compound AC5 was reacted with an organometallic species (such as organotin, organoboron, organozinc, organosilicon, organocopper, organomagnesium, etc.) in the presence of a ligand (such as triphenylphosphine, triphenylarsine, etc) to give Compound AA5.

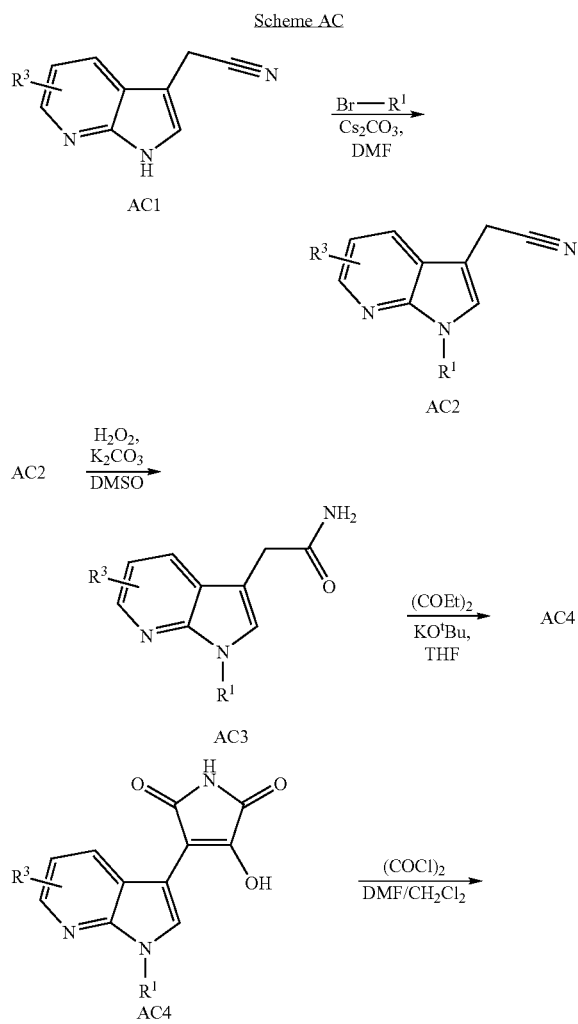

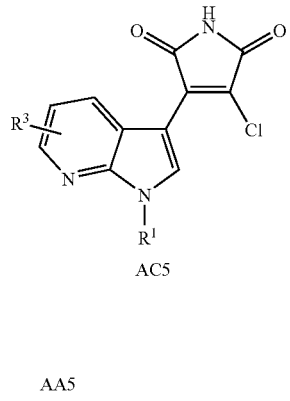

Specific Synthetic Methods

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

All chemicals were obtained from commercial suppliers and used without further purification. $^1$H and $^{13}$C NMR spectra were recorded on a Bruker AC 300B (300 MHz proton) or a Bruker AM-400 (400 MHz proton) spectrometer with $Me_4Si$ as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-μm silica gel plates. Preparative TLC was performed with Analtech 1000-μm silica gel GF plates. Flash column chromatography was conducted with flash column silica gel (40–63 μm) and column chromatography was conducted with standard silica gel. HPLC separations were carried out on three Waters PrepPak® Cartridges (25×100 mm, Bondapak® C18, 15–20 μm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

Compounds are named according to nomenclature conventions well known in the art or, as in the compound names for the examples presented, may be generated using commercial chemical naming software such as the ACD/Index Name (Advanced Chemistry Development, Inc., Toronto, Ontario).

EXAMPLE 1

3-(2-chlorophenyl)-4-[1-(3-hydroxypropyl)-1H-pyr-rolo[2,3-b]pyridin-3-yl]-1H-pyrrole-2,5-dione (Compound 1)

Ethylmagnesium bromide in diethyl ether (3.0 M, 63 mL) was added dropwise to a solution of Compound 1a (20 g, 0.156 mole) in THF (300 mL) cooled in an ice bath. The resulting yellowish mixture of solids was stirred at 65° C. for 1 h, then cooled with an acetone-dry ice bath. A solution of methyl chlorooxoacetate (47.66 g) in THF (40 mL) was added dropwise to the cooled mixture. The cooled temperature was maintained while the mixture was stirred for 30 min. The temperature was warmed up to 0° C. while the mixture was stirred for another 30 min at 0° C. The reaction was quenched with saturated NH$_4$Cl (200 mL) and water (100 mL), then the mixture was filtered and the filtrate extracted with ethyl acetate (2×500 mL). The organic layers were combined and washed with saturated NaHCO$_3$ (2×250 mL), brine (250 mL), dried over anhydrous sodium sulfate and concentrated in vacuo to give 7.64 g (24%) of Compound 1b as a yellow solid. Compound 1b, without further purification, was directly used in the next step. $^1$H NMR (CDCl$_3$) δ 8.78 (dd, J=1.5, 7.9 Hz, 1H), 8.75 (s, 1H), 8.47 (dd, J=1.5, 4.9 Hz, 1H), 7.37 (dd, J=4.9, 7.9 Hz, 1H) 3.99 (s, 1H). ES-MS m/z 205 (MH$^+$).

A mixture of crude Compound 1b (4.0 g, 19.6 mmol) and cesium carbonate (8.298 g, 25.5 mmol) in anhydrous DMF (100 mL) was stirred under nitrogen at 50° C. for one hour, then was treated with (3-bromopropoxy)-tert-butyl-dimethylsilane (4.96 g, 19.6 mmol). The stirring was continued at 50° C. for 5 h. The reaction mixture was then diluted with ethyl acetate (500 mL) and washed with brine (2×100 mL). The organic layer was separated, dried over anhydrous sodium sulfate and concentrated in vacuo. This crude product was purified by flash chromatography on silica (EtOAc/hexane, from 1:7 to 1:4) to give Compound 1c (2.1 g). $^1$H NMR (CDCl$_3$) δ 8.6 (m, 1H), 8.47 (s, 1H), 7.27–7.22 (m, 1H), 4.46–4.41 (t, 2H), 3.9 (s, 3H), 3.58–3.54 (t, 2H), 2.12–2.04 (m, 2H), 0.87 (s, 9H), 0 (s, 6H). ES-MS m/z 377 (MH$^+$).

A mixture of Compound 1c (322 mg, 0.857 mmol) and Compound 1d (121 mg, 0.714 mmol) in 7 mL of anhydrous THF was stirred under nitrogen and cooled in an ice bath while treating dropwise with 2.9 mL of 1 N potassium t-butoxide in THF. The mixture was stirred for 30 minutes in an ice bath then at room temperature for another 30 min. The reddish mixture was then cooled down and then 2 mL of concentrated HCl was added dropwise. The mixture was stirred for 5 min. Ethyl acetate (150 mL) and H$_2$O (30 mL) were added. The organic layer was separated and washed with saturated NaHCO$_3$ and brine, dried over anhydrous sodium sulfate and concentrated in vacuo. The crude product was separated by flash chromatography on silica gel (CH$_2$Cl$_2$/MeOH/NH$_4$OH, from 98:2:0.2 to 95:5:0.5) to yield 150 mg (55%) of Compound 1 as a yellow solid. $^1$H NMR (CDCl$_3$) δ 8.21 (dd, J=1.5, 4.7 Hz, 1H), 8.17 (s, 1H), 7.48–7.33 (m, 4H), 6.78 (dd, J=4.7, 8.1 Hz, 1H), 6.66 (dd, J=1.5, 8.1 Hz, 1H), 4.5 (dd, J=2.6, 7.1 Hz, 2H), 3.41 (t, J=5.5 Hz, 2H), 2.03 (m, 2H). ES-MS m/z 382 (MH$^+$).

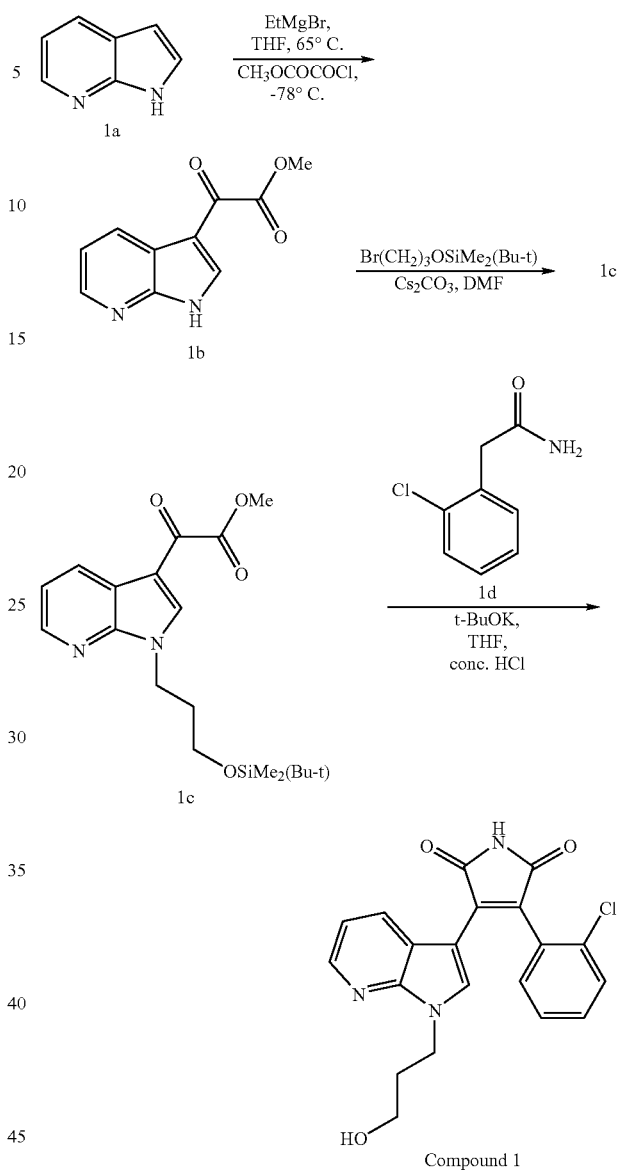

Using the procedure of Example 1 and the appropriate reagents and starting materials known to those skilled in the art, other compounds of the present invention may be prepared including, but not limited to:

| Cpd | Name | ES-MS m/z (MH$^+$) |
|---|---|---|
| 5 | 3-(5-chlorobenzo[b]thien-3-yl)-4-[1-(3-hydroxypropyl)-1H-pyrrolo[2,3-b]pyridin-3-yl]-1H-pyrrole-2,5-dione | 438 |
| 6 | 3-[1-(3-hydroxypropyl)-1H-pyrrolo[2,3-b]pyridin-3-yl]-4-(1H-indazol-3-yl)-1H-pyrrole-2,5-dione | 388 |
| 10 | 3-(2-chloro-4-fluorophenyl)-4-[1-(3-hydroxypropyl)-1H-pyrrolo[2,3-b]pyridin-3-yl]-1H-pyrrole-2,5-dione | 400 |
| 11 | 3-[1-(3-hydroxypropyl)-1H-pyrrolo[2,3-b]pyridin-3-yl]-4-[2-(trifluoromethyl)phenyl]-1H-pyrrole-2,5-dione | 416 |
| 12 | 3-[1-(3-hydroxypropyl)-1H-pyrrolo[2,3-b]pyridin-3-yl]-4-(2-pyridinyl)-1H-pyrrole-2,5-dione | 349 |

-continued

| Cpd | Name | ES-MS m/z (MH+) |
|---|---|---|
| 13 | 3-[3-chloro-5-(trifluoromethyl)-2-pyridinyl]-4-[1-(3-hydroxypropyl)-1H-pyrrolo[2,3-b]pyridin-3-yl]-1H-pyrrole-2,5-dione | 451 |
| 14 | 3-[1-(3-hydroxypropyl)-1H-pyrrolo[2,3-b]pyridin-3-yl]-4-(2-thienyl)-1H-pyrrole-2,5-dione | 354 |
| 15 | 3-(2,5-dichloro-3-thienyl)-4-[1-(3-hydroxypropyl)-1H-pyrrolo[2,3-b]pyridin-3-yl]-1H-pyrrole-2,5-dione | 422 |
| 30 | 3-(2-hydroxyphenyl)-4-[1-(3-methoxypropyl)-1H-pyrrolo[2,3-b]pyridin-3-yl]-1H-pyrrole-2,5-dione | 378 |
| 31 | 3-(3,4-dimethoxyphenyl)-4-[1-(3-methoxypropyl)-1H-pyrrolo[2,3-b]pyridin-3-yl]-1H-pyrrole-2,5-dione | 422 |
| 32 | 3-(3,4-dihydroxyphenyl)-4-[1-(3-hydroxypropyl)-1H-pyrrolo[2,3-b]pyridin-3-yl]-1H-pyrrole-2,5-dione | 380 |

EXAMPLE 2

3-(2-chlorophenyl)-4-[1-[3-(dimethylamino)propyl]-1H-pyrrolo[2,3-b]pyridin-3-yl]-1H-pyrrole-2,5-dione (Compound 2)

To a solution of Compound 1 (45 mg, 0.118 mmol) in THF (5 mL) was added pyridine (41 mg, 0.5 mmol). The mixture was stirred at room temperature for 15 min and then methanesulfonic anhydride (65 mg, 0.37 mmol) was added and the mixture was heated to 50° C. for 2 h. TLC and mass spectra showed the formation of Compound 2a. To the crude product was added excess 1.0 M solution of dimethylamine in THF (1 mL). The mixture was heated from 50 to 65° C. overnight. The solvent was concentrated in vacuo. The crude product was extracted with ethyl acetate (100 mL). The organic phase was washed with saturated NaHCO$_3$, brine, and evaporated in vacuo to give a crude product (50 mg). The crude product was separated by flash chromatography on silica gel (CH$_2$Cl$_2$/MeOH/NH$_4$OH, from 98:2:0.2 to 95:5:0.5) to give 15 mg (31%) of Compound 2 as a yellow solid. $^1$H NMR (DMSO-d$_6$) δ 8.27 (s, 1H), 8.23 (m, 1H), 7.44–7.33 (m, 4H), 6.75–6.71 (m, 1H), 6.62–6.60 (m, 1H), 4.41–4.38 (m, 2H), 2.3–2.28 (m, 2H), 2.25 (s, 6H), 2.12–2.05 (m, 2H). ES-MS m/z 409 (MH+).

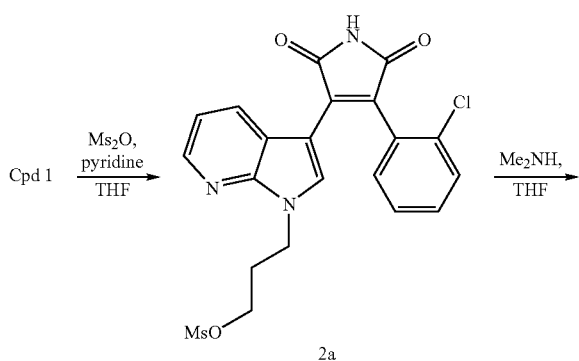

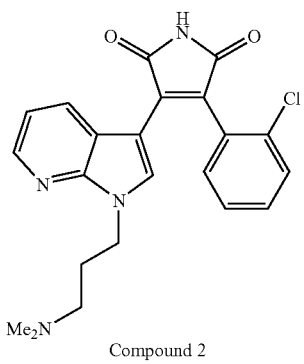

Compound 2

Using the procedures of Examples 1 and 2 and the appropriate reagents and starting materials known to those skilled in the art, other compounds of the present invention may be prepared including, but not limited to:

| Cpd | Name | ES-MS m/z (MH+) |
|---|---|---|
| 38 | 3-(2-methoxyphenyl)-4-[1-[3-(1H-tetrazol-1-yl)propyl]-1H-pyrrolo[2,3-b]pyridin-3-yl]-1H-pyrrole-2,5-dione | 430 |
| 39 | 3-(2-methoxyphenyl)-4-[1-[3-(2H-tetrazol-2-yl)propyl]-1H-pyrrolo[2,3-b]pyridin-3-yl]-1H-pyrrole-2,5-dione | 430 |

EXAMPLE 3

3-[1-(3-hydroxypropyl)-1H-pyrrolo[2,3-b]pyridin-3-yl]-4-(1-naphthalenyl)-1H-pyrrole-2,5-dione (Compound 3)

A mixture of Compound 1c (406 mg, 1.08 mmol) and Compound 3a (154 mg, 0.83 mmol) in 6 mL of anhydrous THF was stirred under nitrogen and cooled in an ice bath while treating dropwise with 4.2 mL of 1 N potassium t-butoxide in THF. The mixture was stirred for 30 minutes in an ice bath then at room temperature for another 30 min. The reddish mixture was then cooled down and then 2 mL of concentrated HCl was added dropwise. The mixture was stirred for 5 min and then ethyl acetate (250 mL) and H$_2$O (50 mL) were added. The organic layer was separated and washed with saturated NaHCO$_3$ and brine, dried over anhydrous sodium sulfate and concentrated in vacuo to give a crude product (0.45 g). The crude product was separated by flash chromatography on silica gel (CH$_2$Cl$_2$/MeOH/NH$_4$OH, from 98:2:0.2 to 95:5:0.5) to give 203.8 mg (48%) of Compound 3 as a yellow solid. $^1$H NMR (DMSO-d$_6$) δ 8.23 (s, 1H), 8.05 (d, J=6.1 Hz, 2H), 7.97 (d, J=8.1 Hz, 1H), 7.69 (d, J=8.4 Hz, 1H), 7.61–7.53 (m, 2H), 7.45 (t, J=7.4 Hz, 1H), 7.31 (t, J=7.5 Hz, 1H), 6.52 (dd, J=4.7, 8.0 Hz, 1H), 6.31 (d, J=7.1 Hz, 1H), 4.35 (t, J=6.9 Hz, 2H), 3.34 (t, J=6.1 Hz, 2H), 1.88 (m, 2H). ES-MS m/z 398 (MH+). Anal. Calcd for $C_{24}H_{19}N_3O_3$: C, 72.54; H, 4.82; N, 10.58. Found: C, 72.29; H, 4.88; N, 10.70.

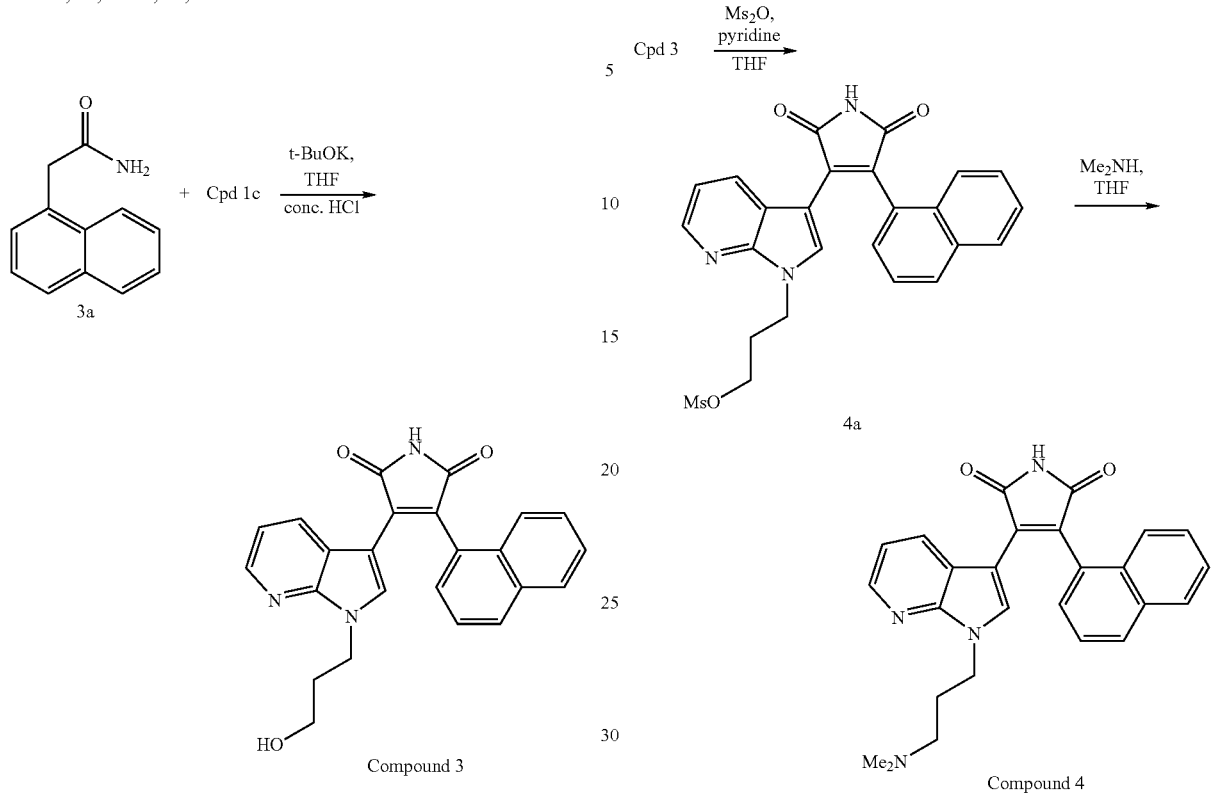

EXAMPLE 4

3-[1-[3-(dimethylamino)propyl]-1H-pyrrolo[2,3-b]pyridin-3-yl]-4-(1-naphthalenyl)-1H-pyrrole-2,5-dione (Compound 4)

To a solution of Compound 3 (25 mg, 0.063 mmol) in THF (5 mL) was added pyridine (24.9 mg, 0.315 mmol). The mixture was stirred at room temperature for 15 min and then methanesulfonic anhydride (43.9 mg, 0.25 mmol) was added and the mixture was heated to 50° C. for 2 h. TLC and mass spectra shown the formation of Compound 4a. To the crude product was added excess 1.0 M solution of dimethylamine in THF (1 mL). The mixture was heated from 50 to 65° C. overnight. The solvent was concentrated in vacuo. The crude product was extracted with ethyl acetate (100 mL). The organic phase was washed with saturated NaHCO$_3$, brine, and evaporated in vacuo to give a crude product (50 mg). The crude product was separated by flash chromatography on silica gel (CH$_2$Cl$_2$/MeOH/NH$_4$OH, from 98:2:0.2 to 95:5:0.5) to give 6 mg (22%) of Compound 4 as a yellow solid. $^1$H NMR (CDCl$_3$) δ 8.33 (s, 1H), 8.08 (dd, J=1.5, 4.7 Hz, 1H), 7.94 (m, 1H), 7.86 (d, J=8.2 Hz, 1H), 7.68 (d, J=8.3 Hz, 1H), 7.54 (m, 2H), 7.41 (t, J=6.9 Hz, 1H), 7.28 (m, 1H), 6.44 (dd, J=4.7, 8.1 Hz, 1H), 6.26 (dd, J=1.5, 8.0 Hz, 1H), 4.37 (t, J=7.1 Hz, 2H), 2.29 (t, J=7.0 Hz, 2H), 2.25 (s, 6H), 2.07 (m, 2H). ES-MS m/z 425 (MH$^+$).

EXAMPLE 5

3-(1-ethyl-1H-pyrrolo[2,3-b]pyridin-3-yl)-4-[1-(3-hydroxypropyl)-1H-pyrrolo[2,3-b]pyridin-3-yl]-1H-pyrrole-2,5-dione (Compound 7)

A mixture of Compound 1b (1.02 g) of and cesium carbonate (2.18 g, 6.5 mmol) in anhydrous DMF (20 mL) was stirred under argon at 50° C. for 5 min, then was treated with EtI (0.78 g, 5.0 mmol). The reaction mixture was stirred at 50° C. for 40 min, then diluted with EtOAc (120 mL). Th solution was washed with H$_2$O (2×30 mL), brine (30 mL), dried over anhydrous sodium sulfate, and concentrated in vacuo to give Compound 5a (0.80 g) as a viscous brown solid. ES-MS m/z 233 (MH$^+$). To a solution of Compound 5a (372 mg) in trifluoroacetic acid (15 mL) was added triethylsilane (1.86 g, 16.0 mmol) in one portion. The reaction mixture was stirred at 55° C. for 18H. The volatiles were removed under vacuo and the residue was dissolved in EtOAc (80 mL). The solution was washed with saturated NaHCO$_3$ (30 mL), brine (30 mL), dried over anhydrous sodium sulfate, and concentrated in vacuo to give Compound 5b (313 mg) as a viscous brown solid. ES-MS m/z 219 (MH$^+$).

A solution (in a pressure tube) of Compound 5b (218 mg) in 2.0 M ammonia in MeOH (8 mL) was stirred at 90° C. for 72H. The volatiles were removed under vacuo and the residue was purified by flash column chromatography (CH$_2$Cl$_2$/MeOH/NH$_4$OH, 95:4.5:0.5) to afford Compound 5c (110 mg) as a light brown solid. $^1$H NMR (CD$_3$OD) δ 8.22 (m, 1H), 8.02 (dd, J=7.9, 1.4 Hz, 1H), 7.36 (s, 1H), 7.10 (dd, J=7.9, 4.8 Hz, 1H), 4.30 (q, J=7.2 Hz, 2H), 3.65 (s, 2H), 1.43 (t, J=7.2 Hz, 3H). ES-MS m/z 204 (MH⁺). A mixture of Compound 5c (60 mg, 0.295 mmol) and Compound 1c (156 mg, 0.413 mmol) in anhydrous THF (2 mL) was stirred under argon and cooled in an ice bath while treating dropwise with 1.0 M potassium t-butoxide in THF (1.2 mL, 1.2 mmol). The reaction mixture was stirred for 1 h in an ice bath then at rt for 1 h. To the dark reaction mixture cooled with an ice bath was added dropwise concentrated HCl (3 mL). The mixture was stirred at rt for 5 min and then diluted with H₂O (30 mL), basified with 6 N aqueous NaOH to pH=10. The solution was extracted with EtOAc (2×40 mL). The combined extracts were washed with, dried over anhydrous sodium sulfate, and concentrated in vacuo. The residue was purified by flash column chromatography (CH₂Cl₂/MeOH/NH₄OH, 93:6:1) to afford Compound 7 (48 mg, 39% yield) as a red-orange solid. ¹H NMR (CDCl₃) δ 8.22 (m, 2H), 7.92 (s, 1H), 7.76 (s, 1H), 7.32 (dd, J=8.0, 1.5 Hz, 1H), 7.08 (dd, J=8.0, 1.5 Hz, 1H), 6.81 (dd, J=8.1, 4.8 Hz, 1H), 6.70 (dd, J=8.0, 4.6 Hz, 1H), 4.50–4.37 (m, 4H), 3.42 (m, 2H), 1.97 (m, 2H), 1.53 (t, J=7.3 Hz, 3H). ES-MS m/z 416 (MH⁺).

while treating dropwise with 1.7 mL of 1 N potassium t-butoxide in THF. The mixture was stirred for 30 minutes in an ice bath then at room temperature for another 30 min. The reddish mixture was then cooled down and then 2 mL of concentrated HCl was added dropwise. The mixture was stirred for 5 min. Ethyl acetate (150 mL) and H₂O (30 mL) were added. The organic layer was separated and washed with saturated NaHCO₃ and brine, dried over anhydrous sodium sulfate and concentrated in vacuo. The crude product was separated by reverse-phase HPLC to give Compound 8 (35 mg, 14%) as a TFA salt, yellow solid. ¹H NMR (DMSO-d₆) δ 8.19 (m, 2H), 7.43 (t, J=7.9 Hz, 1H), 7.30 (d, J=7.6 Hz, 1H), 7.02 (m, 2H), 6.77 (m, 1H), 6.63 (d, J=8.0 Hz, 1H), 4.38 (m, 2H), 3.40 (t, J=6.1 Hz, 2H), 3.30 (s, 3H), 1.95 (m, 2H). ES-MS m/z 378 (MH⁺).

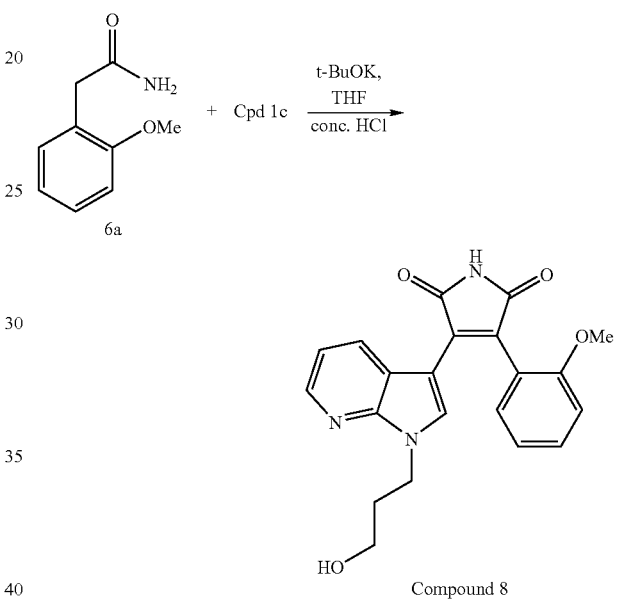

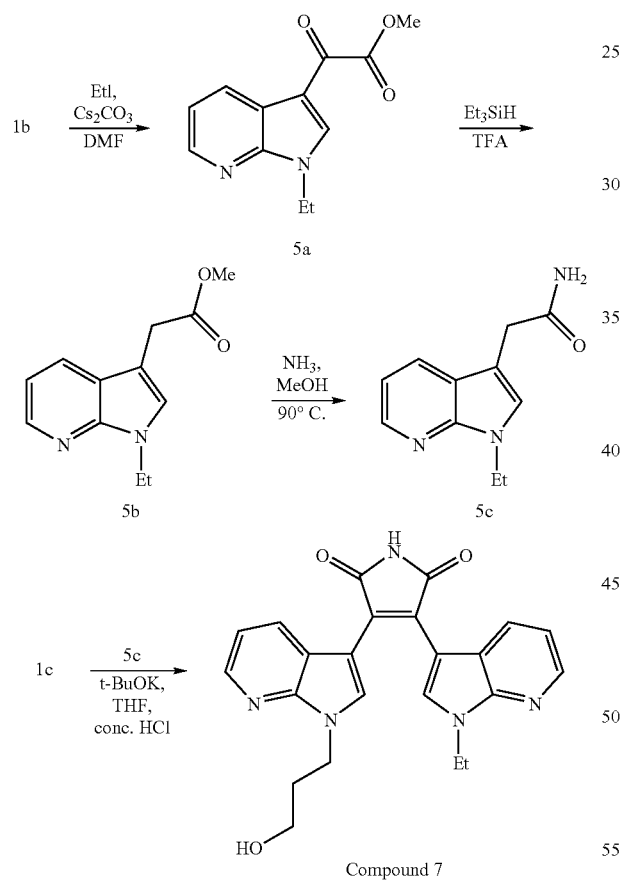

EXAMPLE 6

3-[1-(3-hydroxypropyl)-1H-pyrrolo[2,3-b]pyridin-3-yl]-4-(2-methoxyphenyl)-1H-pyrrole-2,5-dione
(Compound 8)

A mixture of Compound 1c (196.3 mg, 0.520 mmol) and Compound 6a (66.25 mg, 0.40 mmol) in 5 mL of anhydrous THF was stirred under nitrogen and cooled in an ice bath

EXAMPLE 7

3-[1-(3-hydroxypropyl)-1H-pyrrolo[2,3-b]pyridin-3-yl]-4-(3-methoxyphenyl)-1H-pyrrole-2,5-dione
(Compound 9)

A mixture of Compound 1c (203.4 mg, 0.54 mmol) and Compound 6a (68.64 mg, 0.416 mmol) in 5 mL of anhydrous THF was stirred under nitrogen and cooled in an ice bath while treating dropwise with 1.7 mL of 1 N potassium t-butoxide in THF. The mixture was stirred for 30 minutes in an ice bath then at room temperature for another 30 min. The reddish mixture was then cooled down and then 2 mL of concentrated HCl was added dropwise. The mixture was stirred for 5 min. Ethyl acetate (150 mL) and H₂O (30 mL) were added. The organic layer was separated and washed with saturated NaHCO₃ and brine, dried over anhydrous sodium sulfate and concentrated in vacuo. The crude product was separated by Gilson to give Compound 9 (50 mg, 19.3%) as a TFA salt, yellow solid. ¹H NMR (CD₃OD) δ 8.19 (m, 2H), 7.24 (t, J=7.4 Hz, 1H), 7.02 (m, 2H), 6.94 (d, J=8.0 Hz, 1H), 6.85 (m, 2H), 4.48 (t, J=6.8 Hz, 2H), 3.62 (s, 3H), 3.57 (t, J=6.1 Hz, 2H), 2.1 (m, 2H). ES-MS m/z 378 (MH⁺). Anal. Calcd for C₂₁H₁₉N₃O₄·0.85TFA·0.37H₂O: C, 56.69; H, 4.32; N, 8.74; F, 10.08; H₂O, 1.39. Found: C, 56.72; H, 4.32; N, 9.04; F, 10.31; H₂O, 1.79.

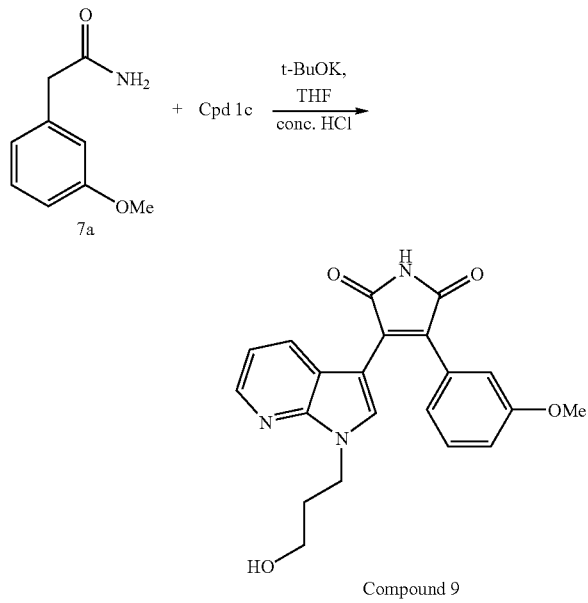

EXAMPLE 8

3-[1-(3-hydroxypropyl)-1H-imidazol-4-yl]-4-[1-(3-hydroxypropyl)-1H-pyrrolo[2,3-b]pyridin-3-yl]-1H-pyrrole-2,5-dione (Compound 18);

3-[1-(2-hydroxyethyl)-1H-imidazol-4-yl]-4-[1-(3-hydroxypropyl)-1H-pyrrolo[2,3-b]pyridin-3-yl]-1H-pyrrole-2,5-dione (Compound 19)

To prepare Compound 1c for use in this example, to a THF solution (20 mL) of 7-azaindole Compound 1a (2.30 g, 19.5 mmol) was added EtMgBr (21.5 mmol, 1 M solution in THF), and the mixture was heated to gentle reflux for 1 h, and cooled to 20° C. Diethyl oxalate (8.0 mL, 58.5 mmol) was dissolved in THF (50 mL) and cooled to −40° C., and the freshly prepared Grignard reagent was introduced slowly via a cannula. After the addition was complete, the mixture was heated to 70° C. for 1.5 h, and cooled to 20° C. It was quenched with 5 mL of saturated NaHCO₃, and diluted with water. The aqueous layer was extracted with EtOAc. The organic layers were combined, dried (MgSO₄) and concentrated. The residue was purified by flash chromatography on silica gel, eluting gradually with Hexane/EtOAc. 1.40 g was recovered and the desired product Compound 1b was isolated as a pale yellow solid (1.0 g): ¹H NMR (300 MHz, CDCl₃) δ 11.8 (s, 1H), 8.75 (dd, J=7.9, 1.5 Hz, 1H), 8.70 (s, 1H), 8.45 (dd, J=4.8, 1.5 Hz, 1H), 7.35 (dd, J=7.9, 4.8 Hz, 1H), 4.44 (q, J=7.1 Hz, 2H), 1.46 (t, J=7.1 Hz, 3H); MS (ES) m/z: 219 (M+H⁺). To a mixture of Compound 1b (318 mg, 1.46 mmol) and Cs₂CO₃ (2.38 g, 7.30 mmol) in DMF (5 mL) was added a DMF (2 mL) solution of (3-bromopropoxy)-tert-butyldimethylsilane (1.85 g, 7.30 mmol) at 80° C. After it was stirred at 80° C. for 10 min, the mixture was cooled, diluted with EtOAc, and filtered through celite. The filtrate was washed with water (4×25 mL), dried (Na₂SO₄) and concentrated. The residue was chromatographed on silica gel, eluting gradually with Hexane/EtOAc. The desired product Compound 1c was isolated as a white crystalline solid (457 mg, 80%): ¹H NMR (300 MHz, CDCl₃) δ 8.61 (dd, J=6.3, 1.5 Hz, 1H), 8.46 (s, 1H), 8.35 (dd, J=4.7, 1.5 Hz, 1H), 7.22 (m, 1H), 4.43 (t, J=6.8 Hz, 2H), 4.38 (q, J=7.1 Hz, 2H), 3.57 (t, J=5.7 Hz, 2H), 2.05 (m, 2H), 1.38 (t, J=7.1 Hz, 3H), 0.87 (s, 9H), 0.00 (s, 6H); MS (ES) m/z: 391 (M+H⁺).

To prepare Compound 8b (where n=2), 1-H-4-imidazoleacetamide Compound 8a (115 mg, 0.92 mmol, prepared as described in Zimmerman, S. C. *Tetrahedron*, 1991, 47, 2649–2660) and Cs₂CO₃ (450 mg, 1.38 mmol) were mixed with DMF (2.0 mL), and (3-bromopropoxy)-tert-butyldimethylsilane (350 mg, 1.38 mmol) in a DMF (1.0 mL) solution was added. The resulting mixture was heated to 70° C. for 5.5 h, and it was then cooled to 20° C. The mixture was diluted with EtOAc and filtered through celite. The filtrate was washed with water, dried (Na₂SO₄) and concentrated in vacuo to give Compound 8b (where n=2) (100 mg) as a sticky yellow oil: ¹H NMR (300 MHz, CDCl₃) δ 7.38 (s, 1H), 6.70 (s, 1H), 3.98 (t, J=6.9 Hz, 2H), 3.52 (t, J=5.6 Hz, 2H), 3.46 (s, 2H), 1.87 (m, 2H), 0.86 (s, 9H), 0.00 (s, 6H); MS (ES) m/z: 298 (M+H⁺).

To prepare Compound 8b (where n=3), a DMF (1.0 mL) solution of (2-bromoethoxy)-tert-butyldimethylsilane (301 mg, 1.26 mmol) was added to a mixture of 1-H-4-imidazoleacetamide Compound 8a (105 mg, 0.84 mmol), Cs₂CO₃ (411 mg, 1.26 mmol) and DMF (2.0 mL). The mixture was heated to reflux for 5 h, and it was then cooled to 20° C. The mixture was diluted with EtOAc and filtered through celite. The filtrate was washed with water, dried (Na₂SO₄) and concentrated in vacuo to give Compound 8b (where n=3) as an oil (149 mg, 63%): ¹H NMR (300 MHz, CDCl₃) δ 7.51 (s, 1H), 6.86 (s, 1H), 4.03 (t, J=4.7 Hz, 2H), 3.86 (t, J=4.8 Hz, 2H), 3.54 (s, 2H), 0.89 (s, 9H), 0.00 (s, 6H); MS (ES) m/z: 284 (M+H⁺).

To prepare Compound 8c (where n=3), KOt-Bu (0.24 mmol, 1 M solution in THF) at 0° C. was added to a THF (0.25 mL) solution of oxolate Compound 1c (48 mg, 0.12 mmol) and imidazole Compound 8b (where n=3), (33 mg, 0.11 mmol). After the mixture was stirred at 0° C. for 15 min, it was warmed to 20° C. for 1 h. After the solvent was removed under reduced pressure, the residue was chromatographed on silica gel, eluting with Hex/EtOAc to give Compound 8c (where n=3) as an orange red oil which crushed out in hexane as a fine yellow powder (32 mg): ¹H NMR (300 MHz, CDCl₃) δ 8.30 (dd, J=4.7, 1.3 Hz, 1H), 8.25 (s, 1H), 7.74 (s, 1H), 7.54 (dd, J=8.0, 1.4 Hz, 1H), 7.44 (s, 1H), 6.96 (dd, J=8.0, 4.7 Hz, 1H), 4.47 (t, J=7.0 Hz, 2H), 4.12 (t, J=6.8 Hz, 2H), 3.72 (t, J=5.8 Hz, 2H), 3.60 (t, J=5.6 Hz, 2H), 2.14 (m, 2H), 1.98 (m, 2H), 0.92 (s, 9H), 0.91 (s, 9H), 0.07 (s, 6H), 0.00 (s, 6H); MS (ES) m/z: 624 (M+H⁺).

To prepare Compound 8c (where n=2), KOt-Bu (1.20 mmol, 1 M in THF) at 0° C. was added to a THF (1.1 mL) solution of oxolate Compound 1c (234 mg, 0.60 mmol) and imidazole Compound 8b (where n=2) (153 mg, 0.54 mmol). The mixture was stirred at 0° C. for 10 min, and then warmed to 20° C. for 1.5 h. It was concentrated and the resulting residue was chromatographed on silica gel, eluting with EtOAc/Hexane to give the desired product Compound 8c (where n=2) (161 mg), which was crystallized from hexane containing a small amount of EtOAc as a red chip: ¹H NMR (400 MHz, DMSO-d₆) δ 10.93 (s, 1H), 8.29 (s, 1H), 8.24 (d, J=4.5 Hz, 1H), 7.91 (s, 1H), 7.61 (s, 1H), 7.59 (d, J=8.1 Hz, 1H), 7.00 (m, 1H), 4.39 (t, J=7.1 Hz, 2H), 4.13 (t, J=4.3 Hz, 2H), 3.83 (t, J=4.5 Hz, 2H), 3.64 (t, J=5.8 Hz, 2H), 2.03 (t, J=6.4 Hz, 2H), 0.87 (s, 9H), 0.81 (s, 9H), 0.01 (s, 6H), −0.01 (s, 6H); MS (ES) m/z: 610 (M+H⁺).

A small amount of Compound 8d (32 mg, 10%) was also isolated in both cases from the reaction mixture as an orange yellow solid: $^1$H NMR (400 MHz, CDCl$_3$) δ 8.30 (s, 1H), 8.23 (s, 1H), 7.70 (s, 1H), 7.53 (d, J=9.5 Hz, 1H), 6.98 (m, 1H), 4.46 (t, J=7.0 Hz, 2H), 4.11 (t, J=5.0 Hz, 2H), 3.89 (t, J=5.0 Hz, 2H), 3.70 (t, J=5.8 Hz, 2H), 3.49 (s, 1H), 2.13 (m, 2H), 0.91 (s, 9H), 0.06 (s, 6H); MS (ES) m/z: 496 (M+H$^+$).

To prepare Compound 18, TBAF (0.40 mmol, 1 M solution in THF) at 20° C. was added to a THF (1.0 mL) solution of Compound 8c (where n=3) (84 mg, 0.14 mmol). After the mixture was stirred for 30 min, the solvent was removed under reduced pressure. The residue was crystallized from MeOH/EtOAc to give Compound 18 as an orange solid (55 mg): $^1$H NMR (300 MHz, DMSO-d$_6$) δ 10.9 (s, 1H), 8.33 (s, 1H), 8.25 (d, J=4.4 Hz, 1H), 7.84 (s, 1H), 7.69 (s, 1H), 7.55 (d, J=7.5 Hz, 1H), 7.02 (m, 1H), 4.65 (s, 1H), 4.64 (s, 1H), 4.39 (t, J=6.7 Hz, 2H), 4.10 (t, J=6.6 Hz, 2H), 3.47 (d, J=5.8 Hz, 2H), 3.38 (d, J=5.5 Hz, 2H), 1.98 (t, J=6.2 Hz, 2H), 1.87 (t, J=6.1 Hz, 2H); MS (ES) m/z: 396 (M+H$^+$).

To prepare Compound 19, TBAF (0.31 mmol, 1 M in THF) at 20° C. was added to a THF (1.0 mL) solution of Compound 8c (where n=2) (86 mg, 0.14 mmol). The mixture was stirred at 20° C. for 2 h, and then concentrated under reduced pressure. The residue was purified by column chromatography eluting with MeOH/CH$_2$Cl$_2$ to give Compound 19 (48 mg), which was crystallized from MeOH/EtOAc as an orange red solid: $^1$H NMR (400 MHz, DMSO-d$_6$) δ 10.96 (s, 1H), 8.35 (s, 1H), 8.26 (d, J=4.3 Hz, 1H), 7.90 (s, 1H), 7.68 (s, 1H), 7.61 (d, J=8.0 Hz, 1H), 7.04 (dd, J=7.9, 4.6 Hz, 1H), 5.00 (t, J=5.1 Hz, 1H), 4.66 (d, J=4.6 Hz, 1H), 4.40 (t, J=6.9 Hz, 2H), 4.08 (t, J=5.1 Hz, 2H), 3.68 (q, J=4.6 Hz, 2H), 3.48 (d, J=4.9 Hz, 2H), 1.99 (m, 2H); MS (ES) m/z: 382 (M+H$^+$).

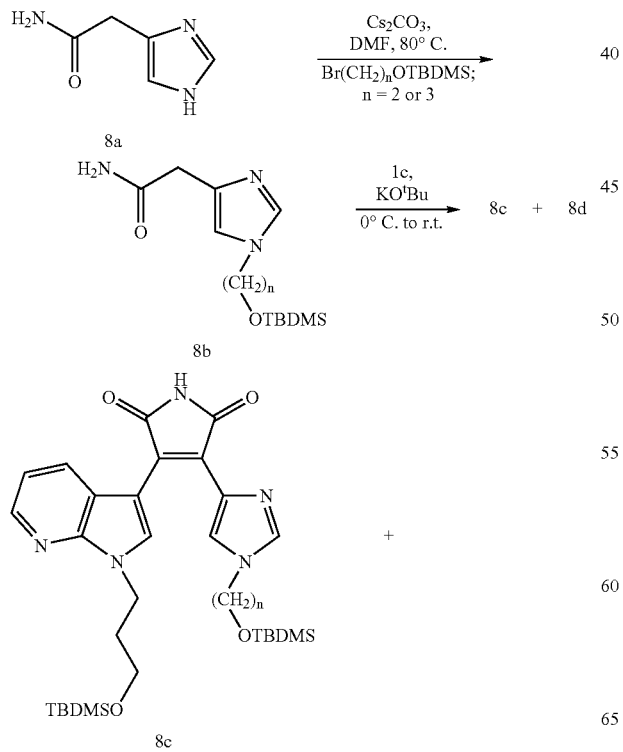

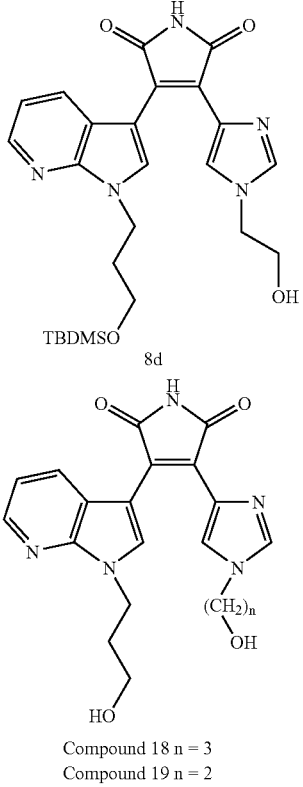

Compound 18 n = 3
Compound 19 n = 2

EXAMPLE 9

3-[1-(3-hydroxypropyl)-1H-pyrazol-3-yl]-4-[1-(3-hydroxypropyl)-1H-pyrrolo[2,3-b]pyridin-3-yl]-1H-pyrrole-2,5-dione (Compound 16)

To prepare Compound 1c for use in this example, ethyl magnesium bromide was added dropwise to a THF solution (40 mL) of 7-azaindole Compound 1a (2 g, 16.9 mmol) at 0° C. The mixture was refluxed for 30 minutes, cooled to 23° C. then transferred via cannula to a THF solution (20 mL) of ethyl chloroacetate (6.2 mL, 55.77 mmol) at −78° C. over 1 hour. The mixture was then warmed to 23° C., refluxed for 1 hour, cooled to 23° C. and quenched with NaHCO$_3$. After extraction with EtOAc (3×50 mL), the combined organic layers were dried (Na$_2$SO$_4$), filtered and concentrated. The product was purified by column chromatography (SiO$_2$) then recrystallized to give 1.9 g of Compound 1b as a white solid: $^1$H NMR (300 MHz, CDCl$_3$) δ 8.81 (dd, J=7.9, 1.5 Hz, 1H), 8.72 (s, 1H), 8.44 (dd, J=4.9, 1.5 Hz, 1H), 7.38 (dd, J=7.9, 4.9 Hz, 1H), 4.47 (q, J=7.2 Hz, 2H), 1.46 (t, J=7.2 Hz, 3H); MS (ES) m/z: 217 (M−H$^+$). To a DMF solution (300 mL) of oxo-(1H-pyrrolo[2,3-b]pyridin-3-yl)acetic acid ethyl ester Compound 1b (1 g, 4.6 mmol) at 23° C. was added cesium carbonate (7.465 g, 22.9 mmol) and (3-bromopropoxy)-tert-butyldimethylsilane (5.3 mL, 5.3 mmol) under nitrogen. The resulting solution was warmed to 70° C. and stirred for 1 hour. After cooling the mixture was diluted with EtOAc (50 mL), filtered through celite and washed with water (5×50 mL). The organic layer was dried (MgSO$_4$), filtered and concentrated in vacuo. The resulting dark oil was purified (SiO$_2$) to give Compound 1c (0.827 g) as a white solid: $^1$H NMR (300 MHz, CDCl$_3$) δ 8.65 (dd, J=7.7, 1.5 Hz, 1H), 8.50 (s, 1H), 8.40 (dd, J=4.7, 1.7 Hz, 1H), 7.3 (dd, J=7.9, 4.7 Hz, 1H), 4.50 (t, J=6.8 Hz, 2H), 4.40 (q, J=7.4 Hz, 2H), 3.61 (t, J=5.7 Hz, 2H), 2.12 (m, J=5.8 Hz, 2H), 1.43 (t, J=7.2 Hz, 3H), 0.91 (s, 9H), 0.03 (s, 6H); MS (ES) m/z: 391 (M+H$^+$).

To a DMF solution (4 mL) of 2-(1H-pyrazol-3-yl)-acetamide Compound 9a (0.2 g, 1.6 mmol; prepared as described in Jones, R. G., J. Am. Chem. Soc. 1953, 75, 4048) at 23° C. was added cesium carbonate (0.782 g, 2.4 mmol) and (3-bromopropoxy)-tert-butyldimethylsilane (0.608 g, 2.4 mmol) under nitrogen. The resulting solution was warmed to 70° C. and stirred for 5 hours. After cooling the mixture was diluted with EtOAc (20 mL), filtered through celite and washed with water (5×10 mL). The organic layer was dried (MgSO$_4$), filtered and concentrated in vacuo. The resulting yellow oil Compound 9b (0.5 g) was used without further purification: $^1$H NMR (400 MHz, CD$_3$OD) δ 7.50 (d, J=2.2 Hz, 1H), 6.20 (d, J=2.2 Hz, 1H), 4.18 (t, J=7 Hz, 2H), 3.59 (s, J=6 Hz, 2H), 3.51 (s, 2H), 2.02 (m, J=6.2 Hz, 2H), 0.89 (s, 9H), 0.05 (s, 6H); MS (ES) m/z: 298 (M–H$^+$). To a THF solution (0.4 mL) of 2-[1-[3-(tert-butyldimethylsilanyloxy)propyl]-1H-pyrazol-3-yl]acetamide Compound 9b (0.147 g, 0.493 mmol) and [-[3-(tert-butyl-dimethylsilanyloxy)propyl]-1H-pyrrolo[2,3-b]pyridin-3-yl]oxo-acetic acid ethyl ester Compound 1c (0.214 g, 0.548 mmol) at 0° C. was added potassium tert-butoxide (1.1 mL, 1 M solution in THF, 1.1 mmol) dropwise under nitrogen. After 15 minutes the mixture was allowed to warm to 23° C. After partial concentration the crude product was purified by column chromatography (SiO$_2$) to give 0.15 g of Compound 9c as a yellow oil: $^1$H NMR (400 MHz, CDCl$_3$) δ 8.28 (m, 2H), 7.45 (d, J=2.2 Hz, 1H), 7.05 (dd, J=8.0, 1.4 Hz, 1H), 6.86 (dd, J=8.0, 1.4 Hz, 1H), 6.94 (dd, J=7.9, 4.6 Hz, 1H), 6.74 (d, J=1.4 Hz, 1H), 4.45 (t, J=6.9 Hz, 2H), 4.13 (t, J=6.9 Hz, 2H), 3.69 (t, J=6.9 Hz, 2H), 3.49 (t, J=6.9 Hz, 2H), 2.14 (m, J=6.8 Hz, 2H), 1.83 (m, J=6 Hz, 2H), 0.91 (s, 9H), 0.88 (s, 9H), 0.06 (s, 6H), 0.01 (s, 6H); MS (ES) m/z: 624 (M+H$^+$).

To prepare Compound 16, tert-butylammonium fluoride (0.303 mL, 1 M solution in THF, 0.303 mmol) was added dropwise under nitrogen to a THF solution (1 mL) of 3-[1-[3-(tert-butyldimethylsilanyloxy)propyl]-1H-pyrazol-3-yl]-4-[1-[3-(tertbutyldimethylsilanyloxy)propyl]-1H-pyrrolo[2,3-b]pyridin-3-yl]pyrrole-2,5-dione Compound 9c (0.06 g, 0.096 mmol) at 23° C. After 2 hours the mixture was concentrated and the crude product was purified by column chromatography (SiO$_2$) to give 0.038 g of Compound 16 as a yellow oil: $^1$H NMR (400 MHz, CD$_3$OD) δ 8.31 (s, 1H), 8.23 (dd, J=4.8, 2.2 Hz, 1H), 7.70 (d, J=2.2 Hz, 1H), 7.15 (dd, J=8, 1.5 Hz, 1H), 6.98 (dd, J=8, 4.8 Hz, 1H), 6.70 (d, J=2.4 Hz, 1H), 4.47 (t, J=7 Hz, 2H), 4.16 (t, J=6.8 Hz, 2H), 3.6 (t, J=6.2 Hz, 2H), 3.45 (t, J=6 Hz, 2H), 2.11 (m, J=6.6 Hz, 2H), 1.86 (m, J=6.2 Hz, 2H); MS (ES) m/z: 396 (M+H$^+$).

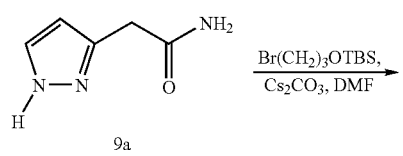

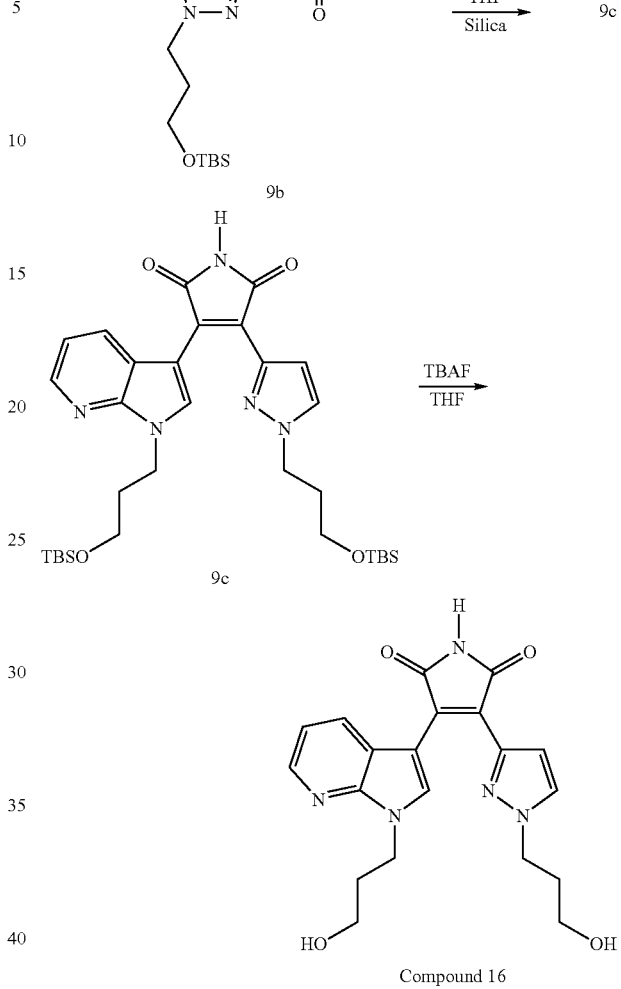

Compound 16

EXAMPLE 10

3-[1-(3-hydroxypropyl)-1H-pyrrolo[2,3-b]pyridin-3-yl]-4-(1H-imidazol-2-yl)-1H-pyrrole-2,5-dione (Compound 17)

To a water solution (20 mL) of KCN (5.46 g, 83.9 mmol) at 0° C. was added 2-chloromethyl-1-(2-trimethylsilanylethoxymethyl)-1H-imidazole Compound 10a (2.3 g, 9.32 mmol; prepared as described in Kania, S. L., PCT Int. Appl. 2001, US18263) in EtOH (40 mL) dropwise. Once addition was complete, the mixture was stirred at 23° C. for 4 hours. The solution was filtered and the precipitate washed with 95% EtOH (100 mL). The filtrate was then concentrated to small volume and water added (20 mL). After extraction of the aqueous layer with CHCl$_3$ (4×50 mL) the combined organic layers were concentrated to give a dark oil which was purified by column chromatography (SiO$_2$) to give 0.813 g (40%) of Compound 10b as a pale oil: $^1$H NMR (300 MHz, CDCl$_3$) δ 6.95 (s, 2H), 5.26 (s, 2H), 3.89 (s, 2H), 3.45 (br t, J=8.4 Hz, 2H), 0.87 (br t, J=8.4 Hz, 2H), –0.06 (s, 9H); MS (ES) m/z: 260 (M+Na$^+$).

To a DMSO solution (3 mL) of [1-(2-trimethylsilanylethoxymethyl)-1H-imidazol-2-yl]acetonitrile (0.813 g, 3.4 mmol) Compound 10b at 0° C. was added K₂CO₃ (0.2 g, 1.7 mmol) in one portion followed by H₂O₂ (0.5 mL, 5.1 mmol) dropwise.

After 5 minutes MeOH (5 mL) was added and the mixture filtered, concentrated and the DMSO removed by a nitrogen stream. The product Compound 10c (0.648 g) was then obtained by recrystallization from Et₂O as pale crystals: ¹H NMR (300 MHz, CD3OD) δ 7.18 (s, 1H), 6.90 (s, 1H), 5.37 (s, 2H), 3.77 (s, 2H), 3.53 (br t, J=7.9 Hz, 2H), 0.89 (br t, J=8.2 Hz, 2H), −0.02 (s, 9H); MS (ES) m/z: 256 (M+H+).
To a THF solution (0.4 mL) of 2-[1-(2-trimethylsilanylethoxymethyl)-1H-imidazol-2-yl]acetamide Compound 10c (0.126 g, 0.493 mmol) and oxo-[1-(2-trimethylsilanylethoxymethyl)-1H-pyrrolo[2,3-b]pyridin-3-yl]acetic acid ethyl ester Compound 1c (prepared according to the procedure of Example 9; where the alkyl group is selected from ethyl) (0.214 g, 0.548 mmol) at 0° C. was added potassium tert-butoxide (1.1 mL, 1 M solution in THF, 1.1 mmol) dropwise under nitrogen. After 15 minutes the mixture was allowed to warm to 23° C. and stirred for 30 minutes. The crude product was then partially concentrated and purified by column chromatography (SiO₂) to give 0.06 g of Compound 10d as a yellow oil: ¹H NMR (400 MHz, CDCl₃) δ 8.51 (s, 1H), 8.31 (m, 2H), 7.32 (m, 1H), 6.91 (dd, J=8, 4.8 Hz, 1H), 6.57 (d, J=7.7 Hz, 1H), 5.21 (s, 2H), 4.50 (t, J=6.8 Hz, 2H), 3.7 (t, J=5.7 Hz, 2H), 3.44 (br t, J=8.2 Hz, 2H), 2.15 (m, J=6.2 Hz, 2H), 0.97 (s, 9H), 0.79 (br t, J=8.2 Hz, 2H), 0.12 (s, 6H), −0.08 (s, 9H); MS (ES) m/z: 583 (M+H⁺).

To a CH₂Cl₂ solution (2 mL) of 3-[1-[3-(tert-butyl-dimethylsilanyloxy)propyl]-1H-pyrrolo[2,3-b]pyridin-3-yl]-4-[1-(2-trimethylsilanylethoxymethyl)-1H-imidazol-2-yl]pyrrole-2,5-dione Compound 10d (0.048 g, 0.082 mmol) at 0° C. was added TFA (1 mL). After 10 minutes toluene (5 mL) was added and the mixture was concentrated. The crude product was purified by column chromatography (SiO₂) to give 0.004 g of Compound 12a as a yellow oil (see Example 12 for characterization of Compound 12a) and a mixture of Compound 12a and Compound 17. To a CH₂Cl₂ solution (1 mL) of the mixture of Compound 12a and Compound 17 (0.03 g) at 23° C. was added TFA (1 mL). After 20 hours toluene (5 mL) was added and the mixture was concentrated. The crude product was purified by column chromatography (SiO₂) to give 0.008 g of Compound 17 as a yellow solid: ¹H NMR (400 MHz, CD₃OD) δ 8.40 (s, 1H), 8.24 (dd, J=4.8, 1.5 Hz, 1H), 7.28 (m, 2H), 7.12 (dd, J=8, 1.5 Hz, 1H), 6.98 (dd, J=7.9, 4.6 Hz, 1H), 4.48 (t, J=6.8 Hz, 2H), 3.61 (t, J=6.2 Hz, 2H), 2.10 (m, J=6.4 Hz, 2H); MS (ES) m/z: 338 (M+H⁺).

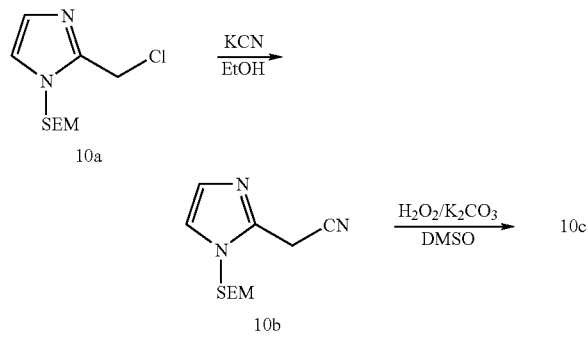

EXAMPLE 11

Intermediate Compound 11e and 11f

To a THF solution (2 mL) of (1H-[1,2,4]triazol-3-yl-acetic acid ethyl ester Compound 11a (0.1 g, 0.65 mmol; prepared as described in Jones, R. G., *J. Am. Chem. Soc.* 1954, 76, 5651) at 0° C. was added sodium hydride (0.034 g, 60% dispersion, 0.84 mmol) under nitrogen. After 30 minutes 2-(trimethylsilyl)ethoxymethyl chloride (0.125 mL, 0.7 mmol) was added. Water (4 mL) was added after 2 hours and the THF was removed in vacuo. The residue was extracted with CHCl₃ (3×10 mL) and the organic layer was dried (MgSO₄) and concentrated. The product Compound 11b (0.07 g) was obtained as an oil without further purification: ¹H NMR (300 MHz, CD₃OD) δ 7.87 (s, 1H), 5.54 (s, 2H), 4.22 (q, J=7.2 Hz, 2H), 3.99 (s, 2H), 3.58 (br t, J=8.3 Hz, 2H), 1.29 (t, J=7.2 Hz, 3H), 0.91 (br t, J=8.5 Hz, 2H), 0.00 (s, 9H); MS (ES) m/z: 284 (M−H⁺). A solution of Compound 11b (0.07 g, 0.234 mmol) in ammonia (2 mL, 2 M in methanol) was stirred at 23° C. for 7 days. The solvent was then removed under vacuum giving 0.06 g (95%) of Compound 11c as a pale oil: ¹H NMR (300 MHz, CD₃OD) δ 7.81 (s, 1H), 7.39 (s, 1H), 6.35 (s, 1H), 5.49 (s, 2H), 3.82 (s, 2H), 3.54 (br t, J=8.3 Hz, 2H), 0.85 (br t, J=8.5 Hz, 2H), −0.07 (s, 9H); MS (ES) m/z: 279 (M+Na⁺).

To a THF solution (5 mL) of oxo-(1H-pyrrolo[2,3-b]pyridin-3-yl)acetic acid ethyl ester Compound 1b (prepared according to the procedure of Example 9; where the alkyl group is selected from ethyl) (0.5 g, 2.29 mmol) and 2-(trimethylsilyl)ethoxymethyl chloride (0.764 g, 4.58 mmol) at 0° C. was added sodium hydride (0.11 g, 60% dispersion, 4.58 mmol) under nitrogen. After 24 hours water (4 mL) was added, the mixture extracted with EtOAc (3×10 mL) and the organic layer dried (MgSO₄) and concentrated. The product was purified by column chromatography (SiO₂) to give the product Compound 11d (0.224 g, 30%) as an oil: $^1$H NMR (300 MHz, CDCl₃) δ 8.65 (dd, J=7.9, 1.7 Hz, 1H), 8.61 (s, 1H), 8.41 (dd, J=4.7, 1.5 Hz, 1H), 7.27 (dd, J=7.9, 4.7 Hz, 1H), 5.71 (s, 2H), 4.40 (q, J=7.2 Hz, 2H), 3.60 (br t, J=8.3 Hz, 2H), 1.41 (t, J=7.2 Hz, 3H), 0.91 (br t, J=8.1 Hz, 2H), −0.09 (s, 9H); MS (ES) m/z: 371 (M+Na⁺).

To a THF solution (0.4 mL) of 2-[1-(2-trimethylsilanylethoxymethyl)-1H-[1,2,4]triazol-3-yl]acetamide Compound 11c (0.03 g, 0.116 mmol) and oxo-[1-(2-trimethylsilanylethoxymethyl)-1H-pyrrolo[2,3-b]pyridin-3-yl]acetic acid ethyl ester Compound 1d (0.04 g, 0.116 mmol) at 0° C. was added potassium tert-butoxide (0.232 mL, 1 M solution in THF, 0.232 mmol) dropwise under nitrogen. After 15 minutes the mixture was allowed to warm to 23° C. and stirred for 1 hour. Conc. HCl (1 mL) was added and the solution stirred for 5 minutes then poured into EtOAc (10 mL). The aqueous layer was extracted with EtOAc (3×10 mL) then the organic layer was dried (MgSO₄) and concentrated. The product was purified by column chromatography (SiO₂) to give 0.017 g of Compound 11e as a yellow solid: $^1$H NMR (300 MHz, CDCl₃) δ 9.13 (s, 1H), 8.40 (dd, J=4.7, 1.5 Hz, 1H), 8.10 (s, 1H), 8.00 (dd, J=8.1, 1.3 Hz, 1H), 7.18 (dd, J=8.1, 4.7 Hz, 1H), 5.80 (s, 2H), 3.68 (br t, J=8.3 Hz, 2H), 0.96 (br t, J=8.3 Hz, 2H), −0.05 (s, 9H); MS (ES) m/z: 433 (M+Na⁺).

To a THF solution (0.4 mL) of 2-[1-(2-trimethylsilanylethoxymethyl)-1H-[1,2,4]triazol-3-yl]acetamide Compound 11c (0.03 g, 0.116 mmol) and oxo-[1-(2-trimethylsilanylethoxymethyl)-1H-pyrrolo[2,3-b]pyridin-3-yl]acetic acid ethyl ester Compound 11d (0.04 g, 0.116 mmol) at 0° C. was added potassium tert-butoxide (0.232 mL, 1 M solution in THF, 0.232 mmol) dropwise under nitrogen. After 15 minutes the mixture was allowed to warm to 23° C. and stirred for 1 hour. Silica gel (1 g) was added and the solution stirred for 5 minutes then EtOAc (10 mL) added and the mixture filtered and concentrated. The product was purified by column chromatography (SiO₂) then recrystallized to give 0.014 g (50%) of Compound 11 f as a yellow solid: $^1$H NMR (300 MHz, CDCl₃) δ 8.54 (s, 1H), 8.33 (dd, J=4.6, 1.3 Hz, 1H), 8.06 (s, 1H), 7.47 (s, 1H), 6.94 (dd, J=8.1, 4.8 Hz, 1H), 6.66 (dd, J=8.1, 1.5 Hz, 1H), 5.72 (s, 2H), 5.49 (s, 2H), 3.62 (br t, J=8.2 Hz, 2H), 3.58 (br t, J=8.5 Hz, 2H), 0.95 (br t, J=8.4 Hz, 2H), 0.75 (br t, J=8.6 Hz, 2H), −0.04 (s, 9H), −0.09 (s, 9H); MS (ES) m/z: 539 (M−H⁺).

Other compounds of the invention may be obtained by substituting Intermediate Compound 11e and Intermediate Compound 11f for Compounds 10d, 9c or 8c in the reactions described for use thereof to provide compounds alkylated on the R₁ and R₂ positions.

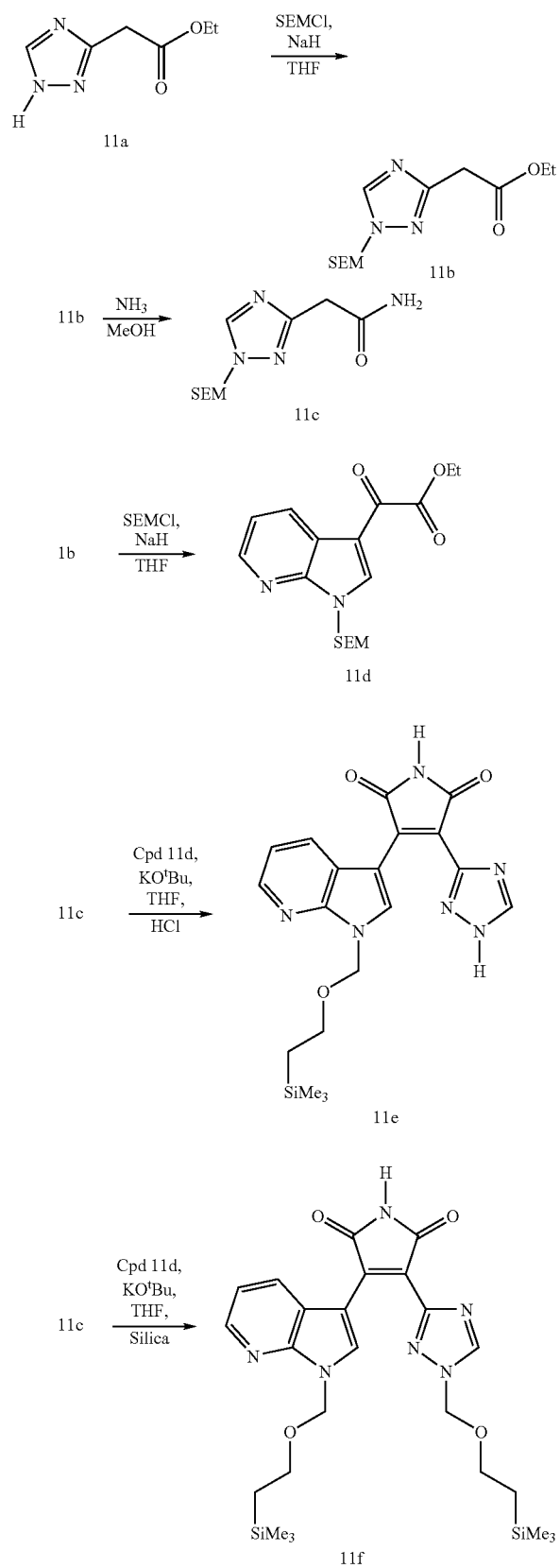

EXAMPLE 12

Intermediate Compound 12a

Prepared by the method of Example 10, the crude product Compound 12a was purified by column chromatography (SiO$_2$) as a yellow oil (0.004 g): $^1$H NMR (400 MHz, CD$_3$OD) δ 8.50 (s, 1H), 8.24 (dd, J=4.8, 1.5 Hz, 1H), 7.45 (d, J=1.3 Hz, 1H), 7.21 (d, J=1.3 Hz, 1H), 6.91 (dd, J=8, 4.8 Hz, 1H), 6.58 (dd, J=8, 1.5 Hz, 1H), 5.22 (s, 2H), 4.48 (t, J=7 Hz, 2H), 3.57 (t, J=6 Hz, 2H), 3.42 (br t, J=8.2 Hz, 2H), 2.09 (m, J=6.4 Hz, 2H), 0.67 (br t, J=8.4 Hz, 2H), −0.15 (s, 9H); MS (ES) m/z: 468 (M+H$^+$).

Other compounds of the invention may be obtained by substituting Intermediate Compound 12a for Compounds 10d, 9c or 8c in the reactions described for use thereof to provide compounds alkylated on the R$_2$ position.

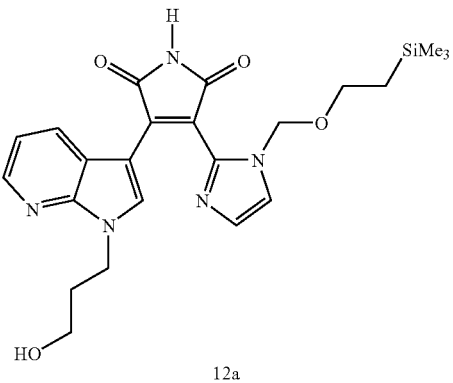

12a

EXAMPLE 13

3-[1-[3-(dimethylamino)propyl]-1H-indazol-3-yl]-4-[1-(2-naphthalenyl)-1H-pyrrolo[2,3-b]pyridin-3-yl]-1H-pyrrole-2,5-dione (Compound 20)

7-Azaindole Compound 1a (2.36 g, 20 mmol) and 2-bromonaphthalene (4.14 g, 20 mmol) were dissolved in DMF (10 mL) and potassium carbonate (2.76 g, 20 mmol) and CuO (300 mg, 3.6 mmol) were added in and the reaction was refluxed under argon for 24 h. The reaction was cooled to room temperature and partitioned between DCM (100 mL) and water (100 mL). The organic layer was separated and the aqueous was extracted again with DCM (100 mL). The combined DCM solution was washed 3 times with water (50 mL), twice with brine (50 mL), dried (Na$_2$SO$_4$) and evaporated in vacuo to a brown oil (3.92 g). This was purified via flash column chromatography (ethyl acetate/hexane 1:6) to give a white solid Compound 13a (2.15 g, 44%). The indole Compound 13a (0.98 g, 4.0 mmol) in DCM (15 mL) was treated with oxalyl chloride (0.52 g, 4.1 mmol) with ice bath cooling and then stirred at ambient temperature for 16 h. The reaction was cooled to 0° C. and a mixture of diisopropylethylamine-DIPEA (0.52 g, 4.0 mmol) was added and the reaction was stirred at ambient temperature for 16 h. Again, the reaction was cooled to 0° C. and oxalyl chloride (125 mg, 1.0 mmol) was added and the reaction stirred at ambient temperature for 24 h. The solution was cooled to −65° C. and sodium methoxide (0.58 g, 10.0 mmol) in methanol (20 mL) was added in slowly, and the reaction was allowed to come to room temperature and stirred for 1.5 h. The reaction was evaporated in vacuo to a solid, which was triturated with chloroform (50 mL) for 30 min, filtered and the filtrate dried (K$_2$CO$_3$) and evaporated in vacuo to a brown solid Compound 13b (1.0 g), which was impure with starting material (20%) and DIPEA. $^1$H NMR (CDCl$_3$) δ 4.00 (s, 3H), 7.38 (m, 1H), 7.58 (m, 2H), 7.95 (m, 4H), 8.21 (s, 1H), 8.50 (m, 1H), 8.79 (m, 1H), 8.89 (s, 1H); ES-MS m/z 331 (MH$^+$).

Indazole acid Compound 13c (5.28 g, 30 mmol) was dissolved in DCM (120 mL) and DMF (30 mL) under argon and HOBT (4.45 g, 33 mmol) and DCC (6.51 g, 32 mmol) were added and the reaction was stirred at ambient temperature for 1 h. Ammonium hydroxide (28%, 2.7 g, 44 mmol) was added over 5 min and the reaction was then stirred at ambient temperature for 16 h. White solid was filtered and the filtrate diluted with DCM (150 mL) and filtered again. The DCM solution was extracted four times with 5% NaHCO$_3$ (150 mL); the combined aqueous solution was treated with sodium chloride (190 g) and extracted with ethyl acetate (300 mL) six times. The organic extract was dried (Na$_2$SO$_4$) and evaporated in vacuo to a solid (6.25 g), which was triturated with diethyl ether (100 mL) and filtered to afford a white solid Compound 13d (3.52 g, 67%). Amide Compound 13d (2.62 g, 15 mmol) in DMF (35 mL) was combined with 3-dimethylaminopropylchloride hydrochloride (2.61 g, 16.5 mmol) and ice bath cooled as 95% sodium hydride (0.80 g, 31.5 mmol) was added portionwise over the next 20 min. The reaction was stirred at ambient temperature for 10 min and then placed in an oilbath at 55° C. for 3 h. After cooling to room temperature, the reaction was diluted with DCM (200 mL) and washed with 0.3N NaOH (200 mL), twice with water (100 mL), brine (50 mL), dried (K$_2$CO$_3$) and evaporated in vacuo to a first crop of light yellow solid (2.50 g). The aqueous solutions were re-extracted with DCM (100 mL) three times and the DCM was washed with brine, dried (K$_2$CO$_3$) and evaporated in vacuo to give a second crop (1.63 g). These two crops were combined and purified by flash column chromatography (DCM:MeOH:NH$_4$OH in a ratio of 90:9:1) to afford a white solid Compound 13e (2.63 g, 64%).

The ester Compound 13b (231 mg, 0.70 mmol) and amide Compound 13e (130 mg, 0.50 mmol) were combined in dry THF (4 mL) under argon and cooled with an ice bath as 1M potassium t-butoxide in THF (2.0 mL, 2.0 mmol) was added with stirring over the next 2 min. After stirring for 2 h at 0° C., the reaction was quenched by slow addition of 12 M HCl (0.80 mL, 9.6 mmol), stirred 15 min and then partitioned between chloroform and saturated NaHCO$_3$. The organic solution was washed once with saturated NaHCO$_3$, once with brine, dried (Na$_2$SO$_4$) and evaporated in vacuo to a flaky solid, which was purified by flash column chromatography (EA:MeOH:NH$_4$OH in a ratio of 80:8:2) to afford a flaky yellow solid Compound 20 (70 mg, 26%). This was dissolved in 20% MeOH in chloroform (10 mL) and 1N HCl in diethyl ether (0.30 mL, 0.30 mm) was added in; the solution was evaporated in vacuo to the HCl salt, which was dissolved in water (10 mL), frozen and lyophilized to an orange fluffy solid. $^1$H NMR (CD$_3$OD) δ 2.35 (m, 2H), 2.86 (s, 6H), 3.29 (m, 2H), 4.65 (t, 2H, J=6.0 Hz), 6.93 (dd, 1H, J=4.8, 8.0 Hz), 7.04 (dd, 1H, J=7.5, 7.7 Hz), 7.16 (m, 1H), 7.5 (m, 5H), 8.15 (m, 6H), 8.50 (s, 1H). ES-MS m/z 541 (MH$^+$).

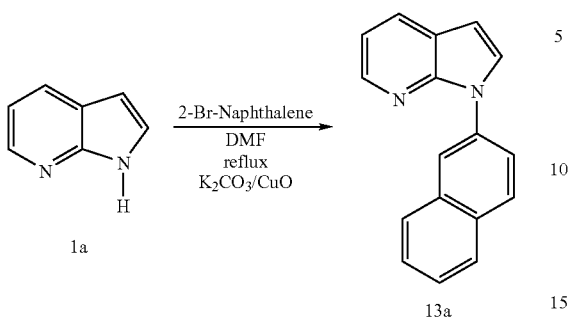

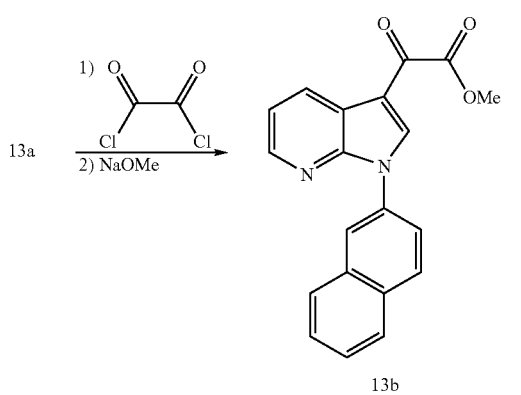

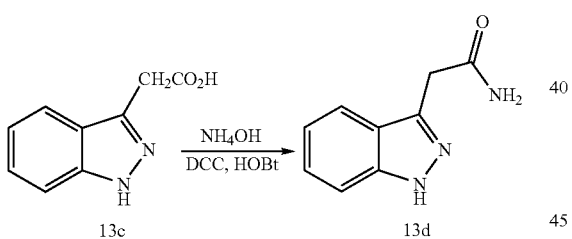

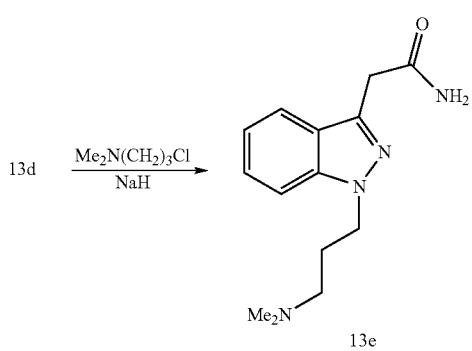

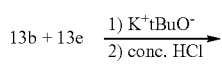

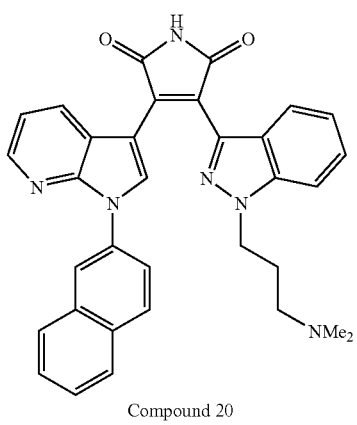

Compound 20

Using the procedure of Example 13 and the appropriate reagents and starting materials known to those skilled in the art, other compounds of the present invention may be prepared including, but not limited to:

| Cpd | Name | ES-MS m/z (MH+) |
|---|---|---|
| 21 | 3-[1-(3-hydroxypropyl)-1H-indazol-3-yl]-4-[1-(2-naphthalenyl)-1H-pyrrolo[2,3-b]pyridin-3-yl]-1H-pyrrole-2,5-dione | 513 |
| 33 | 3-(2-methoxyphenyl)-4-[1-(2-naphthalenyl)-1H-pyrrolo[2,3-b]pyridin-3-yl]-1H-pyrrole-2,5-dione | 446 |

EXAMPLE 14

3-[(E)-2-(4-fluorophenyl)ethenyl]-4-[1-(3-hydroxypropyl)-1H-pyrrolo[2,3-b]pyridin-3-yl]-1H-pyrrole-2,5-dione (Compound 22)

Cesium carbonate (53.48 g, 164.15 mmol) and (3-Bromopropoxy)-tert-butyldimethylsilane (38.14 mL, 164.15 mmol) were added to a DMF solution (100 mL) of a (1H-Pyrrolo[2,3-b]pyridin-3-yl)-acetonitrile Compound 14a (8.6 g, 54.7 mmol; prepared as described in Robison, *J. Amer. Chem. Soc.*, 78, 1956, 1247–1249) and the resulting mixture was stirred at 90° C. After 1 hour the reaction mixture was allowed to cool to 23° C. then filtered through celite, diluted with EtOAc (100 mL) and washed with water (5×100 mL). The organic layer was then dried (MgSO$_4$) and concentrated. The product was purified by column chromatography (SiO$_2$) to give Compound 14b (16.465 g, 92%) as a pale oil. $^1$H NMR (300 MHz, CDCl$_3$) δ 8.36 (dd, J=4.5, 1.3 Hz, 1H), 7.91 (dd, J=7.9, 1.5 Hz, 1H), 7.28 (s, 1H), 7.11 (dd, J=7.9, 4.7 Hz, 1H), 4.38 (t, J=6.8 Hz, 2H), 3.82 (s, 2H), 3.60 (t, J=5.8 Hz, 2H), 2.06 (m, 2H), 0.93 (s, 9H), 0.05 (s, 6H); MS (ES) m/z: 330 (M+H+). K$_2$CO$_3$ (0.34 g, 2.46 mmol) was added to a solution of Compound 14b (1.6 g, 4.9 mmol) in DMSO (2.5 mL) at 0° C., followed by H$_2$O$_2$ (0.84 mL, 7.38 mmol, 30% solution in H₂O) added dropwise. The resulting solution was stirred for 5 mins and EtOAc (50 mL) was added. The organic layer was washed with water (5×50 mL), dried (MgSO₄) and concentrated. The product was purified by column chromatography (SiO₂) to give Compound 14c (1.43 g, 85%) as a pale oil. ¹H NMR (300 MHz, CD₃OD) δ 8.21 (d, J=4.1 Hz, 1H), 8.02 (d, J=7.2 Hz, 1H), 7.32 (s, 1H), 7.11 (dd, J=7.9, 4.9 Hz, 1H), 4.35 (t, J=6.8 Hz, 2H), 3.61 (m, 4H), 2.03 (m, 2H), 0.9 (s, 9H), 0.02 (s, 6H); MS (ES) m/z: 348 (M+H⁺).

Potassium tert-butoxide (0.99 mL, 1 M solution in THF, 0.99 mmol) was added dropwise under nitrogen to a THF solution (1 mL) of Compound 14c (0.173 g, 0.49 mmol) at 0° C. The mixture was stirred for 1 hour, concentrated and then purified by column chromatography (SiO₂) to give Compound 14d (0.14 g, 70%) as a red oil. ¹H NMR (400 MHz, CD₃OD) δ 8.78 (d, J=7.9 Hz, 1H), 8.13 (d, J=3.7 Hz, 1H), 7.83 (s, 1H), 6.99 (dd, J=7.9, 4.8 Hz, 1H), 4.32 (t, J=6.8 Hz, 2H), 3.58 (t, J=6.0 Hz, 2H), 2.00 (m, 2H), 0.87 (s, 9H), −0.01 (s, 6H); MS (ES) m/z: 402 (M+H⁺). Sodium hydride (0.105 g, 60% dispersion, 4.38 mmol) under nitrogen was added to a solution of Compound 14d (0.8 g, 1.99 mmol) at 0° C. in DMF (20 mL). After 30 minutes, the reaction was warmed to 23° C. and stirred for 1.5 hours then recooled to 0° C. Iodomethane (1.35 mL, 2.19 mmol) was added and the mixture stirred for 3 hours at 23° C. After being poured into EtOAc (50 mL) the reaction mixture was washed with 1N HCl (25 mL). The aqueous layer was then back-extracted with EtOAc (25 mL) and the combined organic layers washed with brine (50 mL), dried (MgSO₄) and concentrated. The product was purified by column chromatography (SiO₂) to give the product Compound 14e (0.77 g, 92%) as a red oil. ¹H NMR (300 MHz, CDCl₃) δ 8.59 (d, J=7.4 Hz, 1H), 8.29 (d, J=3.8 Hz, 1H), 8.02 (s, 1H), 7.04 (dd, J=7.4, 4.5 Hz, 1H), 4.40 (t, J=6.6 Hz, 2H), 3.61 (t, J=6.0 Hz, 2H), 3.04 (s, 3H), 2.07 (m, 2H), 0.89 (s, 9H), 0.03 (s, 6H); MS (ES) m/z: 416 (M+H⁺).

Triethylamine (0.64 mL, 4.62 mmol) was added to a solution of Compound 14e (0.77 g, 1.85 mmol) in CH₂Cl₂ (10 mL) at −78° C. under nitrogen followed by (CF₃SO₂)₂O (triflic anhydride) (0.467 mL, 2.78 mmol) added dropwise. After 1 hour, the CH₂Cl₂ was removed and EtOAc added. The mixture was then washed with water (4×20 mL), 0.1 N NaOH (20 mL) and brine (20 mL), then dried (MgSO₄) and concentrated. The crude product was purified by column chromatography (SiO₂) to give an intermediate (0.5 g, 54%) as a red oil. ¹H NMR (300 MHz, CDCl₃) δ 8.42 (dd, J=4.5, 1.3 Hz, 1H), 8.30 (s, 1H), 8.22 (dd, J=8.1, 1.5 Hz, 1H), 7.23 (dd, J=8.1, 4.7 Hz, 1H), 4.50 (t, J=7.0 Hz, 2H), 3.63 (t, J=5.7 Hz, 2H), 3.11 (s, 3H), 2.11 (m, 2H), 0.89 (s, 9H), 0.02 (s, 6H); MS (ES) m/z: 548 (M+H⁺). Trans-2-(4-Fluorophenyl) vinylboronic acid Compound 14f (0.015 g, 0.09 mmol), Pd(OAc)₂ (0.002 g, 0.009 mmol) and KF (0.017 g, 0.3 mmol) were added to a solution of the red oil intermediate (0.05 g, 0.09 mmol) in THF (1 mL) at 23° C. A nitrogen atmosphere was then introduced and tricyclohexyl phosphine (3.8 mg in 50 μL THF, 0.014 mmol) was added dropwise. After 30 minutes, ether (5 mL) was added and the mixture was filtered through celite and concentrated to give Compound 14g (0.046 g, 96%) as a yellow oil. ¹H NMR (300 MHz, CDCl₃) δ 8.38 (dd, J=4.7, 1.5 Hz, 1H), 8.02 (dd, J=8.1, 1.7 Hz, 1H), 7.92 (d, J=16.4 Hz, 1H), 7.86 (s, 1H), 8.02 (m, 2H), 7.14 (m, 1H), 7.03 (m, 3H), 4.49 (t, J=7 Hz, 2H), 3.69 (t, J=5.8 Hz, 2H), 3.11 (s, 3H), 2.15 (m, 2H), 0.87 (s, 9H), 0.04 (s, 6H); MS (ES) m/z: 548 (M+H⁺).

Potassium hydroxide (10 N; 0.25 mL, 2.5 mmol) was added to a solution of Compound 14g (0.045 g, 0.09 mmol) in EtOH (2 mL) at 23° C. The reaction was stirred for 20 minutes, water (5 mL) was added and the mixture was acidified with 2 drops of conc. HCl. After extraction with CH₂Cl₂ (3×10 mL), the organic layers were dried (MgSO₄), filtered and concentrated in vacuo. The resulting yellow oil Compound 14h (0.038 g, 77%) was used without further purification. ¹H NMR (300 MHz, CDCl₃) δ 8.43 (dd, J=4.7, 1.3 Hz, 1H), 8.07 (dd, J=8.1, 1.5 Hz, 1H), 8.00 (s, 1H), 7.94 (d, J=16.4 Hz, 1H), 7.48 (dd, J=8.7, 5.5 Hz, 1H), 7.20 (dd, J=8.1, 4.7 Hz, 2H), 7.09 (m, 3H), 4.53 (t, J=6.8 Hz, 2H), 3.66 (t, J=5.8 Hz, 2H), 2.13 (m, 2H), 0.88 (s, 9H), 0.04 (s, 6H); MS (ES) m/z: 507 (M+H⁺). Hexamethyl disilazine (0.146 mL, 0.65 mmol) in MeOH (0.5 mL) was added to a solution of Compound 14h (0.033 g, 0.065 mmol) in DMF (1 mL) at 23° C. The reaction was warmed to 80° C. and stirred for 6 hours then cooled to 23° C. The mixture was purified (SiO₂) to give Compound 14i (0.020 g, 63%) as a yellow oil. ¹H NMR (300 MHz, CDCl₃) δ 8.41 (dd, J=4.7, 1.3 Hz, 1H), 8.03 (dd, J=7.9, 1.3 Hz, 1H), 7.94 (m, 2H), 7.48 (m, 2H), 7.20 (m, 2H), 7.01 (m, 2H), 4.52 (t, J=6.8 Hz, 2H), 3.69 (t, J=5.8 Hz, 2H), 2.15 (m, 2H), 0.88 (s, 9H), 0.05 (s, 6H); MS (ES) m/z: 506 (M+H⁺). TBAF (0.05 mL, 1 M solution in THF, 0.05 mmol) was added dropwise to a solution of Compound 14i (0.02 g, 0.041 mmol) in THF at 0° C. under nitrogen. After 15 minutes the mixture was allowed to warm to 23° C. and stirred for 18 hours. The crude product was concentrated and purified by column chromatography (SiO₂) to give Compound 22 (0.015 g, 92%) as a yellow oil. ¹H NMR (300 MHz, CDCl₃) δ 8.39 (d, J=4.1 Hz, 1H), 8.08 (d, J=7.9 Hz, 1H), 7.93 (d, J=16.3 Hz, 1H), 7.84 (s, 1H), 7.45 (m, 2H), 7.19 (dd, J=8.1, 4.9 Hz, 1H), 7.04 (m, 3H), 4.55 (t, J=6 Hz, 2H), 3.48 (t, J=5.3 Hz, 2H), 2.06 (m, 2H); MS (ES) m/z: 392 (M+H⁺).

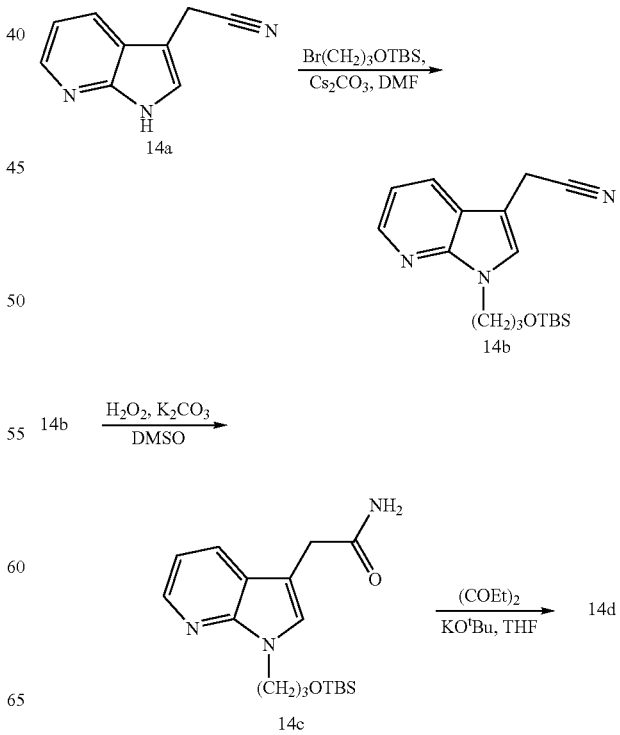

-continued

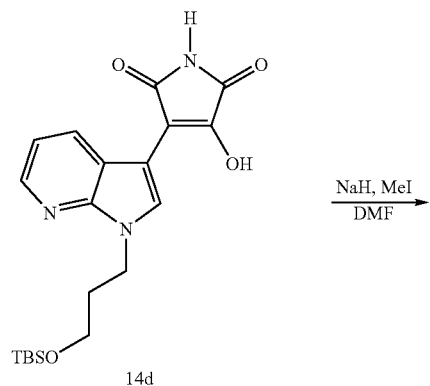
14d

NaH, MeI / DMF →

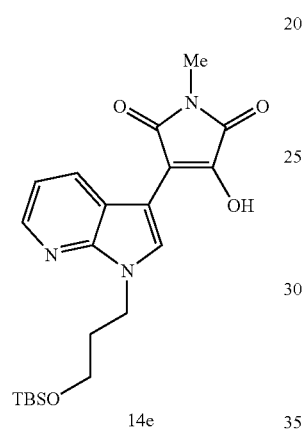
14e

14e
Tf$_2$O, Et$_3$N
CH$_2$Cl$_2$
→
(HO)$_2$B—CH=CH—C$_6$H$_4$F
14f
Pd(OAc)$_2$, PCy$_3$, KF, THF

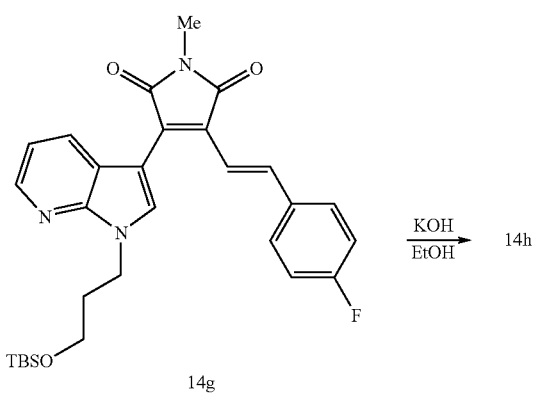
14g

KOH / EtOH → 14h

-continued

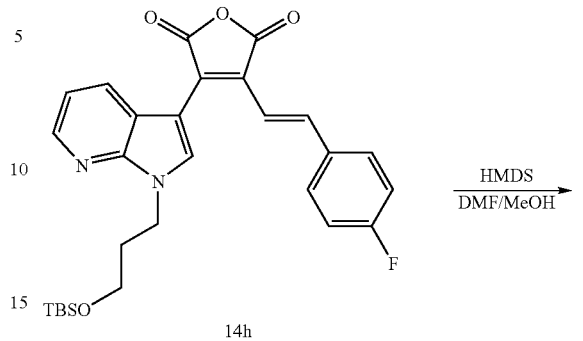
14h

HMDS / DMF/MeOH →

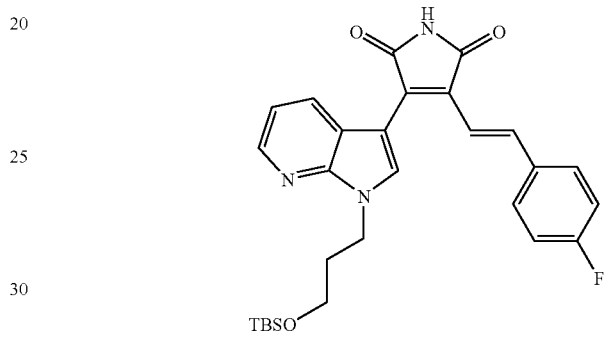
14i

14i TBAF / THF →

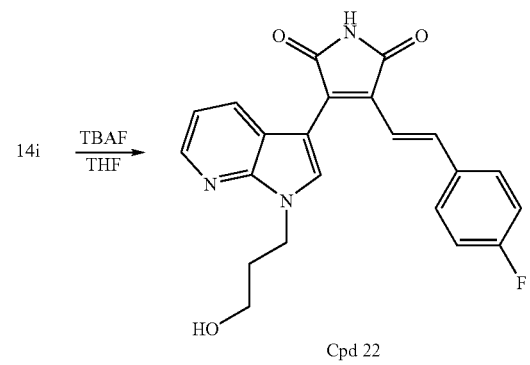
Cpd 22

EXAMPLE 15

3-(3,4-dihydro-2H-pyran-6-yl)-4-[1-(3-hydroxypropyl)-1H-pyrrolo[2,3-b]pyridin-3-yl]-1H-pyrrole-2,5-dione (Compound 23)

Potassium carbonate (3.4 g, 24.7 mmol) was added to a solution of (1H-pyrrolo[2,3-b]pyridin-3-yl)-acetonitrile Compound 14a (7.75 g, 49.4 mmol; prepared as described in Robison, *J. Amer. Chem. Soc.*, 78, 1956, 1247–1249) in DMSO (15 mL) at 0° C., followed by dropwise addition of hydrogen peroxide (8.4 mL, 74 mmol; 30% solution in H$_2$O). The resulting solution was stirred for 10 mins, CH$_2$Cl$_2$ was added and the reaction mixture was then filtered and concentrated. CH₂Cl₂ (100 mL) was added followed by Et₂O (20 mL) and the mixture cooled. The resulting precipitate was filtered off to give Compound 15a (7.212 g, 84%) as a yellow solid. ¹H NMR (300 MHz, DMSO) δ 11.44 (br s, 1H), 8.19 (d, J=4.7, 1.5 Hz, 1H), 7.95 (dd, J=7.9, 1.5 Hz, 1H), 7.39 (br s, 1H), 7.29 (s, 1H), 7.06 (dd, J=7.9, 4.9 Hz, 1H), 6.86 (br s, 1H), 3.50 (s, 2H); MS (ES) m/z: 176 (M+H⁺). Cesium carbonate (0.45 g, 1.37 mmol) and (3-bromopropoxy)-tert-butyl-diphenyl-silane (0.19 g, 0.5 mmol) were added to a solution of 2-(1H-pyrrolo[2,3-b]pyridin-3-yl)-acetamide Compound 15a (0.08 g, 0.46 mmol) in DMF (2 mL) and the resulting mixture was stirred at 70° C. After 6 h, the reaction mixture was filtered through celite, diluted with EtOAc (10 mL) and washed with water (5×10 mL). The organic layer was then dried (MgSO₄) and concentrated. The crude product was purified by column chromatography (SiO₂) to give Compound 15b (0.132 g, 60%) as a clear oil. ¹H NMR (400 MHz, CDCl₃) δ 8.31 (dd, J=4.6, 1.3 Hz, 1H), 7.85 (dd, J=4.6, 1.3 Hz, 1H), 7.64 (m, 4H), 7.38 (m, 6H), 7.05 (m, 2H), 4.42 (t, J=6.6 Hz, 2H), 3.64 (t, J=5.9 Hz, 2H), 3.62 (s, 2H), 2.09 (m, 2H), 1.08 (s, 9H); MS (ES) m/z: 472 (M+H⁺).

Potassium tert-butoxide (0.69 mL, 0.69 mmol; 1 M solution in THF) was added dropwise to a solution of 2-{1-[3-(tert-butyl-diphenyl-silanyloxy)-propyl]-1H-pyrrolo[2,3-b]pyridin-3-yl}-acetamide Compound 15b (0.13 g, 0.35 mmol) and diethyl oxalate (0.101 g, 0.69 mmol) in TMF (2 mL) at 0° C. under nitrogen. After 20 minutes the reaction mixture was concentrated and a crude product was purified by column chromatography (SiO₂) to give Compound 15c (0.117 g, 80%) as a yellow solid. ¹H NMR (300 MHz, CDCl₃) δ 9.44 (s, 1H), 8.69 (dd, J=7.9, 1.3 Hz, 1H), 8.33 (dd, J=4.7, 1.5 Hz, 1H), 8.20 (s, 1H), 7.69 (m, 4H), 7.41 (m, 6H), 7.14 (dd, J=7.9, 4.5 Hz, 1H), 4.6 (t, J=6.8 Hz, 2H), 3.73 (t, J=6.0 Hz, 2H), 2.2 (m, 2H), 1.07 (s, 9H); MS (ES) m/z: 526 (M+H⁺). Oxalyl chloride (0.015 mL, 0.18 mmol) was added in one portion to a solution of 3-{1-[3-(tert-butyl-diphenyl-silanyloxy)-propyl]-1H-pyrrolo[2,3-b]pyridin-3-yl}-4-hydroxy-pyrrole-2,5-dione Compound 15c (0.03 g, 0.06 mmol) in 1:1 CH₂Cl₂/DMF (2 mL) at 23° C. under nitrogen. After one hour the reaction mixture was concentrated and a crude product was purified by column chromatography (SiO₂) to give Compound 15d (0.023 g, 73%) as a yellow solid. ¹H NMR (400 MHz, CDCl₃) δ 10.14 (s, 1H), 8.69 (dd, J=8.1, 1.5 Hz, 1H), 8.4 (dd, J=4.6, 1.5 Hz, 1H), 8.36 (s, 1H), 7.67 (m, 4H), 7.41 (m, 6H), 7.25 (dd, J=8.1, 4.6 Hz, 1H), 4.67 (t, J=6.8 Hz, 2H), 3.74 (t, J=6.0 Hz, 2H), 2.24 (m, 2H), 1.04 (s, 9H); MS (ES) m/z: 544 (M+H⁺).

Tributyl-(5,6-dihydro-4H-pyran-2-yl)-stannane Compound 15e (0.051 mL, 0.13 mmol) was added to a solution of 3-{1-[3-(tert-butyl-diphenyl-silanyloxy)-propyl]-1H-pyrrolo[2,3-b]pyridin-3-yl}-4-chloro-pyrrole-2,5-dione Compound 15d (0.054 g, 0.1 mmol), PdCl₂(PPh₃)₂ (0.007 g, 0.01 mmol) and lithium chloride (0.013 g, 0.3 mmol) in DMF (1.5 mL) at 23° C. under nitrogen. The reaction mixture was heated to 100° C. and stirred for 18 h. After cooling to 23° C., the mixture was diluted with EtOAc (10 mL), washed with H₂O (3×10 mL), sat'd KF (1×10 mL) and brine (1×10 mL), then dried (MgSO₄) and concentrated. The product was purified by column chromatography (SiO₂) to give Compound 15f (0.027 g, 46%) as a yellow solid. ¹H NMR (300 MHz, CDCl₃) δ 8.34 (dd, J=4.7, 1.5 Hz, 1H), 7.96 (dd, J=8.7, 2.3 Hz, 1H), 7.93 (s, 1H), 7.66 (m, 4H), 7.38 (m, 6H), 7.13 (dd, J=7.9, 4.7 Hz, 1H), 5.78 (t, J=4.3 Hz, 2H), 4.52 (t, J=7.0 Hz, 2H), 3.83 (m, 2H), 3.74 (t, J=5.8 Hz, 2H), 2.29 (m, 2H), 2.16 (m, 2H), 1.86 (m, 2H), 1.08 (s, 9H); MS (ES) m/z: 592 (M+H⁺). TBAF (0.07 mL, 0.07 mmol; 1 M solution in THF) was added dropwise to a solution of 3-{1-[3-(tert-butyl-diphenyl-silanyloxy)-propyl]-1H-pyrrolo[2,3-b]pyridin-3-yl}-4-(5,6-dihydro-4H-pyran-2-yl)-pyrrole-2,5-dione Compound 15f (0.027 g, 0.046 mmol) in THF (2 mL) under nitrogen. After 18 hours the mixture was concentrated and purified by column chromatography (SiO₂) to give Compound 23 (0.011 g, 70%) as a yellow solid. ¹H NMR (400 MHz, CDCl₃) δ 8.34 (d, J=4.6 Hz, 1H), 7.99 (d, J=8.1 Hz, 1H), 7.90 (s, 1H), 7.51 (br s, 1H), 7.18 (dd, J=7.9, 4.6 Hz, 1H), 5.87 (t, J=4.2 Hz, 1H), 4.66 (m, 1H), 4.51 (t, J=6.0 Hz, 2H), 3.82 (t, J=4.9 Hz, 2H), 3.43 (m, 2H), 2.31 (m, 2H), 2.04 (m, 2H), 1.85 (m, 2H); MS (ES) m/z: 354 (M+H⁺).

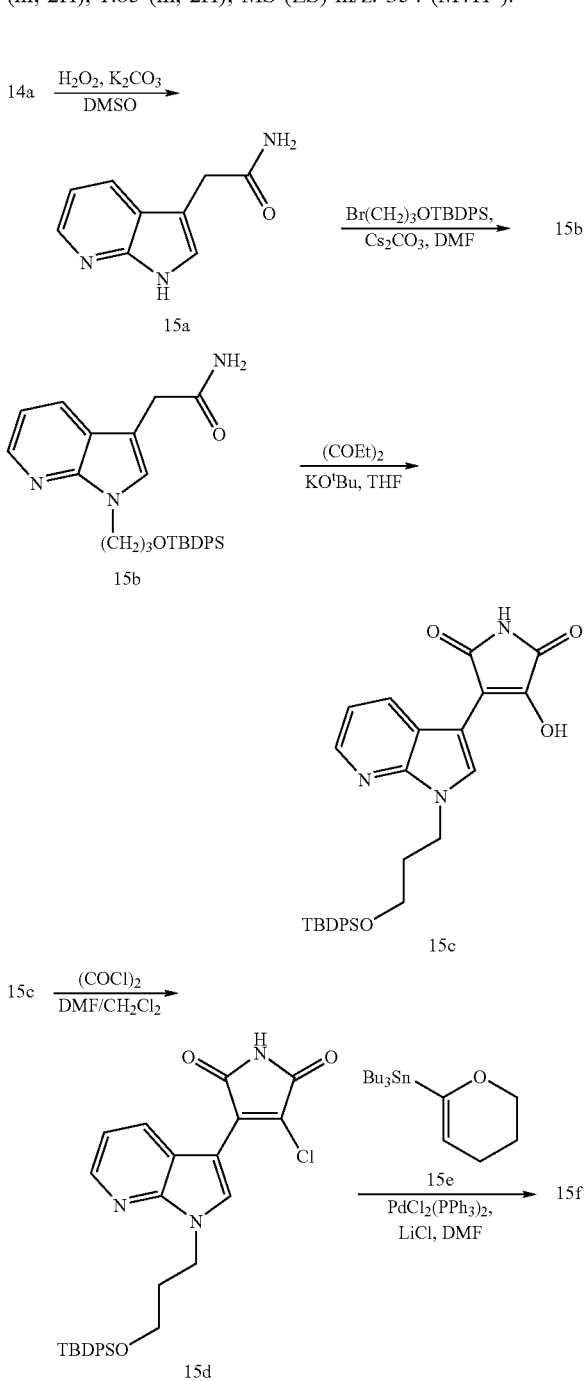

-continued

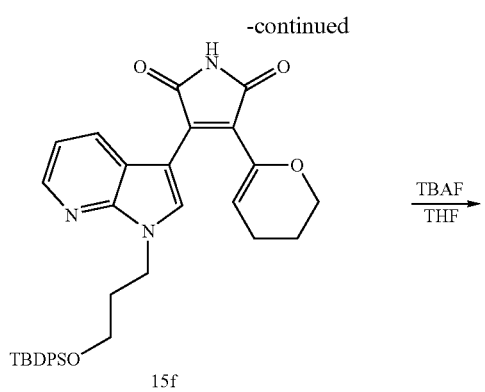

15f

Using the procedure of Example 15 and the appropriate reagents and starting materials known to those skilled in the art, other compounds of the present invention may be prepared including, but not limited to:

| Cpd | Name | ES-MS m/z (MH+) |
|---|---|---|
| 27 | 2,5-dihydro-4-[1-(3-hydroxypropyl)-1H-pyrrolo[2,3-b]pyridin-3-yl]-2,5-dioxo-1H-pyrrole-3-carbonitrile | 296 |

EXAMPLE 16

4-[1-(3-hydroxypropyl)-1H-pyrrolo[2,3-b]pyridin-3-yl]-[3,3'-bi-1H-pyrrole]-2,5-dione (Compound 24)

1-(Triisopropyl)pyrrole-3-boronic acid (0.053 mL, 0.2 mmol) was added to a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (0.054 g, 0.1 mmol), Pd$_2$(dba)$_3$ (5 mg, 0.005 mmol), Pd($^t$Bu$_3$P)$_2$ (5 mg, 0.01 mmol) and potassium fluoride (20 mg, 0.34 mmol) in THF (1 mL) at 23° C. under nitrogen. The mixture was stirred at 23° C. for 18 h, then diluted with EtOAc (10 mL), filtered through celite and concentrated. The product was purified by column chromatography (SiO$_2$) to give Compound 16a (0.044 g, 60%) as a yellow solid. $^1$H NMR (300 MHz, CDCl$_3$) δ 8.28 (d, J=4.9 Hz, 1H), 7.74 (s, 1H), 7.66 (m, 4H), 7.36 (m, 7H), 7.17 (m, 1H), 6.89 (dd, J=8.3, 4.9 Hz, 1H), 6.62 (m, 1H), 6.37 (m, 1H), 4.53 (t, J=6.8 Hz, 2H), 3.7 (t, J=6.0 Hz, 2H), 2.2 (m, 2H), 1.37 (sep, J=7.4 Hz, 3H), 1.09 (s, 9H), 1.05 (s, 9H), 1.02 (s, 9H); MS (ES) m/z: 731 (M+H+).

TBAF (0.12 mL, 1 M solution in THF, 0.12 mmol) as added dropwise to a solution of 3-benzofuran-2-yl-4-{1-[3-(tert-butyldiphenylsilanyloxy)-propyl]-1H-pyrrolo[2,3-b]pyridin-3-yl}-pyrrole-2,5-dione Compound 16a (0.044 g, 0.06 mmol) in THF (1 mL) under nitrogen. After 18 hours the mixture was concentrated and purified by column chromatography (SiO$_2$) to give Compound 24 (0.017 g, 84%) as an orange solid. $^1$H NMR (300 MHz, Acetone-d$_6$) δ 10.47 (s, 1H), 9.57 (s, 1H), 8.3 (dd, J=4.7, 1.5 Hz, 1H), 7.9 (s, 1H), 7.56 (m, 1H), 7.49 (dd, J=7.9, 1.5 Hz, 1H), 7.01 (dd, J=7.9, 4.7 Hz, 1H), 6.75 (m, 1H), 6.22 (m, 1H), 4.55 (t, J=6.6 Hz, 2H), 4.02 (t, J=5.7 Hz, 1H), 3.56 (q, J=5.8 Hz, 2H), 2.11 (m, 2H); MS (ES) m/z: 388 (M+H+).

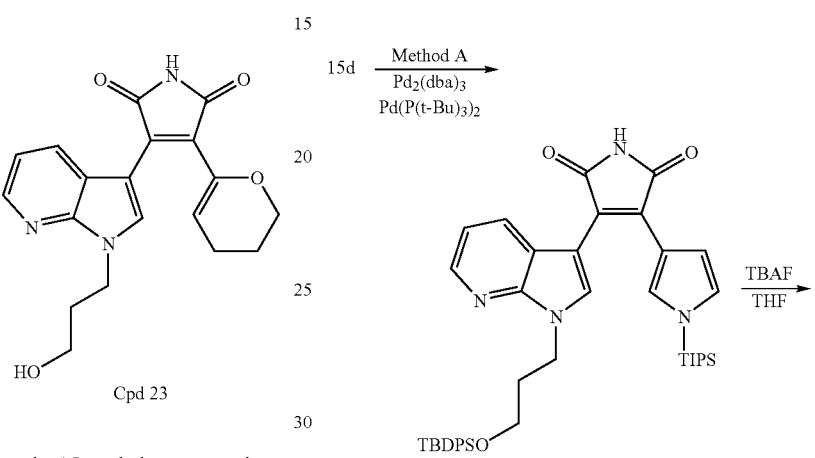

EXAMPLE 17

3-(2-benzofuranyl)-4-[1-(3-hydroxypropyl)-1H-pyrrolo[2,3-b]pyridin-3-yl]-1H-pyrrole-2,5-dione (Compound 25)

2-Benzofuran boronic acid (0.032 mL, 0.2 mmol) was added to a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (0.054 g, 0.1 mmol), Pd$_2$(dba)$_3$ (5 mg, 0.005 mmol), Pd($^t$Bu$_3$P)$_2$ (5 mg, 0.01 mmol) and potassium fluoride (20 mg, 0.34 mmol) in THF (1 mL) at 23° C. under nitrogen. The reaction mixture was stirred at 23° C. for 18 h, diluted with EtOAc (10 mL), then filtered through Celite and concentrated. The product was purified by column chromatography (SiO$_2$) to give Compound 17a (0.040 g, 64%) as a yellow solid. $^1$H NMR (300 MHz, Acetone-d$_6$) δ 8.34 (d, J=3.8 Hz, 1H), 8.26 (m, 1H), 7.77 (m, 1H), 7.68 (m, 6H), 7.40 (m, 6H), 7.29 (m, 2H), 7.16 (m, 1H), 7.13 (dd, J=8.1, 4.7 Hz, 1H), 4.69 (t, J=7.0 Hz, 2H), 3.83 (t, J=6.0 Hz, 2H), 2.3 (m, 2H), 1.06 (s, 9H); MS (ES) m/z: 626 (M+H⁺).

TBAF (0.1 mL, 0.1 mmol; 1 M solution in THF) was added dropwise to a solution of 3-benzofuran-2-yl-4-{1-[3-(tert-butyldiphenylsilanyloxy)-propyl]-1H-pyrrolo[2,3-b]pyridin-3-yl}-pyrrole-2,5-dione Compound 17a (0.04 g, 0.064 mmol) in THF (1 mL) under nitrogen. After 18 hours, the mixture was concentrated and purified by column chromatography (SiO₂) to give Compound 25 (0.022 g, 89%) as an orange solid. ¹H NMR (300 MHz, DMSO-d₆) δ 11.31 (s, 1H), 8.32 (dd, J=4.7, 1.5 Hz, 1H), 8.27 (s, 1H), 7.77 (m, 1H), 7.65 (s, 1H), 7.57 (dd, J=7.9, 1.3 Hz, 1H), 7.29 (m, 3H), 7.02 (dd, J=7.9, 4.5 Hz, 1H), 4.47 (t, J=6.9 Hz, 2H), 3.5 (t, J=6.0 Hz, 2H), 2.05 (m, 2H); MS (ES) m/z: 388 (M+H⁺).

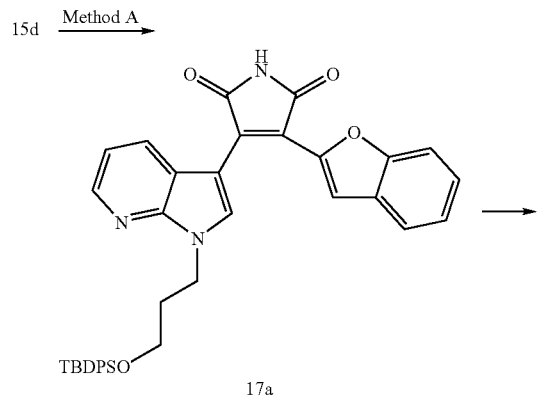

Cpd 25

EXAMPLE 18

3-[1-(3-hydroxypropyl)-1H-pyrrolo[2,3-b]pyridin-3-yl]-4-(1-methyl-1H-pyrazol-3-yl)-1H-pyrrole-2,5-dione (Compound 26)

Cesium carbonate (3.5 g, 10.8 mmol) and iodomethane (0.51 g, 3.6 mmol) were added to a solution of 2-(1H-pyrazol-3-yl)-acetamide Compound 9a (0.45 g, 3.6 mmol) in DMF (5 mL) at 23° C. under nitrogen. The mixture was warmed to 70° C. and stirred for 3 hours. After cooling, the mixture was diluted with EtOAc (20 mL), filtered through celite and washed with water (4×10 mL). The organic layer was dried (MgSO₄), filtered and concentrated to give a first crude product (0.46 g) as a white solid. By chromatography, the first crude product was shown to be a 2:1 mixture of 2-(1-methyl-1H-pyrazol-3-yl)-acetamide and 2-(2-methyl-2H-pyrazol-3-yl)-acetamide.

Potassium tert-butoxide (6.6 mL, 6.6 mmol; 1 M solution in THF) was added dropwise to a solution of the first crude product and Compound 1c (1.36 g, 3.47 mmol) in THF (20 mL) at 0° C. under nitrogen. After warming to 23° C., the reaction was stirred for 2 h then concentrated and purified by column chromatography (SiO₂) to give a second crude product (0.46 g) as a yellow solid which was then recrystallized (EtOAc/Hexanes) to give Compound 18a (0.36 g). ¹H NMR (400 MHz, CDCl₃) δ 8.32 (s, 1H), 8.30 (dd, J=4.8, 1.7 Hz, 1H), 7.42 (d, J=2.2 Hz, 1H), 7.37 (s, 1H), 7.09 (dd, J=7.9, 1.5 Hz, 1H), 6.93 (dd, J=7.9, 4.6 Hz, 1H), 6.73 (d, J=2.2 Hz, 1H), 4.47 (t, J=7.0 Hz, 2H), 3.84 (s, 3H), 3.71 (t, J=5.9 Hz, 2H), 2.15 (m, 2H), 0.92 (s, 9H), 0.07 (s, 6H); MS (ES) m/z: 466 (M+H⁺).

TBAF (1.3 mL, 1 M solution in THF, 1.3 mmol) was added to a solution of 3-[1-(3-hydroxypropyl)-1H-pyrrolo[2,3-b]pyridin-3-yl]-4-(1-methyl-1H-pyrazol-3-yl)-pyrrole-2,5-dione Compound 18a (0.35 g, 0.75 mmol) in THF (15 mL) at 23° C. dropwise under nitrogen. After 18 hours, the mixture was concentrated and a crude product was purified by column chromatography (SiO₂) (0.26 g, 98%) as a yellow solid. The crude product was then recrystallized (CH₂Cl₂: Hexane) to give Compound 26 (0.218 g). ¹H NMR (300 MHz, DMSO-d₆) δ 11.05 (s, 1H). 8.45 (s, 1H), 8.27 (dd, J=4.7, 1.5 Hz, 1H), 7.78 (d, J=2.3 Hz, 1H), 7.27 (dd, J=8, 1.5 Hz, 1H), 7.05 (dd, J=8.1, 4.7 Hz, 1H), 6.67 (d, J=2.3 Hz, 1H), 4.4 (t, J=7 Hz, 2H), 3.79 (s, 3H), 3.46 (t, J=6 Hz, 2H), 1.99 (m, 2H); MS (ES) m/z: 352 (M+H⁺).

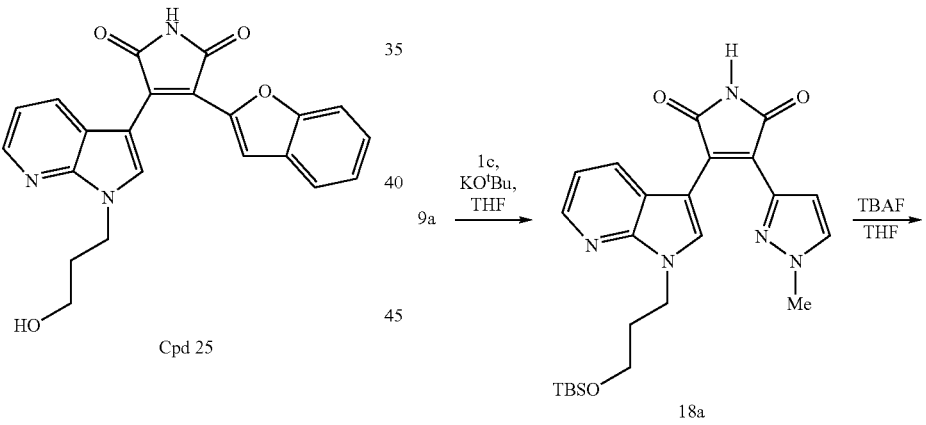

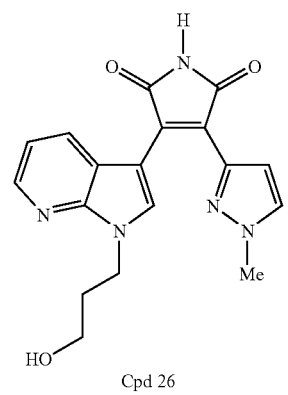

Cpd 26

EXAMPLE 19

3-dibenzo[b,d]thien-4-yl-4-[1-(3-hydroxypropyl)-1H-pyrrolo[2,3-b]pyridin-3-yl]-1H-pyrrole-2,5-dione (Compound 28)

Dibenzothiophene-4-boronic acid (0.046 g, 0.2 mmol) was added to a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (0.054 g, 0.1 mmol), Pd$_2$(dba)$_3$ (5 mg, 0.005 mmol), Pd($^t$Bu$_3$P)$_2$ (5 mg, 0.01 mmol) and potassium fluoride (20 mg, 0.34 mmol) in THF (1 mL) at 23° C. under nitrogen. The reaction mixture was stirred at 23° C. for 18 h, then diluted with EtOAc (10 mL), filtered through celite and concentrated. The product was purified by column chromatography (SiO$_2$) to give Compound 19a (0.039 g 56%) as a yellow solid: $^1$H NMR (300 MHz, CDCl$_3$) δ 8.23 (m, 2H), 8.1 (m, 2H), 7.63 (m, 7H), 7.40 (m, 8H), 6.53 (m, 2H), 4.53 (m, 2H), 3.64 (m, 2H), 2.09 (m, 2H), 1.10 (s, 9H); MS (ES) m/z: 692 (M+H$^+$).

TBAF (0.85 mL, 0.085 mmol; 1 M solution in THF) was added dropwise to a solution of 3-{1-[3-(tert-butyldiphenyl-silanyloxy)-propyl]-1H-pyrrolo[2,3-b]pyridin-3-yl}-4-dibenzothiophen-4-yl-pyrrole-2,5-dione Compound 19a (0.039 g, 0.06 mmol) in THF (1 mL) under nitrogen. After 18 hours the mixture was concentrated and purified by column chromatography (SiO$_2$) to give Compound 28 (0.017 g, 67%) as a yellow solid. $^1$H NMR (300 MHz, CD$_3$OD) δ 8.35 (dd, J=7.7, 1.5 Hz 1H), 8.25 (s, 1H), 8.21 (dd, J=6.8,3, 1.5 Hz, 1H), 8.01 (dd, J=4.7, 1.5 Hz, 1H), 7.68 (m, 3H), 7.39 (m, 2H), 6.68 (dd, J=8.1, 1.5 Hz, 1H), 6.55 (dd, J=8.1, 4.7 Hz, 1H), 4.42 (t, J=6.8 Hz, 2H), 3.49 (t, J=6.2 Hz, 2H), 2.03 (m, 2H); MS (ES) m/z: 454 (M+H$^+$).

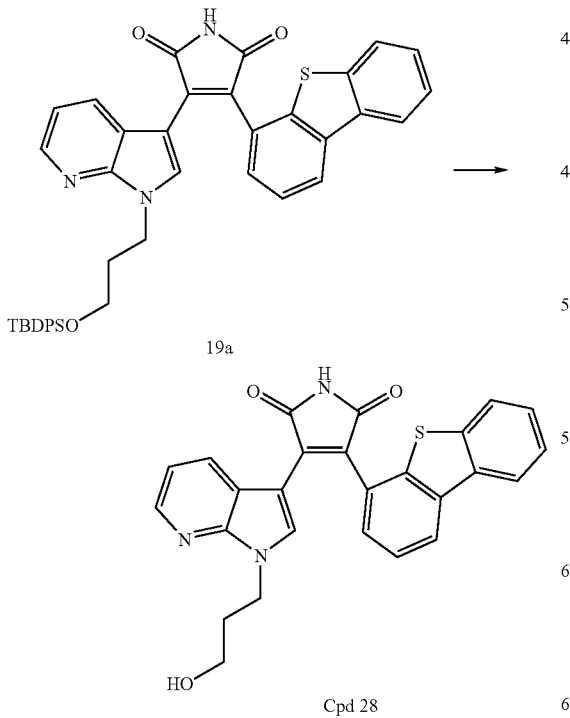

EXAMPLE 20

3-(4-dibenzofuranyl)-4-[1-(3-hydroxypropyl)-1H-pyrrolo[2,3-b]pyridin-3-yl]-1H-pyrrole-2,5-dione (Compound 29)

Dibenzofuran-4-boronic acid (0.042 g, 0.2 mmol) was added to a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (0.054 g, 0.1 mmol), Pd$_2$(dba)$_3$ (5 mg, 0.005 mmol), Pd($^t$Bu$_3$P)$_2$ (5 mg, 0.01 mmol) and potassium fluoride (20 mg, 0.34 mmol) in THF (1 mL) at 23° C. under nitrogen. The reaction mixture was stirred at 23° C. for 18 h, then diluted with EtOAc (10 mL), filtered through celite and concentrated. The crude product was purified by column chromatography (SiO$_2$) to give Compound 20a (0.032 g, 48%) as a yellow solid. $^1$H NMR (300 MHz, CDCl$_3$) δ 8.22 (s, 1H), 8.05 (dd, J=4.0, 2.3 Hz, 1H), 8.00 (dd, J=7.7, 1.1 Hz, 1H), 7.89 (m, 2H), 7.68 (m, 4H), 7.61 (dd, J=5.6, 1.1 Hz, 1H), 7.29 (m, 7H), 7.24 (m, 1H), 7.05 (m, 1H), 6.49 (m, 2H), 4.52 (t, J=6.8 Hz, 2H), 3.68 (t, J=5.7 Hz, 2H), 2.1 (m, 2H), 1.11 (s, 9H); MS (ES) m/z: 676 (M+H$^+$).

TBAF (0.7 mL, 0.06 mmol; 1 M solution in THF) was added dropwise to a solution of 3-{1-[3-(tert-butyldiphenyl-silanyloxy)-propyl]-1H-pyrrolo[2,3-b]pyridin-3-yl}-4-dibenzofuran-4-yl-pyrrole-2,5-dione Compound 20a (0.03 g, 0.04 mmol) in THF (1 mL) under nitrogen. After 18 hours, the mixture was concentrated and purified by column chromatography (SiO$_2$) to give Compound 29 (0.013 g, 71%) as a yellow solid. $^1$H NMR (300 MHz, Acetone-d$_6$) δ 8.28 (s, 1H), 8.18 (dd, J=7.7, 1.3 Hz 1H), 8.02 (ddd, J=8.3, 4.5, 1.5 Hz, 2H), 7.74 (dd, J=7.5, 1.1 Hz, 1H), 7.51 (m, 1H), 7.32 (m, 2H), 7.17 (m, 1H), 6.64 (dd, J=7.9, 1.5 Hz, 1H), 6.53 (dd, J=8.1, 4.7 Hz, 1H), 4.50 (t, J=6.6 Hz, 2H), 3.49 (m, 2H), 2.04 (m, 2H); MS (ES) m/z: 438 (M+H$^+$).

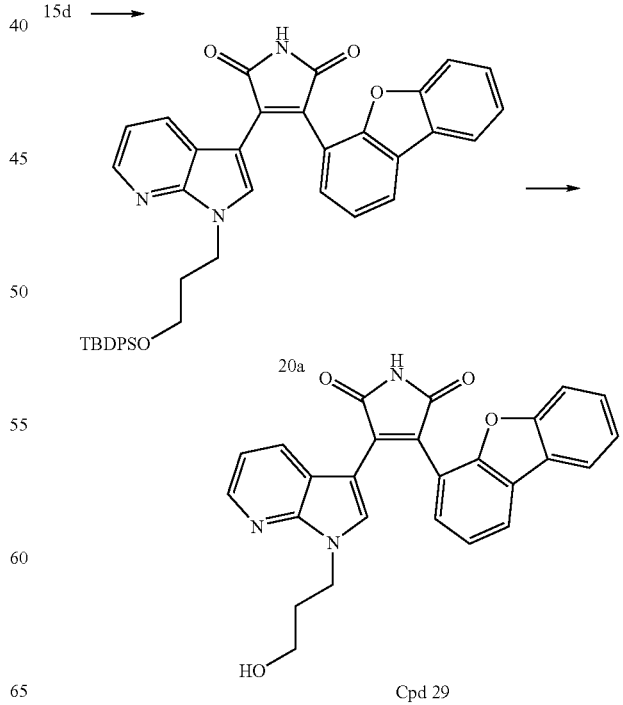

EXAMPLE 21

[3-[3-[2,5-dihydro-4-(2-methoxyphenyl)-2,5-dioxo-1H-pyrrol-3-yl]-1H-pyrrolo[2,3-b]pyridin-1-yl]propyl]-carbamic acid 2-methylpropyl ester (Compound 34)

A mixture of crude Compound 1b (1.3 g, 6.4 mmol), 21a (2.29 g, 9.6 mmol) and cesium carbonate (2.09 g, 6.4 mmol) in anhydrous DMF (15 mL) was stirred under nitrogen at 68° C. for 6 h. The solvent was evaporated. The residue was then diluted with ethyl acetate (250 mL) and washed with brine (2×50 mL). The organic layer was separated, dried over anhydrous sodium sulfate and concentrated in vacuo to give 1.5 g of crude product 21b.

A mixture of Compound 21b (200 mg, 0.55 mmol) and Compound 6a (63 mg, 0.38 mmol) in 6 mL of anhydrous THF was stirred under nitrogen and cooled in an ice bath while treating dropwise with 1.9 mL of 1 N potassium t-butoxide in THF. The mixture was stirred for 30 minutes in an ice bath then at room temperature for another 30 min. The reddish mixture was then cooled down and then 2 mL of concentrated HCl was added dropwise. The mixture was stirred for 5 min and then ethyl acetate (250 mL) and $H_2O$ (50 mL) were added. The organic layer was separated and washed with saturated $NaHCO_3$ and brine, dried over anhydrous sodium sulfate and concentrated in vacuo to give a crude oil, which was separated by flash chromatography on silica gel ($CH_2Cl_2$/MeOH/$NH_4OH$, from 98:2:0.2 to 95:5:0.5) to give 78 mg (43%) of Compound 34 as a yellow solid. $^1$H NMR (CDCl$_3$) δ 8.23 (m, 1 H), 8.12 (s, 1 H), 7.99 (m, 1 H), 7.40 (d, J=7.4 Hz, 1 H), 7.03 (m, 1 H), 6.86 (m, 1 H), 6.72 (m, 2 H), 5.41 (m, 1 H), 4.41 (t, J=6.6 Hz, 2 H), 3.36 (s, 3 H), 3.05 (m, 2 H), 2.06 (m, 2 H), 1.46 (s, 9H). ES-MS m/z 477 (MH$^+$).

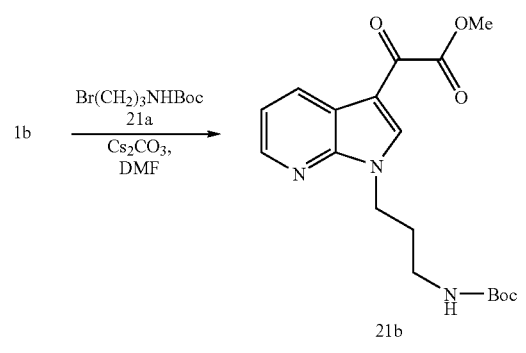

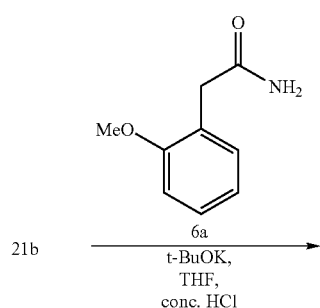

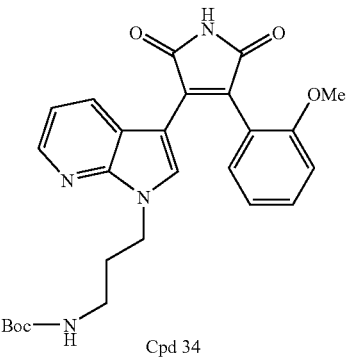

Cpd 34

Using the procedure of Example 21 and the appropriate reagents and starting materials known to those skilled in the art, other compounds of the present invention may be prepared including, but not limited to:

| Cpd | Name | ES-MS m/z (MH$^+$) |
| --- | --- | --- |
| 35 | [3-[3-[2,5-dihydro-4-(2-methoxyphenyl)-2,5-dioxo-1H-pyrrol-3-yl]-1H-pyrrolo[2,3-b]pyridin-1-yl]propyl]-carbamic acid methyl ester | 435 |
| 36 | [3-[3-[2,5-dihydro-4-(2-trifluoromethylphenyl)-2,5-dioxo-1H-pyrrol-3-yl]-1H-pyrrolo[2,3-b]pyridin-1-yl]propyl]-carbamic acid 2-methylpropyl ester | 515 |
| 37 | [3-[3-[2,5-dihydro-4-(2-trifluoromethylphenyl)-2,5-dioxo-1H-pyrrol-3-yl]-1H-pyrrolo[2,3-b]pyridin-1-yl]propyl]-carbamic acid methyl ester | 473 |

EXAMPLE 22

3-[1-(3-aminopropyl)-1H-pyrrolo[2,3-b]pyridin-3-yl]-4-(2-methoxyphenyl)-1H-pyrrole-2,5-dione (Compound 38)

A solution of 20% TFA in $CH_2Cl_2$ was added to the compound 34. The mixture was stirred at room temperature overnight till no more starting material. The solvent was evaporated and purified by flash chromatography on silica gel ($CH_2Cl_2$/MeOH/$NH_4OH$, from 98:2:0.2 to 95:5:0.5) to give 100 mg (84%) of Compound 38 as a yellow solid. $^1$H NMR (CDCl$_3$) δ 8.21 (m, 2 H), 7.40 (m, 2 H), 7.05 (m, 1 H), 6.85 (m, 1 H), 6.69 (m, 2 H), 4.45 (t, J=6.9 Hz, 2 H), 3.33 (s, 3 H), 2.70 (t, J=6.5 Hz, 2 H), 2.06 (m, 2 H). ES-MS m/z 377 (MH$^+$).

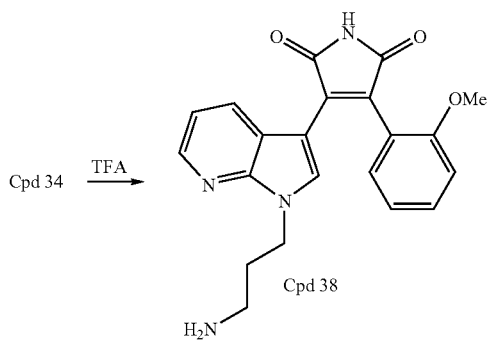

EXAMPLE 23

N-[3-[3-[2,5-dihydro-4-(2-methoxyphenyl)-2,5-dioxo-1H-pyrrol-3-yl]-1H-pyrrolo[2,3-b]pyridin-1-yl]propyl]-sulfamide (Compound 39)

To the mixture of compound 38 (50 mg, 0.133 mmol) in dioxane was added large excess of sulfamide. The mixture was heated to 80° C. overnight. The solvent was evaporated and the residue was purified by flash chromatography on silica gel (CH$_2$Cl$_2$/MeOH/NH$_4$OH, from 99:1:0.1 to 97:3:0.3) to give 10 mg (17%) of Compound 39 as a yellow solid. $^1$H NMR (CD$_3$OD) δ 8.17 (m, 2 H), 7.42 (m, 1 H), 7.34 (d, J=6.0 Hz, 1 H), 7.00 (m, 2 H), 6.75 (m, 2 H), 4.45 (t, J=6.9 Hz, 2 H), 3.36 (s, 3 H), 3.05 (t, J=6.7 Hz, 2 H), 2.13 (t, J=6.8 Hz, 2 H). ES-MS m/z 456 (MH$^+$).

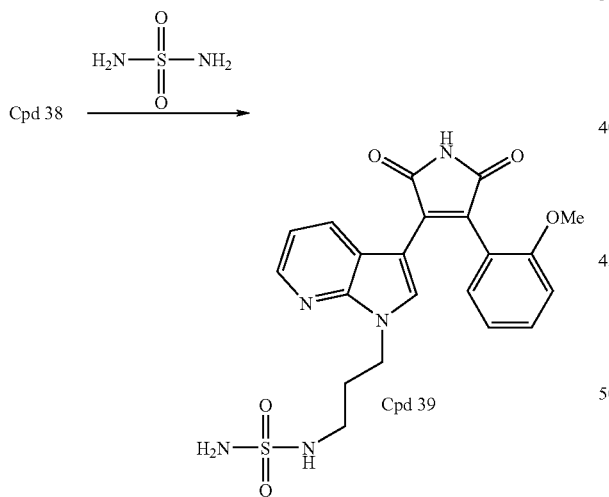

EXAMPLE 24

4-[1-(3-Hydroxy-propyl)-1H-pyrrolo[2,3-b]pyridin-3-yl]-1'H-[3,3']bipyrrolyl-2,5-dione (Compound 40)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (60 mg, 0.11 mmol) and Pd($^t$Bu$_3$P)$_2$ (5 mg, 0.01 mmol) in THF (1 mL) was added boronic acid derivative (0.2 mmol) at 23° C. under nitrogen. The reaction mixture was refluxed at 90° C. for 18 h. Upon cooling, the mixture was diluted with EtOAc (10 mL), then filtered through Celite and concentrated. The product was purified by column chromatography (SiO$_2$) to give Compound 40a (38 mg, 53%). $^1$H NMR (300 MHz, CDCl$_3$) δ 8.49 (s, 1 H), 8.29 (dd, J=4.71, 1.51 Hz, 1 H), 8.13 (s, 1 H), 7.98 (s, 1 H), 7.67 (m, 4 H), 7.39 (m, 6 H), 7.00 (dd, J=7.91, 1.51 Hz, 1 H), 6.87 (dd, J=8.10, 4.71 Hz, 1 H), 4.56 (m, 2 H), 4.04 (s, 3 H), 3.69 (m, 2 H), 3.36 (s, 3 H), 2.17 (m, 2 H), 1.10 (s, 9 H); MS (ES) m/z: 648 (M+H$^+$).

To a solution of 40a (38 mg, 0.06 mmol) in THF (1 mL) was added TBAF (1 M solution in THF, 1.5 eq) dropwise under nitrogen. After 18 hours, the mixture was concentrated and purified by column chromatography (SiO$_2$) to give Compound 40 (16 mg, 67%). $^1$H NMR (300 MHz, CD$_3$OD) δ 8.48 (s, 1 H), 8.26 (dd, J=4.71, 1.51 Hz, 1 H), 8.13 (s, 1 H), 7.20 (dd, J=7.91, 1.32 Hz, 1 H), 6.96 (dd, J=8.10, 4.71 Hz, 1 H), 4.49 (m, 2 H), 4.01 (s, 3 H), 3.56 (m, 2 H), 3.42 (s, 3 H), 2.10 (m, 2 H); MS (ES) m/z: 410 (M+H$^+$).

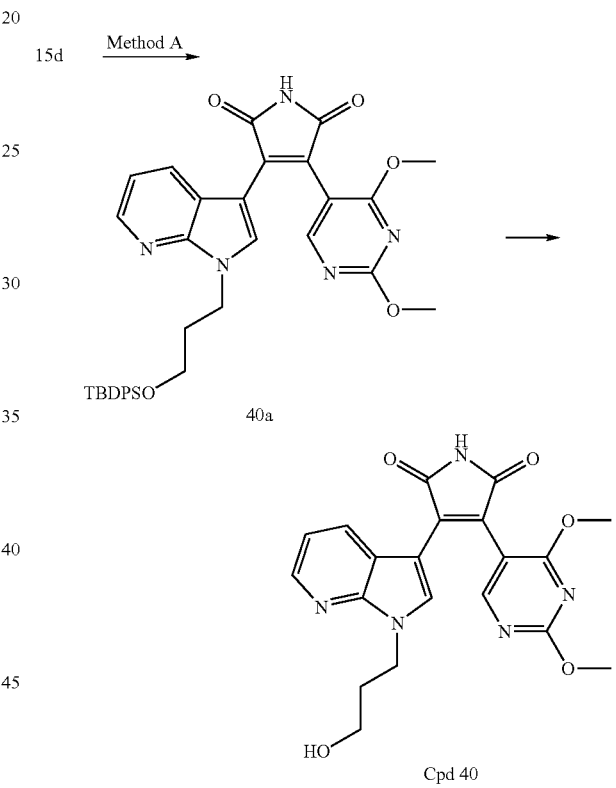

EXAMPLE 25

3-[1-(3-Hydroxy-propyl)-1H-pyrrolo[2,3-b]pyridin-3-yl]-4-pyrimidin-5-yl-pyrrole-2,5-dione (Compound 41)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added boronic acid derivative (0.2 mmol) at 23° C. under nitrogen. The reaction mixture was refluxed at 90° C. for 18 h. Upon cooling, the mixture was diluted with EtOAc (10 mL), then filtered through Celite and concentrated. The product was purified by column chromatography (SiO$_2$) to give Compound 41a (29 mg, 45%) as a yellow solid. $^1$H NMR (300 MHz, CDCl$_3$)

δ 9.19 (s, 1 H), 8.83 (s, 2 H), 8.30 (d, J=4.76 Hz, 1 H), 8.15 (s, 1 H), 7.88 (s, 1 H), 7.66 (m, 5 H), 7.36 (m, 5 H), 6.86 (dd, J=8.05, 4.57 Hz, 1 H), 6.72 (d, J=8.05 Hz, 1 H), 4.55 (m, 2 H), 3.68 (m, 2 H), 2.17 (m, 2 H), 1.10 (s, 9 H); MS (ES) m/z: 588 (M+H$^+$).

To a solution of 41a (29 mg, 0.05 mmol) in THF (1 mL) was added TBAF (1 M solution in THF, 1.5 eq) dropwise under nitrogen. After 18 hours, the mixture was concentrated and purified by column chromatography (SiO$_2$) to give Compound 41 (11 mg, 64%). $^1$H NMR (300 MHz, Acetone-d$_6$) δ 9.11 (s, 1 H), 8.86 (s, 2 H), 8.29 (m, 2 H), 6.95 (m, 2 H), 4.58 (m, 2 H), 3.55 (m, 2 H), 2.11 (m, 2 H); MS (ES) m/z: 348 (M−H$^+$).

Hz, 1 H), 4.48 (m, 2 H), 3.66 (m, 2 H), 2.11 (m, 2 H), 1.08 (s, 9 H); MS (ES) m/z: 637 (M+H$^+$).

To a solution of 42a (37.5 mg, 0.059 mmol) in THF (1 mL) was added TBAF (1 M solution in THF, 1.5 eq) dropwise under nitrogen. After 18 hours, the mixture was concentrated and purified by column chromatography (SiO$_2$) to give Compound 42 (20 mg, 85%) as an orange solid. $^1$H NMR (300 MHz, Acetone-d$_6$) δ 8.69 (dd, J=3.96, 1.70 Hz, 1 H), 8.37 (dd, J=8.48, 1.70 Hz, 1 H), 8.13 (s, 1 H), 8.08 (m, 2 H), 7.78 (dd, J=6.97, 1.51 Hz, 1 H), 7.65 (dd, J=8.10, 7.35 Hz, 1 H), 7.45 (dd, J=8.48, 4.14 Hz, 1 H), 6.52 (m, 2 H), 4.44 (m, 2 H), 3.46 (m, 2 H), 1.99 (m, 2 H); MS (ES) m/z: 399 (M+H$^+$).

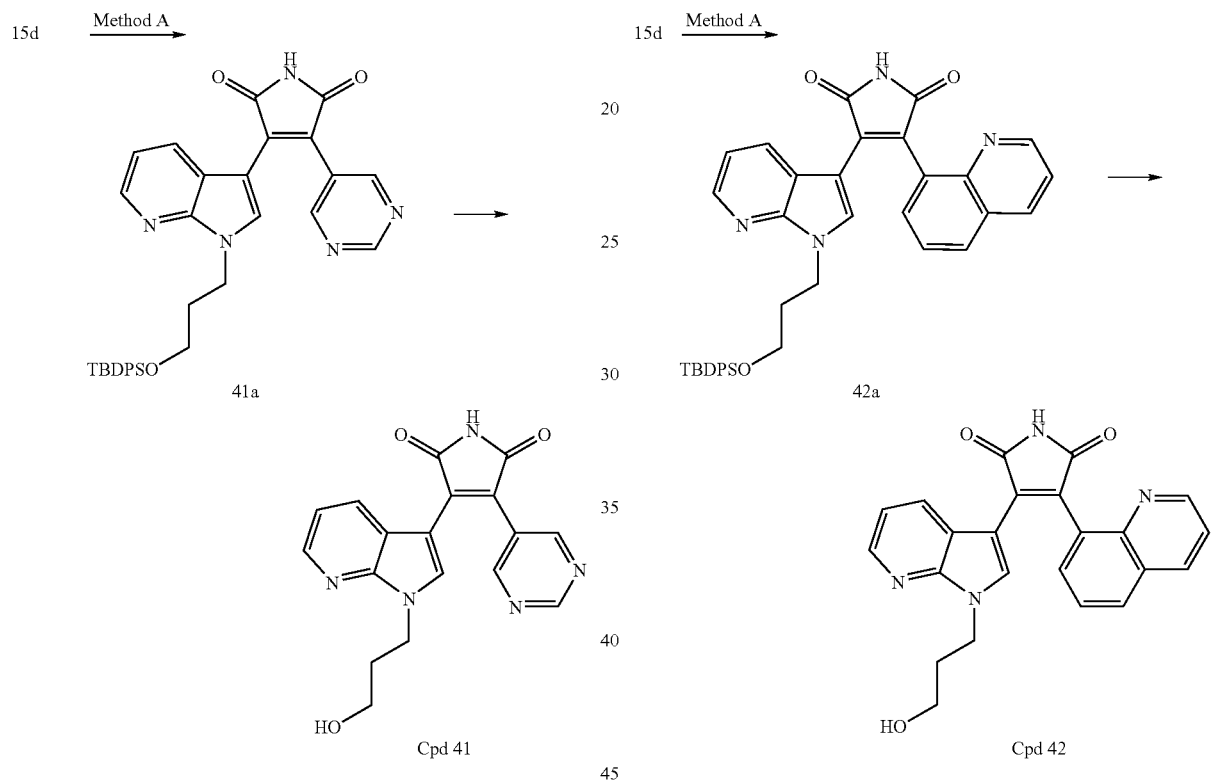

EXAMPLE 26

3-[1-(3-Hydroxy-propyl)-1H-pyrrolo[2,3-b]pyridin-3-yl]-4-quinolin-8-yl-pyrrole-2,5-dione (Compound 42)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added boronic acid derivative (0.2 mmol) at 23° C. under nitrogen. The reaction mixture was refluxed at 90° C. for 18 h. Upon cooling, the mixture was diluted with EtOAc (10 mL), then filtered through Celite and concentrated. The product was purified by column chromatography (SiO$_2$) to give Compound 42a (37.5 mg, 59%) as a yellow solid. $^1$H NMR (300 MHz, CDCl$_3$) δ 8.72 (dd, J=4.14, 1.70 Hz, 1 H), 8.16 (m, 2 H), 8.07 (dd, J=4.71, 1.51 Hz, 1 H), 7.91 (dd, J=8.29, 1.51 Hz, 1 H), 7.83 (s, 1 H), 7.65 (m, 5 H), 7.54 (m, 1 H), 7.36 (m, 7 H), 6.41 (dd, J=8.10, 4.71 Hz, 1 H), 6.25 (dd, J=8.10, 1.51

EXAMPLE 27

3-Benzo[b]thiophen-2-yl-4-[1-(3-hydroxy-propyl)-1H-pyrrolo[2,3-b]pyridin-3-yl]-pyrrole-2,5-dione (Compound 43)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added boronic acid derivative (0.2 mmol) at 23° C. under nitrogen. The reaction mixture was refluxed at 90° C. for 18 h. Upon cooling, the mixture was diluted with EtOAc (10 mL), then filtered through Celite and concentrated. The product was purified by column chromatography (SiO$_2$) to give Compound 43a (40 mg, 61%). $^1$H NMR (300 MHz, CDCl$_3$) 8.48 (dd, J=8.10, 1.70 Hz, 1 H), 8.40 (d, J=4.71 Hz, 1 H), 8.21 (s, 1 H), 7.68 (m, 7 H), 7.38 (m, 9 H), 7.20 (m, 1 H), 4.63 (m, 2 H), 3.75 (m, 2 H), 2.18 (m, 2 H), 1.10 (s, 9 H); MS (ES) m/z: 662 (M+H$^+$).

To a solution of 43a (40 mg, 0.06 mmol) in THF (1 mL) was added TBAF (1 M solution in THF, 1.5 eq) dropwise under nitrogen. After 18 hours, the mixture was concentrated and purified by column chromatography (SiO$_2$) to give Compound 43 (16 mg, 66%). $^1$H NMR (300 MHz, Acetone-d$_6$) δ 8.52 (dd, J=8.10, 1.51 Hz, 1H), 8.39 (m, 2 H), 8.32 (dd, J=4.71, 1.51 Hz, 1H), 8.18 (s, 1 H), 7.83 (m, 1 H), 7.39 (m, 2 H), 7.27 (dd, J=8.10, 4.71 Hz, 1 H), 6.97 (dd, J=8.10, 4.71 Hz, 1 H), 4.59 (m, 2 H), 3.58 (m, 2 H), 2.14 (m, 2 H); MS (ES) m/z: 404 (M+H$^+$).

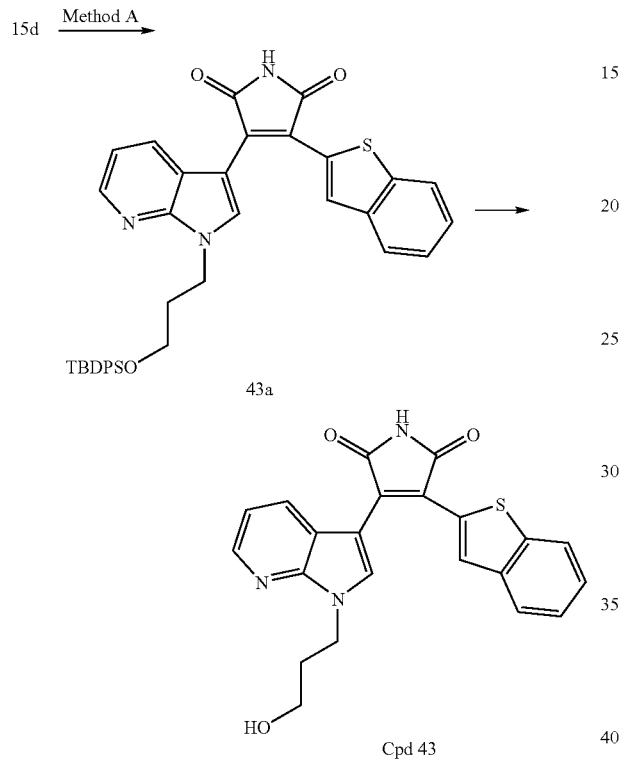

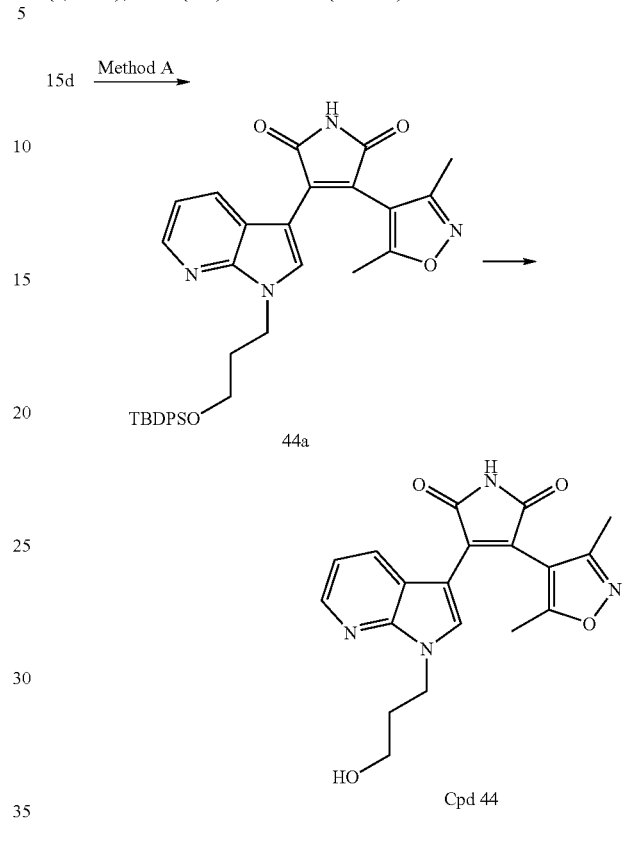

EXAMPLE 28

3-(3,5-Dimethyl-isoxazol-4-yl)-4-[1-(3-hydroxy-propyl)-1H-pyrrolo[2,3-b]pyridin-3-yl]-pyrrole-2,5-dione (Compound 44)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol), Pd($^t$Bu$_3$P)$_2$ (5 mg, 0.01 mmol) in THF (1 mL) was added boronic acid derivative (0.2 mmol) at 23° C. under nitrogen. The reaction mixture was refluxed at 90° C. for 18 h. Upon cooling, the mixture was diluted with EtOAc (10 mL), then filtered through Celite and concentrated. The product was purified by column chromatography (SiO$_2$) to give Compound 44a (9 mg, 15%). $^1$H NMR (300 MHz, CDCl$_3$), 8.32 (d, J=3.11 Hz, 1 H), 8.21 (s, 1 H), 7.64 (m, 4 H), 7.58 (s, 1 H), 7.35 (m, 6 H), 6.99 (m, 2 H), 4.59 (m, 2 H), 3.64 (m, 2 H), 2.16 (m, 2 H), 1.09 (s, 9 H); MS (ES) m/z: 605 (M+H$^+$).

To a solution of 44a (9 mg, 0.015 mmol) in THF (1 mL) was added TBAF (1 M solution in THF, 1.5 eq) dropwise under nitrogen. After 18 hours, the mixture was concentrated and purified by column chromatography (SiO$_2$) to give Compound 44 (3.5 mg, 64%). $^1$H NMR (300 MHz, Acetone-d$_6$) δ 8.33 (dd, J=4.57, 1.46 Hz, 1 H), 8.24 (s, 1 H), 7.24 (dd, J=8.05, 1.65 Hz, 1 H), 7.03 (dd, J=8.05, 4.76 Hz, 1 H), 4.56 (m, 2 H), 3.53 (m, 2 H), 2.11 (m, 2 H), 2.08 (s, 3 H), 2.02 (s, 3 H); MS (ES) m/z: 365 (M–H$^+$).

EXAMPLE 29

3-[1-(3-Hydroxy-propyl)-1H-pyrrolo[2,3-b]pyridin-3-yl]-4-(2-oxo-2H-pyran-3-yl)-pyrrole-2,5-dione (Compound 45)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 45a (30 mg, 50%). $^1$H NMR (300 MHz, CDCl$_3$) 8.32 (d, J=4.71 Hz, 1 H), 8.17 (s, 1 H), 7.96 (s, 1 H), 7.67 (m, 5 H), 7.65 (dd, J=5.09, 2.07 Hz, 1 H), 7.37 (m, 7 H), 6.99 (dd, J=7.91, 4.71 Hz, 1 H), 6.39 (m, 1 H), 4.52 (m, 2 H), 3.44 (m, 2 H), 2.06 (m, 2 H), 1.05 (s, 9 H); MS (ES) m/z: 604 (M+H$^+$).

To a solution of 45a (38 mg, 0.063 mmol) in THF (1 mL) was added TBAF (1 M solution in THF, 1.5 eq) dropwise under nitrogen. After 18 hours, the mixture was concentrated and purified by column chromatography (SiO$_2$) to give Compound 45 (3 mg, 13%) as an orange solid. $^1$H NMR (300 MHz, Acetone-d$_6$) δ 8.30 (dd, J=4.71, 1.51 Hz, 1 H), 8.11 (s, 1 H), 7.80 (dd, J=6.78, 2.26 Hz, 1 H), 7.61 (dd, J=5.09, 2.07 Hz, 1 H), 7.50 (dd, J=7.91, 1.32 Hz, 1 H), 7.02

(dd, J=7.91, 4.71 Hz, 1 H), 6.46 (dd, J=6.78, 5.09 Hz, 1 H), 4.52 (m, 2 H), 3.44 (m, 2 H), 2.06 (m, 2 H); MS (ES) m/z: 366 (M+H$^+$).

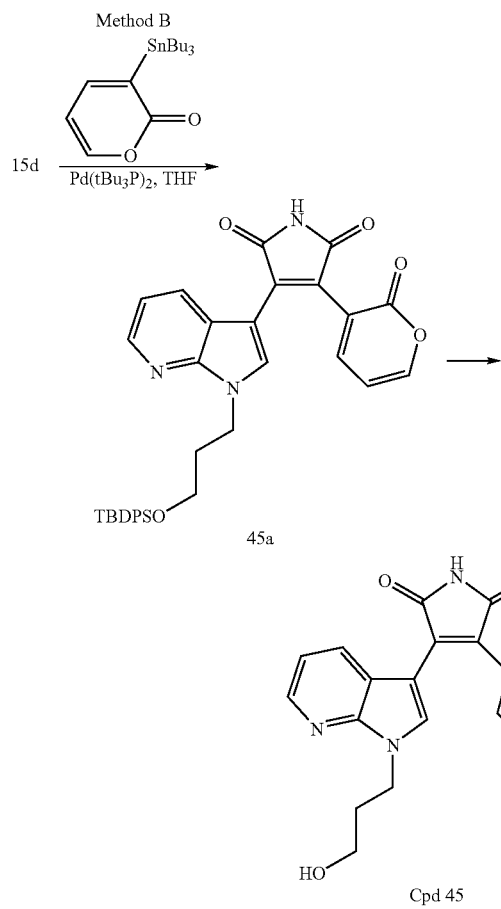

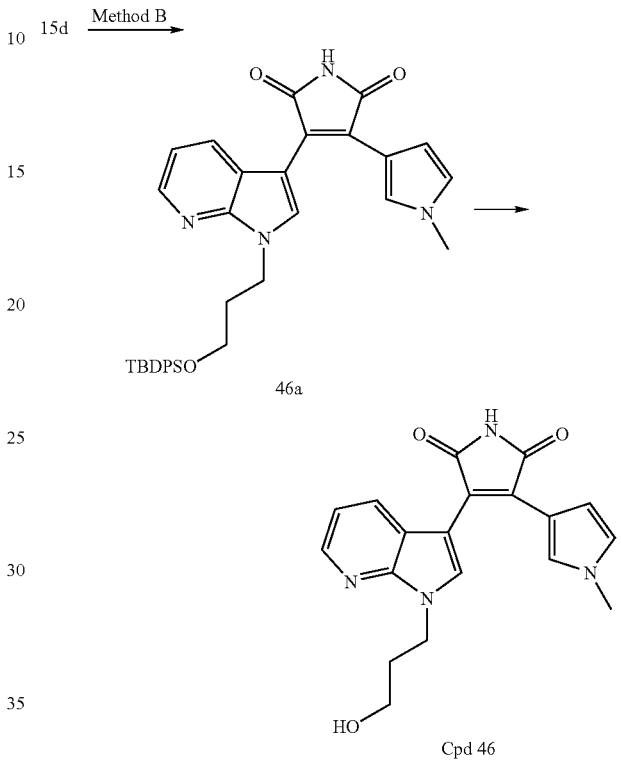

(300 MHz, Acetone-d$_6$) δ 9.54 (s, 1 H), 8.30 (dd, J=4.71, 1.51 Hz, 1 H), 7.89 (s, 1 H), 7.50 (dd, J=8.10, 1.70 Hz, 1 H), 7.44 (m, 1 H), 7.02 (dd, J=7.91, 4.71 Hz, 1 H), 6.60 (m, 1 H), 6.11 (dd, J=2.83, 1.70 Hz, 1 H), 4.54 (m, 2 H), 4.01 (m, 1 H), 3.70 (s, 3 H), 3.55 (m, 2 H), 2.11 (m, 2 H); MS (ES) m/z: 351 (M+H$^+$).

EXAMPLE 30

4-[1-(3-Hydroxy-propyl)-1H-pyrrolo[2,3-b]pyridin-3-yl]-1'-methyl-1'H-[3,3']bipyrrolyl-2,5-dione (Compound 46)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 46a (35 mg, 60%) as a yellow solid. $^1$H NMR (300 MHz, CDCl$_3$) δ 8.34 (dd, J=4.71, 1.51 Hz, 1 H), 7.74 (s, 1 H), 7.64 (m, 4 H), 7.35 (m, 9 H), 6.97 (dd, J=7.91, 4.71 Hz, 1 H), 6.43 (m, 1 H), 6.12 (m, 1 H), 4.53 (m, 2 H), 4.01 (m, 1 H), 3.72 (m, 2 H), 3.66 (s, 3 H), 2.18 (m, 2 H), 1.09 (s, 9 H); MS (ES) m/z: 589 (M+H$^+$).

To a solution of 46a (35 mg, 0.06 mmol) in THF (1 mL) was added TBAF (1 M solution in THF, 1.5 eq) dropwise under nitrogen. After 18 hours, the mixture was concentrated and purified by column chromatography (SiO$_2$) to give Compound 46 (15 mg, 71%) as an orange solid. $^1$H NMR

EXAMPLE 31

4-[1-(3-Hydroxy-propyl)-1H-pyrrolo[2,3-b]pyridin-3-yl]-1'-methyl-1'H-[3,3']bipyrrolyl-2,5-dione (Compound 47)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 47a (47 mg, 72%). $^1$H NMR (300 MHz, Acetone-d$_6$) δ 8.95 (s, 1 H), 8.54 (s, 2 H), 8.34 (s, 1 H), 8.28 (dd, J=4.52, 1.32 Hz, 1 H), 7.76 (s, 1 H), 7.64 (m, 6 H), 7.38 (m, 4 H), 6.82 (dd, J=8.10, 4.71 Hz, 1 H), 6.66 (dd, J=8.10, 1.51 Hz, 1 H), 4.54 (m, 2 H), 3.75 (m, 2 H), 2.16 (m, 2 H), 1.09 (s, 9 H); MS (ES) m/z: 588 (M+H$^+$).

To a solution of 47a (47 mg, 0.08 mmol) in THF (1 mL) was added TBAF (1 M solution in THF, 1.5 eq) dropwise under nitrogen. After 18 hours, the mixture was concentrated and purified by column chromatography (SiO$_2$) to give Compound 47 (18 mg, 64%). $^1$H NMR (300 MHz, Acetone-d$_6$) δ 9.01 (s, 1 H), 8.58 (m, 1 H), 8.42 (s, 1 H), 8.27 (dd, J=4.39, 1.83 Hz, 1 H), 6.94 (m, 2 H), 4.54 (m, 2 H), 3.57 (m, 2 H), 2.11 (m, 2 H); MS (ES) m/z: 351 (M+H⁺).

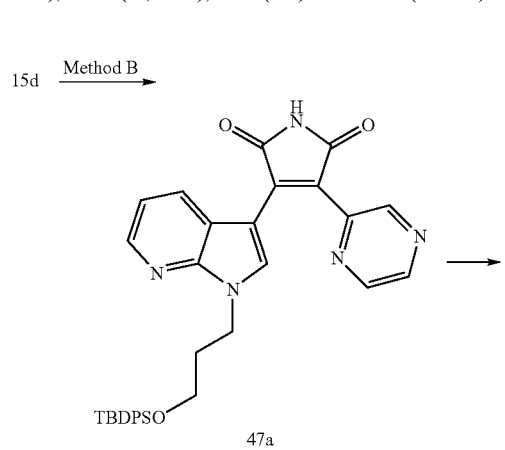

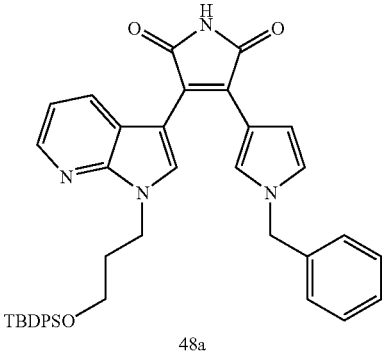

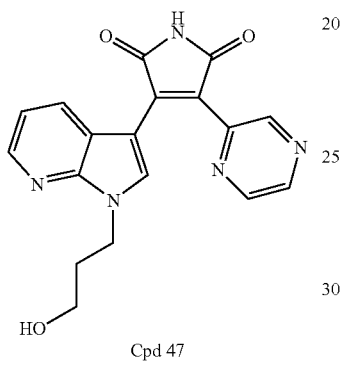

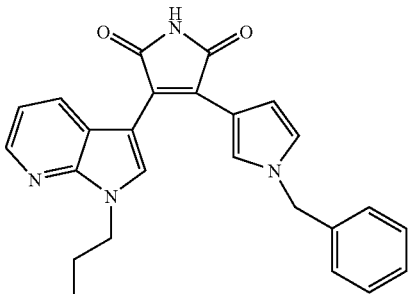

EXAMPLE 32

1'-Benzyl-4-[1-(3-hydroxy-propyl)-1H-pyrrolo[2,3-b]pyridin-3-yl]-1'H-[3,3']bipyrrolyl-2,5-dione (Compound 48)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd(ᵗBu₃P)₂ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H₂O, KF, brine and dried. After concentration, the crude product was purified by column chromatography (SiO₂) to give Compound 48a (40 mg, 60%). ¹H NMR (300 MHz, CDCl₃) δ 8.29 (d, J=4.57 Hz, 1 H), 7.75 (s, 1 H), 7.65 (m, 4 H), 7.37 (m, 12 H), 7.11 (d, J=6.40 Hz, 2 H), 6.89 (dd, J=7.87, 4.57 Hz, 1 H), 6.53 (m, 1 H), 6.27 (m, 1 H), 5.00 (s, 2 H), 4.56 (m, 2 H), 3.72 (m, 2 H), 2.17 (m, 2 H), 1.08 (s, 9 H); MS (ES) m/z: 665 (M+H⁺).

To a solution of 48a (40 mg, 0.06 mmol) in THF (1 mL) was added TBAF (1 M solution in THF, 1.5 eq) dropwise under nitrogen. After 18 hours, the mixture was concentrated and purified by column chromatography (SiO₂) to give Compound 48 (16 mg, 64%). ¹H NMR (300 MHz, CDCl₃) δ 8.28 (d, J=4.76 Hz, 1 H), 7.76 (s, 1 H), 7.59 (s, 1 H), 7.42 (m, 2 H), 7.32 (m, 3 H), 7.12 (d, J=6.59 Hz, 1 H), 6.94 (dd, J=7.87, 4.76 Hz, 1 H), 6.55 (m, 1 H), 6.25 (m, 1 H), 5.02 (s, 2 H), 4.51 (m, 2 H), 3.46 (m, 2 H), 2.05 (m, 2 H); MS (ES) m/z: 427 (M+H⁺).

EXAMPLE 33

3-[1-(3-Hydroxy-propyl)-1H-pyrrolo[2,3-b]pyridin-3-yl]-4-(2-phenyl-oxazol-5-yl)-pyrrole-2,5-dione (Compound 49)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (60 mg, 0.11 mmol) and Pd(ᵗBu₃P)₂ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H₂O, KF, brine and dried. After concentration, the crude product was purified by column chromatography (SiO₂) to give Compound 49a (45 mg, 63%). ¹H NMR (300 MHz, CDCl₃) δ 8.36 (dd, J=4.52, 1.51 Hz, 1 H), 8.08 (s, 1 H), 8.01 (s, 1 H), 7.64 (m, 4 H), 7.53 (m, 2 H), 7.36 (m, 11 H), 6.95 (dd, J=7.91, 4.71 Hz, 1 H), 4.64 (m, 2 H), 3.74 (m, 2 H), 2.22 (m, 2 H), 1.06 (s, 9 H); MS (ES) m/z: 653 (M+H⁺).

To a solution of 49a (45 mg, 0.069 mmol) in THF (1 mL) was added TBAF (1 M solution in THF, 1.5 eq) dropwise under nitrogen. After 18 hours, the mixture was concentrated and purified by column chromatography (SiO₂) to give Compound 49 (21 mg, 74%). ¹H NMR (300 MHz, Acetone-d₆) δ 8.37 (dd, J=4.76, 1.46 Hz, 1 H), 8.27 (s, 1 H), 7.98 (s, 1 H), 7.76 (dd, J=7.87, 1.46 Hz, 1 H), 7.48 (m, 3 H), 7.37 (m, 2 H), 7.08 (dd, J=7.87, 4.57 Hz, 1 H), 4.65 (m, 2 H), 3.60 (m, 2 H), 2.16 (m, 2 H); MS (ES) m/z: 415 (M+H⁺).

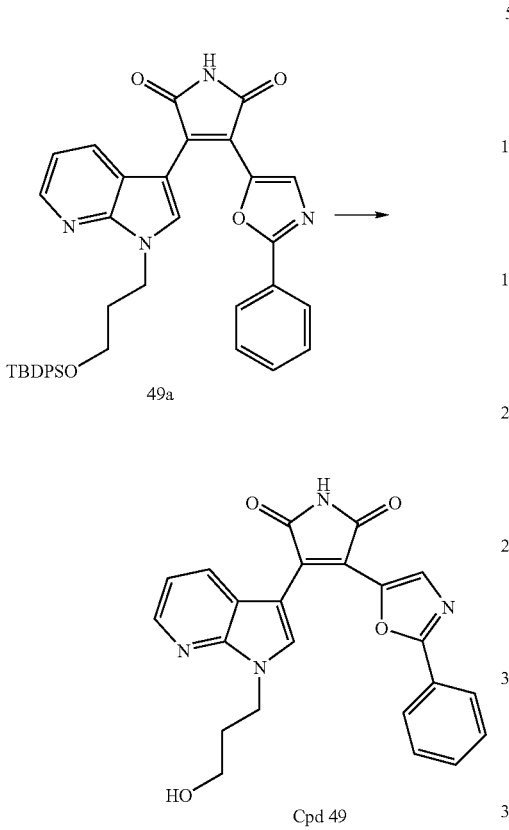

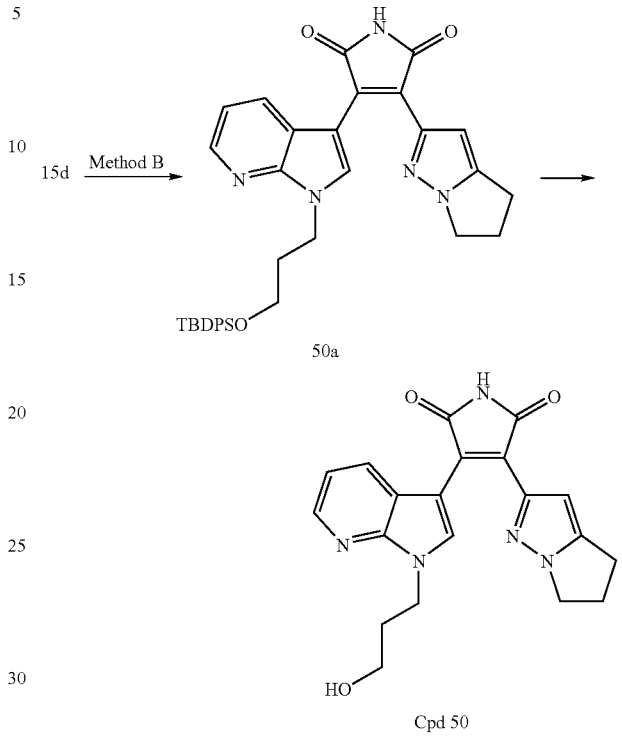

EXAMPLE 34

3-(5,6-Dihydro-4H-pyrrolo[1,2-b]pyrazol-2-yl)-4-[1-(3-hydroxy-propyl)-1H-pyrrolo[2,3-b]pyridin-3-yl]-pyrrole-2,5-dione (Compound 50)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (60 mg, 0.11 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 50a (63 mg, 93%). $^1$H NMR (300 MHz, CDCl$_3$) δ 8.30 (m, 2 H), 7.92 (s, 1 H), 7.66 (m, 4 H), 7.37 (m, 6 H), 7.22 (dd, J=7.54, 6.03 Hz, 1 H), 6.92 (dd, J=7.91, 4.71 Hz, 1 H), 6.43 (s, 1 H), 4.54 (m, 2 H), 4.02 (m, 2 H), 3.78 (m, 2 H), 2.90 (m, 2 H), 2.17 (m, 2 H), 1.08 (s, 9 H); MS (ES) m/z: 616 (M+H$^+$).

To a solution of 50a (63 mg, 0.10 mmol) in THF (1 mL) was added TBAF (1 M solution in THF, 1.5 eq) dropwise under nitrogen. After 18 hours, the mixture was concentrated and purified by column chromatography (SiO$_2$) to give Compound 50 (36 mg, 93%). $^1$H NMR (300 MHz, Acetone-d$_6$) δ 8.29 (m, 2 H), 7.76 (s, 1 H), 7.24 (d, J=8.48 Hz, 1 H), 6.96 (dd, J=7.91, 4.71 Hz, 1 H), 6.51 (s, 1 H), 4.50 (m, 2 H), 4.04 (m, 2 H), 3.51 (m, 2 H), 2.95 (m, 2 H), 2.61 (m, 2 H), 2.06 (m, 2 H); MS (ES) m/z: 378 (M+H$^+$).

EXAMPLE 35

3-(5,6-Dihydro-[1,4]dioxin-2-yl)-4-[1-(3-hydroxy-propyl)-1H-pyrrolo[2,3-b]pyridin-3-yl]-pyrrole-2,5-dione (Compound 51)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (59 mg, 0.11 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 51a (41 mg, 63%). $^1$H NMR (300 MHz, CDCl$_3$) δ 8.34 (dd, J=4.57, 1.46 Hz, 1 H), 7.89 (dd, J=7.87, 1.46 Hz, 1 H), 7.77 (s, 1 H), 7.66 (m, 4 H), 7.38 (m, 8 H), 7.13 (dd, J=8.05, 4.76 Hz, 1 H), 4.51 (m, 2 H), 4.12 (m, 2 H), 3.88 (m, 2 H), 3.74 (m, 2 H), 2.14 (m, 2 H), 1.08 (s, 9 H); MS (ES) m/z: 594 (M+H$^+$).

To a solution of 51a (41 mg, 0.069 mmol) in THF (1 mL) was added TBAF (1 M solution in THF, 1.5 eq) dropwise under nitrogen. After 18 hours, the mixture was concentrated and purified by column chromatography (SiO$_2$) to give Compound 51 (19 mg, 77%). $^1$H NMR (300 MHz, CDCl$_3$) δ 8.32 (dd, J=4.71, 1.32 Hz, 1 H), 7.93 (dd, J=7.91, 1.32 Hz, 1 H), 7.76 (s, 1 H), 7.39 (s, 1 H), 7.16 (dd, J=7.91, 4.90 Hz, 1 H), 4.49 (m, 2 H), 4.14 (m, 2 H), 3.89 (m, 2 H), 3.46 (m, 2 H), 2.05 (m, 2 H); MS (ES) m/z: 356 (M+H$^+$).

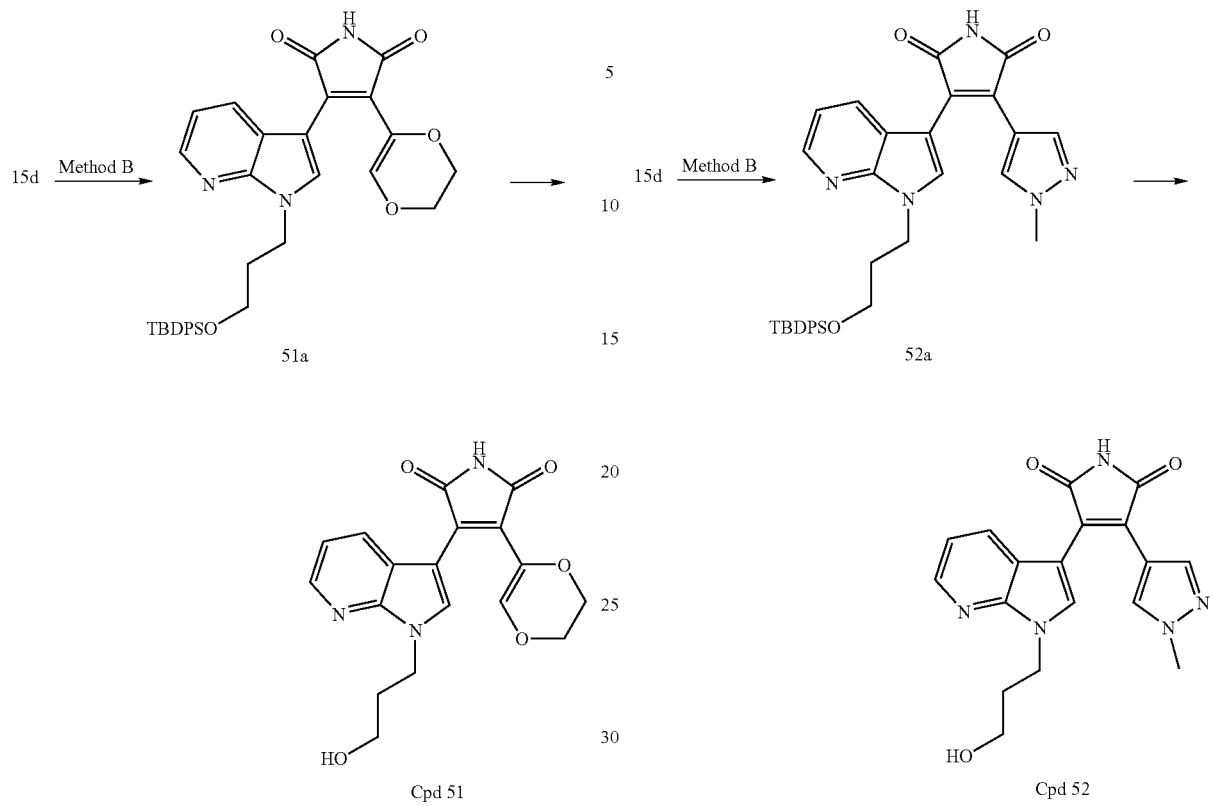

EXAMPLE 36

3-[1-(3-Hydroxy-propyl)-1H-pyrrolo[2,3-b]pyridin-3-yl]-4-(1-methyl-1H-pyrazol-4-yl)-pyrrole-2,5-dione (Compound 52)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 52a (18 mg, 31%). $^1$H NMR (300 MHz, CDCl$_3$) δ 8.32 (s, 1 H), 8.29 (m, 1 H), 7.8 (s, 1 H), 7.65 (m, 5 H), 7.39 (m, 8 H), 6.89 (dd, J=8.1, 4.7 Hz, 1 H), 6.49 (m, 2 H), 4.54 (m, 2 H), 3.67 (m, 2 H), 3.46 (s, 3 H), 2.16 (m, 2 H), 1.11 (s, 9 H); MS (ES) m/z: 590 (M+H$^+$).

To a solution of 52a (18 mg, 0.314 mmol) in THF (1 mL) was added TBAF (1 M solution in THF, 1.5 eq) dropwise under nitrogen. After 18 hours, the mixture was concentrated and purified by column chromatography (SiO$_2$) to give Compound 52 (11 mg, 100%). $^1$H NMR (300 MHz, Acetone-d$_6$) δ 8.38 (s, 1 H), 8.29 (m, 1 H), 8.07 (s, 1 H), 7.51 (s, 1 H), 6.9 (dd, J=8.1, 4.7 Hz, 1 H), 6.67 (d, J=2.3 Hz, 1 H), 6.42 (s, 1 H), 4.56 (m, 2 H), 3.51 (m, 5 H), 2.05 (m, 2 H); MS (ES) m/z: 352 (M+H$^+$).

EXAMPLE 37

3-Furan-2-yl-4-[1-(3-hydroxy-propyl)-1H-pyrrolo[2,3-b]pyridin-3-yl]-pyrrole-2,5-dione (Compound 53)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 53a (42 mg, 73%). $^1$H NMR (300 MHz, CDCl$_3$) δ 8.33 (dd, J=4.71, 1.51 Hz, 1 H), 7.92 (s, 1 H), 7.76 (s, 1 H), 7.64 (m, 4 H), 7.48 (dd, J=7.91, 1.32 Hz, 1 H), 7.35 (m, 7 H), 7.26 (m, 1 H), 6.99 (dd, J=8.10, 4.71 Hz, 1 H), 6.55 (dd, J=3.58, 1.88 Hz, 1 H), 4.58 (m, 2 H), 3.77 (m, 2 H), 2.18 (m, 2 H), 1.07 (s, 9 H); MS (ES) m/z: 576 (M+H$^+$).

To a solution of 53a (41 mg, 0.07 mmol) in THF (1 mL) was added TBAF (1 M solution in THF, 1.5 eq) dropwise under nitrogen. After 18 hours, the mixture was concentrated and purified by column chromatography (SiO$_2$) to give Compound 53 (21 mg, 87%). $^1$H NMR (300 MHz, CDCl$_3$) δ 8.31 (dd, J=4.71, 1.32 Hz, 1 H), 7.96 (s, 1 H), 7.57 (s, 1 H), 7.51 (dd, J=8.10, 1.51 Hz, 1 H), 7.39 (d, J=1.13 Hz, 1 H), 7.31 (d, J=3.58 Hz, 1 H), 7.03 (dd, J=8.10, 4.71 Hz, 1 H), 6.58 (dd, J=3.58, 1.70 Hz, 1 H), 4.54 (m, 2 H), 3.50 (m, 2 H), 2.07 (m, 2 H); MS (ES) m/z: 338 (M+H$^+$).

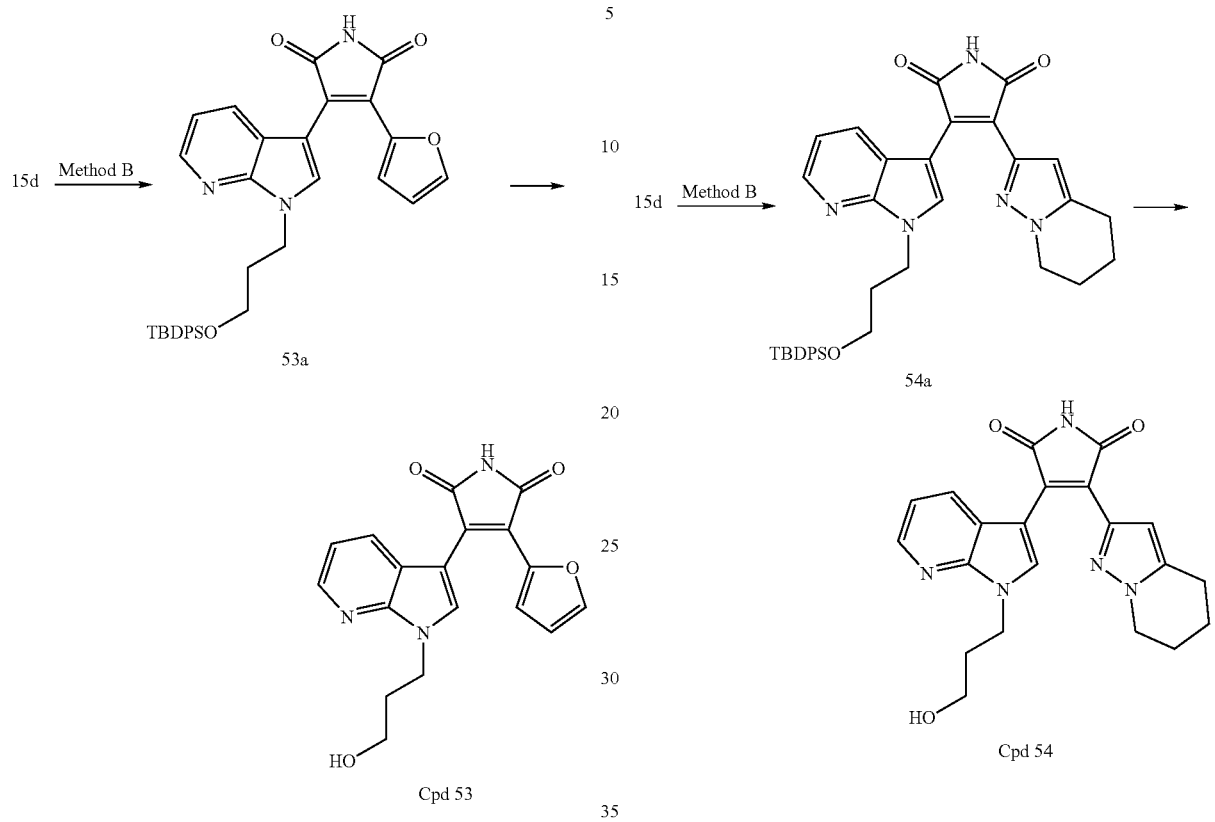

EXAMPLE 38

3-[1-(3-Hydroxy-propyl)-1H-pyrrolo[2,3-b]pyridin-3-yl]-4-(4,5,6,7-tetrahydro-pyrazolo[1,5-a]pyridin-2-yl)-pyrrole-2,5-dione (compound 54)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (60 mg, 0.11 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 54a (53 mg, 76%). $^1$H NMR (300 MHz, CDCl$_3$) δ 8.39 (s, 1 H), 8.30 (dd, J=4.71, 1.51 Hz, 1 H), 7.90 (s, 1 H), 7.66 (m, 4 H), 7.37 (m, 6 H), 7.19 (dd, J=8.10, 1.51 Hz, 1 H), 6.93 (dd, J=7.91, 4.71 Hz, 1 H), 6.46 (s, 1 H), 4.53 (m, 2 H), 4.00 (m, 2 H), 3.76 (m, 2 H), 2.82 (m, 2 H), 2.17 (m, 2 H), 1.99 (m, 2 H), 1.85 (m, 2 H), 1.07 (s, 9 H); MS (ES) m/z: 630 (M+H$^+$).

To a solution of 54a (53 mg, 0.084 mmol) in THF (1 mL) was added TBAF (1 M solution in THF, 1.5 eq) dropwise under nitrogen. After 18 hours, the mixture was concentrated and purified by column chromatography (SiO$_2$) to give Compound 54 (31 mg, 94%). $^1$H NMR (300 MHz, CDCl$_3$) δ 8.33 (s, 1 H), 8.27 (dd, J=4.71, 1.32 Hz, 1 H), 7.53 (s, 1 H), 7.19 (dd, J=8.10, 1.51 Hz, 1 H), 6.98 (dd, J=8.10, 4.71 Hz, 1 H), 6.51 (s, 1 H), 4.50 (m, 2 H), 4.00 (m, 2 H), 3.48 (m, 2 H), 2.85 (m, 2 H), 2.06 (m, 4 H), 1.89 (m, 2 H); MS (ES) m/z: 392 (M+H$^+$).

EXAMPLE 39

3-[1-(3-Hydroxy-propyl)-1H-pyrrolo[2,3-b]pyridin-3-yl]-4-thiazol-2-yl-pyrrole-2,5-dione (Compound 55)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (54 mg, 0.1 mmol) and Pd($^t$Bu$_3$P)$_2$ (5 mg, 0.01 mmol) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 55a (6.5 mg, 11%). $^1$H NMR (300 MHz, CDCl$_3$) δ 8.69 (s, 1 H), 8.34 (dd, J=4.71, 1.51 Hz, 1 H), 7.87 (d, J=2.3 Hz, 1 H), 7.64 (m, 4 H), 7.36 (m, 9 H), 7.03 (dd, J=7.91, 4.71 Hz, 1 H), 4.57 (m, 2 H), 3.73 (m, 2 H), 2.18 (m, 2 H), 1.08 (s, 9 H); MS (ES) m/z: 593 (M+H$^+$).

To a solution of 55a (5.4 mg, 0.009 mmol) in THF (1 mL) was added TBAF (1 M solution in THF, 1.5 eq) dropwise under nitrogen. After 18 hours, the mixture was concentrated and purified by column chromatography (SiO$_2$) to give Compound 55 (2.6 mg, 80%). $^1$H NMR (300 MHz, Acetone-d$_6$) δ 8.89 (s, 1 H), 8.33 (d, J=2.1 Hz, 1 H), 7.94 (m, 2 H), 7.71 (d, J=2.3 Hz, 1 H), 7.1 (dd, J=8.1, 4.7 Hz, 1 H), 4.58 (m, 2 H), 3.99 (m, 1 H), 3.61 (m, 2 H), 2.14 (m, 2 H); MS (ES) m/z: 355 (M+H$^+$).

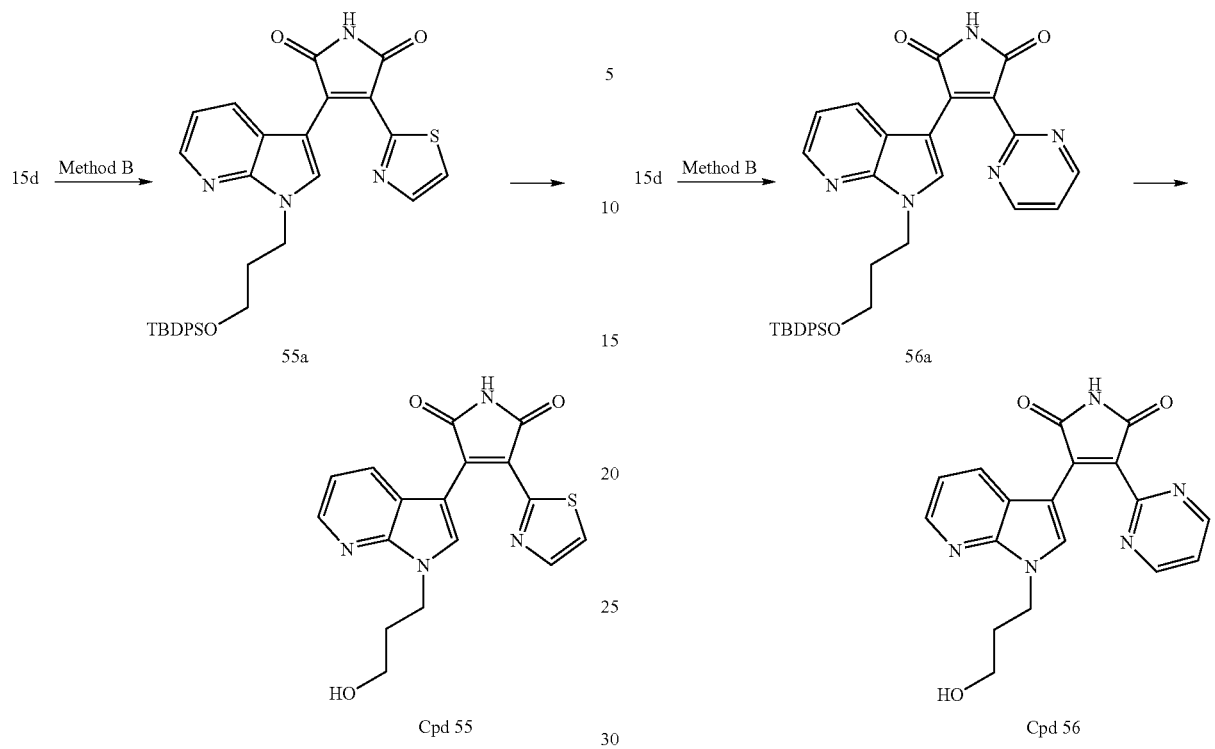

EXAMPLE 40

3-[1-(3-Hydroxy-propyl)-1H-pyrrolo[2,3-b]pyridin-3-yl]-4-pyrimidin-2-yl-pyrrole-2,5-dione (Compound 56)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (60 mg, 0.1 mmol) and Pd($^t$Bu$_3$P)$_2$ (5 mg, 0.01 mmol) in THF (1 mL) was added stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 56a (45 mg, 70%). $^1$H NMR (300 MHz, CDCl$_3$) δ 8.83 (m, 2 H), 8.33 (s, 1 H), 8.26 (dd, J=4.52, 1.13 Hz, 1 H), 8.16 (s, 1 H), 7.66 (m, 4 H), 7.38 (m, 6 H), 7.25 (m, 1 H), 6.78 (dd, J=4.71, 3.39 Hz, 1 H), 6.53 (dd, J=8.10, 1.32 Hz, 1 H), 4.52 (m, 2 H), 3.77 (m, 2 H), 2.16 (m, 2 H), 1.08 (s, 9 H); MS (ES) m/z: 588 (M+H$^+$).

To a solution of 56a (45 mg, 0.077 mmol) in THF (1 mL) was added TBAF (1 M solution in THF, 1.5 eq) dropwise under nitrogen. After 18 hours, the mixture was concentrated and purified by column chromatography (SiO$_2$) to give Compound 56 (28 mg, 100%). $^1$H NMR (300 MHz, CD$_3$OD) δ 8.85 (d, J=4.94 Hz, 2 H), 8.32 (s, 1 H), 8.21 (d, J=4.03 Hz, 1 H), 7.49 (m, 1 H), 6.87 (dd, J=8.05, 4.76 Hz, 1 H), 6.68 (d, J=7.87 Hz, 1 H), 4.47 (m, 2 H), 3.56 (m, 2 H), 2.08 (m, 2 H); MS (ES) m/z: 349 (M−H$^+$).

EXAMPLE 41

3-(2,4-Dimethoxy-pyrimidin-5-yl)-4-[1-(3-phenyl-propyl)-1H-pyrrolo[2,3-b]pyridin-3-yl]-pyrrole-2,5-dione (Compound 57)

To a solution of the amide 15a (0.5 g, 2.7 mmol) in DMF (10 mL) was added Cs$_2$CO$_3$ (3 eq) and 3-phenyl-propyl bromide (1.5 eq). The reaction was heated at 70° C. for 2 hours. After cooling down, the solution was diluted with EtOAc and washed with H$_2$O. The organic layer was dried (MgSO$_4$), concentrated and chromatographed on silica to give 57a (0.412 g, 49%) as a white solid. $^1$H NMR (300 MHz, CDCl$_3$) δ 8.36 (dd, J=4.71, 1.51 Hz, 1 H), 7.88 (dd, J=7.91, 1.51 Hz, 1 H), 7.22 (m, 6 H), 7.10 (m, 1 H), 4.32 (m, 2 H), 3.70 (s, 2 H), 2.66 (m, 2 H); MS (ES) m/z: 316 (M+H$^+$).

To a solution of 57a (0.412 g, 1.3 mmol) in DMF (10 mL) at 0° C. was added (CO$_2$Et)$_2$ (2 eq), and then $^t$BuOK (2 eq, 1 M in THF) was added dropwise. The resulting red solution was stirred for 15 minutes then concentrated and chromatographed on silica. The product 57b (0.393 g, 81%) was obtained as a yellow solid. $^1$H NMR (300 MHz, Acetone-d$_6$) δ 9.11 (s, 1 H), 8.75 (m, 1 H), 8.10 (m, 1 H), 7.97 (s, 1 H), 7.12 (m, 5 H), 6.88 (m, 1 H), 4.15 (m, 2 H), 2.45 (m, 2 H), 2.04 (m, 2 H); MS (ES) m/z: 374 (M−H$^+$).

To a solution of 57b (0.393 g, 1.05 mmol) in DMF and CH$_2$Cl$_2$ (1:1) was added (COCl)$_2$ (3 eq) in one portion at 0° C. The reaction was followed by TLC until starting material disappeared (~1 hour), then NaHCO$_3$ solution was added. The mixture was diluted with EtOAc and washed with water, dried, concentrated and chromatographed on silica giving the product 57c (0.372 g, 89%) as a yellow solid. $^1$H NMR (300 MHz, CDCl$_3$) δ 8.46 (dd, J=8.10, 1.51 Hz, 1 H), 8.43

(dd, J=4.71, 1.51 Hz, 1 H), 7.75 (s, 1 H), 7.24 (m, 7 H), 4.41 (m, 2 H), 2.70(m, 2 H), 2.30 (m, 2 H); MS (ES) m/z: 366 (M+H⁺).

To a solution of 57c (30 mg, 0.082 mmol) and Pd(ᵗBu₃P)₂ (0.1 eq) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H₂O, KF, brine and dried. After concentration, the crude product was purified by column chromatography (SiO₂) to give Compound 57 (6 mg, 16%). ¹H NMR (300 MHz, CDCl₃) δ 8.50 (s, 1 H), 8.31 (dd, J=4.71, 1.51 Hz, 1 H), 8.09 (s, 1 H), 7.59 (s, 1 H), 7.31 (m, 2 H), 7.20 (m, 4 H), 7.05 (dd, J=7.91, 1.32 Hz, 1 H), 6.90 (dd, J=7.91, 4.71 Hz, 1 H), 4.41 (m, 2 H), 4.04 (s, 3 H), 3.43 (s, 3 H), 2.69 (m, 2 H), 2.29 (m, 2 H); MS (ES) m/z: 470 (M+H⁺).

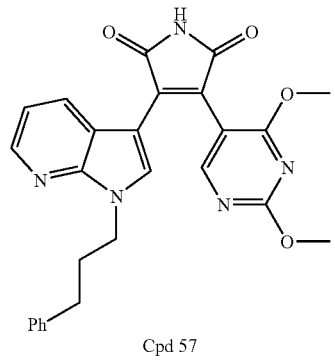

Cpd 57

EXAMPLE 42

3-[1-(3-Phenyl-propyl)-1H-pyrrolo[2,3-b]pyridin-3-yl]-4-pyrimidin-5-yl-pyrrole-2,5-dione (Compound 58)

To a solution of 57c (30 mg, 0.083 mmol) and Pd(ᵗBu₃P)₂ (0.1 eq) in THF (1 mL) was added boronic acid derivative (2 eq) and KF (3 eq) at 23° C. under nitrogen. The reaction mixture was refluxed at 90° C. for 18 h. Upon cooling, the mixture was diluted with EtOAc (10 mL), then filtered through Celite and concentrated. The product was purified by column chromatography (SiO₂) to give Compound 58 (13 mg, 36%) as a yellow solid. ¹H NMR (300 MHz, CDCl₃) δ 9.20 (s, 1 H), 8.89 (s, 2 H), 8.33 (dd, J=4.71, 1.51 Hz, 1 H), 8.16 (s, 1 H), 7.23 (m, 6 H), 6.90 (dd, J=7.91, 4.71 Hz, 1 H), 6.74 (dd, J=8.10, 1.32 Hz, 1 H), 4.42 (m, 2 H), 2.73 (m, 2 H), 2.35 (m, 2 H); MS (ES) m/z: 437 (M+H⁺).

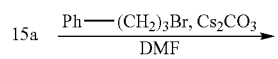

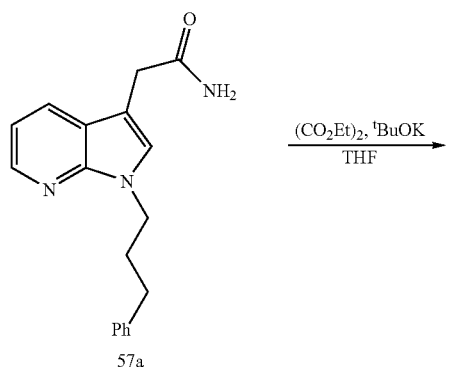

57a

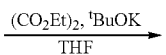

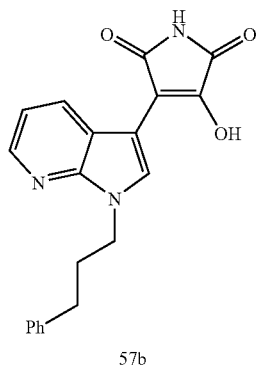

57b

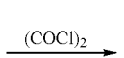

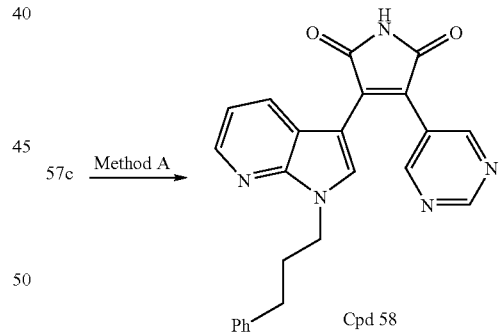

Cpd 58

EXAMPLE 43

3-(5,6-Dihydro-4H-pyrrolo[1,2-b]pyrazol-2-yl)-4-[1-(3-phenyl-propyl)-1H-pyrrolo[2,3-b]pyridin-3-yl]-pyrrole-2,5-dione (Compound 59)

To a solution of 57c (30 mg, 0.082 mmol) and Pd(ᵗBu₃P)₂ (0.1 eq) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H₂O, KF, brine and dried. After concentration, the crude product was purified by

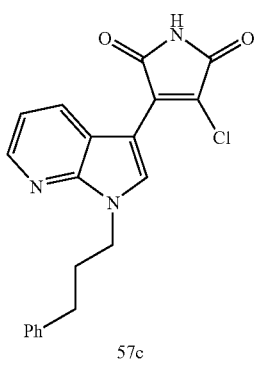

57c

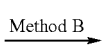

column chromatography (SiO$_2$) to give Compound 59 (32 mg, 89%). $^1$H NMR (300 MHz, CDCl$_3$) δ 8.32 (m, 2 H), 7.50 (s, 1 H), 7.24 (m, 6 H), 6.95 (dd, J=8.10, 4.71 Hz, 1 H), 6.45 (s, 1 H), 4.38 (m, 2 H), 4.03 (m, 2 H), 2.93 (m, 2 H), 2.74 (m, 2 H), 2.59 (m, 2 H), 2.30 (m, 2 H); MS (ES) m/z: 438 (M+H$^+$).

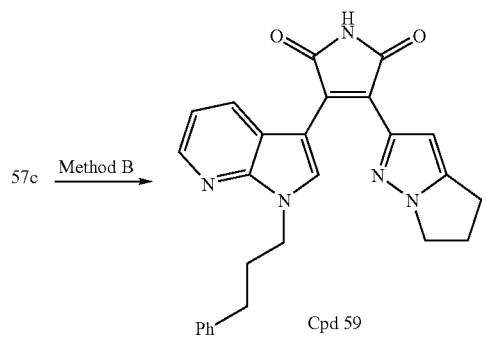

EXAMPLE 44

3-[1-(3-Phenyl-propyl)-1H-pyrrolo[2,3-b]pyridin-3-yl]-4-pyrazin-2-yl-pyrrole-2,5-dione (Compound 60)

To a solution of 57c (30 mg, 0.083 mmol) and Pd($^t$Bu$_3$P)$_2$ (0.1 eq) in THF (1 mL) was added the stannane derivative (2 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 60 (20 mg, 59%). $^1$H NMR (300 MHz, CDCl$_3$) δ 9.01 (d, J=1.32 Hz, 1 H), 8.55 (m, 2 H), 8.30 (m, 2 H), 7.73 (s, 1 H), 7.26 (m, 5 H), 6.85 (dd, J=7.91, 4.71 Hz, 1 H), 6.64 (dd, J=7.91, 1.51 Hz, 1 H), 4.39 (m, 2 H), 2.74 (m, 2 H), 2.31 (m, 2 H); MS (ES) m/z: 410 (M+H$^+$).

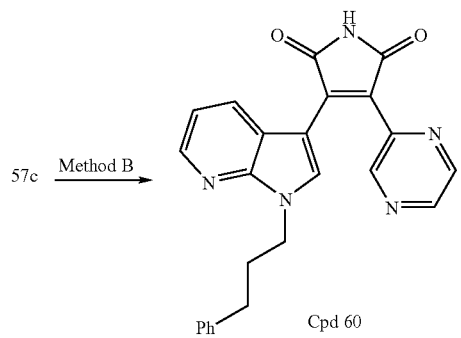

EXAMPLE 45

3-(5,6-Dihydro-4H-pyran-2-yl)-4-[1-(3-phenyl-propyl)-1H-pyrrolo[2,3-b]pyridin-3-yl]-pyrrole-2,5-dione (Compound 61)

To a solution of 57c (30 mg, 0.083 mmol) and Pd($^t$Bu$_3$P)$_2$ (0.1 eq) in THF (1 mL) was added the stannane derivative (1.5 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 61 (29 mg, 85%). $^1$H NMR (300 MHz, CDCl$_3$) δ 8.39 (dd, J=4.71, 1.32 Hz, 1 H), 8.18 (s, 1 H), 7.97 (dd, J=7.91, 1.32 Hz, 1 H), 7.92 (s, 1 H), 7.22 (m, 6 H), 5.82 (m, 1 H), 4.38 (m, 2 H), 3.83 (m, 2 H), 2.71 (m, 2 H), 2.29 (m, 4 H), 1.85 (m, 2 H); MS (ES) m/z: 414 (M+H$^+$).

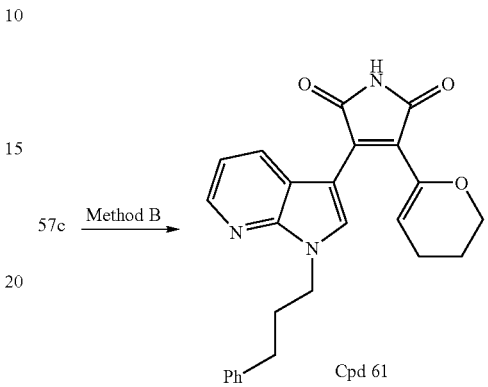

EXAMPLE 46

4-{3-[4-(2,4-Dimethoxy-pyrimidin-5-yl)-2,5-dioxo-2,5-dihydro-1H-pyrrol-3-yl]-pyrrolo[2,3-b]pyridin-1-yl}-butyronitrile (Compound 62)

To a solution of the amide 15a (0.25 g, 1.43 mmol) in DMF (5 mL) was added Cs$_2$CO$_3$ (3 eq) and 3-cyano-propyl bromide (1.5 eq). The reaction was heated at 80° C. for 2 hours. After cooling down, the solution was filtered through celite and then concentrated and chromatographed on silica to give 62a (0.146 g, 42%). $^1$H NMR (300 MHz, CDCl$_3$) δ 8.33 (dd, J=4.71, 1.51 Hz, 1 H), 7.91 (dd, J=7.91, 1.51 Hz, 1 H), 7.20 (s, 1 H), 7.13 (dd,J=7.91, 4.71 Hz, 1 H), 4.47 (m, 2 H), 3.71 (s, 2 H), 2.38 (m, 2 H), 2.29 (m, 2 H); MS (ES) m/z: 243 (M+H$^+$).

To a solution of 62a (0.146 g, 0.6 mmol) in THF (10 mL) at 0° C. was added (CO$_2$Et)$_2$ (2 eq), and then $^t$BuOK (2 eq, 1 M in THF) was added dropwise. After stirring for 1 hour, the solution was concentrated and chromatographed on silica gel. The product 62b (0.131 g, 73%) was obtained as a yellow solid. $^1$H NMR (300 MHz, CD$_3$OD) δ 8.65 (dd, J=8.05, 1.65 Hz, 1 H), 8.17 (dd, J=4.76, 1.46 Hz, 1 H), 7.69 (s, 1 H), 7.06 (dd, J=7.87, 4.76 Hz, 1 H), 4.38 (m, 2 H), 2.43 (m, 2 H), 2.21 (m, 2 H); MS (ES) m/z: 297 (M+H$^+$).

To a solution of 62b (0.131 g, 0.44 mmol) in DMF and CH$_2$Cl$_2$ (1:1) was added (COCl)$_2$ (3 eq) dropwise at room temperature. The reaction was followed by TLC until the starting material disappeared. NaHCO$_3$ solution was added and the aqueous layer was discarded. The organic layer was washed with water, dried, concentrated and chromatographed on silica giving the product 62c (0.107 g, 77%) as an orange solid. $^1$H NMR (300 MHz, CD$_3$OD) δ 8.52 (dd, J=8.10, 1.51 Hz, 1 H), 8.39 (dd, J=4.71, 1.51 Hz, 1 H), 8.32 (s, 1 H), 7.26 (dd, J=8.10, 4.71 Hz, 1 H), 4.53 (m, 2 H), 2.51 (m, 2 H), 2.28 (m, 2 H); MS (ES) m/z: 315 (M+H$^+$).

To a solution of 62c (30 mg, 0.095 mmol) and Pd($^t$Bu$_3$P)$_2$ (0.1 eq) in THF (3 mL) was added the stannane derivative (2 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 62 (17 mg, 43%). $^1$H NMR (300 MHz, CDCl$_3$) δ 8.46 (s, 1 H), 8.29 (dd, J=4.71, 1.51 Hz, 1 H), 8.07 (s, 1 H), 7.07 (dd, J=7.91, 1.51 Hz, 1 H), 6.92 (dd, J=7.91, 4.71 Hz, 1 H), 4.50 (s, 2 H), 4.04 (s, 3 H), 3.48 (s, 3 H) 2.36 (m, 4 H); MS (ES) m/z: 419 (M+H$^+$).

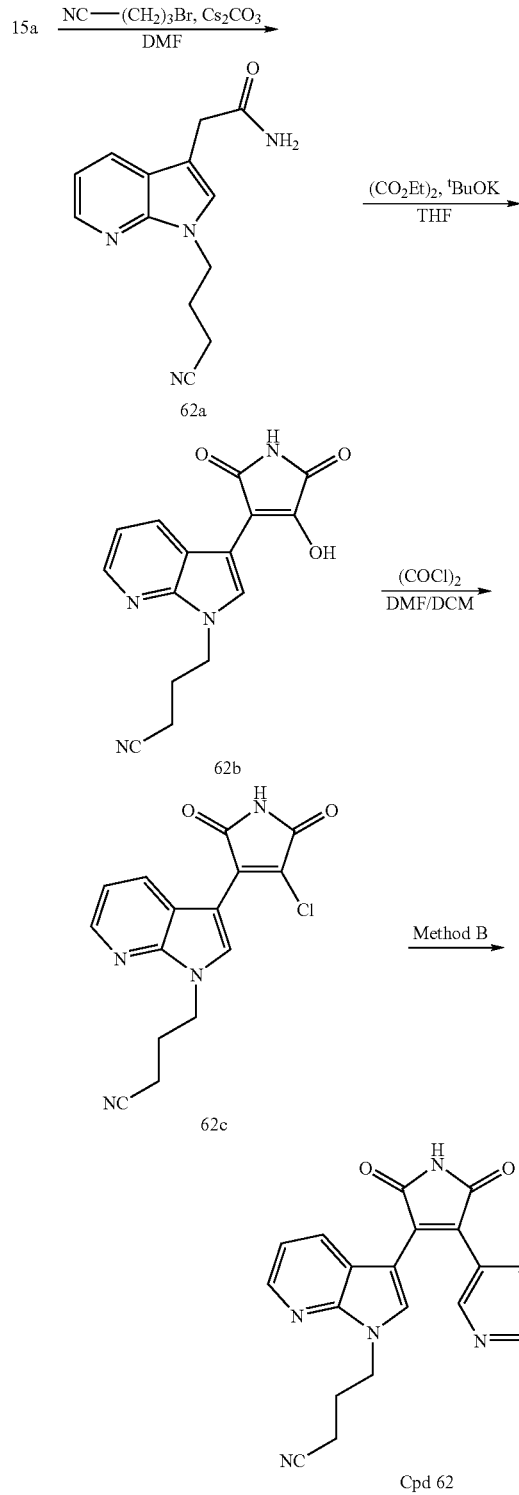

EXAMPLE 47

4-[3-(2,5-Dioxo-4-pyrazin-2-yl-2,5-dihydro-1H-pyrrol-3-yl)-pyrrolo[2,3-b]pyridin-1-yl]-butyronitrile (Compound 63)

To a solution of 62c (30 mg, 0.094 mmol) and Pd($^t$Bu$_3$P)$_2$ (0.1 eq) in THF (3 mL) was added the stannane derivative (2 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 63 (23 mg, 68%). $^1$H NMR (300 MHz, CDCl$_3$) δ 9.04 (s, 1 H), 8.57 (s, 2 H), 8.30 (m, 2 H), 7.82 (s, 1 H), 6.89 (dd, J=7.87, 4.39 Hz, 1 H), 6.75 (d, J=7.87 Hz, 1 H), 4.52 (m, 2 H), 2.44 (m, 2 H), 2.37 (m, 2 H); MS (ES) m/z: 357 (M–H$^+$).

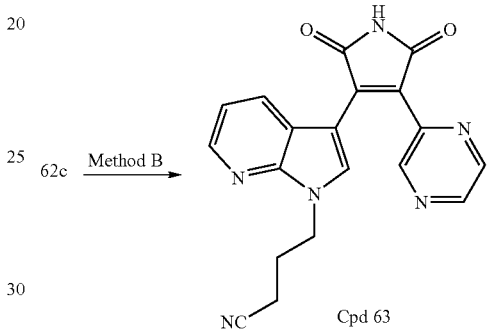

EXAMPLE 48

4-{3-[4-(1-Methyl-1H-pyrazol-3-yl)-2,5-dioxo-2,5-dihydro-1H-pyrrol-3-yl]-pyrrolo[2,3-b]pyridin-1-yl}-butyronitrile (Compound 64)

To a solution of 62c (60 mg, 0.19 mmol) and Pd($^t$Bu$_3$P)$_2$ (0.1 eq) in THF (3 mL) was added the stannane derivative (2 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by column chromatography (SiO$_2$) to give Compound 64 (23 mg, 33%). $^1$H NMR (300 MHz, CDCl$_3$) δ 8.31 (m, 2 H), 7.45 (m, 2 H), 7.22 (dd, J=8.05, 1.46 Hz, 1 H), 6.99 (dd, J=8.05, 4.76 Hz, 1 H), 6.80 (d, J=2.38 Hz, 1 H), 4.51 (s, 2 H), 3.85 (s, 3 H), 2.44 (m, 2 H), 2.36 (s, 2 H); MS (ES) m/z: 361 (M+H$^+$).

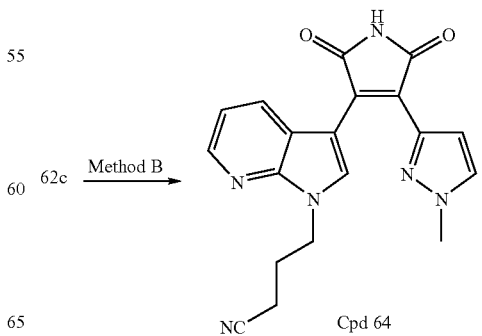

EXAMPLE 49

3-(5,6-Dihydro-4H-pyrrolo[1,2-b]pyrazol-2-yl)-4-[1-(3-phenoxy-propyl)-1H-pyrrolo[2,3-b]pyridin-3-yl]-pyrrole-2,5-dione (Compound 65)

To a solution of the amide 15a (0.25 g, 1.44 mmol) in DMF (5 mL) was added $Cs_2CO_3$ (3 eq) and 3-phenoxyl-propyl bromide (1.5 eq). The reaction was heated at 80° C. for 2 hours. After cooling down, the solution was filtered through celite and then concentrated and chromatographed on silica to give 65a (0.12 g, 27%). $^1$H NMR (300 MHz, $CDCl_3$) δ 8.33 (dd, J=4.57, 1.28 Hz, 1 H), 7.89 (dd, J=7.87, 1.28 Hz, 1 H), 7.26 (m, 2 H), 7.16 (s, 1 H), 7.08 (dd, J=7.87, 4.57 Hz, 1 H), 6.94 (m, 1 H), 6.86 (m, 2 H), 4.49 (m, 2 H), 3.92 (m, 2 H), 3.64 (s, 2 H), 2.36 (m, 2 H); MS (ES) m/z: 310 (M+H$^+$).

To a solution of 65a (0.12 g, 0.39 mmol) in THF (10 mL) at 0° C. was added $(CO_2Et)_2$ (2 eq), and then $^t$BuOK (2 eq, 1 M in THF) was added dropwise. After stirring for 1 hour, the solution was concentrated and chromatographed on silica gel. The product 65b (74 mg, 53%) was obtained as a yellow solid. $^1$H NMR (300 MHz, $CDCl_3$) δ 8.50 (m, 1 H), 8.41 (m, 1 H), 8.17 (s, 1 H), 7.25 (m, 4 H), 7.21 (m, 1 H), 6.86 (m, 2 H), 4.62 (m, 2 H), 3.98 (m, 2 H), 2.44 (m, 2 H); MS (ES) m/z: 364 (M+H$^+$).

To a solution of 65b (74 mg, 0.2 mmol) in DMF and $CH_2Cl_2$ (1:1) was added $(COCl)_2$ (3 eq) dropwise at room temperature. The reaction was followed by TLC until the starting material disappeared. $NaHCO_3$ solution was added and the aqueous layer was discarded. The organic layer was washed with water, dried, concentrated and chromatographed on silica giving the product 65c (61 mg, 78%) as a yellow solid. $^1$H NMR (300 MHz, $CDCl_3$) δ 8.39 (dd, J=4.90, 1.51 Hz, 1 H), 7.97 (dd, J=7.91, 1.51 Hz, 1 H), 7.25 (m, 4 H), 7.14 (dd, J=7.91, 4.90 Hz, 1 H), 6.95 (m, 1 H), 6.86 (m, 2 H), 4.53 (m, 2 H), 3.95 (m, 2 H), 2.35 (m, 2 H); MS (ES) m/z: 382 (M+H$^+$).

To a solution of 65c (30 mg, 0.079 mmol) and $Pd(^tBu_3P)_2$ (0.1 eq) in THF (3 mL) was added the stannane derivative (2 eq) at 23° C. under nitrogen. The reaction mixture was refluxed for 18 h. Upon cooling, the mixture was diluted with EtOAc (10 mL) and washed with $H_2O$, KF, brine and dried. After concentration, the crude product was purified by column chromatography ($SiO_2$) to give Compound 65 (12 mg, 34%). $^1$H NMR (300 MHz, $CDCl_3$) δ 8.32 (m, 2 H), 7.49 (s, 1 H), 7.26 (m, 3 H), 6.94 (m, 4 H), 6.46 (s, 1 H), 4.59 (m, 2 H), 4.05 (m, 4 H), 2.92 (m, 2 H), 2.59 (m, 2 H), 2.43 (m, 2 H); MS (ES) m/z: 454 (M+H$^+$).

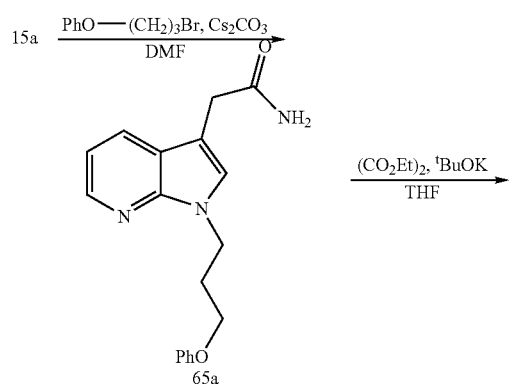

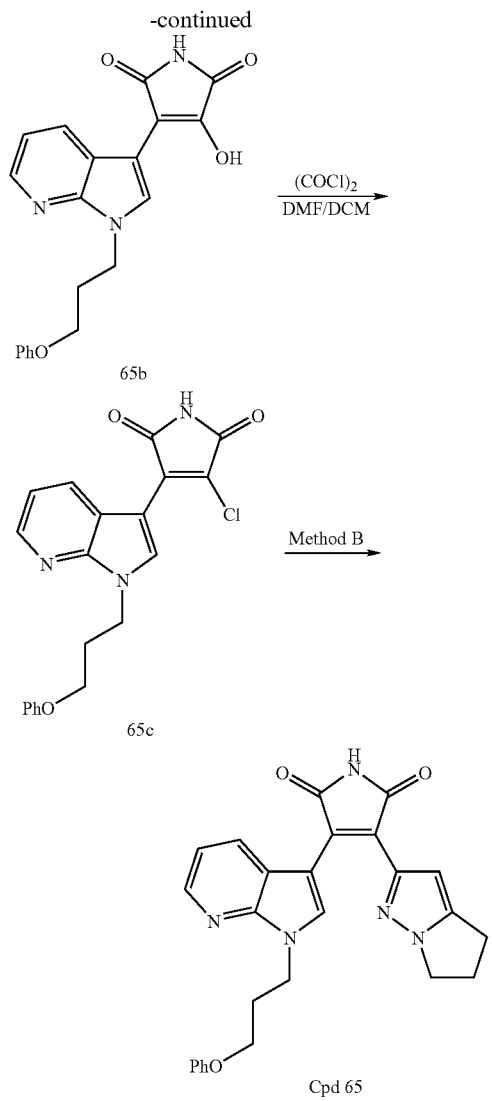

EXAMPLE 50

3-[1-(3-Hydroxy-propyl)-1H-pyrrolo[2,3-b]pyridin-3-yl]-4-(2-methyl-2H-pyrazol-3-yl)-pyrrole-2,5-dione (Compound 66)

Cesium carbonate (3.5 g, 10.8 mmol) and iodomethane (0.51 g, 3.6 mmol) were added to a solution of 2-(1H-pyrazol-3-yl)-acetamide Compound 9a (0.45 g, 3.6 mmol) in DMF (5 mL) at 23° C. under nitrogen. The mixture was warmed to 70° C. and stirred for 3 hours. After cooling, the mixture was diluted with EtOAc (20 mL), filtered through celite and washed with water (4×10 mL). The organic layer was dried ($MgSO_4$), filtered and concentrated to give a first crude product (0.46 g) as a white solid. By chromatography, the first crude product was shown to be a 2:1 mixture of 2-(1-methyl-1H-pyrazol-3-yl)-acetamide and 2-(2-methyl-2H-pyrazol-3-yl)-acetamide.

Potassium tert-butoxide (6.6 mL, 6.6 mmol; 1 M solution in THF) was added dropwise to a solution of the first crude product and Compound 1c (1.36 g, 3.47 mmol) in THF (20 mL) at 0° C. under nitrogen. After warming to 23° C., the reaction was stirred for 2 h then concentrated and purified by column chromatography (SiO$_2$) to give a second crude product (0.46 g) as a yellow solid which was then recrystallized (EtOAc/Hexanes) to give Compound 66a, $^1$H NMR (300 MHz, CDCl$_3$) δ 8.72 (s, 1 H), 8.30 (s, 1 H), 8.25 (dd, J=4.76, 1.46 Hz, 1 H), 7.56 (d, J=2.01 Hz, 1 H), 6.83 (dd, J=8.05, 4.57 Hz, 1 H), 6.47 (dd, J=8.05, 1.46 Hz, 1 H), 6.45 (d, J=1.83 Hz, 1 H), 4.43 (m, 2 H), 3.61 (m, 2 H), 3.47 (s, 3 H), 2.07 (m, 2 H), 0.87 (s, 9 H), 0.00 (s, 6 H); MS (ES) m/z: 466 (M+H$^+$).

TBAF (1.3 mL, 1 M solution in THF, 1.3 mmol) was added to a solution of 66a (92 mg, 0.20 mmol) in THF (15 mL) at 23° C. dropwise under nitrogen. After 18 hours, the mixture was concentrated and the crude product was then recrystallized (CH$_2$Cl$_2$:Hexane) to give Compound 66 (64 mg, 91%) as a yellow solid. $^1$H NMR (300 MHz, CDCl$_3$) δ 8.28 (m, 2 H), 7.62 (d, J=1.88 Hz, 1 H), 6.94 (dd, J=8.48, 5.09 Hz, 1 H), 6.59 (dd, J=8.10, 1.32 Hz, 1 H), 6.51 (d, J=1.70 Hz, 1 H), 4.53 (m, 2 H), 4.13 (m, 1 H), 3.54 (s, 3 H), 3.43 (m, 2 H), 2.07 (m, 2 H); MS (ES) m/z: 352 (M+H$^+$).

23° C. for 18 h, diluted with EtOAc (10 mL), then filtered through Celite and concentrated. The product was purified by column chromatography (SiO$_2$) to give Compound 67a (40 mg, 68%) as a yellow solid. $^1$H NMR (300 MHz, CDCl$_3$) δ 8.36 (d, J=3.20, 1.32 Hz, 1 H), 8.11 (s, 1 H), 8.05 (s, 1 H), 7.85 (s, H), 7.63 (m, 4 H), 7.36 (m, 8 H), 7.02 (dd, J=7.91, 4.71 Hz, 1 H), 6.32 (d, J=1.32 Hz, 1 H), 4.57 (m, 2 H), 3.72 (m, 2 H), 2.19 (m, 2 H), 1.08 (s, 9 H); MS (ES) m/z: 576 (M+H$^+$).

To a solution of 67a (39 mg, 0.064 mmol) in THF (1 mL) was added TBAF (1 M solution in THF, 1.5 eq) dropwise under nitrogen. After 18 hours, the mixture was concentrated and purified by column chromatography (SiO$_2$) to give Compound 67 (20 mg, 87%) as an orange solid. $^1$H NMR (300 MHz, Acetone-d$_6$) δ 8.34 (d, J=4.52, 1.51 Hz, 1 H), 8.16 (m, 1 H), 8.01 (s, 1 H), 7.53 (m, H), 7.11 (dd, J=8.10, 4.71 Hz, 1 H), 6.47 (dd, J=2.07, 0.75 Hz, 1 H), 4.56 (m, 2 H), 3.59 (m, 2 H), 2.13 (m, 2 H); MS (ES) m/z: 338 (M+H$^+$).

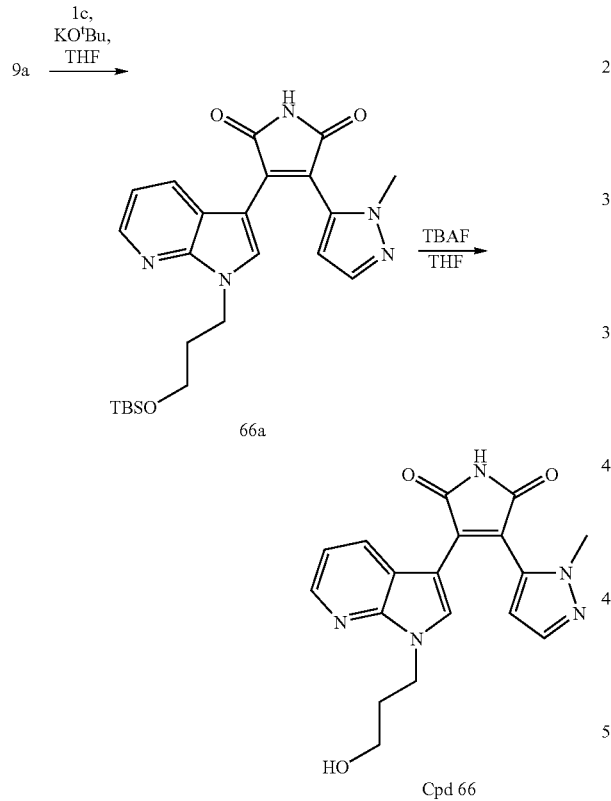

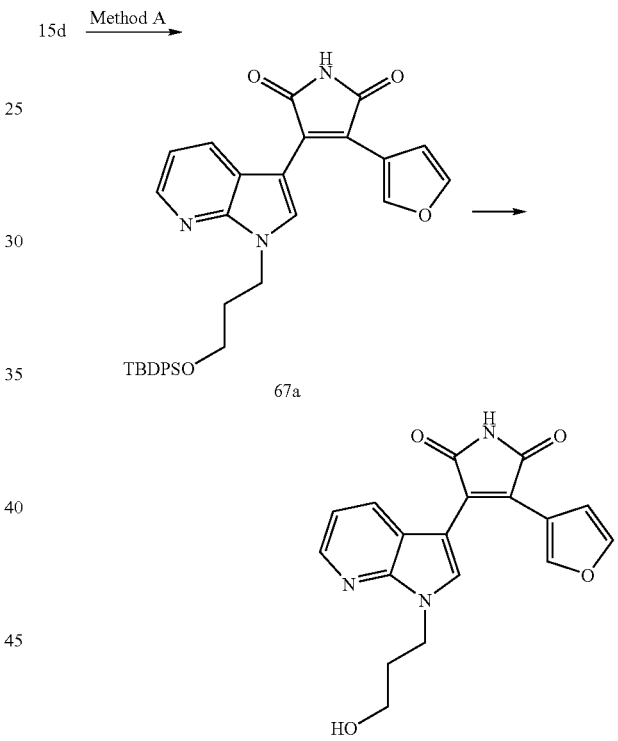

EXAMPLE 51

3-Furan-3-yl-4-[1-(3-hydroxy-propyl)-1H-pyrrolo[2,3-b]pyridin-3-yl]-pyrrole-2,5-dione (Compound 67)

The boronic acid derivative (0.032 mL, 0.2 mmol) was added to a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (0.054 g, 0.1 mmol), Pd$_2$(dba)$_3$ (5 mg, 0.005 mmol), Pd($^t$Bu$_3$P)$_2$ (5 mg, 0.01 mmol) and potassium fluoride (20 mg, 0.34 mmol) in THF (1 mL) at 23° C. under nitrogen. The reaction mixture was stirred at

EXAMPLE 52

5-{4-[1-(3-Hydroxy-propyl)-1H-pyrrolo[2,3-b]pyridin-3-yl]-2,5-dioxo-2,5-dihydro-1H-pyrrol-3-yl}-1H-pyrimidine-2,4-dione (Compound 68)

To a solution of 40 (14 mg, 0.034 mmol) in MeOH (1 mL) at room temperature was added HCl (2 M in Et$_2$O, 2 eq) and the mixture was stirred at 60° C. for 180 minutes. After concentration and vacuum drying, 68 was obtained as a yellow solid (10 mg, 77%); $^1$H NMR (300 MHz, DMSO-d$_6$) δ 11.40 (d, J=5.65 Hz, 1 H), 11.13 (s, 1 H), 11.06 (s, 1 H), 8.29 (d, J=3.96 Hz, 1 H), 8.09 (s, 1 H), 7.74 (dd, J=11.87, 8.29 Hz, 2 H), 7.13 (dd, J=7.91, 4.71 Hz, 1 H), 4.40 (m, 2 H), 3.39 (m, 2 H), 1.95 (m, 2 H); MS (ES) m/z: 382 (M+H$^+$).

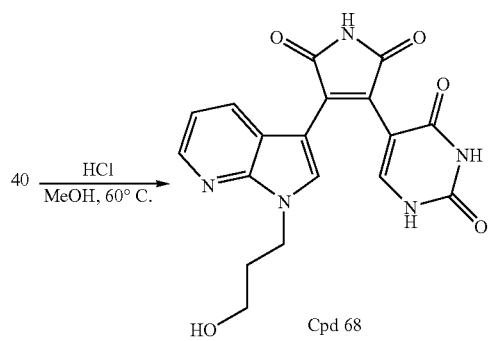

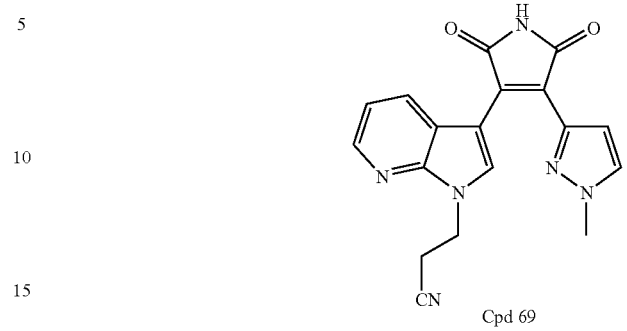

EXAMPLE 53

3-{3-[4-(1-Methyl-1H-pyrazol-3-yl)-2,5-dioxo-2,5-dihydro-1H-pyrrol-3-yl]-pyrrolo[2,3-b]pyridin-1-yl}-propionitrile (Compound 69)

To a solution of the amide 15a (125 mg, 0.58 mmol) in DMF (5 mL) was added $Cs_2CO_3$ (3 eq) and 2-cyano-ethyl bromide (1.5 eq). The reaction was heated at 80° C. for 2 hours. After cooling down, the solution was filtered through celite and then concentrated and the crude product was carried through to the next step.

To a solution of the above crude intermediate in THF (10 mL) at 0° C. was added $(CO_2Et)_2$ (2 eq), and then $^tBuOK$ (2 eq, 1 M in THF) was added dropwise. After stirring for 1 hour, the solution was concentrated and the crude product was carried through to the next step.

To a solution of the above intermediate in DMF and $CH_2Cl_2$ (1:1) was added $(COCl)_2$ (3 eq) dropwise at room temperature. The reaction was followed by TLC until starting material disappeared. $NaHCO_3$ solution was added and the aqueous layer was discarded. The organic layer was washed with water, dried, concentrated and the crude product was carried through to the next step.

To a solution of the above intermediate and $Pd(^tBu_3P)_2$ (0.1 eq) in THF (3 mL) was added the stannane derivative (2 eq) at 23° C. under nitrogen. The reaction mixture was refluxed for 18 h. Upon cooling, the mixture was diluted with EtOAc (10 mL) and washed with $H_2O$, KF, brine and dried. After concentration, the crude product was purified by column chromatography ($SiO_2$) to give Compound 69 (20 mg, 10% for the total yield of 4 steps). $^1H$ NMR (300 MHz, $CD_3OD$) δ 8.37 (s, 1 H), 8.28 (dd, J=4.71, 1.51 Hz, 1 H), 7.67 (d, J=2.26 Hz, 1 H), 7.14 (dd, J=7.91, 1.51 Hz, 1 H), 7.02 (dd, J=7.91, 4.71 Hz, 1 H), 6.68 (d, J=2.26 Hz, 1 H), 4.69 (m, 2 H), 3.81 (s, 3 H), 3.13 (m, 2 H); MS (ES) m/z: 345 (M−H$^+$).

EXAMPLE 54

3-Butyl-4-[1-(3-hydroxy-propyl)-1H-pyrrolo[2,3-b]pyridin-3-yl]-pyrrole-2,5-dione (Compound 70)

To a solution of 3-{1-[3-(tert-butyldiphenylsilanyloxy)-propyl]-1H-pyrrolo[2,3-b]pyridin-3-yl}-4-chloro-pyrrole-2,5-dione Compound 15d (0.96 g, 1.77 mmol) and $Pd(^tBu_3P)_2$ (0.1 eq) in THF (1 mL) was added boronic acid derivative (2 eq) at 23° C. under nitrogen. The reaction mixture was refluxed at 90° C. for 18 h. Upon cooling, the mixture was diluted with EtOAc (10 mL), then filtered through Celite and concentrated. The product was purified by column chromatography ($SiO_2$) to give Compound 70a (0.3 g, 30%) as a yellow solid. $^1H$ NMR (300 MHz, $CDCl_3$) δ 8.38 (dd, J=3.29, 0.91 Hz, 1 H), 8.03 (dd, J=8.05, 1.10 Hz, 1 H), 7.65 (m, 1 H), 7.39 (m, 1 H), 7.16 (dd, J=7.87, 4.57 Hz, 1 H), 4.55 (m, 2 H), 3.71 (m, 2 H), 2.62 (m, 2 H), 2.14 (s, 2 H), 1.60 (m, 2 H), 1.35 (m, 2 H), 1.09 (s, 9 H), 0.88 (t, J=7.32 Hz, 3 H); MS (ES) m/z: 566 (M+H$^+$).

To a solution of 70a (50 mg, 0.088 mmol) in THF (1 mL) was added TBAF (1 M solution in THF, 1.5 eq) dropwise under nitrogen. After 18 hours, the mixture was concentrated and purified by column chromatography ($SiO_2$) to give Compound 70 (20 mg, 69%) as an orange solid. $^1H$ NMR (300 MHz, $CDCl_3$) δ 8.35 (d, J=4.57 Hz, 1 H), 8.06 (d, J=8.05, 1 H), 7.65 (s, 1 H), 7.21 (dd, J=8.05, 4.76 Hz, 1 H), 4.51 (m, 2 H), 3.47 (m, 2 H), 2.64 (m, 2 H), 2.04 (m, 2 H), 1.62 (m, 2 H), 1.37 (m, 2 H), 0.88 (t, J=7.32 Hz, 3 H); MS (ES) m/z: 328 (M+H$^+$).

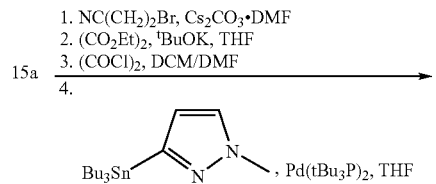

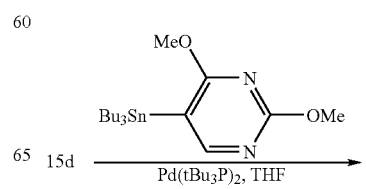

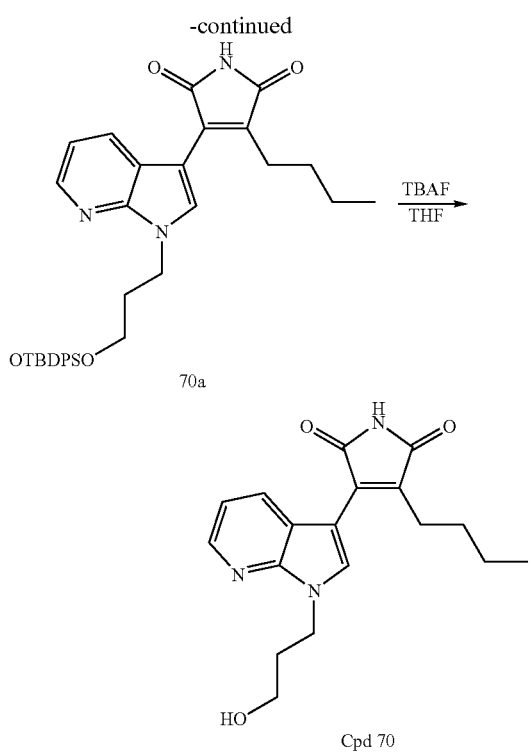

EXAMPLE 55

3-(2,4-Dimethoxy-pyrimidin-5-yl)-4-[1-(2-methoxy-ethyl)-1H-pyrrolo[2,3-b]pyridin-3-yl]-pyrrole-2,5-dione (Compound 71)

To a solution of the amide 15a (0.25 g, 1.42 mmol) in DMF (5 mL) was added, $Cs_2CO_3$ (3 eq) and 2-methoxy-ethyl bromide (1.5 eq). The reaction was heated at 80° C. for 2 hours. After cooling down, the solution was filtered through celite and then concentrated and the crude product was carried through to the next step.

To a solution of the above crude intermediate in THF (10 mL) at 0° C. was added $(CO_2Et)_2$ (2 eq), and then $^tBuOK$ (2 eq, 1 M in THF) was added dropwise. After stirring for 1 hour, the solution was concentrated and the crude product was carried through to the next step.

To a solution of the above intermediate in DMF and $CH_2Cl_2$ (1:1) was added $(COCl)_2$ (3 eq) dropwise at room temperature. The reaction was followed by TLC until the starting material disappeared. $NaHCO_3$ solution was added and the aqueous layer was discarded. The organic layer was washed with water, dried, concentrated and purified by column chromatography to get compound 71a (0.2 g, total yield 46% for the 3 steps). $^1$H NMR (300 MHz, $CD_3OD$) δ 8.49 (dd, J=8.10, 1.51 Hz, 1 H), 8.41 (dd, J=4.71, 1.51 Hz, 1 H), 8.29 (s, 1 H), 7.47 (s, 1 H), 7.22 (dd, J=8.10, 4.71 Hz, 1 H), 4.57 (m, 2 H), 3.78 (m, 2 H), 3.36 (s, 3 H); MS (ES) m/z: 306 (M+H$^+$).

To a solution of 71a (20 mg, 0.065 mmol) and Pd($^tBu_3P$)$_2$ (0.1 eq) in THF (3 mL) was added the stannane derivative (2 eq) at 23° C. under nitrogen. The reaction mixture was refluxed for 18 h. Upon cooling, the mixture was diluted with EtOAc (10 mL) and washed with $H_2O$, KF, brine and dried. After concentration, the crude product was purified by column chromatography ($SiO_2$) to give Compound 71 (8 mg, 30%). $^1$H NMR (300 MHz, $CD_3OD$) δ 8.50 (s, 1 H), 8.29 (dd, J=4.57, 0.91 Hz, 1 H), 8.10 (s, 1 H), 7.83 (s, 1 H), 7.13 (dd, J=7.87, 1.10 Hz, 1 H), 6.92 (dd, J=8.05, 4.76 Hz, 1 H), 4.54 (m, 2 H), 4.05 (s, 3 H), 3.78 (m, 2 H), 3.45 (s, 3 H), 3.33 (s, 3 H); MS (ES) m/z: 410 (M+H$^+$).

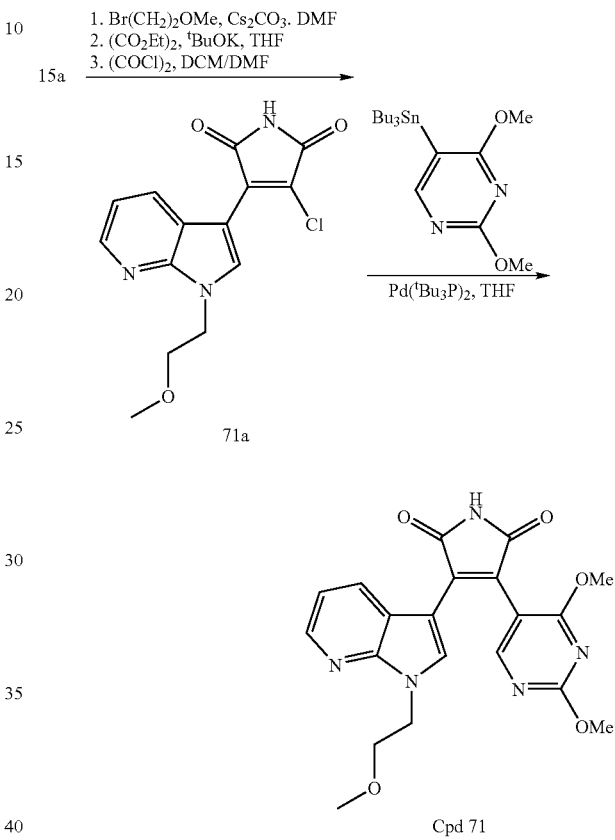

EXAMPLE 56

3-(1-Benzyl-1H-pyrrolo[2,3-b]pyridin-3-yl)-4-(2,4-dimethoxy-pyrimidin-5-yl)-pyrrole-2,5-dione (Compound 72)

A solution EtMgBr (26.6 mL, 3 M in $Et_2O$) was added dropwise under argon to a well-stirred solution of 7-azaindole (9 g, 76 mmol) in dry toluene (270 mL) at room temperature. After 1 h, a solution of the dichloromaleimide (4.5 g, 38 mmol) in toluene (240 mL) was slowly added. After 15 min, anhydrous $CH_2Cl_2$ (300 mL) was added and the reaction mixture was heated at 50° C. for 24 h. Hydrolysis was performed by a saturated solution of $NH_4Cl$ till pH 7. After extraction with EtOAc (2×400 mL), the combined organic layers were dried over $MgSO_4$, filtered and the solvent was removed under reduced pressure. Compound 72a was precipitated from methanol, filtered, washed with methanol and dried under vacuum. Compound 72a was obtained as an orange solid (2.12 g, 21%). $^1$H NMR (300 MHz, DMSO-$d_6$) δ 12.71 (s, 1 H), 8.34 (m, 2 H), 8.21 (s, 2 H), 7.21 (m, 1 H), 2.98 (s, 3 H); MS (ES) m/z: 262 (M+H$^+$).

To a solution of 72a (125 mg, 0.478 mmol) in anhydrous DMF (7 mL) was added NaH (1 eq, 60% dispersion in oil) under $N_2$. After stirring 10 minutes, the bromide (3 eq) was added and the reaction mixture was stirred at room temperature for 20 minutes. Water was added and the solution was extracted with EtOAc (3 times). The organic layers were combined, dried and concentrated. The product was purified by column chromatography to give 72b (127 mg, 76%) as a yellow solid. $^1$H NMR (300 MHz, $CDCl_3$) δ 8.50 (dd, J=8.1, 1.5 Hz, 1 H), 8.44 (dd, J=4.7, 1.5 Hz, 1 H), 8.14 (s, 1 H), 7.32–7.28 (m, 5 H), 7.26–7.21 (m, 1 H), 5.58 (s, 2 H), 3.14 (s, 3 H); MS (ES) m/z: 352 (M+H$^+$).

Compound 72b (51 mg, 0.145 mmol), $Pd_2(dba)_3$ (0.1 eq), organo-tin compound (1.5 eq) and P($^t$Bu)$_3$ (0.6 eq) was mixed in anhydrous THF and DMF (10:1 by volume). The mixture was sealed in a tube and microwaved for 350 seconds at 200° C. After concentration, the product was purified by column chromatography to give 72c (47 mg, 71%). $^1$H NMR (300 MHz, $CDCl_3$) δ 8.49 (s, 1 H), 8.32 (dd, J=4.7, 1.5 Hz, 1 H), 8.02 (s, 1 H), 7.32–7.29 (m, 5 H), 7.09 (dd, J=8.0, 1.5 Hz, 1 H), 6.93–6.89 (m, 1 H), 5.55 (s, 2 H), 4.04 (s, 3 H), 3.34 (s, 3 H), 3.14 (s, 3 H); MS (ES) m/z: 456 (M+H$^+$).

To a solution of 72c (47 mg, 0.1 mmol) in EtOH (2 mL) was added KOH aqueous solution (10 N, ~70 eq) and the reaction was stirred for 2 hours. Water (5 mL) was added and the mixture was acidified with 10% citric acid. After extraction with $CH_2Cl_2$ (3 times), the organic layers were dried and concentrated to give the crude product (46 mg).

To the above intermediate (46 mg) in anhydrous DMF (1.5 mL) was added HMDS (10 eq) in 0.8 mL MeOH. The reaction was heated at 80° C. for 2 hours then cooled slowly. After concentration, the product was purified by column chromatography to give 72 (12 mg, 26% for two steps). $^1$H NMR (300 MHz, $CDCl_3$) δ 8.50 (s, 1 H), 8.33 (dd, J=4.7, 1.5 Hz, 1 H), 8.02 (s, 1 H), 7.46 (s, 1 H), 7.33–7.29 (m, 5 H), 7.09 (dd, J=8.0, 1.5 Hz, 1 H), 6.94–6.90 (m, 1 H), 5.56 (s, 2 H), 4.04 (s, 3 H), 3.34 (s, 3 H); MS (ES) m/z: 442 (M+H$^+$).

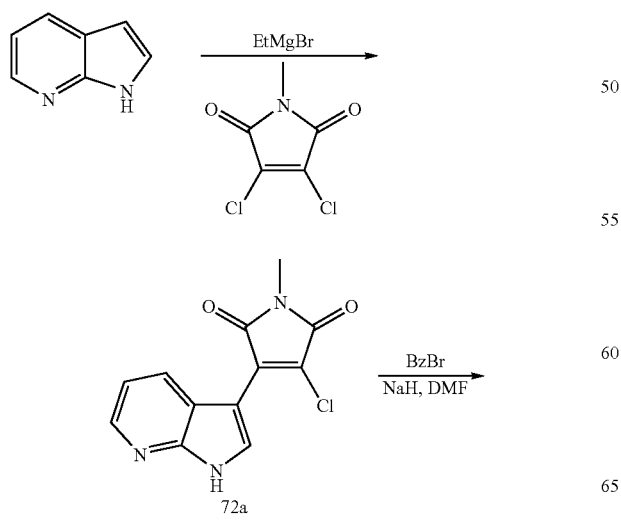

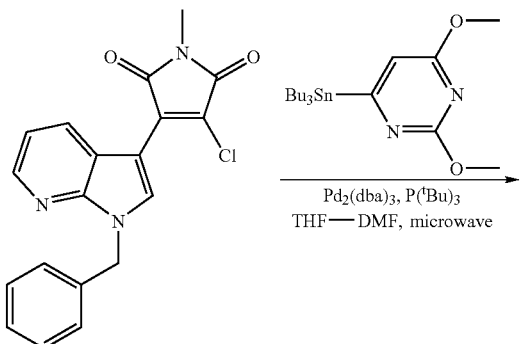

72b

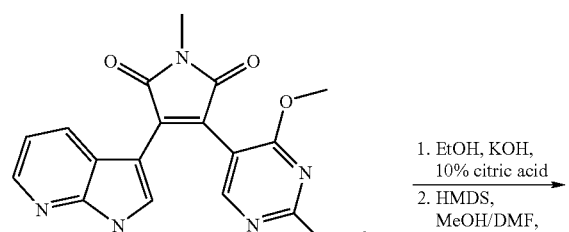

72c

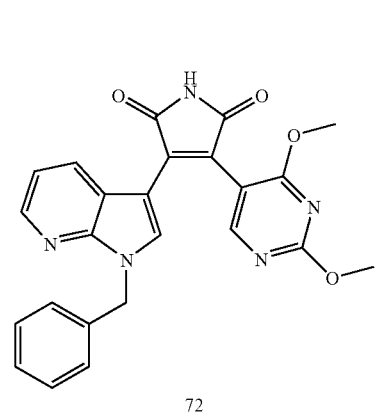

72

EXAMPLE 57

3-(2,4-Dimethoxy-pyrimidin-5-yl)-4-(1-phenethyl-1H-pyrrolo[2,3-b]pyridin-3-yl)-pyrrole-2,5-dione (Compound 73)

To a solution of 72a (250 mg, 0.96 mmol) in anhydrous DMF (15 mL) was added NaH (5 eq, 60% dispersion in oil) under $N_2$. After stirring 10 minutes, the bromide (2 eq) was added and the reaction mixture was heated at 70° C. for 90 minutes. Water (15 mL) was added at 20° C. followed by EtOAc (50 mL). The aqueous layer was acidified with 1 N HCl then extracted with EtOAc (3 times). The organic layers were combined, dried and concentrated. The product was purified by column chromatography to give 73a (37 mg, 11%). ¹H NMR (300 MHz, CDCl₃) δ 8.51 (dd, J=8.1, 1.5 Hz, 1 H), 8.43 (dd, J=4.7, 1.5 Hz, 1 H), 7.90 (s, 1 H), 7.26–7.20 (m, 3 H), 7.14–7.06 (m, 3 H), 4.62 (t, J=7.2 Hz, 2 H), 3.22 (t, J=7.2 Hz, 2 H), 3.14 (s, 3 H); MS (ES) m/z: 366 (M+H⁺).

Compound 73a (38 mg, 0.1 mmol), Pd₂(dba)₃ (0.1 eq), organo-tin compound (1.5 eq) and P(ᵗBu)₃ (0.6 eq) were mixed in anhydrous THF and DMF (10:1 by volume). The mixture was sealed in a tube and microwaved for 350 seconds at 200° C. After concentration, the product was purified by column chromatography to give 73b (27 mg, 55%). ¹H NMR (300 MHz, CDCl₃) δ 8.46 (s, 1 H), 8.31 (dd, J=4.7, 1.5 Hz, 1 H), 7.91 (s, 1 H), 7.31–7.23 (m, 3 H), 7.18–7.15 (m, 2 H), 7.01 (dd, J=8.0, 1.5 Hz, 1 H), 6.91–6.87 (m, 1 H), 4.62 (t, J=7.3 Hz, 2 H), 4.07 (s, 3 H), 3.44 (s, 3 H), 3.24 (t, J=7.1 Hz, 2 H); MS (ES) m/z: 470 (M+H⁺).

To a solution of 73b (27 mg, 0.058 mmol) in EtOH (2 mL) was added KOH aqueous solution (10 N, ~70 eq) and the reaction was stirred for 2 hours. Water (5 mL) was added and the mixture was acidified with 10% citric acid. After extraction with CH₂Cl₂ (3 times), the organic layers were dried and concentrated to give the crude product (23 mg).

To the above intermediate (23 mg) in anhydrous DMF (1.5 mL) was added HMDS (10 eq) in 0.8 mL MeOH. The reaction was heated at 80° C. for 2 hours then cooled slowly. The solvent was removed and the residue was purified by column chromatography to give product 73 (9.2 mg, 35% for both steps). ¹H NMR (300 MHz, CDCl₃) δ 8.52 (s, 1 H), 8.35 (dd, J=4.7, 1.5 Hz, 1 H), 7.98 (s, 1 H), 7.28–7.23 (m, 3 H), 7.14–7.12 (m, 2 H), 6.99–6.95 (m, 2 H), 4.64 (t, J=7.2 Hz, 2 H), 4.05 (s, 3 H), 3.41 (s, 3 H), 3.24 (t, J=7.2 Hz, 2 H); MS (ES) m/z: 456 (M+H⁺).

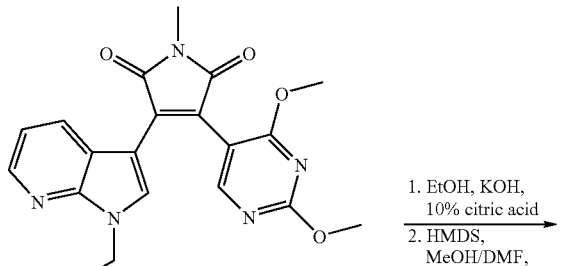

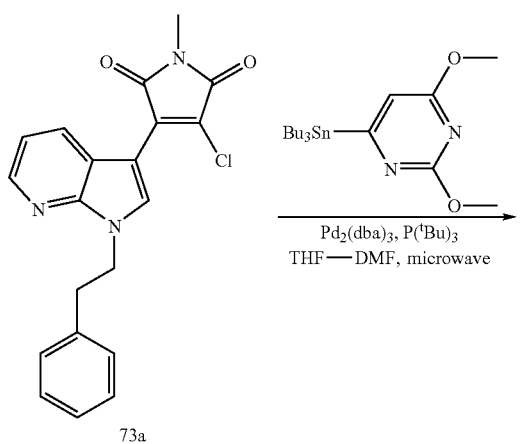

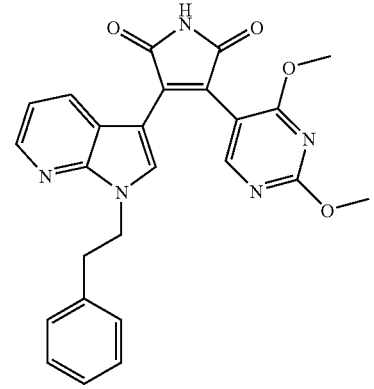

EXAMPLE 58

3-(2,4-Dimethoxy-pyrimidin-5-yl)-4-[1-(3-thiophen-2-yl-propyl)-1H-pyrrolo[2,3-b]pyridin-3-yl]-pyrrole-2,5-dione (Compound 74)

To a solution of 72a (50 mg, 0.19 mmol) in anhydrous CH₃CN (5 mL) was added K₂CO₃ (4 eq) under N₂. The reaction mixture turned red. After stirring 10 minutes the bromide (2 eq) was added and the reaction mixture was heated at 70° C. for 3 hours. Water was added at 20° C. and the solution was extracted with EtOAc (3 times). The organic layers were combined, dried and concentrated. The product was purified by column chromatography to give 74a (25 mg, 34%) as a yellow solid. ¹H NMR (300 MHz, CDCl₃) δ 8.50 (dd, J=8.1, 1.3 Hz, 1 H), 8.42 (d, J=4.4 Hz, 1 H), 8.16 (s, 1 H), 7.22–7.20 (m, 1 H), 7.14 (dd, J=5.1, 1.0 Hz, 1 H), 6.93 (m, 1 H), 6.84 (s, 1 H), 4.44 (t, J=7.0 Hz, 2 H), 3.16 (s, 3 H), 2.91 (t, J=7.4 Hz, 2 H), 2.35 (m, 2 H); MS (ES) m/z: 386 (M+H⁺).

Compound 74a (39 mg, 0.1 mmol), Pd₂(dba)₃ (0.1 eq), organo-tin compound (1.5 eq) and P(ᵗBu)₃ (0.6 eq) were mixed in anhydrous THF and DMF (10:1 by volume). The mixture was sealed in a tube and microwaved for 350 seconds at 200° C. After cooling down and concentration, the product was purified by column chromatography to give 74b (28 mg, 57%). $^1$H NMR (300 MHz, CDCl$_3$) δ 8.49 (s, 1 H), 8.42 (dd, J=8.1, 1.3 Hz, 1 H), 8.29 (d, J=4.4 Hz, 1 H), 8.09 (s, 1 H), 7.18–7.13 (m, 1 H), 7.07 (dd, J=5.1, 1.0 Hz, 1 H), 6.92 (m, 1 H), 6.84 (s, 1 H), 4.42 (t, J=7.0 Hz, 2 H), 4.04 (s, 3 H), 3.44 (s, 3 H), 3.17 (s, 3 H), 2.89 (t, J=7.4 Hz, 2 H), 2.33 (m, 2 H); MS (ES) m/z: 490 (M+H$^+$).

To a solution of 74b (25 mg, 0.05 mmol) in EtOH (2 mL) was added KOH aqueous solution (10 N, ~70 eq) and the reaction was stirred for 2 hours. Water (5 mL) was added and the mixture was acidified with 10% citric acid. After extraction with CH$_2$Cl$_2$ (3 times), the organic layers were dried and concentrated to give the crude product (24 mg).

To the above intermediate (24 mg) in anhydrous DMF (1.5 mL) was added HMDS (10 eq) in 0.8 mL MeOH. The reaction was heated at 80° C. for 2 hours then cooled down slowly. The solvent was removed and the residue was purified by flash column to give product 74 (6 mg, 25% for both steps). $^1$H NMR (300 MHz, CDCl$_3$) δ 8.52 (s, 1 H), 8.42 (dd, J=8.1, 1.3 Hz, 1 H), 8.31 (d, J=4.4 Hz, 1 H), 8.11 (s, 1 H), 7.18–7.16 (m, 1 H), 7.07 (dd, J=7.8, 1.5 Hz, 1 H), 6.95 (m, 1 H), 6.86 (s, 1 H), 4.44 (t, J=7.0 Hz, 2 H), 4.06 (s, 3 H), 3.46 (s, 3 H), 2.91 (t, J=7.6 Hz, 2 H), 2.36 (m, 2 H); MS (ES) m/z: 476 (M+H$^+$).

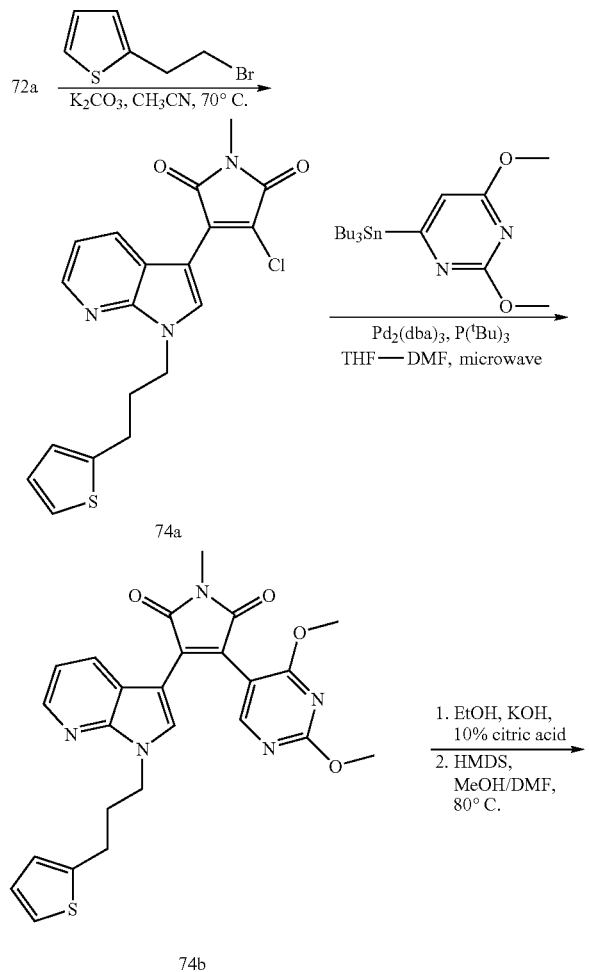

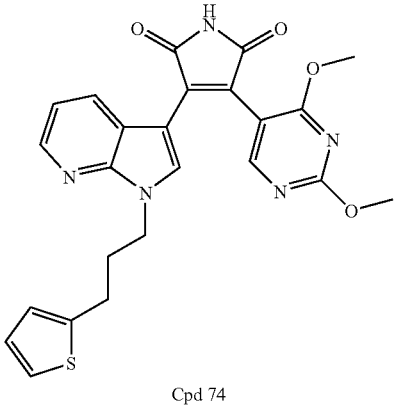

Cpd 74

EXAMPLE 59

3-(2,4-Dimethoxy-pyrimidin-5-yl)-4-{1-[2-(4-fluoro-phenoxy)-ethyl]-1H-pyrrolo[2,3-b]pyridin-3-yl}-pyrrole-2,5-dione (Compound 75)

To a solution of 72a (50 mg, 0.19 mmol) in anhydrous CH$_3$CN (5 mL) was added K$_2$CO$_3$ (4 eq) under N$_2$. The reaction mixture turned red. After stirring 10 minutes the bromide (2 eq) was added and the reaction mixture was heated at 70° C. for 3 hours. Water was added at 20° C. and the solution was extracted with EtOAc (3 times). The organic layers were combined and dried. After concentration, the product was purified by column chromatography to give 75a (26 mg, 34%) as a yellow solid. $^1$H NMR (300 MHz, CDCl$_3$) δ 8.49 (dd, J=8.1 Hz, 1.5 Hz, 1 H), 8.40 (dd, J=4.7, 1.5 Hz, 1 H), 8.35 (s, 1 H), 7.24–7.20 (m, 1 H), 6.98–6.95 (m, 2 H), 6.94–6.90 (m, 2 H), 4.77 (t, J=5.0 Hz, 2 H), 4.33 (t, J=5.0 Hz, 2 H), 3.16 (s, 3 H); MS (ES) m/z: 400 (M+H$^+$).

Compound 75a (50 mg, 0.125 mmol), Pd$_2$(dba)$_3$ (0.1 eq), organo-tin compound (1.5 eq) and P($^t$Bu)$_3$ (0.6 eq) were mixed in anhydrous THF and DMF (10:1 by volume). The mixture was sealed in a tube and microwaved for 350 seconds at 200° C. After concentration, the residue was purified by flash chromatography to get pure product 75b (20 mg, 32%). $^1$H NMR (300 MHz, CDCl$_3$) δ 8.50 (s, 1 H), 8.30 (dd, J=4.7, 1.5 Hz, 1 H), 8.24 (s, 1 H), 7.10 (dd, J=7.9, 1.5 Hz, 1 H), 6.99–6.90 (m, 3 H), 6.86–6.82 (m, 2 H), 4.77 (t, J=5.1 Hz, 2 H), 4.35 (t, J=5.0 Hz, 2 H), 4.05 (s, 3 H), 3.38 (s, 3 H), 3.20 (s, 3 H); MS (ES) m/z: 504 (M+H$^+$).

To a solution of 75b (20 mg, 0.04 mmol) in EtOH (2 mL) was added KOH aqueous solution (10 N, ~70 eq) and the reaction was stirred for 2 hours. Water (5 mL) was added and the mixture was acidified with 10% citric acid. After extraction with CH$_2$Cl$_2$ (3 times), the organic layers were dried and concentrated to give the crude product (19 mg).

To the above intermediate (19 mg) in anhydrous DMF (1.5 mL) was added HMDS (10 eq) in 0.8 mL MeOH. The reaction was heated at 80° C. for 2 hours then cooled slowly. The solvent was removed and the residue was purified by column chromatography to get product 75 (5 mg, 26% for both steps). $^1$H NMR (300 MHz, CDCl$_3$) δ 8.51 (s, 1 H), 8.30 (d, J=4.7, 1.5 Hz, 1 H), 8.24 (s, 1 H), 7.10 (dd, J=7.9, 1.5 Hz, 1 H), 6.96–6.93 (m, 3 H), 6.87–6.83 (m, 2 H), 4.77 (t, J=5.1 Hz, 2 H), 4.36 (t, J=5.0 Hz, 2 H), 4.05 (s, 3 H), 3.38 (s, 3 H), 3.20 (s, 3 H); MS (ES) m/z: 490 (M+H$^+$).

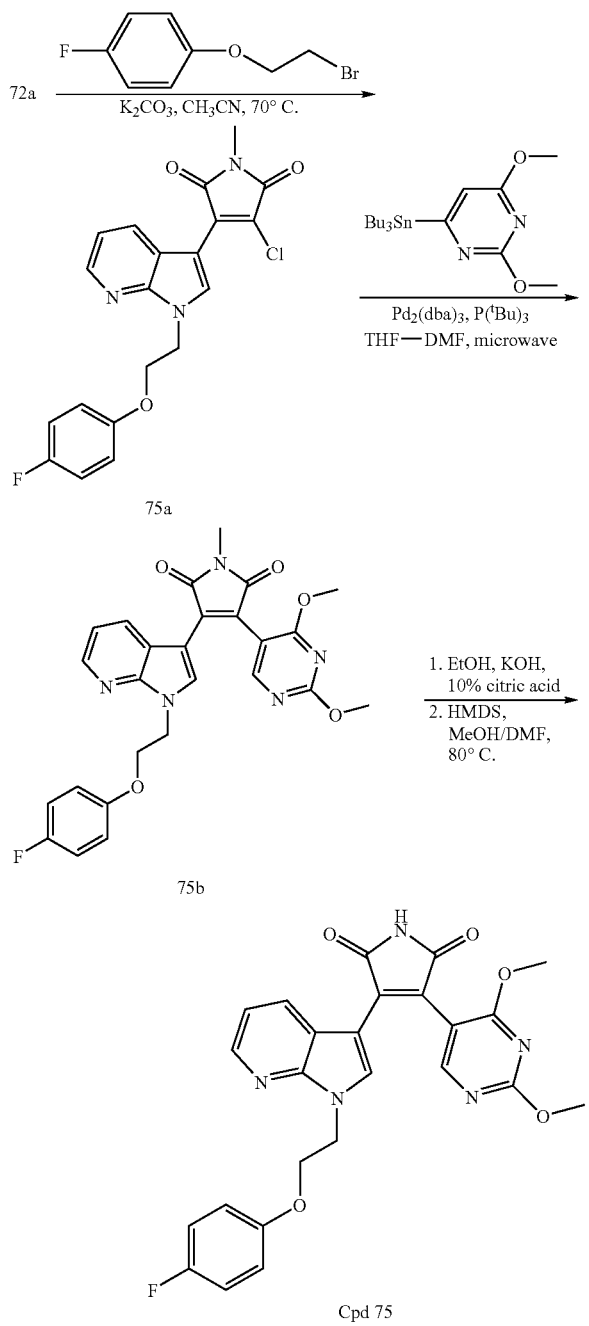

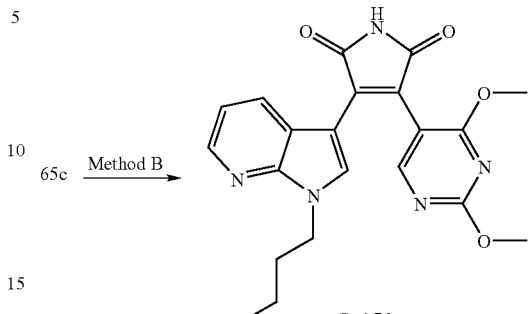

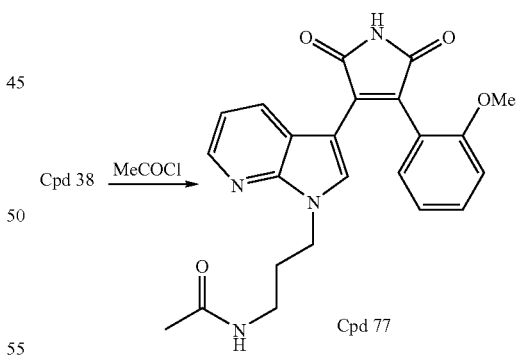

column chromatography (SiO$_2$) to give Compound 76 (9 mg, 23%). MS (ES) m/z: 486 (M+H$^+$).

EXAMPLE 61

N-[3-[3-[2,5-dihydro-4-(2-methoxyphenyl)-2,5-dioxo-1H-pyrrol-3-yl]-1H-pyrrolo[2,3-b]pyridin-1-yl]propyl]-acetamide (Compound 77)

A mixture of compound 38 (TFA salt) (577.8 mg, 0.95 mmol) in pyridine was cooled to 0° C., to which was added dropwise acetyl chloride (90 mg, 1.14 mmol). The mixture was stirred at 0° C. for 10 min, and then room temperature for 1 h. The reaction was quenched with sat'd NaHCO$_3$, extracted several times with EtOAc. The orgaic layers were combined, dried (Na$_2$SO$_4$) and concentrated to give the crude product, which was purified by flash chromatography on silica gel (CH$_2$Cl$_2$/MeOH/NH$_4$OH, from 99:1:0.1 to 97:3:0.3) to give 134 mg of Compound 77 as a yellow solid. Compound 77 was converted to its mesylate salt. $^1$H NMR (CD$_3$OD) δ 8.34 (m, 1 H), 8.22 (s, 1 H), 7.45 (m, 1 H), 7.39 (m, 1 H), 7.30 (m, 1 H), 7.06 (m, 3 H), 4.44 (t, J=6.9 Hz, 2 H), 3.42 (s, 3 H), 3.22 (t, J=6.7 Hz, 2 H), 2.11 (m, 2 H), 1.96 (s, 3 H). ES-MS m/z 419 (MH$^+$).

EXAMPLE 60

3-(2,4-Dimethoxy-pyrimidin-5-yl)-4-[1-(3-phenoxy-propyl)-1H-pyrrolo[2,3-b]pyridin-3-yl]-pyrrole-2,5-dione (Compound 76)

To a solution of 65c (30 mg, 0.079 mmol) and Pd($^t$Bu$_3$P)$_2$ (0.1 eq) in THF (3 mL) was added the stannane derivative (2 eq) at 23° C. under nitrogen. The reaction mixture was refluxed for 18 h. Upon cooling, the mixture was diluted with EtOAc (10 mL) and washed with H$_2$O, KF, brine and dried. After concentration, the crude product was purified by

EXAMPLE 62

N-[3-[3-[2,5-dihydro-4-(2-methoxyphenyl)-2,5-dioxo-1H-pyrrol-3-yl]-1H-pyrrolo[2,3-b]pyridin-1-yl]propyl]-formamide (Compound 78)

To a mixture of compound 38 (48.3 mg, 0.128 mmol) in DMF was added excess of butyl formate. The mixture was heated at 80° C. for 5 h. The solvent was evaporated and the residue was extracted with EtOAc. The organic layers were combined, washed with H₂O and brine, dried (Na₂SO₄) and concentrated to give the crude 78, which was then purified by flash chromatography on silica gel (CH₂Cl₂/MeOH/NH₄OH, from 99:1:0.1 to 97:3:0.3) to give 31 mg of Compound 78 as a yellow solid. $^1$H NMR (CDCl₃) δ 8.27 (s, 1H), 8.21 (dd, J=1.7, 4.5 Hz, 1 H), 8.12 (s, 1 H), 7.45 (m, 2 H), 7.04 (t, J=7.4 Hz, 1 H), 6.87 (d, J=8.2 Hz, 1 H), 6.75 (m, 2 H), 4.43 (t, J=2.4 Hz, 2 H), 3.38 (s, 3 H), 3.16 (dd, J=6.3, 12.2 Hz, 2 H), 2.10 (dd, J=6.3, 12.3 Hz, 2 H). ES-MS m/z 405 (MH⁺).

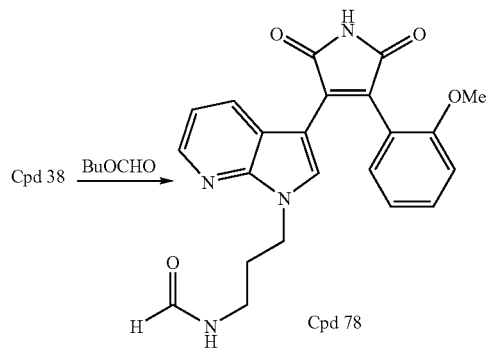

EXAMPLE 63

N-[3-[3-[2,5-dihydro-4-(2-methoxyphenyl)-2,5-dioxo-1H-pyrrol-3-yl]-1H-pyrrolo[2,3-b]pyridin-1-yl]propyl]-formamide (Compound 79)

To a mixture of compound 38 (21.2 mg, 0.056 mmol) in THF was added pyridine (13.3 mg, 0.168 mmol) and methanesufonic anhydride (19.6 mg, 0.113 mmol). The mixture was heated at 50° C. for 3 h. The solvent was evaporated and the residue was extracted with EtOAc. The organic layers were combined, washed with H₂O and brine, dried (Na₂SO₄) and concentrated to give the crude 79, which was then purified by flash chromatography on silica gel (CH₂Cl₂/MeOH/NH₄OH, from 99:1:0.1 to 97:3:0.3) to give 11.5 mg of Compound 79 as a yellow solid. $^1$H NMR (CD₃OD) δ 8.17 (m, 1 H), 8.15 (s, 1 H), 7.42 (t, J=7.9 Hz, 1 H), 7.33 (d, J=7.5 Hz, 1 H), 6.98 (t, J=8.9 Hz, 2 H), 6.76 (m, 2 H), 4.44 (t, J=6.8 Hz, 2 H), 3.36 (s, 3 H), 3.08 (t, J=6.7 Hz, 2 H), 2.91 (s, 3 H), 2.12 (m, 2 H). ES-MS m/z 455 (MH⁺).

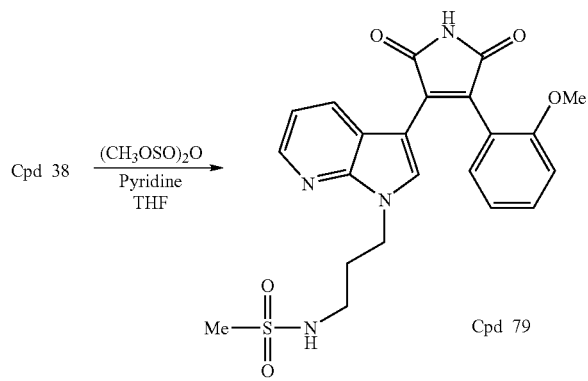

EXAMPLE 64

As a specific embodiment of an oral composition, 100 mg of Compound 4 prepared according to Example 4 is formulated with sufficient finely divided lactose to provide a total amount of 580 to 590 mg to fill a size O hard gel capsule.

Biological Experimental Examples

The utility of the compounds to treat kinase or dual-kinase mediated disorders (in particular, kinases selected from glycogen synthase kinase-3 and protein kinase C; and, more particularly, kinases selected from glycogen synthase kinase-3β, protein kinase C α, protein kinase C β-II, or protein kinase C γ) was determined using the following procedures.

Glycogen Synthase Kinase-3 Assay

Compounds were tested for the ability to inhibit recombinant rabbit GSK-3β protein using the following protocol. The test compound was added to a reaction mixture containing Protein Phosphatase Inhibitor-2 (PPI-2) (Calbiochem) (45 ng), rabbit GSK-3β protein (New England Biolabs) (0.75 units) and $^{33}$P-ATP (1 μCi) in 50 mM Tris-HCl (pH 8.0), 10 mM MgCl₂, 0.1% BSA, 1 mM DTT and 100 μM Sodium Vanadate. The mixture was reacted for 90 minutes at 30° C. to allow phosphorylation of the PPI-2 protein and then the protein in the reaction was precipitated using 10% TCA. The precipitated protein was collected on filter plates (MultiScreen-DV/Millipore), which were subsequently washed. Finally, the radioactivity was quantified using a TopCount Scintillation Counter (Packard). GSK-3 inhibitory compounds resulted in less phosphorylated PPI-2 and thus a lower radioactive signal in the precipitated protein. Staurosporine or Valproate, known inhibitors of GSK-3β, were used as a positive control for screening.

Protein Kinase C Histone-Based Assay

Compounds were evaluated for PKC isozyme selectivity using histone III as the substrate. PKC isozymes α, β-II or γ were added to a reaction mixture that contained 20 mM HEPES, (pH 7.4), 940 μM CaCl₂, 10 mM MgCl₂, 1 mM EGTA. 100 μg/mL phosphatidylserine, 20 μg/mL diacylglycerol, 30 μM ATP, 1 μCi [$^{33}$P]ATP and 200 μg/mL histone III. The reaction was incubated for 10 min at 30° C. Reactions were terminated by TCA precipitation and spotting on Whatman P81 filters. Filters were washed in 75 mM phosphoric acid and the radioactivity quantified by liquid scintillation counting.

Table 2 shows the biological activity in the GSK-3β and PKC (histone) assays as an IC₅₀ value (μM) or in % inhibition (data obtained on different days when two numbers are present) for representative compounds of the present invention.

TABLE 2

| | Biological Activity (IC₅₀ μM, or % inhibition) | | | |
|---|---|---|---|---|
| Cpd | GSK-3β | PKC-α | PKC-βII | PKC-γ |
| 1 | 0.009/0.010 | 18% @1 μM | 14% @1 μM | 48% @1 μM |
| | | 2% @10 μM | 81% @10 μM | 43% @10 μM |
| 2 | 0.019 | 0% @1 μM | 22% @1 μM | 46% @1 μM |
| | | 1% @10 μM | 50% @10 μM | 54% @10 μM |
| 3 | 0.030/0.031 | 0% @1 μM | 30% @1 μM | 20% @1 μM |
| | | 51% @10 μM | 89% @10 μM | 31% @10 μM |
| 4 | 51% @100 nM | 0% @1 μM | 47% @1 μM | 48% @1 μM |
| | | 34% @10 μM | 84% @10 μM | 59% @10 μM |
| 5 | 56% @400 nM | 0% @1 μM | 21% @1 μM | 44% @1 μM |
| | | 34% @10 μM | 81% @10 μM | 57% @10 μM |

TABLE 2-continued

Biological Activity (IC$_{50}$ μM, or % inhibition)

| Cpd | GSK-3β | PKC-α | PKC-βII | PKC-γ |
|---|---|---|---|---|
| 6 | 56% @100 nM | | | |
| 7 | 0.051 | | | |
| 8 | 0.003 | | | |
| 9 | 0.011 | | | |
| 10 | 0.010 | | | |
| 11 | 0.004 | | | |
| 13 | 0.036 | | | |
| 14 | 0.006 | | | |
| 15 | 0.006 | | | |
| 16 | 0.1 | | | |
| 17 | 19% @100 nM | | | |
| 18 | 29% @200 nM | | | |
| 19 | 25% @200 nM | | | |
| 20 | 21% @1 μM | 0.053 | 0.002 | 0.151 |
| 21 | 44% @1 μM | 1.44 | 0.036 | 0.859 |
| 22 | 0.33 | | | |
| 23 | 0.158/0.051 | | | |
| 24 | 0.015/0.008 | | | |
| 25 | 0.071/0.044 | | | |
| 26 | 0.07/0.12 | | | |
| 30 | 0.04/0.05 | | | |
| 32 | 0.067/0.095 | | | |
| 34 | 0.005/0.009 | 0.452 | 39% @1 μM | 43% @1 μM |
| 35 | 0.008/0.011 | 31% @10 μM | 35% @1 μM | 35% @10 μM |
| 36 | 0.067/0.067 | | | |
| 37 | 0.014/0.019 | 5.27 | 0.342 | 4.75 |
| 38 | 0.031/0.043 | 32% @1 μM | 26% @1 μM | 24% @1 μM |
| 39 | 0.023/0.016 | 41% @10 μM | 52% @1 μM | 41% @10 μM |
| 40 | 0.009/0.015 | | | |
| 41 | 0.037/0.042 | | | |
| 42 | 0.123/0.106 | | | |
| 43 | 0.198/0.126 | | | |
| 44 | 32% @1 μM/ 25% @1 μM | | | |
| 45 | 0.028/0.018 | | | |
| 46 | 0.038/0.037 | | | |
| 47 | 0.046/0.054 | | | |
| 48 | 0.047/0.038 | | | |
| 49 | 0.056/0.058 | | | |
| 50 | 0.088/0.107 | | | |
| 51 | 0.150/0.187 | | | |
| 52 | 0.179/0.212 | | | |
| 53 | 0.211/0.143 | | | |
| 54 | 0.232/0.161 | | | |
| 55 | 4% @1 μM/ 13% @1 μM | | | |
| 56 | 23% @1 μM/ 20% @1 μM | | | |
| 57 | 0.015/0.010 | | | |
| 58 | 0.366/0.344 | | | |
| 59 | 0.519/0.424 | | | |
| 60 | 0.625 | | | |
| 61 | 0.714/0.635 | | | |
| 62 | 0.036/0.035 | | | |
| 63 | 0.077/0.102 | | | |
| 64 | 0.077/0.128 | | | |
| 65 | 0.188/0.244 | | | |
| 66 | 0.48/0.66 | | | |
| 67 | 0.140/0.059 | | | |
| 68 | 43% @1 μM/ 40% @1 μM | | | |
| 69 | 0.1 | | | |
| 70 | 0.38 | | | |
| 71 | 0.36 | | | |
| 72 | 54% @1 μM | | | |
| 73 | 0.1 | | | |
| 74 | 39% @1 μM | | | |
| 75 | 0.24 | | | |
| 76 | 0.043/0.059 | | | |
| 77 | 0.002/0.003 | 26% @10 μM | 49% @1 μM | |
| 78 | 0.007/0.009 | 33% @10 μM | 21% @1 μM | 48% @10 μM |

The results from the foregoing indicate that a compound of the present invention would be expected to be useful in treating or ameliorating a kinase or dual-kinase mediated disorder.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

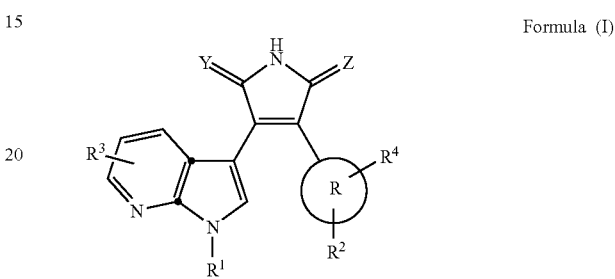

Formula (I)

wherein

R is a 6-membered heterocyclyl;

$R^1$ is selected from the group consisting of hydrogen, —$C_{1-8}$alkyl-$R^5$, —$C_{2-8}$alkenyl-$R^5$, —$C_{2-8}$alkynyl-$R^5$, —C(O)—($C_{1-8}$)alkyl-$R^9$, —C(O)-aryl-$R^8$, —C(O)—O—($C_{1-8}$)alkyl-$R^9$, —C(O)—O-aryl-$R^8$, —C(O)—NH($C_{1-8}$alkyl-$R^9$), —C(O)—NH(aryl-$R^8$), —C(O)—N($C_{1-8}$alkyl-$R^9$)$_2$, —$SO_2$—($C_{1-8}$)alkyl-$R^9$, —$SO_2$-aryl-$R^8$, -cycloalkyl-$R^6$, -heterocyclyl-$R^6$, -aryl-$R^6$ and -heteroaryl-$R^6$; wherein heterocyclyl and heteroaryl are attached to the azaindole nitrogen atom in the one position via a heterocyclyl or heteroaryl ring carbon atom;

$R^2$ is one substituent attached to a carbon or nitrogen atom selected from the group consisting of hydrogen, —$C_{1-8}$alkyl-$R^5$, —$C_{2-8}$alkenyl-$R^5$, —$C_{1-8}$alkynyl-$R^5$, —C(O)H, —C(O)—($C_{1-8}$)alkyl-$R^9$, —C(O)—NH$_2$, —C(O)—NH($C_{1-8}$alkyl-$R^9$), —C(O)—N($C_{1-8}$alkyl-$R^9$)$_2$, —C(O)—NH(aryl-$R^8$), —C(O)-cycloalkyl-$R^8$, —C(O)-heterocyclyl-$R^8$, —C(O)-aryl-$R^8$, —C(O)-heteroaryl-$R^8$, —$CO_2$H, —C(O)—O—($C_{1-8}$)alkyl-$R^9$, —C(O)—O-aryl-$R^8$, —$SO_2$—($C_{1-8}$)alkyl-$R^9$, —$SO_2$-aryl-$R^8$, -cycloalkyl-$R^6$, -aryl-$R^6$ and —($C_{1-8}$)alkyl-N—$R^7$;

with the proviso that, when $R^2$ is attached to a carbon atom, $R^2$ is further selected from the group consisting of —$C_{1-8}$alkoxy-$R^5$, —N—$R^7$, cyano, halogen, hydroxy, nitro, oxo, -heterocyclyl-$R^6$ and -heteroaryl-$R^6$;

$R^3$ is 1 to 3 substituents attached to a carbon atom independently selected from the group consisting of hydrogen, —$C_{1-8}$alkyl-$R^{10}$, —$C_{2-8}$alkenyl-$R^{10}$, —$C_{2-8}$alkynyl-$R^{10}$, —$C_{1-8}$alkoxy-$R^{10}$, —C(O)H, —C(O)—($C_{1-8}$)alkyl-$R^9$, —C(O)—NH$_2$, —C(O)—NH($C_{1-8}$alkyl-$R^9$), —C(O)—N($C_{1-8}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—NH$_2$, —$CO_2$H, —C(O)—O—($C_{1-8}$)alkyl-$R^9$, —C(O)—O-aryl-$R^8$, —$SO_2$-($C_{1-8}$)alkyl-$R^9$, —$SO_2$-aryl-$R^8$, —N—$R^7$, cyano, halogen, hydroxy, nitro, -cycloalkyl-$R^8$, -heterocyclyl-$R^8$, -aryl-$R^8$ and -heteroaryl-$R^8$;

R$^4$ is 1 to 4 substituents attached to a carbon atom independently selected from the group consisting of hydrogen, —C$_{1-8}$alkyl-R$^{10}$, —C$_{2-8}$alkenyl-R$^{10}$, —C$_{2-8}$alkynyl-R$^{10}$, —C$_{1-8}$alkoxy-R$^{10}$, —C(O)H, —C(O)—(C$_{1-8}$)alkyl-R$^9$, —C(O)—NH$_2$, —C(O)—NH(C$_{1-8}$alkyl-R$^9$), —C(O)—N(C$_{1-8}$alkyl-R$^9$)$_2$, —C(O)-cycloalkyl-R$^8$, —C(O)-heterocyclyl-R$^8$, —C(O)-aryl-R$^8$, —C(O)-heteroaryl-R$^8$, —C(NH)—NH$_2$, —CO$_2$H, —C(O)—O—(C$_{1-8}$)alkyl-R$^9$, —C(O)—O-aryl-R$^8$, —SH, —S—(C$_{1-8}$)alkyl-R$^{10}$, —SO$_2$—(C$_{1-8}$)alkyl-R$^9$, —SO$_2$-aryl-R$^8$, —SO$_2$—NH$_2$, —SO$_2$—NH(C$_{1-8}$alkyl-R$^9$), —SO$_2$—N(C$_{1-8}$alkyl-R$^9$)$_2$, —N—R$^7$, cyano, halogen, hydroxy, nitro, -cycloalkyl-R$^8$, -heterocyclyl-R$^8$, -aryl-R$^8$ and -heteroaryl-R$^8$;

R$^5$ is 1 to 2 substituents independently selected from the group consisting of hydrogen, —O—(C$_{1-8}$)alkyl, —O-aryl-R$^6$, —O—(C$_{1-8}$)alkyl-OH, —O—(C$_{1-8}$)alkyl-O—(C$_{1-8}$)alkyl, —O—(C$_{1-8}$)alkyl-NH$_2$, —O—(C$_{1-8}$)alkyl-NH(C$_{1-8}$alkyl), —O—(C$_{1-8}$)alkyl-N(C$_{1-8}$alkyl)$_2$, —O—(C$_{1-8}$)alkyl-S—(C$_{1-8}$)alkyl, —O—(C$_{1-8}$)alkyl-SO$_2$—(C$_{1-8}$)alkyl, —O—(C$_{1-8}$)alkyl-SO$_2$—NH$_2$, —O—(C$_{1-8}$)alkyl-SO$_2$—NH(C$_{1-8}$alkyl), —O—(C$_{1-8}$)alkyl-SO$_2$—N(C$_{1-8}$alkyl)$_2$, —O—C(O)H, —O—C(O)—(C$_{1-8}$)alkyl, —O—C(O)—NH$_2$, —O—C(O)—NH(C$_{1-8}$alkyl), —O—C(O)—N(C$_{1-8}$alkyl)$_2$, —O—(C$_{1-8}$)alkyl-C(O)H, —O—(C$_{1-8}$)alkyl-C(O)—(C$_{1-8}$)alkyl, —O—(C$_{1-8}$)alkyl-CO$_2$H, —O—(C$_{1-8}$)alkyl-C(O)—O—(C$_{1-8}$)alkyl, —O—(C$_{1-8}$)alkyl-C(O)—NH$_2$, —O—(C$_{1-8}$)alkyl-C(O)—NH(C$_{1-8}$alkyl), —O—(C$_{1-8}$)alkyl-C(O)—N(C$_{1-8}$alkyl)$_2$, —C(O)H, —C(O)—(C$_{1-8}$)alkyl, —CO$_2$H, —C(O)—O—(C$_{1-8}$)alkyl, —C(O)—NH$_2$, —C(NH)—NH$_2$, —C(O)—NH(C$_{1-8}$alkyl), —C(O)—N(C$_{1-8}$alkyl)$_2$, —SH, —S—(C$_{1-8}$)alkyl, —S—(C$_{1-8}$)alkyl-S—(C$_{1-8}$)alkyl, —S—(C$_{1-8}$)alkyl-O—(C$_{1-8}$)alkyl, —S—(C$_{1-8}$)alkyl-O—(C$_{1-8}$)alkyl-OH, —S—(C$_{1-8}$)alkyl-O—(C$_{1-8}$)alkyl-NH$_2$, —S—(C$_{1-8}$)alkyl-O—(C$_{1-8}$)alkyl-NH(C$_{1-8}$alkyl), —S—(C$_{1-8}$)alkyl-O—(C$_{1-8}$)alkyl-N(C$_{1-8}$alkyl)$_2$, —S—(C$_{1-8}$)alkyl-NH(C$_{1-8}$alkyl), —SO$_2$—(C$_{1-8}$)alkyl, —SO$_2$—NH$_2$, —SO$_2$—NH(C$_{1-8}$alkyl), —SO$_2$—N(C$_{1-8}$alkyl)$_2$, —N—R$^7$, cyano, (halo)$_{1-3}$, hydroxy, nitro, oxo, -cycloalkyl-R$^6$, -heterocyclyl-R$^6$, -aryl-R$^6$ and -heteroaryl-R$^6$;

R$^6$ is 1 to 4 substituents attached to a carbon or nitrogen atom independently selected from the group consisting of hydrogen, —C$_{1-8}$alkyl, —C$_{2-8}$alkenyl, —C$_{2-8}$alkynyl, —C(O)H, —C(O)—(C$_{1-8}$)alkyl, —CO$_2$H, —C(O)—O—(C$_{1-8}$)alkyl, —C(O)—NH$_2$, —C(NH)—NH$_2$, —C(O)—NH(C$_{1-8}$alkyl), —C(O)—N(C$_{1-8}$alkyl)$_2$, —SO$_2$—(C$_{1-8}$)alkyl, —SO$_2$—NH$_2$, —SO$_2$—NH(C$_{1-8}$alkyl), —SO$_2$—N(C$_{1-8}$alkyl)$_2$, —(C$_{1-8}$)alkyl-N—R$^7$, —(C$_{1-8}$)alkyl-(halo)$_{1-3}$, —(C$_{1-8}$)alkyl-OH, -aryl-R$^8$, —(C$_{1-8}$)alkyl-aryl-R$^8$ and —(C$_{1-8}$)alkyl-heteroaryl-R$^8$;

with the proviso that, when R$^6$ is attached to a carbon atom, R$^6$ is further selected from the group consisting of —C$_{1-8}$alkoxy, —(C$_{1-8}$)alkoxy-(halo)$_{1-3}$, —SH, —S—(C$_{1-8}$)alkyl, —N—R$^7$, cyano, halo, hydroxy, nitro, oxo and -heteroaryl-R$^8$;

R$^7$ is 2 substituents independently selected from the group consisting of hydrogen, —C$_{1-8}$alkyl, —C$_{2-8}$alkenyl, —C$_{2-8}$alkynyl, —(C$_{1-8}$)alkyl-OH, —(C$_{1-8}$)alkyl-O—(C$_{1-8}$)alkyl, —(C$_{1-8}$)alkyl-NH$_2$, —(C$_{1-8}$)alkyl-NH(C$_{1-8}$alkyl), —(C$_{1-8}$)alkyl-N(C$_{1-8}$alkyl)$_2$, —(C$_{1-8}$)alkyl-S—(C$_{1-8}$)alkyl, —C(O)H, —C(O)—(C$_{1-8}$)alkyl, —C(O)—O—(C$_{1-8}$)alkyl, —C(O)—NH$_2$, —C(O)—NH(C$_{1-8}$alkyl), —C(O)—N(C$_{1-8}$alkyl)$_2$, —SO$_2$—(C$_{1-8}$)alkyl, —SO$_2$—NH$_2$, —SO$_2$—NH(C$_{1-8}$alkyl), —SO$_2$—N(C$_{1-8}$ alkyl)$_2$, —C(N)—NH$_2$, -cycloalkyl-R$^8$, —(C$_{1-8}$)alkyl-heterocyclyl-R$^8$, -aryl-R$^8$, —(C$_{1-8}$)alkyl-aryl-R$^8$ and —(C$_{1-8}$)alkyl-heteroaryl-R$^8$;

R$^8$ is 1 to 4 substituents attached to a carbon or nitrogen atom independently selected from the group consisting of hydrogen, —C$_{1-8}$alkyl, —(C$_{1-8}$)alkyl-(halo)$_{1-3}$ and —(C$_{1-8}$)alkyl-OH;

with the proviso that, when R$^8$ is attached to a carbon atom, R$^8$ is further selected from the group consisting of —C$_{1-8}$alkoxy, —NH$_2$, —NH(C$_{1-8}$alkyl), —N(C$_{1-8}$ alkyl)$_2$, cyano, halo, —(C$_{1-8}$)alkoxy-(halo)$_{1-3}$, hydroxy and nitro;

R$^9$ is 1 to 2 substituents independently selected from the group consisting of hydrogen, —C$_{1-8}$alkoxy, —NH$_2$, —NH(C$_{1-8}$alkyl), —N(C$_{1-8}$alkyl)$_2$, cyano, (halo)$_{1-3}$, hydroxy and nitro;

R$^{10}$ is 1 to 2 substituents independently selected from the group consisting of hydrogen, —NH$_2$, —NH(C$_{1-8}$ alkyl), —N(C$_{1-8}$alkyl)$_2$, cyano, (halo)$_{1-3}$, hydroxy, nitro and oxo; and Y and Z is each O;

and pharmaceutically acceptable salts thereof.

2. The compound of claim 1 wherein R$^5$ is 1 to 2 substituents independently selected from the group consisting of hydrogen, —O—(C$_{1-4}$)alkyl, —O-aryl-R$^6$, —O—(C$_{1-4}$)alkyl-OH, —O—(C$_{1-4}$)alkyl-O—(C$_{1-4}$)alkyl, —O—(C$_{1-4}$)alkyl-NH$_2$, —O—(C$_{1-4}$)alkyl-NH(C$_{1-4}$alkyl), —O—(C$_{1-4}$)alkyl-N(C$_{1-4}$alkyl)$_2$, —O—(C$_{1-4}$)alkyl-S—(C$_{1-4}$)alkyl, —O—(C$_{1-4}$)alkyl-SO$_2$—(C$_{1-4}$)alkyl, —O—(C$_{1-4}$)alkyl-SO$_2$—NH$_2$, —O—(C$_{1-4}$)alkyl-SO$_2$—NH(C$_{1-4}$alkyl), —O—(C$_{1-4}$)alkyl-SO$_2$—N(C$_{1-4}$alkyl)$_2$, —O—C(O)H, —O—C(O)—(C$_{1-4}$)alkyl, —O—C(O)—NH$_2$, —O—C(O)—NH(C$_{1-4}$alkyl), —O—C(O)—N(C$_{1-4}$alkyl)$_2$, —O—(C$_{1-4}$)alkyl-C(O)H, —O—(C$_{1-4}$)alkyl-C(O)—(C$_{1-4}$)alkyl, —O—(C$_{1-4}$)alkyl-CO$_2$H, —O—(C$_{1-4}$)alkyl-C(O)—O—(C$_{1-4}$)alkyl, —O—(C$_{1-4}$)alkyl-C(O)—NH$_2$, —O—(C$_{1-4}$)alkyl-C(O)—NH(C$_{1-4}$alkyl), —O—(C$_{1-4}$)alkyl-C(O)—N(C$_{1-4}$alkyl)$_2$, —C(O)H, —C(O)—(C$_{1-4}$)alkyl, —CO$_2$H, —C(O)—O—(C$_{1-4}$)alkyl, —C(O)—NH$_2$, —C(NH)—NH$_2$, —C(O)—NH(C$_{1-4}$alkyl), —C(O)—N(C$_{1-4}$alkyl)$_2$, —SH, —S—(C$_{1-4}$)alkyl, —S—(C$_{1-4}$)alkyl-S—(C$_{1-4}$)alkyl, —S—(C$_{1-4}$)alkyl-O—(C$_{1-4}$)alkyl, —S—(C$_{1-4}$)alkyl-O—(C$_{1-4}$)alkyl-OH, —S—(C$_{1-4}$)alkyl-O—(C$_{1-4}$)alkyl-NH$_2$, —S—(C$_{1-4}$)alkyl-O—(C$_{1-4}$)alkyl-NH(C$_{1-4}$alkyl), —S—(C$_{1-4}$)alkyl-O—(C$_{1-4}$)alkyl-N(C$_{1-4}$alkyl)$_2$, —S—(C$_{1-4}$)alkyl-NH(C$_{1-4}$alkyl), —SO$_2$—(C$_{1-4}$)alkyl, —SO$_2$—NH$_2$, —SO$_2$—NH(C$_{1-4}$alkyl), —SO$_2$—N(C$_{1-4}$alkyl)$_2$, —N—R$^7$, cyano, (halo)$_{1-3}$, hydroxy, nitro, oxo, -cycloalkyl-R$^6$, -heterocyclyl-R$^6$, -aryl-R$^6$ and -heteroaryl-R$^6$.

3. The compound of claim 1 wherein R$^5$ is 1 to 2 substituents independently selected from the group consisting of hydrogen, —O—(C$_{1-4}$)alkyl, —O-aryl-R$^6$, —N—R$^7$, hydroxy, and -heteroaryl-R$^6$.

4. The compound of claim 1 wherein R$^5$ is 1 to 2 substituents independently selected from the group consisting of hydrogen, —O—(C$_{1-4}$)alkyl, —O-aryl-R$^6$, —N—R$^7$, hydroxy, -imidazolyl-R$^6$, -triazolyl-R$^6$, and -tetrazolyl-R$^6$.

5. The compound of claim 1 wherein R$^6$ is 1 to 4 substituents attached to a carbon or nitrogen atom independently selected from the group consisting of hydrogen, —C$_{1-4}$alkyl, —C$_{2-4}$alkenyl, —C$_{2-4}$alkynyl, —C(O)H, —C(O)—(C$_{1-4}$)alkyl, —CO$_2$H, —C(O)—O—(C$_{1-4}$)alkyl, —C(O)—NH$_2$, —C(NH)—NH$_2$, —C(O)—NH(C$_{1-4}$alkyl), —C(O)—N(C$_{1-4}$)alkyl)$_2$, —SO$_2$—(C$_{1-4}$)alkyl, —SO$_2$—NH$_2$, —SO$_2$—NH(C$_{1-4}$alkyl), —SO$_2$—N(C$_{1-4}$alkyl)$_2$, —(C$_{1-4}$)alkyl-N—R$^7$, —(C$_{1-4}$)alkyl-(halo)$_{1-3}$, —(C$_{1-4}$)alkyl-OH, -aryl-R$^8$, —(C$_{1-4}$)alkyl-aryl-R$^8$ and —(C$_{1-4}$)alkyl-heteroaryl-R$^8$;

with the proviso that, when R$^6$ is attached to a carbon atom, R$^6$ is further selected from the group consisting of —C$_{1-4}$alkoxy, —(C$_{1-4}$)alkoxy-(halo)$_{1-3}$, —SH, —S—($C_{1-4}$)alkyl, —N—$R^7$, cyano, halo, hydroxy, nitro, oxo and -heteroaryl-$R^8$.

6. The compound of claim 1 wherein $R^7$ is 2 substituents independently selected from the group consisting of hydrogen, —$C_{1-4}$alkyl, —$C_{2-4}$alkenyl, —$C_{2-4}$alkynyl, —($C_{1-4}$)alkyl-OH, —($C_{1-4}$)alkyl-O—($C_{1-4}$)alkyl, —($C_{1-4}$)alkyl-NH$_2$, —($C_{1-4}$)alkyl-NH($C_{1-4}$alkyl), —($C_{1-4}$)alkyl-N($C_{1-4}$ alkyl)$_2$, —($C_{1-4}$)alkyl-S—($C_{1-4}$)alkyl, —C(O)H, —C(O)—($C_{1-4}$)alkyl, —C(O)—O—($C_{1-4}$)alkyl, —C(O)—NH$_2$, —C(O)—NH($C_{1-4}$alkyl), —C(O)—N($C_{1-4}$alkyl)$_2$, —SO$_2$—($C_{1-4}$)alkyl, —SO$_2$—NH$_2$, —SO$_2$—NH($C_{1-4}$alkyl), —SO$_2$—N($C_{1-4}$alkyl)$_2$, —C(N)—NH$_2$, -cycloalkyl-$R^8$, —($C_{1-4}$)alkyl-heterocyclyl-$R^8$, -aryl-$R^8$, —($C_{1-4}$)alkyl-aryl-$R^8$, and —($C_{1-4}$)alkyl-heteroaryl-$R^8$.

7. The compound of claim 1 wherein $R^7$ is 2 substituents independently selected from the group consisting of of hydrogen, —$C_{1-4}$alkyl, —C(O)H, —C(O)—($C_{1-4}$)alkyl, —C(O)—O—($C_{1-4}$)alkyl, —SO$_2$—NH$_2$, —SO$_2$—NH($C_{1-4}$ alkyl), and —SO$_2$—N($C_{1-4}$alkyl)$_2$.

8. The compound of claim 1 wherein $R^8$ is 1 to 4 substituents attached to a carbon or nitrogen atom independently selected from the group consisting of hydrogen, —$C_{1-4}$alkyl, —($C_{1-4}$)alkyl-(halo)$_{1-3}$, and —($C_{1-4}$)alkyl-OH; with the proviso that, when $R^8$ is attached to a carbon atom, $R^8$ is further selected from the group consisting of —$C_{1-4}$alkoxy, —NH$_2$, —NH($C_{1-4}$alkyl), —N($C_{1-4}$ alkyl)$_2$, cyano, halo, —($C_{1-4}$)alkoxy-(halo)$_{1-3}$, hydroxy, and nitro.

9. The compound of claim 1 wherein $R^9$ is 1 to 2 substituents independently selected from the group consisting of hydrogen, —$C_{1-4}$alkoxy, —NH$_2$, —NH($C_{1-4}$alkyl), —N($C_{1-4}$alkyl)$_2$, cyano, (halo)$_{1-3}$, hydroxy, and nitro.

10. The compound of claim 1 wherein $R^6$, $R^8$, and $R^9$ are hydrogen.

11. The compound of claim 1 wherein $R^2$ is one substituent attached to a carbon or nitrogen atom selected from the group consisting of hydrogen, —$C_{1-4}$alkyl-$R^5$, —$C_{2-4}$alkenyl-$R^5$, —$C_{2-4}$alkynyl-$R^5$, —CO$_2$H, —C(O)—O—($C_{1-4}$) alkyl-$R^9$, —C(O)—NH$_2$, —C(O)—NH($C_{1-4}$alkyl-$R^9$), —C(O)—N($C_{1-4}$alkyl-$R^9$)$_2$, —C(O)—NH(aryl-$R^8$), —C(O)-cycloalkyl-$R^8$, —C(O)-heterocyclyl-$R^8$, —C(O)-aryl-$R^8$, —C(O)-heteroaryl-$R^8$, —CO$_2$H, —C(O)—O—($C_{1-4}$)alkyl-$R^9$, —C(O)—O-aryl-$R^8$, —SO$_2$—($C_{1-4}$)alkyl-$R^9$, —SO$_2$-aryl-$R^8$, -cycloalkyl-$R^6$, -aryl-$R^6$ and —($C_{1-4}$)alkyl-N—$R^7$;
with the proviso that, when $R^2$ is attached to a carbon atom, $R^2$ is further selected from the group consisting of —$C_{1-4}$alkoxy-$R^5$, —N—$R^7$, cyano, halogen, hydroxy, nitro, oxo, -heterocyclyl-$R^6$ and -heteroaryl-$R^6$.

12. The compound of claim 1 wherein $R^2$ is one substituent attached to a carbon or nitrogen atom selected from the group consisting of hydrogen, —$C_{1-4}$alkyl-$R^5$, —$C_{2-4}$alkenyl-$R^5$, —$C_{2-4}$alkynyl-$R^5$, —CO$_2$H, —C(O)—O—($C_{1-4}$) alkyl-$R^9$, -cycloalkyl-$R^6$, -alkyl-$R^6$ and —($C_{1-4}$)alkyl-N—$R^7$;
with the proviso that, when $R^2$ is attached to a nitrogen atom, a quaternium salt is not formed; and, with the proviso that, when $R^2$ is attached to a carbon atom, $R^2$ is further selected from the group consisting of —$C_{1-4}$ alkoxy-$R^5$, —N—$R^7$, cyano, halogen, hydroxy, nitro, oxo, -heterocyclyl-$R^6$ and -heteroaryl-$R^6$.

13. The compound of claim 1 wherein $R^2$ is one substituent attached to a carbon or nitrogen atom selected from the group consisting of hydrogen, —$C_{1-4}$alkyl-$R^5$ and -aryl-$R^6$; with the proviso that when $R^2$ is attached to a nitrogen atom, a quaternium salt is not formed; and, with the proviso that when $R^2$ is attached to a carbon atom, $R^2$ is further selected from the group consisting of —N—$R^7$, halogen, hydroxy and -heteroaryl-$R^6$.

14. The compound of claim 1 wherein $R_3$ is 1 to 3 substituents attached to a carbon atom independently selected from the group consisting of hydrogen, —$C_{1-4}$ alkyl-$R^{10}$, —$C_{2-4}$alkenyl-$R^{10}$, —$C_{2-4}$alkynyl-$R^{10}$, —$C_{1-4}$ alkoxy-$R^{10}$, —C(O)H, —C(O)—($C_{1-4}$)alkyl-$R^9$, —C(O)—NH$_2$, —C(O)—NH($C_{1-4}$alkyl-$R^9$), —C(O)—N($C_{1-4}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—NH$_2$, —CO$_2$H, —C(O)—O—($C_{1-4}$)alkyl-$R^9$, —C(O)—O-aryl-$R^8$, —SO$_2$—($C_{1-8}$)alkyl-$R^9$, —SO$_2$-aryl-$R^8$, —N—$R^7$, —($C_{1-4}$)alkyl-N—$R^7$, cyano, halogen, hydroxy, nitro, -cycloalkyl-$R^8$, -heterocyclyl-$R^8$, -aryl-$R^8$ and -heteroaryl-$R^8$.

15. The compound of claim 1 wherein $R^3$ is one substituent attached to a carbon atom selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —CO$_2$H, —NH$_2$, —NH($C_{1-4}$alkyl), —N($C_{1-4}$alkyl)$_2$, cyano, halogen, hydroxy, and nitro.

16. The compound of claim 1 wherein $R^3$ is one substituent attached to a carbon atom selected from the group consisting of hydrogen, —$C_{1-4}$alkyl-$R^{10}$, —NH$_2$, —NH ($C_{1-4}$ alkyl), —N($C_{1-4}$alkyl)$_2$, halogen, and hydroxy.

17. The compound of claim 1 wherein $R^4$ is 1 to 4 substituents attached to a carbon atom independently selected from the group consisting of hydrogen, —$C_{1-4}$ alkyl-$R^{10}$, —$C_{2-4}$alkenyl-$R^{10}$, —$C_{2-4}$alkynyl-$R^{10}$, —$C_{1-4}$ alkoxy-$R^{10}$, —C(O)H, —C(O)—($C_{1-4}$)alkyl-$R^9$, —C(O)—NH$_2$, —C(O)—NH($C_{1-4}$alkyl-$R^9$), —C(O)—N($C_{1-4}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—NH$_2$, —CO$_2$H, —C(O)—O—($C_{1-4}$)alkyl-$R^9$, —C(O)—O-aryl-$R^8$, —SH, —S—($C_{1-4}$)alkyl-$R^{10}$, —SO$_2$—($C_{1-4}$)alkyl-$R^9$, —SO$_2$-aryl-$R^8$, —SO$_2$—NH$_2$, —SO$_2$—NH($C_{1-4}$alkyl-$R^9$), —SO$_2$—N($C_{1-4}$alkyl-$R^9$)$_2$, —N—$R^7$, cyano, halogen, hydroxy, nitro, -cycloalkyl-$R^8$, -heterocyclyl-$R^8$, -aryl-$R^8$ and -heteroaryl-$R^8$.

18. The compound of claim 1 wherein $R^4$ is 1 to 4 substituents attached to a carbon atom independently selected from the group consisting of hydrogen, —$C_{1-4}$ alkyl-$R^{10}$, —$C_{2-4}$alkenyl-$R^{10}$, —$C_{2-4}$alkynyl-$R^{10}$, —$C_{1-4}$ alkoxy-$R^{10}$, —C(O)H, —CO$_2$H, —NH$_2$, —NH($C_{1-4}$alkyl), —N($C_{1-4}$alkyl)$_2$, cyano, halogen, hydroxy, nitro, -cycloalkyl, -heterocyclyl, -aryl and -heteroaryl.

19. The compound of claim 1 wherein $R^4$ is 1 to 4 substituents attached to a carbon atom independently selected from the group consisting of hydrogen, $C_{1-4}$alkyl-$R^{10}$, $C_{1-4}$alkoxy-$R^{10}$, —NH$_2$, —NH($C_{1-4}$alkyl), —N($C_{1-4}$ alkyl)$_2$, halogen, and hydroxy.

20. The compound of claim 1 wherein $R^4$ is 1 to 4 substituents attached to a carbon atom independently selected from the group consisting of hydrogen, $C_{1-4}$alkyl-$R^{10}$, $C_{1-4}$alkoxy-$R^{10}$, —NH$_2$, —NH($C_{1-4}$alkyl), —N($C_{1-4}$ alkyl)$_2$, chlorine, fluorine, and hydroxy.

21. The compound of claim 1 wherein $R^{10}$ is 1 to 2 substituents independently selected from the group consisting of hydrogen, —NH$_2$, —NH($C_{1-4}$alkyl), —N($C_{1-4}$alkyl)$_2$, cyano, (halo)$_{1-3}$, hydroxy, nitro, and oxo.

22. The compound of claim 1 wherein $R^{10}$ is 1 to 2 substituents independently selected from the group consisting of hydrogen and (halo)$_{1-3}$.

23. The compound of claim 1 wherein $R^{10}$ is 1 to 2 substituents independently selected from the group consisting of hydrogen and (fluoro)$_3$.

24. The compound of claim 1 wherein the compound of Formula (I) is a compound selected from Formula (Ia):

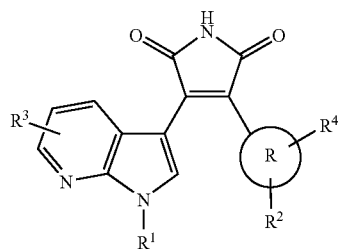

Formula (Ia)

wherein R, R¹, R², R³, and R⁴ are dependently selected from:

| R¹ | R³ | R | R² | R⁴ |
|---|---|---|---|---|
| HO(CH$_2$)$_3$ | H | 2-pyridinyl | H | H; |
| HO(CH$_2$)$_3$ | H | 2-pyridinyl | H | 3-Cl-5-CF$_3$; |
| HO(CH$_2$)$_3$ | H | 3,4-dihydro-2H-pyran-6-yl | H | H; |
| HO(CH$_2$)$_3$ | H | pyrimidin-5-yl | 2-OMe | 4-OMe |
| HO(CH$_2$)$_3$ | H | pyrimidin-5-yl | H | H |
| HO(CH$_2$)$_3$ | H | 2-oxo-2H-pyran-3-yl | H | H |
| HO(CH$_2$)$_3$ | H | pyrazin-2-yl | H | H |
| HO(CH$_2$)$_3$ | H | 5,6-dihydro-[1,4]dioxin-2-yl | H | H |
| HO(CH$_2$)$_3$ | H | pyrimidin-2-yl | H | H |
| Ph(CH$_2$)$_3$ | H | pyrimidin-5-yl | 2-MeO | 4-MeO |
| Ph(CH$_2$)$_3$ | H | pyrimidin-5-yl | H | H |
| Ph(CH$_2$)$_3$ | H | pyrazin-2-yl | H | H |
| Ph(CH$_2$)$_3$ | H | 5,6-dihydro-4H-pyran-2-yl | H | H |
| NC(CH$_2$)$_3$ | H | pyrimidin-5-yl | 2-Meo | 4-MeO |
| NC(CH$_2$)$_3$ | H | pyrazin-2-yl | H | H |
| HO(CH$_2$)$_3$ | H | 1H-pyrimidine-2,4-dione-5-yl | H | H |
| MeO(CH$_2$)$_2$ | H | pyrimidin-5-yl | 2-MeO | 4-MeO |
| PhCH$_2$ | H | pyrimidin-5-yl | 2-MeO | 4-MeO |
| Ph(CH$_2$)$_2$ | H | pyrimidin-5-yl | 2-MeO | 4-MeO |
| 3-thiophen-2-yl-propyl | H | pyrimidin-5-yl | 2-MeO | 4-MeO |
| 2-(4-fluoro-phenoxy)-ethyl | H | pyrimidin-5-yl | 2-MeO | 4-MeO and |
| PhO(CH$_2$)$_3$ | H | pyrimidin-5-yl | 2-MeO | 4-MeO. |

25. A pharmaceutical composition comprising a compound of claim 1 and a pharmaceutically acceptable carrier.

26. A method for preparing a pharmaceutical composition comprising mixing a compound of claim 1 and a pharmaceutically acceptable carrier.

\* \* \* \* \*